(12) United States Patent
Brogdon et al.

(10) Patent No.: US 10,927,184 B2
(45) Date of Patent: Feb. 23, 2021

(54) TREATMENT OF CANCER USING HUMANIZED ANTI-CD19 CHIMERIC ANTIGEN RECEPTOR

(71) Applicants: Novartis AG, Basel (CH); The Trustees of the University of Pennsylvania, Philadelphia, PA (US)

(72) Inventors: Jennifer Brogdon, Sudbury, MA (US); Carl H. June, Merion Station, PA (US); Andreas Loew, Boston, MA (US); Marcela Maus, Lexington, MA (US); John Scholler, Narberth, PA (US)

(73) Assignees: Novartis AG, Basel (CH); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/192,375

(22) Filed: Nov. 15, 2018

(65) Prior Publication Data
US 2019/0135940 A1    May 9, 2019

Related U.S. Application Data

(62) Division of application No. 14/214,728, filed on Mar. 15, 2014, now Pat. No. 10,221,245.

(60) Provisional application No. 61/838,537, filed on Jun. 24, 2013, provisional application No. 61/802,629, filed on Mar. 16, 2013.

(51) Int. Cl.
| | |
|---|---|
| *C07K 16/28* | (2006.01) |
| *C07K 16/30* | (2006.01) |
| *C07K 14/725* | (2006.01) |
| *C07K 14/705* | (2006.01) |
| *C12N 5/0783* | (2010.01) |
| *A61K 39/00* | (2006.01) |

(52) U.S. Cl.
CPC ...... *C07K 16/3061* (2013.01); *C07K 14/7051* (2013.01); *C07K 14/70503* (2013.01); *C07K 14/70578* (2013.01); *C07K 16/2803* (2013.01); *C12N 5/0636* (2013.01); *A61K 2039/505* (2013.01); *C07K 2317/24* (2013.01); *C07K 2317/565* (2013.01); *C07K 2317/622* (2013.01); *C07K 2317/73* (2013.01); *C07K 2317/94* (2013.01); *C07K 2319/00* (2013.01); *C07K 2319/03* (2013.01); *C12N 2510/02* (2013.01)

(58) Field of Classification Search
None
See application file for complete search history.

(56) References Cited

U.S. PATENT DOCUMENTS

| | | |
|---|---|---|
| 5,359,046 A | 10/1994 | Capon et al. |
| 5,686,281 A | 11/1997 | Roberts |
| 5,712,149 A | 1/1998 | Roberts |
| 5,786,464 A | 7/1998 | Seed |
| 5,874,240 A | 2/1999 | Ni et al. |
| 5,906,936 A | 5/1999 | Eshhar et al. |
| 6,103,521 A | 8/2000 | Capon et al. |
| 6,111,090 A | 8/2000 | Gorman et al. |
| 6,114,148 A | 9/2000 | Seed et al. |
| 6,319,494 B1 | 11/2001 | Capon et al. |
| 6,355,779 B1 | 3/2002 | Goodwin et al. |
| 6,410,319 B1 | 6/2002 | Raubitschek et al. |
| 6,569,997 B1 | 5/2003 | Kwon |
| 7,049,136 B2 | 5/2006 | Seed et al. |
| 7,052,906 B1 | 5/2006 | Lawson et al. |
| 7,070,995 B2 | 7/2006 | Jensen |
| 7,132,255 B2 | 11/2006 | Blumberg |
| 7,265,209 B2 | 9/2007 | Jensen |
| 7,319,143 B2 | 1/2008 | Gross et al. |
| 7,320,787 B2 | 1/2008 | Seed et al. |
| 7,402,431 B2 | 7/2008 | Har-Noy |
| 7,446,190 B2 | 11/2008 | Sadelain et al. |
| 7,446,191 B2 | 11/2008 | Jensen |
| 7,514,537 B2 | 4/2009 | Jensen |
| 7,638,325 B2 | 12/2009 | June et al. |
| 7,638,326 B2 | 12/2009 | June et al. |
| 7,741,465 B1 | 6/2010 | Eshhar et al. |
| 7,745,140 B2 | 6/2010 | June et al. |
| 7,754,482 B2 | 7/2010 | Riley et al. |
| 7,994,298 B2 | 8/2011 | Zhang et al. |
| 8,008,449 B2 | 8/2011 | Korman et al. |
| 8,124,084 B2 | 2/2012 | Lefrancois et al. |
| 8,211,422 B2 | 7/2012 | Eshhar et al. |
| 8,252,914 B2 | 8/2012 | Zhang et al. |

(Continued)

FOREIGN PATENT DOCUMENTS

| | | |
|---|---|---|
| EP | 215576 A1 | 3/1987 |
| EP | 0574512 A1 | 12/1993 |
| EP | 0871495 A1 | 10/1998 |
| EP | 1226244 A2 | 7/2002 |
| JP | 2003517301 A | 5/2003 |
| JP | 2004529636 A | 9/2004 |

(Continued)

OTHER PUBLICATIONS

Kofler et al., Mol Ther. Apr. 2011;19(4):760-7. (Year: 2011).*

(Continued)

*Primary Examiner* — Zachary S Skelding
(74) *Attorney, Agent, or Firm* — Lando & Anastasi, LLP

(57) ABSTRACT

The invention provides compositions and methods for treating diseases associated with expression of CD19. The invention also relates to chimeric antigen receptor (CAR) specific to CD19, vectors encoding the same, and recombinant T cells comprising the CD19 CAR. The invention also includes methods of administering a genetically modified T cell expressing a CAR that comprises a CD19 binding domain.

26 Claims, 8 Drawing Sheets

Specification includes a Sequence Listing.

(56) References Cited

U.S. PATENT DOCUMENTS

| | | |
|---|---|---|
| 8,383,778 B2 | 2/2013 | Hsieh et al. |
| 8,389,282 B2 | 3/2013 | Sadelain et al. |
| 8,399,645 B2 | 3/2013 | Campana et al. |
| 8,465,743 B2 | 6/2013 | Rosenberg et al. |
| 8,637,307 B2 | 1/2014 | June et al. |
| 8,722,400 B2 | 5/2014 | Riley et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,394,368 B2 | 7/2016 | Brogdon et al. |
| 9,464,140 B2 | 10/2016 | June et al. |
| 9,481,728 B2 | 11/2016 | June et al. |
| 9,499,629 B2 | 11/2016 | June et al. |
| 9,573,988 B2 | 2/2017 | Brogdon et al. |
| 9,745,368 B2 | 8/2017 | Milone et al. |
| 9,777,061 B2 | 10/2017 | Ebersbach et al. |
| 9,815,901 B2 | 11/2017 | Brogdon et al. |
| 10,357,514 B2 | 7/2019 | June et al. |
| 2003/0060444 A1 | 3/2003 | Finney et al. |
| 2003/0077249 A1 | 4/2003 | Bebbington et al. |
| 2003/0148982 A1 | 8/2003 | Brenner et al. |
| 2003/0224520 A1 | 12/2003 | June et al. |
| 2004/0038886 A1 | 2/2004 | Finney et al. |
| 2004/0043401 A1 | 3/2004 | Sadelain et al. |
| 2005/0113564 A1 | 5/2005 | Campana et al. |
| 2005/0129671 A1 | 6/2005 | Cooper et al. |
| 2007/0036773 A1 | 2/2007 | Cooper et al. |
| 2008/0131415 A1 | 6/2008 | Riddell et al. |
| 2009/0082299 A1 | 3/2009 | Felber et al. |
| 2009/0257994 A1 | 10/2009 | Jensen |
| 2010/0233200 A1 | 9/2010 | Medin |
| 2010/0247521 A1 | 9/2010 | Jones et al. |
| 2011/0052554 A1 | 3/2011 | Zakrzewski et al. |
| 2011/0081311 A1 | 4/2011 | Pavlakis et al. |
| 2012/0141413 A1 | 6/2012 | Pavlakis et al. |
| 2012/0148552 A1 | 6/2012 | Jensen |
| 2012/0177598 A1 | 7/2012 | Lefrancois et al. |
| 2012/0321667 A1 | 12/2012 | Sentman |
| 2013/0071409 A1 | 3/2013 | Riley et al. |
| 2013/0071414 A1 | 3/2013 | Dotti et al. |
| 2013/0149337 A1 | 6/2013 | Cooper et al. |
| 2013/0155909 A1 | 6/2013 | Jackson et al. |
| 2013/0287748 A1 | 10/2013 | June et al. |
| 2013/0288368 A1 | 10/2013 | June et al. |
| 2014/0050708 A1 | 2/2014 | Powell et al. |
| 2014/0099309 A1 | 4/2014 | Powell, Jr. et al. |
| 2014/0099340 A1 | 4/2014 | June et al. |
| 2014/0106449 A1 | 4/2014 | June et al. |
| 2014/0186947 A1 | 7/2014 | June et al. |
| 2014/0212446 A1 | 7/2014 | Riley et al. |
| 2014/0219975 A1 | 8/2014 | June et al. |
| 2014/0227237 A1 | 8/2014 | June et al. |
| 2014/0271582 A1 | 9/2014 | Forman et al. |
| 2014/0271635 A1 | 9/2014 | Brogdon et al. |
| 2014/0322169 A1 | 10/2014 | Harper et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0370017 A1 | 12/2014 | June et al. |
| 2014/0370045 A1 | 12/2014 | June et al. |
| 2015/0017141 A1 | 1/2015 | June et al. |
| 2015/0050729 A1 | 2/2015 | June et al. |
| 2015/0093822 A1 | 4/2015 | June et al. |
| 2015/0099299 A1 | 4/2015 | June et al. |
| 2015/0118202 A1 | 4/2015 | June et al. |
| 2015/0140019 A1 | 5/2015 | June et al. |
| 2015/0166661 A1 | 6/2015 | Chen et al. |
| 2015/0190428 A1 | 7/2015 | June et al. |
| 2015/0202286 A1 | 7/2015 | June et al. |
| 2015/0238631 A1 | 8/2015 | Kim et al. |
| 2015/0283178 A1 | 10/2015 | June et al. |
| 2015/0290207 A1 | 10/2015 | Kutok et al. |
| 2015/0290244 A1 | 10/2015 | June et al. |
| 2015/0342994 A1 | 12/2015 | Riley et al. |
| 2016/0046724 A1 | 2/2016 | Brogdon et al. |
| 2016/0051651 A1 | 2/2016 | Brogdon et al. |
| 2016/0068601 A1 | 3/2016 | Brogdon et al. |
| 2016/0096892 A1 | 4/2016 | Brogdon et al. |
| 2016/0130355 A1 | 5/2016 | June et al. |
| 2016/0159907 A1 | 6/2016 | June et al. |
| 2016/0185861 A1 | 6/2016 | Bedoya et al. |
| 2016/0194404 A1 | 7/2016 | June et al. |
| 2016/0208012 A1 | 7/2016 | June et al. |
| 2016/0311907 A1 | 10/2016 | Brogdon et al. |
| 2016/0311917 A1 | 10/2016 | Beatty et al. |
| 2016/0340406 A1 | 11/2016 | Zhao et al. |
| 2016/0362472 A1 | 12/2016 | Bitter et al. |
| 2017/0008963 A1 | 1/2017 | Brogdon et al. |
| 2017/0081411 A1 | 3/2017 | Engels et al. |
| 2017/0137783 A1 | 5/2017 | Bedoya et al. |
| 2017/0183415 A1 | 6/2017 | Brogdon et al. |
| 2017/0209492 A1 | 7/2017 | June et al. |
| 2017/0211055 A1 | 7/2017 | Brogdon et al. |
| 2017/0226495 A1 | 8/2017 | Guimaraes |
| 2017/0239294 A1 | 8/2017 | Thomas-Tikhonenko et al. |
| 2017/0260268 A1 | 9/2017 | Beatty et al. |
| 2017/0274014 A1 | 9/2017 | Brogdon et al. |
| 2017/0306416 A1 | 10/2017 | Bedoya et al. |
| 2017/0335281 A1 | 11/2017 | Loew et al. |
| 2018/0022795 A1 | 1/2018 | Milone et al. |
| 2018/0044423 A1 | 2/2018 | Ebersbach et al. |
| 2018/0044424 A1 | 2/2018 | June et al. |
| 2018/0118834 A1 | 5/2018 | Brogdon et al. |
| 2018/0125892 A1 | 5/2018 | Brannetti et al. |
| 2018/0133296 A1 | 5/2018 | Barrett et al. |
| 2018/0140602 A1 | 5/2018 | Angst et al. |
| 2018/0230193 A1 | 8/2018 | Loew et al. |
| 2018/0252727 A1 | 9/2018 | Garfall et al. |
| 2018/0258149 A1 | 9/2018 | Motz et al. |
| 2018/0298068 A1 | 10/2018 | Albelda |
| 2018/0312595 A1 | 11/2018 | Brogdon et al. |
| 2019/0000880 A1 | 1/2019 | Motz et al. |
| 2019/0000944 A1 | 1/2019 | Brogdon et al. |
| 2019/0151365 A1 | 5/2019 | Anak et al. |
| 2019/0153061 A1 | 5/2019 | Brogdon et al. |
| 2019/0161542 A1 | 5/2019 | Gill et al. |
| 2019/0263914 A1 | 8/2019 | Brogdon et al. |
| 2019/0292238 A1 | 9/2019 | Bitter et al. |
| 2019/0292257 A1 | 9/2019 | Bedoya et al. |
| 2019/0298715 A1 | 10/2019 | Motz et al. |
| 2019/0330356 A1 | 10/2019 | Brogdon et al. |
| 2019/0336504 A1 | 11/2019 | Gill et al. |
| 2019/0375815 A1 | 12/2019 | Engels et al. |
| 2019/0382500 A1 | 12/2019 | Abujoub et al. |
| 2019/0388471 A1 | 12/2019 | June et al. |
| 2019/0389928 A1 | 12/2019 | Posey et al. |
| 2020/0048359 A1 | 2/2020 | Albelda et al. |
| 2020/0055948 A1 | 2/2020 | Daley et al. |
| 2020/0061113 A1 | 2/2020 | Kassim et al. |
| 2020/0085869 A1 | 3/2020 | Schuster et al. |
| 2020/0087376 A1 | 3/2020 | Fraietta et al. |

FOREIGN PATENT DOCUMENTS

| | | |
|---|---|---|
| WO | 1992015322 A1 | 9/1992 |
| WO | 9507984 A1 | 3/1995 |
| WO | 199530014 A1 | 11/1995 |
| WO | 9623814 A1 | 8/1996 |
| WO | 9624671 A1 | 8/1996 |
| WO | 1997015669 A1 | 5/1997 |
| WO | 9723613 A2 | 7/1997 |
| WO | 9818809 A1 | 5/1998 |
| WO | 9900494 A2 | 1/1999 |
| WO | 99015555 A1 | 4/1999 |
| WO | 9921581 A1 | 5/1999 |
| WO | 9957268 A1 | 11/1999 |
| WO | 0014257 A1 | 3/2000 |
| WO | 200134843 A1 | 5/2001 |
| WO | 2002033101 A1 | 4/2002 |
| WO | 02077029 A2 | 10/2002 |

(56) References Cited

FOREIGN PATENT DOCUMENTS

| WO | 02088334 A1 | 11/2002 |
|---|---|---|
| WO | 2003057171 A2 | 7/2003 |
| WO | 2004/003019 A2 | 1/2004 |
| WO | 2005019429 A2 | 3/2005 |
| WO | 2005044996 A2 | 5/2005 |
| WO | 2005/118788 A2 | 12/2005 |
| WO | 2006050491 A2 | 5/2006 |
| WO | 2006060878 A1 | 6/2006 |
| WO | 08039218 A2 | 4/2008 |
| WO | 2008045437 A2 | 4/2008 |
| WO | 2008049928 A1 | 5/2008 |
| WO | 2009091826 A2 | 7/2009 |
| WO | 2010019570 A2 | 2/2010 |
| WO | 2010025177 A1 | 3/2010 |
| WO | 2010085660 A2 | 7/2010 |
| WO | 2010095031 A2 | 8/2010 |
| WO | 2011059836 A2 | 5/2011 |
| WO | 2011097477 A1 | 8/2011 |
| WO | 2012058460 A2 | 5/2012 |
| WO | 2012079000 A1 | 6/2012 |
| WO | 2012082841 A2 | 6/2012 |
| WO | 2012/099973 A2 | 7/2012 |
| WO | 2012127464 A2 | 9/2012 |
| WO | 2012129514 A1 | 9/2012 |
| WO | 2012135854 A2 | 10/2012 |
| WO | 2012138858 A1 | 10/2012 |
| WO | 2013019615 A2 | 2/2013 |
| WO | 2013033626 A2 | 3/2013 |
| WO | 2013040371 A2 | 3/2013 |
| WO | 2013040557 A2 | 3/2013 |
| WO | 2013059593 A1 | 4/2013 |
| WO | 2013/126712 A1 | 8/2013 |
| WO | 2013126729 A1 | 8/2013 |
| WO | 2013126733 A1 | 8/2013 |
| WO | 2014/011984 A1 | 1/2014 |
| WO | 2014/011987 A1 | 1/2014 |
| WO | 2014/011993 A2 | 1/2014 |
| WO | 2014/012001 A2 | 1/2014 |
| WO | 2014011988 A2 | 1/2014 |
| WO | 2014011996 A1 | 1/2014 |
| WO | 2014031687 A1 | 2/2014 |
| WO | 2014039513 A2 | 3/2014 |
| WO | 2014/055442 A2 | 4/2014 |
| WO | 2014055657 A1 | 4/2014 |
| WO | 2014130635 A1 | 8/2014 |
| WO | 2014/145252 A2 | 9/2014 |
| WO | 2014153270 A1 | 9/2014 |
| WO | 2015079417 A1 | 6/2015 |
| WO | 2015090229 A1 | 6/2015 |
| WO | 2015090230 A1 | 6/2015 |
| WO | 2015112626 A1 | 7/2015 |
| WO | 2015/142661 A1 | 9/2015 |
| WO | 2015142675 A2 | 9/2015 |
| WO | 2015157252 A1 | 10/2015 |
| WO | 2016014501 A1 | 1/2016 |
| WO | 2016014530 A1 | 1/2016 |
| WO | 2016014535 A1 | 1/2016 |
| WO | 2016014553 A1 | 1/2016 |
| WO | 2016014565 A2 | 1/2016 |
| WO | 2016014576 A1 | 1/2016 |
| WO | 2016019300 A1 | 2/2016 |
| WO | 2016025880 A1 | 2/2016 |
| WO | 2016028896 A1 | 2/2016 |
| WO | 2016044605 A1 | 3/2016 |
| WO | 2016/164580 A1 | 10/2016 |

OTHER PUBLICATIONS

Bell et al., J Exp Med. Jan. 1, 1996;183(1):169-78. (Year: 1996).*
Kawamata et al., vol. 273, No. 10, pp. 5808-5814, 1998. (Year: 1998).*
Kaizuka et al., J Cell Biol. May 4, 2009;185(3):521-34. (Year: 2009).*
Arch et al. (MCB, Jan. 1998, p. 558-565). (Year: 1998).*
Barao et al. (Front Immunol. Jan. 4, 2013;3:402). (Year: 2013).*
Akinleye et al. "Iburtinib and novel BTK inhibitors in clinical development" Journal of Hematology & Oncology (2013) vol. 6, No. 59, pp. 1-9.
ClinicalTrials.gov "Phase IIa Study of Redirected Autologous T Cells Engineered to Contain Anti-CD19 Attached to TCRz and 4-Signaling Domains in Patients With Chemotherapy Relapsed or Refractory CD19+ Lymphomas" Clinical Trials Identifier: NCT02030834; Updated Feb. 19, 2019.
ClinicalTrials.gov "Pilot Trial of Autologous T Cells Engineered to Express Anti-CD19 Chimeric Antigen Receptor (CART19) in Combination With Iburtinib in Patients With Relapsed or Refractory CD19+ Chronic Lymphocytic Leukemia (CLL) or Small Lymphocytic Lymphoma (SLL)" ClinicalTrials.gov Identifier: NCT02640209; Last Updated Sep. 27, 2016.
Fraietta et al. "Iburtinib enhances chimeric antigen receptor T-cell engraftment and efficacy in leukemia" Blood (2016) vol. 127, No. 9, pp. 1117-1127.
Jain et al. "Overview of recent developments in chronic lymphocytic leukemia" South Asian Journal of Cancer (2012) vol. 1, No. 2, pp. 84-89.
Pakula "Genetic Analysis of Protein Stability and Function" Annu. Rev. Genet. (1989) vol. 23, pp. 289-310.
"Pilot study for Patients with chemotherapy resistant or refractory CD19 Leukemia and Lymphoma (CART-19)" ClinicalTrials.gov Identifier NCT00891215; Retrieved from the internet on Sep. 2, 2015 Found at http://web.archive.org/web/20090903002304/http://clinicaltrials.gov/ct2/show/study/NCT00891215.
A NCBI Direct Submission NP 000725 dated Nov. 21, 2010.
A NCBI Direct Submission NP 932170.1 dated Nov. 21, 2010.
Accession No. NM_001178098.
Acuto et al. "CD28-Mediated Co-Stimulation: A Quantitative Support for TCR Signalling" Nature Reviews Immunology (2003) vol. 3, pp. 939-951.
Advani et al., "Bruton tyrosine kinase inhibitor ibrutinib (PCI-32765) has significant activity in patients with relapsed/refractory B-cell malignancies." Journal of Clinical Oncology (2012) vol. 31 No. 1 pp. 88-94.
Advani et al., "Bruton tyrosine kinase inhibitor ibrutinib (PCI-32765) has significant activity in patients with relapsed/refractory B-cell malignancies." Journal of Clinical Oncology (2013) vol. 31 No. 1 pp. 88-94.
Agata et al. "Expression of the PD-1 antigen on the surface of stimulated mouse T and B lymphocytes", International Immunology (1996) vol. 8 No. 5 pp. 765-772.
Akiba et al. "CD27, a Member of the Tumor Necrosis Factor Receptor Superfamily, Activates NF-kB and Stress-activated Protein Kinase/c-Jun N-terminal Kinase via TRAF2, TRAF5, and NF-kB-inducing Kinase" The Journal of Biological Chemistry (1998) vol. 273, No. 21, pp. 13353-13358.
Alabanza et al. "Function of Novel Anti-CD19 Chimeric Antigen Receptors with Human Variable Regions Is Affected by Hinge and Transmembrane Domains" Molecular Therapy (2017) vol. 25, No. 11, pp. 1-14.
AppliChem product sheet for RPMI-1640, 2 pages, downloaded Dec. 28, 2015.
Awan and Byrd, "New Strategies in Chronic Lymphocytic Leukemia: Shifting Treatment Paradigms" Clinical Cancer Research (2014) vol. 20 No. 23 pp. 5869-5874.
Baeksgaard & Sorensen, "Acute tumor lysis syndrome in solid tumors—a case report and review of the literature" Cancer Chemotherapy Pharmacology (2003) vol. 51 pp. 187-192.
Batzer et al. "Enhanced evolutionary PCR using oligonucleotides with inosine at the 3'-terminus" (1991) vol. 19, No. 18, pp. 5081.
Bierer et al., "Cyclosporin A and FK506: molecular mechanisms of immunosuppression and probes for transplantation biology" Current Opinion in Immunology (1992) vol. 5 pp. 763-773.
Blank et al. "Interaction of PD-L1 on tumor cells with PD-1 on tumor-specific T cells as a mechanism of immune evasion: implications for tumor immunotherapy." Cancer Immunol Immunother (2005) vol. 54 No. 4 pp. 307-314.

(56) References Cited

OTHER PUBLICATIONS

Bondanza et al. "Suicide gene therapy of graft-versus-host disease induced by central memory human T lymphocytes" Blood (2006) vol. 107 No. 5 pp. 1828-1836.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Novel cellular therapies for leukemia: CAR-modified T cells targeted to the CD19 antigen" Hematology (2012) pp. 143-151.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Bridgeman et al. "The Optimal Antigen Response of Chimeric Antigen Receptors Harboring the CD3 Transmembrane Domain Is Dependent upon Incorporation of the Receptor into the Endogenous TCR/CD3 Complex" J. Immunol. (2010) vol. 184, pp. 6938-6949.
Brocker and Karjalainen, "Signals through T Cell Receptor-Chain alone Are Insufficient to Prime Resting T Lymphocytes" J. Exp. Med. (1995) vol. 181 pp. 1653-1659.
Brown J R et al: "Novel Treatments for Chronic Lymphocytic Leukemia and Moving Forward",American Society of Clinical Oncology Educational Book,vol. 34, 2014, pp. e317-e325,XP05520 1368,ISSN: 1548-8748, DOI:10.14694/EdBook_AM.2014..34. e317 the whole document.
Byrd et al., "Targeting BTK with ibrutinib in relapsed chronic lymphocytic leukemia." New England Journal of Medicine (2013) vol. 369 No. 1 pp. 32-42.
Call & Wucherpfennig, "The T Cell Receptor: Critical Role of the Membrane Environment in Receptor Assembly and Function" Annu. Rev. Immunol. (2005) vol. 23 pp. 101-125.
Campana et al., 2003 Blood 102(11); abstract #223.
Carpenito et al. "Control of large, established tumor xenografts with genetically retargeted human T cells containing CD28 and CD137 domains", Proc Natl Acad Sci USA (2009) vol. 106 pp. 3360-3365.
Carter et al. "PD-1:PD-L inhibitory pathway affects both CD4+ and CD8+ T cells and is overcome by IL-2" Eur. J. Immunol. (2002) vol. 32 pp. 634-643.
Casulo et al., "A phase I study of PRO131921, a novel anti-CD20 monoclonal antibody in patients with relapsed/refractory CD20+ indolent NHL: correlation between clinical responses and AUC pharmacokinetics." Clinical Immunology (2014) vol. 154 No. 1 pp. 37-46.
Cheadle et al "Natural Expression of the CD19 Antigen Impacts the Long-Term Engraftment but Not Antitumor Activity of CD19-Specific Engineered T Cells" The Journal of Immunology (2010) vol. 184, No. 4, pp. 1885-1896.
Cheson et al., "Report of an International Workshop to Standardize Response Criteria for Non-Hodgkin's Lymphomas" Journal of Clinical Oncology (1999) vol. 17 pp. 1244-1253.
Chothia et al. "Canonical structures for the hypervariable regions of immunoglobulins" Journal of Molecular Biology (1987) vol. 196, No. 4, pp. 901-917.

Chung et al. "All TRAFs are not created equal: common and distinct molecular mechanisms of TRAF-mediated signal transduction" Journal of Cell Science (2002) vol. 115, pp. 679-688.
Colman et al. "Effects of amino acid sequence changes on antibody-antigen interactions" Research in Immunology (1994) vol. 145, pp. 33-36.
Cooper et al. "Test-driving CARs" Blood (2008) vol. 112, No. 5, pp. 2172-2173.
Cruz et al. "Adverse events following infusion of T cells for adoptive immunotherapy: a 10-year experience" Cytotherapy (2010) vol. 12, No. 6, pp. 743-749.
Davila et al, "T Cells Genetically Targeted to CD19 Eradicate B-All in a Novel Syngeneic Mouse Disease Model" 2010 ASH Abstract No. 171, presented Dec. 6, 2010 (poster abstract).
Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meting and Exposition (2010) Oral and Poster Abstract.
De Visser et al., "De novo carcinogenesis promoted by chronic inflammation is B lymphocyte dependent." Cancer Cell (2005) vol. 7 No. 5 pp. 411-423.
Di Stasi et al., "Inducing apoptosis as a safety switch for adoptive cell therapy" New England Journal of Medicine (2011) vol. 365 No. 18 pp. 1673-1683.
Diamond et al. "Somatic mutation of the T15 heavy chain gives rise to an antibody with autoantibody specificity" PNAS (1984) vol. 81, pp. 5841-5844.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dong et al. "B7-H1 pathway and its role in the evasion of tumor immunity." J Mol Med (2003) vol. 81 No. 5 pp. 281-287.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dubovsky et al., "Ibrutinib is an irreversible molecular inhibitor of ITK driving a Th1-selective pressure in T lymphocytes." Blood (2013) vol. 122 No. 15. pp. 2539-2549.
Dudley et al. "Malignancy Persisting After Allogeneic Hematopoietic Stem Cell Transplantation" Blood (2013) vol. 122, No. 21, pp. 151—Abstract Only.
Milone et al, "Chimeric Receptors Containing CD137 Signal Transduction Domains Mediate Enhanced Survival of T Cells and Increased Antileukemic Efficacy in Vivo" Molecular Therapy (2009) vol. 17 No. 8 pp. 1453-1464.
Milone et al, Supplementary Materials and Methods, Mol. Ther (2009) vol. 17, 7 pages.
Moeini et al., "Emerging signaling pathways in hepatocellular carcinoma." Liver Cancer (2012) vol. 1 No. 2 pp. 83-93.
Molina, "A Decade of Rituximab: Improving Survival Outcomes in Non-Hodgkin's Lymphoma" Annu. Rev. Med. (2008) vol. 59 pp. 237-250.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).

(56) References Cited

OTHER PUBLICATIONS

Ochoa et al, "Immune Defects in T Cells from Cancer Patients, Parallels in Infectious Diseases" Cancer Immunotherapy at the Crossroads: how tumors evade immunity and what can be done (current clinical oncology), edited by James H. Finke, Ronald M. Bukowski, 2004 edition.
Ohno, et al. "Antigen-binding specificities of antibodies are preimarily determined by seven residues of VH" PNAS (1985) vol. 82, pp. 2945-2949.
Ohtsuka et al. "An Alternative Approach to Deoxyoligonucleotides as Hybridization Probes by Insertion of Deoxyinosine at Ambiguous Codon Positions" The Journal of Biological Chemistry (1985) vol. 260, No. 5, pp. 2605-2608.
Pardoll, "The blockade of immune checkpoints in cancer immunotherapy" Cancer (2012) vol. 12 pp. 252-264.
Parikh et al., "How we treat Richter syndrome." Blood (2014) vol. 123 No. 11 pp. 1647-1657.
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Parry et al. "CD28 and Inducible Costimulatory Protein Src Homology 2 Binding Domains Show Distinct Regulation of Phisphatidylinositol 3-Kinase, Bcl-xL, and IL-2 Expession in Primary Human CD4 T Lymphocytes" The Journal of Immunology (2003) vol. 171, pp. 166-174.
Patel et al., "Impact of chimeric immune receptor extracellular protein domains on T cell function" Gene Therapy (1999) vol. 6 pp. 412-419.
Ponader et al., "The Bruton tyrosine kinase inhibitor PCI-32765 thwarts chronic lymphocytic leukemia cell survival and tissue homing in vitro and in vivo" Blood (2012) vol. 119 No. 5 pp. 1182-1189.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric antigen receptor T cells persist and induce sustained remissions in relapsed refractory chronic lymphocytic leukemia" Science Translational Medicine (2015) vol. 7 No. 303 303ra139.
Porter et al., "Chimeric Antigen Receptor Therapy for B-cell Malignancies" Journal of Cancer (2011) vol. 2 pp. 331-332.
Porter et al., "Randomized, Phase II Dose Optimization Study of Chimeric Antigen Receptor Modified T Cells Directed Against CD19 (CTL019) in Patients with Relapsed, Refractory CLL" Blood (2014) vol. 124 No. 21.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Pytonteck et al., "CSF-1R inhibition alters macrophage polarization and blocks glioma progression." Natural Medicine (2013) vol. 19 No. 10 pp. 1264-1272.
Rapoport et al., "Restoration of immunity in lymphopenic individuals with cancer by vaccination and adoptive T-cell transfer" Nature Medicine (2005) vol. 11 No. 11 pp. 1230-1237.
Robak & Robak, "New Anti-CD20 Monoclonal Antibodies for the Treatment of B-Cell Lymphoid Malignancies" Biodrugs (2011) vol. 25 No. 1 pp. 13-25.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).

Romisher et al., "Bruton's Tyrosine Kinase Inhibition Is Associated with Manageable Cardiac Toxicity" Blood (2015) vol. 126 No. 23.
Rossolini et al. "Use of deoxyinosine-containing primers vs degenerate primers for polymerase chain reaction based on ambiguous sequence information" Molecular and Cellular Probes (1994) vol. 8, No. 2, pp. 91-98.
Rudikoff et al. "Single amino acid substitutuion altering antigen-binding specificity" Proc. Natl. Acad. Sci. (1982) vol. 79, pp. 1979-1983.
Ruella and Gill, "How to train your T cell: genetically engineered chimeric antigen receptor T cells versus bispecific T-cell engagers to target CD19 in B acute lymphoblastic leukemia." (2015) vol. 15 No. 6 pp. 761-766.
Ruella et al., "Combination of Ibrutinib and Anti-CD19 Chimeric Antigen Receptor T Cells for the Treatment of Relapsing/Refractory Mantle Cell Lymphoma (MCL)" Haematologica (2015) vol. 100 pp. 287-288.
Ruella et al., "The Addition of the BTK Ibrutinib to Anti-CD19 Chimeric Antigen Receptor T Cells (CART19) Improves Responses against Mantle Cell Lymphoma" Clinical Cancer Research (2016) 1-13.
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Sagiv-Barfi, et al., "Ibrutinib enhances the antitumor immune response induced by intratumoral injection of a TLR9 ligand in mouse lymphoma" Blood, 125(13):2079-2086 (2015).
Sagiv-Barfi, et al., "Therapeutic antitumor immunity by checkpoint blockade is enhanced by ibrutinib, an inhibitor of both BTK and ITK" PNAS, 112(9):E966-E972 (2015).
Salvadori, "Antineoplastic effects of mammalian target of rapamycine inhibitors." World Journal of Transplantation (2012) vol. 2 No. 5 pp. 74-83.
Santoni et al., "Role of natural and adaptive immunity in renal cell carcinoma response to VEGFR-TKIs and mTOR Inhibitor" International Journal of Cancer (2014) vol. 134 No. 12 pp. 2772-2777.
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Scott et al., "Monoclonal antibodies in cancer therapy" Cancer Immunity (2012) vol. 12 p. 14.
Sebestyen et al., "Human TCR That Incorporate CD3 Induce Highly Preferred Pairing between TCR and Chains following Gene Transfer" Journal of Immunology (2008) vol. 180 pp. 7736-7746.
SHI et al. "Chimeric antigen receptor for adoptive immunotherapy of cancer: latest research and future prospects" Molecular Cancer (2014) vol. 13, No. 219, pp. 1-8.
Shirasu et al. "Functional Design of Chimeric T-Cell Antigen Receptors for Adoptive Immunotherapy of Cancer: Architecture and Outcomes" Anticancer Research (2012) vol. 32, pp. 2377-2384.
Shirasu et al., "Functional Design of Chimeric T-Cell Antigen Receptors for Adoptive Immunotherapy of Cancer: Architecture and Outcomes," AntiCancer Res. 32: 2377-2384 (2012).
Beckman et al. "Antibody Constructs in Cancer Therapy" Cancer (2007) vol. 109, No. 2, pp. 170-179.
Cespedes et al. "Mouse models in oncogenesis and cancer therapy" Clin. Transl. Oncol. (2006) vol. 8, No. 5, pp. 318-329.
D'Cruz et al, "Novel Bruton's tyrosine kinase inhibitors currently in development", Oncotargets and Therapy (2013) vol. 6, pp. 161-176.
Dennis "Off by a whisker" Nature (2006) vol. 442, pp. 739-741.
Extended European Search Report for European Application No. 19158368.1 dated Jul. 5, 2019.
Fujimori et al. "A Modeling Analysis of Monoclonal Antibody Percolation Through Tumors: A Binding Site Barrier" (1990) J. Nuc. Med. vol. 31, pp. 1191-1198.
Kochenderfer et al. "Donor-Derived Anti-CD19 Chimeric-Antigen-Receptor-Expressing T Cells Cause Regression of Malignancy

(56) References Cited

OTHER PUBLICATIONS

Persisting After Allogeneic Hematopoietic Stem Cell Transplantation" Blood (2013) vol. 122, No. 21, Abstract 151, pp. 1-6.
MedChem Express PCI-32765 data sheet (pp. 1-3, Jul. 8, 2016).
Park and Brentjens, "Are All Chimeric Antigen Receptors Created Equal?" J Clin Oncol (2015) vol. 33, No. 6, pp. 651-653.
Rudnick et al. "Affinity and Avidity in Antibody-Based Tumor Targeting" Can. Biotherp. & Radiopharm. (2009) vol. 24 pp. 155-162.
Sun et al. "Abstract 2597: BGB-3111 is a novel and highly selective Bruton's tyrosine kinase (BTK) inhibitor" Experimental and Molecular Therapeutics (2015) vol. 75, Suppl 15, Abstract 2597, pp. 1-5.
Talmadge et al. "Murine Models to Evaluate Novel and Conventional Therapeutic Strategies for Cancer" Am. J. Pathol (2007) vol. 170, No. 3, pp. 793-804.
Thurber et al. "Antibody tumor penetration: Transport opposed by systemic and antigen-mediated clearance" Adv. Drug Deliv. Rev. (2008) vol. 60, pp. 1421-1434.
Voskoglou-Nomikos et al. "Clinical Predictive Value of the in Vitro Cell Line, Human Xenograft, and Mouse Allograft Preclinical Cancer Models" Clinical Cancer Research (2003) vol. 9, pp. 4227-4239.
Wu et al "Blinatumomab: a bispecific T cell engager (BiTe) antibody against CD19/CD3 for refractory acute lymphoid leukemia." Journal of Hematology & Oncology (2015) vol. 8, No. 104, pp. 1-7.
Sidaway, "Ibrutinib supercharges CAR T cells" Nature Reviews Clinical Oncology (2016) Abstract.
Singapore search report and written opinion for Singapore Application No. 11201506603P dated May 31, 2017.
Singapore Search Report and Written Opinion for Singapore Application No. 11201606909R dated Oct. 24, 2017.
Smith-Gill et al., "Contributions of Immunoglobulin Heavy and Light Chains to Antibody Specificity for Lysozyme and Two Haptens" The Journal of Immunology (1987) vol. 139, pp. 4135-4144.
Song et al. "CD27 costimulation augments the survival and antitumor activity of redirected human T cells in vivo" Blood (2012) vol. 119, No. 3, pp. 696-706.
Song et al. "Light Chain of Natural Antibody Plays a Dominant Role in Protein Antigen Binding" Biochemical and Biophysical Research Communications (2000) vol. 268, pp. 390-394.
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Tammana Syam et al., "4-1BB and CD28 Signaling plays a synergistic role in redirecting umbibical cord blood T cells against B-cell malignancies" Human Gene Therapy (2010) vol. 21, pp. 75-86.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Trinh et al. "Optimization of codon pair use within the (GGGGS)3 linker sequence results in enhanced protein expression" Molecular Immunology (2004) vol. 40, pp. 717-722.
Uckun et al., "Detailed studies on expression and function of CD19 surface determinant by using B43 monoclonal antibody and the clinical potential of anti-CD19 immunotoxins" Blood (1988) vol. 71 pp. 13-29.
UniProt/Swiss-Prot Accession No. P15391.
Vajdos et al. "Comprehensive Functional Maps of the Antigen-binding Site of an Anti-ErbB2 Antibody Obtained with Shotgun Scanning Mutagenesis" Journal of Molecular Biology (2002) vol. 320, pp. 415-428.
Vinay & Kwon, "Role of 4-1BB in immune responses" Immunology (1998) vol. 10 pp. 481-489.
Wang et al. "Vista, a novel mouse Ig superfamily ligand that negatively regulates T cell responses" The Journal of Experimental Medicine (2011) vol. 208, No. 3, 577-592.

Wang et al., "Targeting BTK with ibrutinib in relapsed or refractory mantle-cell lymphoma." New England Journal of Medicine (2013) vol. 369 No. 6 pp. 507-516.
Wang et al., "Utilization of Next Generation Sequencing Identifies Potentially Actionable Mutations with Prognostic Significance in Chronic Lymphocytic Leukemia" Blood (2015) vol. 126 No. 23.
Ward et al. "Binding activities of a repertoire of single immunoglobulin variable domains secreted from *Escherichia coli*" Nature (1989) vol. 341, pp. 544-546.
Willemsen et al., "Genetic Engineering of T Cell Specificity for Immunotherapy of Cancer" Human Immunology (2003) vol. 64 pp. 56-68.
Woyach et al., "Resistance mechanisms for the Bruton's tyrosine kinase inhibitor ibrutinib." New England Journal of Medicine (2014) vol. 370 No. 24 pp. 2286-2294.
Xu et al. "γc Cytokines IL7 and IL15 Expanded Chimeric Antigen Receptor-Redirected T Cells (CAR-T) with Superior Antitumor Activity in Vivo" Molecular Therapy (2013) vol. 21, pp. S20-S21.
Xu V et al: "Closely related T-memory stem cells correlate with in vivo expansion of CAR.CD19-T cells and are preserved by IL-7 and IL-15", Blood, vol. 123, No. 24, Apr. 29, 2014 (Apr. 29, 2014), pp. 3750-3759, XP055201372, ISSN: 0006-4971, DOI:10.1182/blood-2014-01-552174.
Yamamoto et al. "NF-kB Activation in CD27 Signaling: Involvement of TNF Receptor-Associated Factors in Its Signaling and Identification of Functional Region of CD27" The Journal of Immunology (1998) vol. 161, pp. 4753-4759.
Younes et al., "Phase 2 study of rituximab plus ABVD in patients with newly diagnosed classical Hodgkin lymphoma." Blood (2012) vol. 119 No. 18 pp. 4123-4128.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.
Irving et al., "The cytoplasmic domain of the T cell receptor zeta chain is sufficient to couple to receptor-associated signal transduction pathways," Cell 64: 891-901 (1991).
Jang et al. "Human 4-1BB (CD137) Signals Are Mediated by TRAF2 and Activate Nuclear Factor-kB" Biochemical and Biophysical Research Communications (1998)) vol. 242, pp. 613-620.
Jena et al. "Chimeric Antigen Receptor (CAR)-Specific Monoclonal Antibody to Detect CD19-Specific T Cells in clinical Trials" PLOS One (2013) vol. 8, No. 3, e57838, pp. 1-12.
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
Jones et al., "Circulating clonotypic B cells in classic Hodgkin lymphoma." Blood (2009) vol. 113 No. 23 pp. 5920-5926.
Joo et al., "Targeted cancer therapy—are the days of systemic chemotherapy numbered?" Maturitas (2013) vol. 76 No. 4 pp. 308-314.
June et al., "Engineering lymphocyte subsets: tools, trials and tribulations" Nat Rev Immunol (2009) vol. 9 No. 10 pp. 704-716.
June, "Adoptive T cell therapy for cancer in the clinic" Journal of Clinical Investigation (2007) vol. 117 No. 6 pp. 1466-1476.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kalos et al.,"T cells with chimeric antigen receptors have potent antitumor effects and can establish memory in patients with advanced leukemia." Science Translational Medicine (2011) vol. 3 No. 95 95ra73.

(56) References Cited

OTHER PUBLICATIONS

Kappos et al., "Ocrelizumab in relapsing-remitting multiple sclerosis: a phase 2, randomised, placebo-controlled, multicentre trial." Lancet (2011) vol. 378 No. 9805 pp. 1779-1787.
Karlsson et al. "Combining CAR T cells and the Bcl-2 family apoptosis inhibitor ABT-737 for treating B-cell malignancy" Cancer Gene Therapy (2013) vol. 20, pp. 386-393.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kharfan-Dabaja et al. "Immunotherapy for chronic lymphocytic leukemia in the era of BTK inhibitors" Leukemia (2014) vol. 28, pp. 507-517.
Kim et al. "B-cell Depletion Using an Anti-CD20 Antibody Augments Antitumor Immune Responses and Immunotherapy in Nonhematopoetic Murine Tumor Models" Journal of Immunotherapy (2008) vol. 31 No. 5 pp. 446-457.
Kim et al., "Human 4-1BB regulates CD28 co-stimulation to promote Th1 cell responses" Eur. J. Immunol. (1998) vol. 28 pp. 881-890.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52ND Annual Meeting of the American-Society-of-Hematology (ASH), Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 689-702.
Kochenderfer et al., "Eradication of B-lineage cells and regression of lymphoma in a patient treated with autologous T cells genetically-engineered to recognize CD19," Blood 116: 4099-4102 (2010).
Kochenderfer et al., "Novel Antigen-Specific Expansion of T Cells Transduced with a CD19 Chimeric Antigen Receptor" 2010 ASH Meeting Abstract No. 3262, presented Dec. 6, 2010 (poster abstract).
Kochenderfer, et al. "Adoptive transfer of syngeneic T cells transduced with a chimeric antigen receptor that recognizes murine CD19 can eradicate lymphoma and normal B cells" Blood (2010) vol. 116, No. 9, pp. 3875-3886.
Kofler et al. "CD28 Costimulation Impairs the Efficacy of a Redirected T-cell Antitumor Attack in the Presence of Regulatory T cells Which Can Be Overcome by Preventing Lck Activation" Molecular Therapy (2001) vol. 19, No. 4, 760-767.
Kohn et al. "CARs on Track in the Clinic", Molecular Therapy (2011) vol. 19, No. 3, pp. 432-438.
Konishi et al. "B7-H1 Expression on Non-Small Cell Lung Cancer Cells and Its Relationship with Tumor-Infiltrating Lymphocytes and Their PD-1 Expression" Clinical Cancer Research (2004) vol. 10 pp. 5094-5100.
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Kumar et al. "Molecular Cloning and Expression of the Fabs of Human Autoantibodies in *Escherichia coli*" The Journal of Biological Chemistry (2000) vol. 275, No. 45, pp. 35129-35136.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.
Lamers et al. "Immune responses to transgene and retroviral vector in patients treated with ex vivo-engineered T cells" Blood (2011) vol. 117, No. 1, pp. 72-82.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Latchman et al. "PD-L2 is a second ligand for PD-1 and inhibits T cell activation", Nat Immunol (2001) vol. 2 No. 3 pp. 261-268.
Lee et al. "Xenograft models for the preclinical evaluation of new therapies in acute leukemia" Leukemia & Lymphoma (2007) vol. 48, No. 4, pp. 659-668.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.
Lim et al., "Anti-CD20 monoclonal antibodies: historical and future perspectives." Haematologica (2010) vol. 95 No. 1 pp. 135-143.
Liu et al., "Calcineurin is a common target of cyclophilin-cyclosporin A and FKBP-FK506 complexes." Cell (1991) vol. 66 No. 4 pp. 807-815.
Macallan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
Martz et al. "Overcoming ibrutinib resistance" SciBX (2014) vol. 7, No. 33, pp. 1-3.
Marzec et al., "Mantle cell lymphoma cells express predominantly cyclin D1a isoform and are highly sensitive to selective inhibition of CDK4 kinase activity." Blood (2006) vol. 108 No. 5 pp. 1744-1750.
Mato et al., "Favorable Outcomes in CLL Pts with Alternate Kinase Inhibitors Following Ibrutinib or Idelalisib Discontinuation: Results from a Large Multi-Center Study" Blood (2015) vol. 126 No. 23.
Mato et al., "Ibrutinib-induced pneumonitis in patients with chronic lymphocyticleukemia" Blood (2016) vol. 127 No. 8 pp. 1064-1067.
Maude et al., "Chimeric Antigen Receptor T Cells for Sustained Remissions in Leukemia" The New England Journal of Medicine (2014) vol. 371 No. 16 pp. 1507-1517.
Maude, "217 Efficacy of Humanized CD19-Targeted Chimeric Antigen Receptor (CAR)-Modified T Cells in Children and Young Adults with Relapsed/Refractory Acute Lymphoblastic Leukemia" 58th Annual Meeting & Exposition—Dec. 3, 2016; Abstract.
McGuinness et al., "Anti-tumor activity of human T cells expressing the CC49-zeta chimeric immune receptor," Hum. Gene Ther. 10: 165-173 (1999).
Dull et al, "A Third-Generation Lentivirus Vector with a Conditional Packaging System" Journal of Virology (1998) vol. 72 No. 11 pp. 8463-8471.
Durie et al. "International uniform response criteria for multiple myeloma" Leukemia (2006) vol. 20, No. 9, pp. 1467-1473.
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).
Evans et al., "Evolution to Plasmablastic Lymphoma (PBL) after CAR-T Cell Therapy in a Case of SLL/CLL with Richter's Transformation" Blood (2014) vol. 124 No. 21.
FDA: Highlights of Prescribing Information for Arzerra (2009).
FDA: Highlights of Prescribing Information for Gazyva (2013).
FDA: Highlights of Prescribing Information for Rituxan (2010).
Finn et al., "Current and Future Treatment Strategies for Patients with Advanced Hepatocellular Carcinoma: Role of mTOR Inhibition." Liver Cancer (2012) vol. 1 No. 3-4 pp. 247-256.
Finney et al., "Activation of resting human primary T cells with chimeric receptors: costimulation from CD28, inducible costimula-

(56) References Cited

OTHER PUBLICATIONS tor, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol. 161: 2791-2797 (1998).
Forero-Torres et al., "Results of a phase 1 study of AME-133v (LY2469298), an Fc-engineered humanized monoclonal anti-CD20 antibody, in Fc?RIIIa-genotyped patients with previously treated follicular lymphoma." Clinical Cancer Research (2012) vol. 18 No. 5 pp. 1395-1403.
Fraietta et al., "Ibrutinib enhances chimeric antigen receptor T-cell engraftment and efficacy in leukemia" Blood (2016) vol. 127 No. 9 pp. 1117-1127.
Fraietta et al., "P.D.14.19—Longitudinal Effects of Ibrutinib Therapy on T Lymphocytes: Implications for Combination Adoptive Cell Strategies to Treat Chronic Lymphocytic Leukemia (CLL)" The 4th European Congress of Immunology (2015) Presentation Abstract.
Freeman et al "Engagement of the PD-1 Immunoinhibitory Receptor by a Novel B7 Family Member Leads to Negative Regulation of Lymphocyte Activation", Journal of Exp Med (2000) vol. 192 No. 7 pp. 1027-1034.
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093 (2005).
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and costimulatory activity enhances signal transduction through single-chain chimeric receptors in T lymphocytes," Blood 98(8): 2364-2371 (2001).
GenBank Acc. No. AAA62478.2 (41bb).
GenBank Acc. No. BAG36664.1 (zeta).
GenBank Accession No. NM_000734 "Homo sapiens CD247 molecule (CD247), transcript variant 2, mRNA" Dec. 7, 2009.
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Goldenberg et al., "Veltuzuman (humanized anti-CD20 monoclonal antibody): characterization, current clinical results, and future prospects" Leukemia & Lymphoma (2010) vol. 51 No. 5 pp. 747-755.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.

Guest et al. "The Role of Extracellular Spacer Regions in the Optimal Design of Chimeric Immune Receptors Evaluation of Four Different scFvs and Antigens" J. Immunother. (2005) vol. 28, No. 3, pp. 203-211.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors by Adoptive Transfer of Cytotoxic T Lymphocytes Reprogrammed by CD44V6-Specific SCFV:~-Chimera" Int J. Cancer (1996) vol. 68 pp. 232-238.
Henderson et al., "Comparison of the effects of FK-506, cyclosporin A and rapamycin on IL-2 production." Immunology (1991) No. 73 vol. 3 pp. 316-321.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Hombach et al. "OX40 costimulation by a chimeric antigen receptor abrogates CD28 and IL-2 induced IL-10 secretion by redirected CD4+ T cells" OncoImmunology (2012) vol. 1, No. 4, pp. 458-466.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Honigberg et al., "The Bruton tyrosine kinase inhibitor PCI-32765 blocks B-cell activation and is efficacious in models of autoimmune disease and B-cell malignancy." Proc Natl Acad Sci (2010) vol. 107 No. 29 pp. 13075-13080.
Hutchinson et al. "Breaking good: the inexorable rise of BTK inhibitors in the treatment of chronic lymphocytic leukaemia" British Journal of Haematology (2014) vol. 166, pp. 12-22.
Huye E L et al: 'Combining mTor Inhibitors With Rapamycin-resistant T Cells: A Two-pronged Approach to Tumor Elimination',Molecular Therapy,vol. 19, No. 12,Aug. 30, 2011 (Aug. 30, 2011), pp. 2239-2248, XP055191016, GB, ISSN: 1525-0016, DOI: 10.1038/mt.2011.179 the whole document.
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Preliminary Report on Patentability for International Application No. PCT/US2014/029943 dated Sep. 22, 2015.
International Search Report and Written Opinion for International Application No. PCT/US2014/029943 dated Jul. 17, 2014.
International Search Report and Written Opinion for International application No. PCT/US2015/024671, dated Jul. 31, 2015.
International Search Report and Written Opinion for International Application No. PCT/US2016/026437 dated Jun. 29, 2016.
International Search Report from PCT/US2011/064191 dated Jan. 5, 2012.
Intlekofer et al. "At the Bench: Preclinical rationale for CTLA-4 and PD-1 blockade as cancer immunotherapy" J Leukoc Biol (2013) vol. 94, No. 1, pp. 25-39.
Irving et al. "Functional Characterization of a Signal Transducing Motif Present in the T Cell Antigen Receptor Chain" Journal of Experimental Medicine (1993) vol. 177, pp. 1093-1103.
Boissel et al. "Retargeting NK-92 cells by means of CD19- and CD20-specific chimeric antigen receptors compares favorably with antibody-dependent cellular cytotoxicity" OncoImmunology (2013) vol. 2, No. 10, e26527, pp. 1-8.
Deniger et al. "Bispecific T-cells Expressing Polyclonal Repertoire of Endogenous ?? T-cell Receptors and Introduced CD19-specific Chimeric Antigen Receptor" Molecular Therapy (2013) vol. 21 No. 3, pp. 638-647.

\* cited by examiner

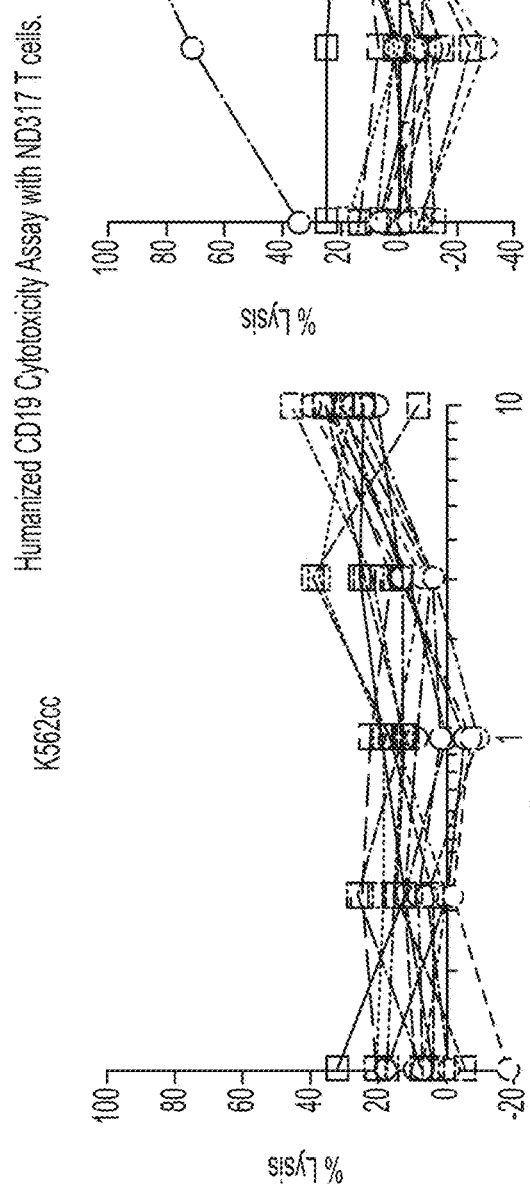
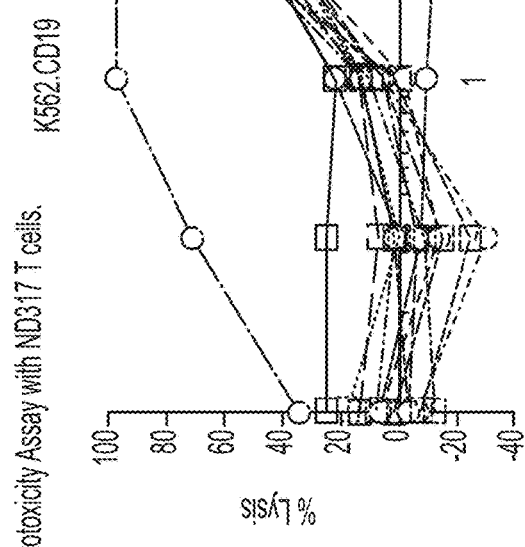
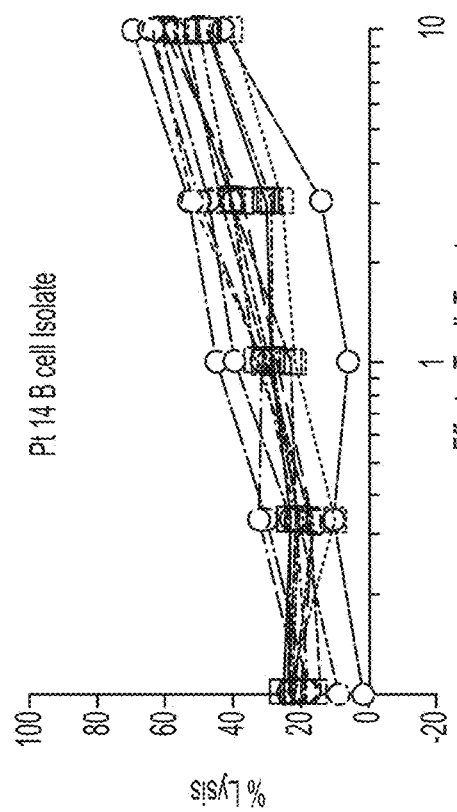
FIG. 1A
FIG. 1B
FIG. 1C

CD138+ CD45 dim tumor cells stained for CD19 (x-axis) and CD38 (y-axis)

TREATMENT OF CANCER USING HUMANIZED ANTI-CD19 CHIMERIC ANTIGEN RECEPTOR

This application is a divisional of U.S. application Ser. No. 14/214,728, filed Mar. 15, 2014, which claims priority to U.S. Ser. No. 61/802,629, filed Mar. 16, 2013, and U.S. Ser. No. 61/838,537 filed Jun. 24, 2013, the entire contents of each of these applications is incorporated herein by reference.

SEQUENCE LISTING

The instant application contains a Sequence Listing which has been submitted electronically in ASCII format and is hereby incorporated by reference in its entirety. Said ASCII copy, created on Mar. 10, 2014, is named N2067-7002WO_SL.txt and is 219,793 bytes in size.

FIELD OF THE INVENTION

The present invention relates generally to the use of T cells engineered to express a Chimeric Antigen Receptor (CAR) to treat a disease associated with expression of the Cluster of Differentiation 19 protein (CD19).

BACKGROUND OF THE INVENTION

Many patients with B cell malignancies are incurable with standard therapy. In addition, traditional treatment options often have serious side effects. Attempts have been made in cancer immunotherapy, however, several obstacles render this a very difficult goal to achieve clinical effectiveness. Although hundreds of so-called tumor antigens have been identified, these are generally derived from self and thus are poorly immunogenic. Furthermore, tumors use several mechanisms to render themselves hostile to the initiation and propagation of immune attack.

Recent developments using chimeric antigen receptor (CAR) modified autologous T cell (CART) therapy, which relies on redirecting T cells to a suitable cell-surface molecule on cancer cells such as B cell malignancies, show promising results in harnessing the power of the immune system to treat B cell malignancies and other cancers (see, e.g., Sadelain et al., Cancer Discovery 3:388-398 (2013)). The clinical results of the murine derived CART19 (i.e., "CTL019") have shown promise in establishing complete remissions in patients suffering with CLL as well as in childhood ALL (see, e.g., Kalos et al., Sci Transl Med 3:95ra73 (2011), Porter et al., NEJM 365:725-733 (2011), Grupp et al., NEJM 368:1509-1518 (2013)). Besides the ability for the chimeric antigen receptor on the genetically modified T cells to recognize and destroy the targeted cells, a successful therapeutic T cell therapy needs to have the ability to proliferate and persist over time, and to further monitor for leukemic cell escapees. The variable quality of T cells whether it's a result of anergy, suppression or exhaustion will have effects on CAR-transformed T cells' performance but for which skilled practitioners have limited control over at this time. To be effective, CAR transformed patient T cells need to persist and maintain the ability to proliferate in response to the CAR's antigen. It has been shown that ALL patient T cells perform can do this with CART19 comprising a murine scFv (see, e.g., Grupp et al., NEJM 368:1509-1518 (2013)).

SUMMARY OF THE INVENTION

The invention addresses controlling an immune response in patients by providing optimized and humanized antibody fragments (e.g., scFv) that bind the Cluster of Differentiation 19 protein (CD19) integrated into a Chimeric Antigen Receptor (CAR) construct that will not elicit an immune response in patients, is safe to use long term, and maintains or has better clinical effectiveness as compared to known CART therapy for treatment of B cell derived cancers. The invention further pertains to the use of T cells engineered to express a humanized antibody fragment that binds CD19 integrated into a CAR to treat a hematologic cancer associated with expression of CD19 (OMIM Acc. No. 107265, Swiss Prot. Acc No. P15391).

Accordingly, in one aspect, the invention pertains to an isolated nucleic acid molecule encoding a chimeric antigen receptor (CAR), wherein the CAR comprises an antibody or antibody fragment which includes a humanized anti-CD19 binding domain, a transmembrane domain, and an intracellular signaling domain (e.g., an intracellular signaling domain comprising a costimulatory domain and/or a primary signaling domain). In one embodiment, the CAR comprises an antibody or antibody fragment which includes a humanized anti-CD19 binding domain described herein, a transmembrane domain described herein, and an intracellular signaling domain described herein (e.g., an intracellular signaling domain comprising a costimulatory domain and/or a primary signaling domain).

In one embodiment, the encoded humanized anti-CD19 binding domain comprises one or more (e.g., all three) light chain complementary determining region 1 (LC CDR1), light chain complementary determining region 2 (LC CDR2), and light chain complementary determining region 3 (LC CDR3) of a humanized anti-CD19 binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized anti-CD19 binding domain described herein, e.g., a humanized anti-CD19 binding domain comprising one or more, e.g., all three, LC CDRs and one or more, e.g., all three, HC CDRs. In one embodiment, the humanized anti-CD19 binding domain comprises at least HC CDR2. In one embodiment, the encoded humanized anti-CD19 binding domain comprises one or more (e.g., all three) heavy chain complementary determining region 1 (HC CDR1), heavy chain complementary determining region 2 (HC CDR2), and heavy chain complementary determining region 3 (HC CDR3) of a humanized anti-CD19 binding domain described herein, e.g., the encoded humanized anti-CD19 binding domain has two variable heavy chain regions, each comprising a HC CDR1, a HC CDR2 and a HC CDR3 described herein. In one embodiment, the humanized anti-CD19 binding domain comprises at least HC CDR2. In one embodiment, the encoded light chain variable region comprises one, two, three or all four framework regions of VK3_L25 germline sequence. In one embodiment, the encoded light chain variable region has a modification (e.g., substitution, e.g., a substitution of one or more amino acid found in the corresponding position in the light chain variable region of SEQ ID NO: 58, e.g., a substitution at one or more of positions 71 and 87). In one embodiment, the encoded heavy chain variable region comprises one, two, three or all four framework regions of VH4_4-59 germline sequence. In one embodiment, the encoded heavy chain variable region has a modification (e.g., substitution, e.g., a substitution of one or more amino acid found in the corresponding position in the heavy chain variable region of SEQ ID NO: 58, e.g., a substitution at one or more of positions 71, 73 and 78). In one embodiment, the encoded humanized anti-CD19 binding domain comprises a humanized light chain variable region described herein (e.g., in Table 3) and/or a humanized heavy chain variable region described herein (e.g., in Table 3). In one embodiment, the encoded humanized anti-CD19 binding domain comprises a humanized heavy chain variable region described herein (e.g., in Table 3), e.g., at least two humanized heavy chain variable regions described herein (e.g., in Table 3). In one embodiment, the encoded anti-CD19 binding domain is a scFv comprising a light chain and a heavy chain of an amino acid sequence of Table 3. In an embodiment, the anti-CD19 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 3, or a sequence with 95-99% identity with an amino acid sequence of Table 3; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 3, or a sequence with 95-99% identity to an amino acid sequence of Table 3. In one embodiment, the encoded humanized anti-CD19 binding domain comprises a sequence selected from a group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, or a sequence with 95-99% identify thereof. In one embodiment, the nucleic acid sequence encoding the humanized anti-CD19 binding domain comprises a sequence selected from a group consisting of SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:70, SEQ ID NO:71 and SEQ ID NO:72, or a sequence with 95-99% identify thereof. In one embodiment, the encoded humanized anti-CD19 binding domain is a scFv, and a light chain variable region comprising an amino acid sequence described herein, e.g., in Table 3, is attached to a heavy chain variable region comprising an amino acid sequence described herein, e.g., in Table 3, via a linker, e.g., a linker described herein. In one embodiment, the encoded humanized anti-CD19 binding domain includes a (Gly$_4$-Ser)n linker, wherein n is 1, 2, 3, 4, 5, or 6, preferably 3 or 4 (SEQ ID NO:53). The light chain variable region and heavy chain variable region of a scFv can be, e.g., in any of the following orientations: light chain variable region-linker-heavy chain variable region or heavy chain variable region-linker-light chain variable region.

In one embodiment, the encoded transmembrane domain is a transmembrane domain of a protein selected from the group consisting of the alpha, beta or zeta chain of the T-cell receptor, CD27, CD28, CD3 epsilon, CD45, CD4, CD5, CD8, CD9, CD16, CD22, CD33, CD37, CD64, CD80, CD86, CD134, CD137 and CD154. In one embodiment, the encoded transmembrane domain comprises a sequence of SEQ ID NO: 15. In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO:15, or a sequence with 95-99% identity to an amino acid sequence of SEQ ID NO:15. In one embodiment, the nucleic acid sequence encoding the transmembrane domain comprises a sequence of SEQ ID NO:56, or a sequence with 95-99% identify thereof.

In one embodiment, the encoded anti-CD19 binding domain is connected to the transmembrane domain by a hinge region, e.g., a hinge region described herein. In one embodiment, the encoded hinge region comprises SEQ ID NO:14 or SEQ ID NO:45 or SEQ ID NO:47, or a sequence with 95-99% identity thereof. In one embodiment, the nucleic acid sequence encoding the hinge region comprises a sequence of SEQ ID NO:55 or SEQ ID NO:46 or SEQ ID NO:48, or a sequence with 95-99% identify thereof.

In one embodiment, the isolated nucleic acid molecule further comprises a sequence encoding a costimulatory domain. In one embodiment, the costimulatory domain is a functional signaling domain obtained from a protein selected from the group consisting of OX40, CD2, CD27, CD28, CDS, ICAM-1, LFA-1 (CD11a/CD18), ICOS (CD278), and 4-1BB (CD137). In one embodiment, the encoded costimulatory domain comprises a sequence of SEQ ID NO:16. In one embodiment, the encoded costimulatory domain comprises an amino acid sequence having at least one, two or three modifications (e.g., substitutions) but not more than 20, 10 or 5 modifications (e.g., substitutions) of an amino acid sequence of SEQ ID NO:16, or a sequence with 95-99% identity to an amino acid sequence of SEQ ID NO:16. In one embodiment, the nucleic acid sequence encoding the costimulatory domain comprises a sequence of SEQ ID NO:60, or a sequence with 95-99% identify thereof. In one embodiment, the isolated nucleic acid molecule further comprises a sequence encoding an intracellular signaling domain, e.g., an intracellular signaling domain described herein. In one embodiment, the encoded intracellular signaling domain comprises a functional signaling domain of 4-1BB and/or a functional signaling domain of CD3 zeta. In one embodiment, the encoded intracellular signaling domain comprises a functional signaling domain of CD27 and/or a functional signaling domain of CD3 zeta. In one embodiment, the encoded intracellular signaling domain comprises the sequence of SEQ ID NO: 16 or SEQ ID NO:51 and/or the sequence of SEQ ID NO:17 or SEQ ID NO:43. In one embodiment, the intracellular signaling domain comprises an amino acid sequence having at least one, two or three modifications (e.g., substitutions) but not more than 20, 10 or 5 modifications (e.g., substitutions) of an amino acid sequence of SEQ ID NO:16 or SEQ ID NO:51 and/or an amino acid sequence of SEQ ID NO:17 or SEQ ID NO:43, or a sequence with 95-99% identity to an amino acid sequence of SEQ ID NO:16 or SEQ ID NO:51 and/or an amino acid sequence of SEQ ID NO:17 or SEQ ID NO:43. In one embodiment, the encoded intracellular signaling domain comprises the sequence of SEQ ID NO:16 or SEQ ID NO:51 and the sequence of SEQ ID NO:17 or SEQ ID NO:43, wherein the sequences comprising the intracellular signaling domain are expressed in the same frame and as a single polypeptide chain. In one embodiment, the nucleic acid sequence encoding the intracellular signaling domain comprises a sequence of SEQ ID NO:60, or a sequence with 95-99% identity thereof, and/or a sequence of SEQ ID NO:101 or SEQ ID NO:44, or a sequence with 95-99% identity thereof. In one embodiment, the nucleic acid sequence encoding the intracellular signaling domain comprises a sequence of SEQ ID NO:52, or a sequence with 95-99% identity thereof, and/or a sequence of SEQ ID NO:101 or SEQ D NO:44, or a sequence with 95-99% identity thereof.

In another aspect, the invention pertains to an isolated nucleic acid molecule encoding a CAR construct comprising a leader sequence, e.g., a leader sequence described herein, e.g., of SEQ ID NO:13; a humanized anti-CD19 binding domain described herein, e.g., a humanized anti-CD19 binding domain comprising a LC CDR1, a LC CDR2, a LC CDR3, a HC CDR1, a HC CDR2 and a HC CDR3 described herein, e.g., a humanized anti-CD19 binding domain described in Table 3, or a sequence with 95-99% identify thereof; a hinge region described herein, e.g., of SEQ ID NO:14 or SEQ ID NO:45; a transmembrane domain described herein, e.g., a transmembrane domain comprising SEQ ID NO:15; and an intracellular signaling domain, e.g., an intracellular signaling domain described herein. In one embodiment, the encoded intracellular signaling domain comprises a costimulatory domain, e.g., a costimulatory domain described herein, e.g., a 4-1BB costimulatory domain having a sequence of SEQ ID NO:16 or SEQ ID NO:51, and/or a primary signaling domain, e.g., a primary signaling domain described herein, e.g., a CD3 zeta stimulatory domain having a sequence of SEQ ID NO:17 or SEQ ID NO:43. In one embodiment, the isolated nucleic acid molecule encoding the CAR construct includes a leader sequence encoded by the nucleic acid sequence of SEQ ID NO:54, or a sequence with 95-99% identity thereto. In one embodiment, the isolated nucleic acid molecule encoding the CAR construct includes a humanized anti-CD19 binding domain sequence encoded by the nucleic acid sequence of SEQ ID NO:61, SEQ ID NO:62, SEQ ID NO:63, SEQ ID NO:64, SEQ ID NO:65, SEQ ID NO:66, SEQ ID NO:67, SEQ ID NO:69, SEQ ID NO:70, SEQ ID NO:71, and SEQ ID NO:72, or a sequence with 95-99% identity thereto. In one embodiment, the isolated nucleic acid molecule encoding the CAR construct includes a transmembrane sequence encoded by the nucleic acid sequence of SEQ ID NO:56, or a sequence with 95-99% identity thereto. In one embodiment, the isolated nucleic acid molecule encoding the CAR construct includes an intracellular signaling domain sequence encoded by the nucleic acid sequence of SEQ ID NO:60, or a sequence with 95-99% identity thereto and/or a nucleic acid sequence of SEQ ID NO:101 or SEQ ID NO:44, or a sequence with 95-99% identity thereto.

In one embodiment, the isolated nucleic acid molecule comprises (e.g., consists of) a nucleic acid encoding a CAR amino acid sequence of SEQ ID NO:31, SEQ ID NO:32, SEQ ID NO: 33, SEQ ID NO:34, SEQ ID NO: 35, SEQ ID NO:36, SEQ ID NO:37, SEQ ID NO:38, SEQ ID NO:39, SEQ ID NO:40, SEQ ID NO:41 or SEQ ID NO:42, or an amino acid sequence having at least one, two, three, four, five, 10, 15, 20 or 30 modifications (e.g., substitutions) but not more than 60, 50 or 40 modifications (e.g., substitutions) of an amino acid sequence of, or an amino acid sequence having 85%, 90%, 95%, 96%, 97%, 98% or 99% identity to an amino acid sequence of SEQ ID NO:31, SEQ ID NO:32, SEQ ID NO: 33, SEQ ID NO:34, SEQ ID NO: 35, SEQ ID NO:36, SEQ ID NO:37, SEQ ID NO:38, SEQ ID NO:39, SEQ ID NO:40, SEQ ID NO:41 or SEQ ID NO:42.

In one embodiment, the isolated nucleic acid molecule comprises (e.g., consists of) a nucleic acid sequence of SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, or SEQ ID NO:96 or a nucleic acid sequence having 85%, 90%, 95%, 96%, 97%, 98% or 99% identity to a nucleic acid sequence of SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, or SEQ ID NO:96.

In one aspect, the invention pertains to an isolated nucleic acid molecule encoding a humanized anti-CD19 binding domain, wherein the anti-CD19 binding domain comprises one or more (e.g., all three) light chain complementary determining region 1 (LC CDR1), light chain complementary determining region 2 (LC CDR2), and light chain complementary determining region 3 (LC CDR3) of an anti-CD19 binding domain described herein, and one or more (e.g., all three) heavy chain complementary determining region 1 (HC CDR1), heavy chain complementary determining region 2 (HC CDR2), and heavy chain complementary determining region 3 (HC CDR3) of an anti-CD19 binding domain described herein, e.g., a humanized anti-CD19 binding domain comprising one or more, e.g., all three, LC CDRs and one or more, e.g., all three, HC CDRs. In one embodiment, the humanized anti-CD19 binding domain comprises at least HC CDR2. In one embodiment, the light chain variable region comprises one, two, three or all four framework regions of VK3_L25 germline sequence. In one embodiment, the light chain variable region has a modification (e.g., substitution, e.g., a substitution of one or more amino acid found in the corresponding position in the murine light chain variable region of SEQ ID NO: 58, e.g., a substitution at one or more of positions 71 and 87). In one embodiment, the heavy chain variable region comprises one, two, three or all four framework regions of VH4_4-59 germline sequence. In one embodiment, the heavy chain variable region has a modification (e.g., substitution, e.g., a substitution of one or more amino acid found in the corresponding position in the murine heavy chain variable region of SEQ ID NO: 58, e.g., a substitution at one or more of positions 71, 73 and 78). In one embodiment, the encoded humanized anti-CD19 binding domain comprises a light chain variable region described herein (e.g., in SEQ ID NO:1, 2, 3, 4, 5, 6, 7, 8, 9, 10, 11 or 12) and/or a heavy chain variable region described herein (e.g., in SEQ ID NO:1, 2, 3, 4, 5, 6, 7, 8, 9, 10, 11 or 12). In one embodiment, the encoded humanized anti-CD19 binding domain is a scFv comprising a light chain and a heavy chain of an amino acid sequence of in SEQ ID NO:1, 2, 3, 4, 5, 6, 7, 8, 9, 10, 11 or 12. In an embodiment, the humanized anti-CD19 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in SEQ ID NO:1, 2, 3, 4, 5, 6, 7, 8, 9, 10, 11 or 12, or a sequence with 95-99% identity with an amino acid sequence of SEQ ID NO:1, 2, 3, 4, 5, 6, 7, 8, 9, 10, 11 or 12; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in SEQ ID NO:1, 2, 3, 4, 5, 6, 7, 8, 9, 10, 11 or 12, or a sequence with 95-99% identity to an amino acid sequence SEQ ID NO:1, 2, 3, 4, 5, 6, 7, 8, 9, 10, 11 or 12. In one embodiment, the humanized anti-CD19 binding domain comprises a sequence selected from a group consisting of SEQ ID NO:1, 2, 3, 4, 5, 6, 7, 8, 9, 10, 11 or 12, or a sequence with 95-99% identify thereof. In one embodiment, the nucleic acid sequence encoding the humanized anti-CD19 binding domain comprises a sequence selected from a group consisting of SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71 and SEQ ID NO:72, or a sequence with 95-99% identify thereof.

In another aspect, the invention pertains to an isolated polypeptide molecule encoded by the nucleic acid sequence. In one embodiment, the isolated polypeptide molecule comprises a sequence selected from the group consisting of SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42. In one embodiment, the isolated polypeptide comprises a sequence of SEQ ID NO:31. In one embodiment, the isolated polypeptide comprises a sequence of SEQ ID NO:32. In one embodiment, the isolated polypeptide molecule comprises a sequence of SEQ ID NO:35. In one embodiment, the isolated polypeptide molecule comprises a sequence of SEQ ID NO:36. In one embodiment, the isolated polypeptide molecule comprises a sequence of SEQ ID NO:37.

In another aspect, the invention pertains to an isolated chimeric antigen receptor (CAR) molecule comprising a humanized anti-CD19 binding domain (e.g., a humanized antibody or antibody fragment that specifically binds to CD19), a transmembrane domain, and an intracellular signaling domain (e.g., an intracellular signaling domain comprising a costimulatory domain and/or a primary signaling domain). In one embodiment, the CAR comprises an antibody or antibody fragment which includes a humanized anti-CD19 binding domain described herein (e.g., a humanized antibody or antibody fragment that specifically binds to CD19 as described herein), a transmembrane domain described herein, and an intracellular signaling domain described herein (e.g., an intracellular signaling domain comprising a costimulatory domain and/or a primary signaling domain described herein).

In one embodiment, the humanized anti-CD19 binding domain comprises one or more (e.g., all three) light chain complementary determining region 1 (LC CDR1), light chain complementary determining region 2 (LC CDR2), and light chain complementary determining region 3 (LC CDR3) of a humanized anti-CD19 binding domain described herein, and one or more (e.g., all three) heavy chain complementary determining region 1 (HC CDR1), heavy chain complementary determining region 2 (HC CDR2), and heavy chain complementary determining region 3 (HC CDR3) of a humanized anti-CD19 binding domain described herein, e.g., a humanized anti-CD19 binding domain comprising one or more, e.g., all three, LC CDRs and one or more, e.g., all three, HC CDRs. In one embodiment, the humanized anti-CD19 binding domain comprises at least HC CDR2. In one embodiment, the humanized anti-CD19 binding domain comprises one or more (e.g., all three) heavy chain complementary determining region 1 (HC CDR1), heavy chain complementary determining region 2 (HC CDR2), and heavy chain complementary determining region 3 (HC CDR3) of a humanized anti-CD19 binding domain described herein, e.g., the humanized anti-CD19 binding domain has two variable heavy chain regions, each comprising a HC CDR1, a HC CDR2 and a HC CDR3 described herein. In one embodiment, the humanized anti-CD19 binding domain comprises at least HC CDR2. In one embodiment, the light chain variable region comprises one, two, three or all four framework regions of VK3_L25 germline sequence. In one embodiment, the light chain variable region has a modification (e.g., substitution, e.g., a substitution of one or more amino acid found in the corresponding position in the murine light chain variable region of SEQ ID NO: 58, e.g., a substitution at one or more of positions 71 and 87). In one embodiment, the heavy chain variable region comprises one, two, three or all four framework regions of VH4_4-59 germline sequence. In one embodiment, the heavy chain variable region has a modification (e.g., substitution, e.g., a substitution of one or more amino acid found in the corresponding position in the murine heavy chain variable region of SEQ ID NO: 58, e.g., a substitution at one or more of positions 71, 73 and 78). In one embodiment, the humanized anti-CD19 binding domain comprises a light chain variable region described herein (e.g., in Table 3) and/or a heavy chain variable region described herein (e.g., in Table 3). In one embodiment, the humanized anti-CD19 binding domain is a scFv comprising a light chain and a heavy chain of an amino acid sequence of Table 3. In an embodiment, the humanized anti-CD19 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 3, or a sequence with 95-99% identity with an amino acid sequence of Table 3; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 3, or a sequence with 95-99% identity to an amino acid sequence of Table 3. In one embodiment, the humanized anti-CD19 binding domain comprises a sequence selected from a group consisting of SEQ ID NO:1, SEQ ID NO:2, SEQ ID NO:3, SEQ ID NO: 4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12, or a sequence with 95-99% identify thereof. In one embodiment, the humanized anti-CD19 binding domain is a scFv, and a light chain variable region comprising an amino acid sequence described herein, e.g., in Table 3, is attached to a heavy chain variable region comprising an amino acid sequence described herein, e.g., in Table 3, via a linker, e.g., a linker described herein. In one embodiment, the humanized anti-CD19 binding domain includes a (Gly$_4$-Ser)n linker, wherein n is 1, 2, 3, 4, 5, or 6, preferably 3 or 4 (SEQ ID NO: 53). The light chain variable region and heavy chain variable region of a scFv can be, e.g., in any of the following orientations: light chain variable region-linker-heavy chain variable region or heavy chain variable region-linker-light chain variable region.

In one embodiment, the isolated CAR molecule comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO: 15. In one embodiment, the transmembrane domain comprises an amino acid sequence having at least one, two or three modifications (e.g., substitutions) but not more than 20, 10 or 5 modifications (e.g., substitutions) of an amino acid sequence of SEQ ID NO: 15, or a sequence with 95-99% identity to an amino acid sequence of SEQ ID NO: 15.

In one embodiment, the humanized anti-CD19 binding domain is connected to the transmembrane domain by a hinge region, e.g., a hinge region described herein. In one embodiment, the encoded hinge region comprises SEQ ID NO:14 or SEQ ID NO:45, or a sequence with 95-99% identity thereof.

In one embodiment, the isolated CAR molecule further comprises a sequence encoding a costimulatory domain, e.g., a costimulatory domain described herein. In one embodiment, the costimulatory domain comprises a functional signaling domain of a protein selected from the group consisting of OX40, CD2, CD27, CD28, CDS, ICAM-1, LFA-1 (CD11a/CD18) and 4-1BB (CD137). In one embodiment, the costimulatory domain comprises a sequence of SEQ ID NO: 16. In one embodiment, the costimulatory domain comprises a sequence of SEQ ID NO:51. In one embodiment, the costimulatory domain comprises an amino acid sequence having at least one, two or three modifications (e.g., substitutions) but not more than 20, 10 or 5 modifications (e.g., substitutions) of an amino acid sequence of SEQ ID NO: 16 or SEQ ID NO:51, or a sequence with 95-99% identity to an amino acid sequence of SEQ ID NO: 16 or SEQ ID NO:51.

In one embodiment, the isolated CAR molecule further comprises a sequence encoding an intracellular signaling domain, e.g., an intracellular signaling domain described herein. In one embodiment, the intracellular signaling domain comprises a functional signaling domain of 4-1BB and/or a functional signaling domain of CD3 zeta. In one embodiment, the intracellular signaling domain comprises the sequence of SEQ ID NO: 16 and/or the sequence of SEQ ID NO:17. In one embodiment, the intracellular signaling domain comprises the sequence of SEQ ID NO:16 and/or the sequence of SEQ ID NO:43. In one embodiment, the intracellular signaling domain comprises a functional signaling domain of CD27 and/or a functional signaling domain of CD3 zeta. In one embodiment, the intracellular signaling domain comprises the sequence of SEQ ID NO: 51 and/or the sequence of SEQ ID NO:17. In one embodiment, the intracellular signaling domain comprises the sequence of SEQ ID NO:51 and/or the sequence of SEQ ID NO:43. In one embodiment, the intracellular signaling domain comprises an amino acid sequence having at least one, two or three modifications (e.g., substitutions) but not more than 20, 10 or 5 modifications (e.g., substitutions) of an amino acid sequence of SEQ ID NO:16 or SEQ ID NO:51 and/or an amino acid sequence of SEQ ID NO:17 or SEQ ID NO:43, or a sequence with 95-99% identity to an amino acid sequence of SEQ ID NO:16 or SEQ ID NO:51 and/or an amino acid sequence of SEQ ID NO:17 or SEQ ID NO:43. In one embodiment, the intracellular signaling domain comprises the sequence of SEQ ID NO:16 or SEQ ID NO:51 and the sequence of SEQ ID NO: 17 or SEQ ID NO:43, wherein the sequences comprising the intracellular signaling domain are expressed in the same frame and as a single polypeptide chain.

In one embodiment, the isolated CAR molecule further comprises a leader sequence, e.g., a leader sequence described herein. In one embodiment, the leader sequence comprises an amino acid sequence of SEQ ID NO: 13, or a sequence with 95-99% identity to an amino acid sequence of SEQ ID NO:13.

In another aspect, the invention pertains to an isolated CAR molecule comprising a leader sequence, e.g., a leader sequence described herein, e.g., a leader sequence of SEQ ID NO: 13, or having 95-99% identity thereof; a humanized anti-CD19 binding domain described herein, e.g., a humanized anti-CD19 binding domain comprising a LC CDR1, a LC CDR2, a LC CDR3, a HC CDR1, a HC CDR2 and a HC CDR3 described herein, e.g., a humanized anti-CD19 binding domain described in Table 3, or a sequence with 95-99% identify thereof; a hinge region, e.g., a hinge region described herein, e.g., a hinge region of SEQ ID NO:14 or having 95-99% identity thereof; a transmembrane domain, e.g., a transmembrane domain described herein, e.g., a transmembrane domain having a sequence of SEQ ID NO:15 or a sequence having 95-99% identity thereof; an intracellular signaling domain, e.g., an intracellular signaling domain described herein (e.g., an intracellular signaling domain comprising a costimulatory domain and/or a primary signaling domain). In one embodiment, the intracellular signaling domain comprises a costimulatory domain, e.g., a costimulatory domain described herein, e.g., a 4-1BB costimulatory domain having a sequence of SEQ ID NO:16 or SEQ ID NO:51, or having 95-99% identity thereof, and/or a primary signaling domain, e.g., a primary signaling domain described herein, e.g., a CD3 zeta stimulatory domain having a sequence of SEQ ID NO:17 or SEQ ID NO:43, or having 95-99% identity thereof.

In one embodiment, the isolated CAR molecule comprises (e.g., consists of) an amino acid sequence of SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41 or SEQ ID NO:42, or an amino acid sequence having at least one, two, three, four, five, 10, 15, 20 or 30 modifications (e.g., substitutions) but not more than 60, 50 or 40 modifications (e.g., substitutions) of an amino acid sequence of SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41 or SEQ ID NO:42, or an amino acid sequence having 85%, 90%, 95%, 96%, 97%, 98% or 99% identity to an amino acid sequence SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41 or SEQ ID NO:42.

In one aspect, the invention pertains to a humanized anti-CD19 binding domain comprising one or more (e.g., all three) light chain complementary determining region 1 (LC CDR1), light chain complementary determining region 2 (LC CDR2), and light chain complementary determining region 3 (LC CDR3) of an anti-CD19 binding domain described herein, and one or more (e.g., all three) heavy chain complementary determining region 1 (HC CDR1), heavy chain complementary determining region 2 (HC CDR2), and heavy chain complementary determining region 3 (HC CDR3) of a humanized anti-CD19 binding domain described herein, e.g., a humanized anti-CD19 binding domain comprising one or more, e.g., all three, LC CDRs and one or more, e.g., all three, HC CDRs. In one embodiment, the humanized anti-CD19 binding domain having at least HC CDR2. In one embodiment, the light chain variable region comprises one, two, three or all four framework regions of VK3_L25 germline sequence. In one embodiment, the light chain variable region has a modification (e.g., substitution, e.g., a substitution of one or more amino acid found in the corresponding position in the murine light chain variable region of SEQ ID NO: 58, e.g., a substitution at one or more of positions 71 and 87). In one embodiment, the heavy chain variable region comprises one, two, three or all four framework regions of VH4_4-59 germline sequence. In one embodiment, the heavy chain variable region has a modification (e.g., substitution, e.g., a substitution of one or more amino acid found in the corresponding position in the heavy chain variable region of SEQ ID NO: 58, e.g., a substitution at one or more of positions 71, 73 and 78). In one embodiment, the humanized anti-CD19 binding domain comprises a light chain variable region described herein (e.g., in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12) and/or a heavy chain variable region described herein (e.g. in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12). In one embodiment, the humanized anti-CD19 binding domain is a scFv comprising a light chain and a heavy chain of an amino acid sequence of in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12. In an embodiment, the humanized anti-CD19 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided, in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12 or a sequence with 95-99% identity with an amino acid sequence in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, or a sequence with 95-99% identity to an amino acid sequence in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.

In another aspect, the invention pertains to a vector comprising a nucleic acid sequence encoding a CAR. In one embodiment, the vector is selected from the group consisting of a DNA, a RNA, a plasmid, a lentivirus vector, adenoviral vector, or a retrovirus vector.

In one embodiment, the vector is a lentivirus vector. In one embodiment, the vector further comprises a promoter. In one embodiment, the promoter is an EF-1 promoter. In one embodiment, the EF-1 promoter comprises a sequence of SEQ ID NO: 100.

In one embodiment, the vector is an in vitro transcribed vector, e.g., a vector that transcribes RNA of a nucleic acid molecule described herein. In one embodiment, the nucleic acid sequence in the vector further comprises a poly(A) tail, e.g., a poly A tail described herein, e.g., comprising about 150 adenosine bases (SEQ ID NO:104). In one embodiment, the nucleic acid sequence in the vector further comprises a 3′UTR, e.g., a 3′ UTR described herein, e.g., comprising at least one repeat of a 3′UTR derived from human beta-globulin. In one embodiment, the nucleic acid sequence in the vector further comprises promoter, e.g., a T2A promoter.

In another aspect, the invention pertains to a cell comprising the vector. In one embodiment, the cell is a human T cell. In one embodiment, the cell is a cell described herein, e.g., a human T cell, e.g., a human T cell described herein. In one embodiment, the human T cell is a CD8+ T cell.

In another embodiment, the CAR-expressing cell described herein can further express another agent, e.g., an agent which enhances the activity of a CAR-expressing cell. For example, in one embodiment, the agent can be an agent which inhibits an inhibitory molecule. Examples of inhibitory molecules include PD1, PD-L1, CTLA4, TIM3, LAG3, VISTA, BTLA, TIGIT, LAIR1, CD160, 2B4 and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, LAG3, CTLA4, CD160, BTLA, LAIR1, TIM3, 2B4 and TIGIT, or a fragment of any of these (e.g., at least a portion of the extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In another aspect, the invention pertains to a method of making a cell comprising transducing a T cell with a vector of comprising a nucleic acid encoding a CAR, e.g., a CAR described herein.

The present invention also provides a method of generating a population of RNA-engineered cells, e.g., cells described herein, e.g., T cells, transiently expressing exogenous RNA. The method comprises introducing an in vitro transcribed RNA or synthetic RNA into a cell, where the RNA comprises a nucleic acid encoding a CAR molecule described herein.

In another aspect, the invention pertains to a method of providing an anti-tumor immunity in a mammal comprising administering to the mammal an effective amount of a cell comprising a CAR molecule, e.g., a cell expressing a CAR molecule described herein. In one embodiment, the cell is an autologous T cell. In one embodiment, the cell is an allogeneic T cell. In one embodiment, the mammal is a human.

In another aspect, the invention pertains to a method of treating a mammal having a disease associated with expression of CD19 comprising administering to the mammal an effective amount of the cell of comprising a CAR molecule, e.g., a CAR molecule described herein.

In one embodiment, the disease associated with CD19 expression is selected from a proliferative disease such as a cancer or malignancy or a precancerous condition such as a myelodysplasia, a myelodysplastic syndrome or a preleukemia, or is a non-cancer related indication associated with expression of CD19. In one embodiment, the disease is a hematologic cancer. In one embodiment, the hematologic cancer is leukemia. In one embodiment, the cancer is selected from the group consisting of one or more acute leukemias including but not limited to B-cell acute lymphoid leukemia ("BALL"), T-cell acute lymphoid leukemia ("TALL"), acute lymphoid leukemia (ALL); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and to disease associated with CD19 expression include, but not limited to atypical and/or non-classical cancers, malignancies, precancerous conditions or proliferative diseases expressing CD19; and any combination thereof.

In one embodiment, lymphocyte infusion, for example allogeneic lymphocyte infusion, is used in the treatment of the cancer, wherein the lymphocyte infusion comprises at least one CD19 CAR-expressing cell. In one embodiment, autologous lymphocyte infusion is used in the treatment of the cancer, wherein the autologous lymphocyte infusion comprises at least one CD19-expressing cell.

In one embodiment, the CD19 CAR expressing cell, e.g., T cell, is administered to a subject that has received a previous stem cell transplantation, e.g., autologous stem cell transplantation.

In one embodiment, the CD19 CAR expressing cell, e.g., T cell, is administered to a subject that has received a previous dose of melphalan.

In one embodiment, the cells expressing a CAR molecule, e.g., a CAR molecule described herein, are administered in combination with an agent that increases the efficacy of a cell expressing a CAR molecule, e.g., an agent described herein.

In one embodiment, the cells expressing a CAR molecule, e.g., a CAR molecule described herein, are administered in combination with an agent that ameliorates one or more side effect associated with administration of a cell expressing a CAR molecule, e.g., an agent described herein.

In one embodiment, the cells expressing a CAR molecule, e.g., a CAR molecule described herein, are administered in combination with an agent that treats the disease associated with CD19, e.g., an agent described herein.

In one embodiment, the cells expressing a CAR molecule, e.g., a CAR molecule described herein, are administered at a dose and/or dosing schedule described herein.

In one embodiment, the CAR molecule is introduced into T cells, e.g., using in vitro transcription, and the subject (e.g., human) receives an initial administration of cells comprising a CAR molecule, and one or more subsequent administrations of cells comprising a CAR molecule, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of cells comprising a CAR molecule are administered to the subject (e.g., human) per week, e.g., 2, 3, or 4 administrations of cells comprising a CAR molecule are administered per week. In one embodiment, the subject (e.g., human subject) receives more than one administration of cells comprising a CAR molecule per week (e.g., 2, 3 or 4 administrations per week) (also referred to herein as a cycle), followed by a week of no administration of cells comprising a CAR molecule, and then one or more additional administration of cells comprising a CAR molecule (e.g., more than one administration of the cells comprising a CAR molecule per week) is administered to the subject. In another embodiment, the subject (e.g., human subject) receives more than one cycle of cells comprising a CAR molecule, and the time between each cycle is less than 10, 9, 8, 7, 6, 5, 4, or 3 days. In one embodiment, the cells comprising a CAR molecule are administered every other day for 3 administrations per week. In one embodiment, the cells comprising a CAR molecule are administered for at least two, three, four, five, six, seven, eight or more weeks.

In one embodiment, the cells expressing a CAR molecule, e.g., a CAR molecule described herein, are administered as a first line treatment for the disease, e.g., the cancer, e.g., a cancer described herein. In another embodiment, the cells expressing a CAR molecule, e.g., a CAR molecule described herein, are administered as a second, third, fourth line treatment for the disease, e.g., the cancer, e.g., the cancer described herein.

In one embodiment, a population of cells described herein is administered.

In another aspect, the invention pertains to the isolated nucleic acid molecule encoding a CAR of the invention, the isolated polypeptide molecule of a CAR of the invention, the vector comprising a CAR of the invention, and the cell comprising a CAR of the invention for use as a medicament.

In another aspect, the invention pertains to a the isolated nucleic acid molecule encoding a CAR of the invention, the isolated polypeptide molecule of a CAR of the invention, the vector comprising a CAR of the invention, and the cell comprising a CAR of the invention for use in the treatment of a disease expressing CD19.

In one aspect, the invention includes a population of autologous cells that are transfected or transduced with a vector comprising a nucleic acid molecule encoding a CD19-CAR molecule, e.g., as described herein. In one embodiment, the vector is a retroviral vector. In one embodiment, the vector is a self-inactivating lentiviral vector as described elsewhere herein. In one embodiment, the vector is delivered (e.g., by transfecting or electroporating) to a cell, e.g., a T cell, wherein the vector comprises a nucleic acid molecule encoding a CD19 CAR molecule as described herein, which is transcribed as an mRNA molecule, and the CD19 CAR molecule is translated from the RNA molecule and expressed on the surface of the cell.

In another aspect, the present invention provides a population of CAR-expressing cells, e.g., CART cells. In some embodiments, the population of CAR-expressing cells comprises a mixture of cells expressing different CARs. For example, in one embodiment, the population of CART cells can include a first cell expressing a CAR having an anti-CD19 binding domain described herein, and a second cell expressing a CAR having a different anti-CD19 binding domain, e.g., an anti-CD19 binding domain described herein that differs from the anti-CD19 binding domain in the CAR expressed by the first cell. As another example, the population of CAR-expressing cells can include a first cell expressing a CAR that includes an anti-CD19 binding domain, e.g., as described herein, and a second cell expressing a CAR that includes an antigen binding domain to a target other than CD19 (e.g., CD123). In one embodiment, the population of CAR-expressing cells includes, e.g., a first cell expressing a CAR that includes a primary intracellular signaling domain, and a second cell expressing a CAR that includes a secondary signaling domain.

In another aspect, the present invention provides a population of cells wherein at least one cell in the population expresses a CAR having an anti-CD19 domain described herein, and a second cell expressing another agent, e.g., an agent which enhances the activity of a CAR-expressing cell. For example, in one embodiment, the agent can be an agent which inhibits an inhibitory molecule. Examples of inhibitory molecules include PD1, PD-L1, CTLA4, TIM3, LAG3, VISTA, BTLA, TIGIT, LAIR1, CD160, 2B4 and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, LAG3, CTLA4, CD160, BTLA, LAIR1, TIM3, 2B4 and TIGIT, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one embodiment, the nucleic acid molecule encoding a CD19 CAR molecule, e.g., as described herein, is expressed as an mRNA molecule. In one embodiment, the genetically modified CD19 CAR-expressing cells, e.g., T cells, can be generated by transfecting or electroporating an RNA molecule encoding the desired CARs (e.g., without a vector sequence) into the cell. In one embodiment, a CD19 CAR molecule is translated from the RNA molecule once it is incorporated and expressed on the surface of the recombinant cell.

BRIEF DESCRIPTION OF THE DRAWINGS

FIGS. 1A, 1B and 1C are graphic representations of cytotoxicity as assayed in ND317 (normal donor) T cell transduced with mouse anti-CD19 CAR or the humanized anti-CD19 CARs of the invention and cultured with either control K562 cells that do not express CD19 (K562cc) as shown in FIG. 1A, K562 cells transformed with CD19 (K562.CD19) as shown in FIG. 1B or malignant B cells isolated from a CLL patient (Pt 14 B cell isolate) as shown in FIG. 1C.

DETAILED DESCRIPTION

Definitions

Figure 2A:
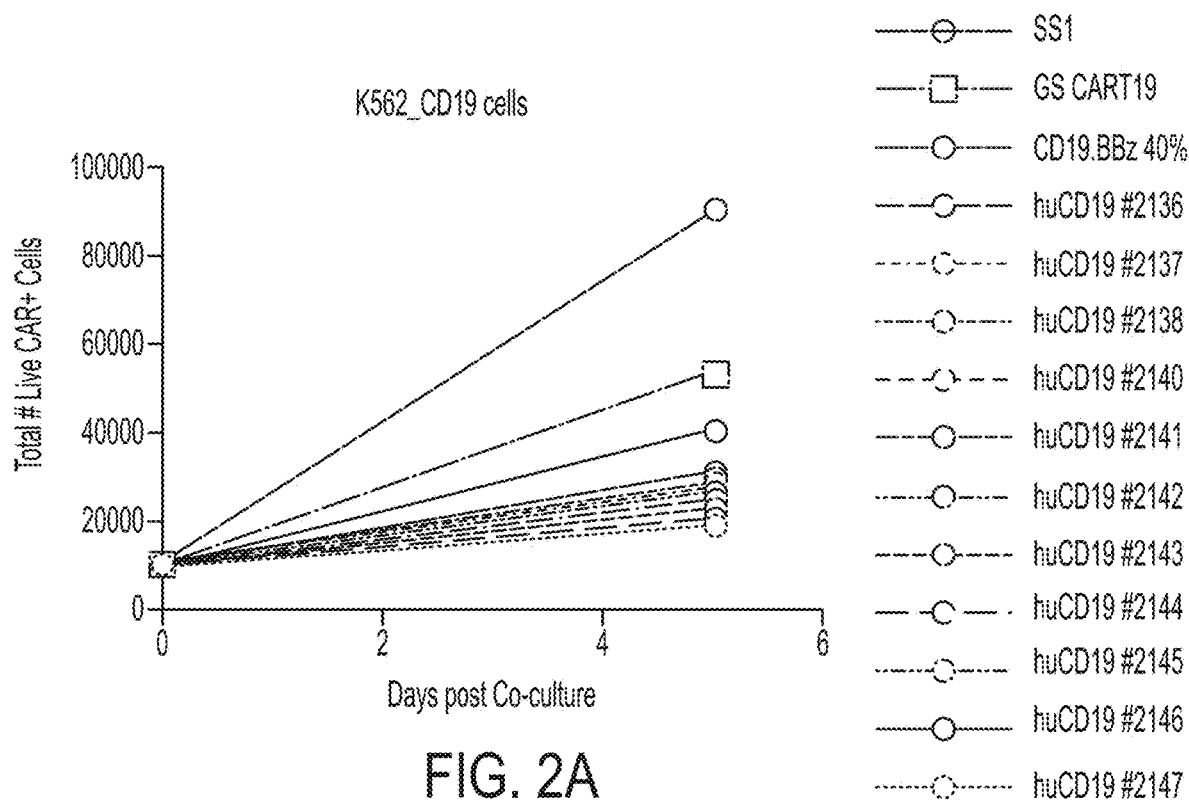
FIGS. 2A and 2B are graphs showing the proliferative response of humanized and mouse anti-CD19CAR-expressing cells to CD19+ cells, where higher number of viable CAR+ T cells correlates with populations showing maximal CD4+ and CD8+ T cell proliferation to primary CLL cells.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances±10%, or in some instances±5%, or in some instances±1%, or in some instances±0.1% from the specified value, as such variations are appropriate to perform the disclosed methods.

The term "Chimeric Antigen Receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the costimulatory molecule is chosen from 4-1BB (i.e., CD137), CD27 and/or CD28. In one aspect, the CAR comprises a chimeric fusion protein comprising an extracellular antigen recognition domain, a transmembrane domain and an intracellular signaling domain comprising a functional signaling domain derived from a stimulatory molecule. In one aspect, the CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. In one aspect, the CAR comprises a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen recognition domain, wherein the leader sequence is optionally cleaved from the antigen recognition domain (e.g., aa scFv) during cellular processing and localization of the CAR to the cellular membrane.

The term "signaling domain" refers to the functional portion of a protein which acts by transmitting information within the cell to regulate cellular activity via defined signaling pathways by generating second messengers or functioning as effectors by responding to such messengers.

As used herein, the term "CD19" refers to the Cluster of Differentiation 19 protein, which is an antigenic determinant detectable on leukemia precursor cells. The human and murine amino acid and nucleic acid sequences can be found in a public database, such as GenBank, UniProt and Swiss-Prot. For example, the amino acid sequence of human CD19 can be found as UniProt/Swiss-Prot Accession No. P15391 and the nucleotide sequence encoding the human CD19 can be found at Accession No. NM_001178098. CD19 is expressed on most B lineage cancers, including, e.g., acute lymphoblastic leukaemia, chronic lymphocyte leukaemia and non-Hodgkin's lymphoma. Other cells with express CD19 are provided below in the definition of "disease associated with expression of CD19." It is also an early marker of B cell progenitors. See, e.g., Nicholson et al. Mol. Immun. 34 (16-17): 1157-1165 (1997). In one aspect the antigen-binding portion of the CART recognizes and binds an antigen within the extracellular domain of the CD19 protein. In one aspect, the CD19 protein is expressed on a cancer cell.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')2, and Fv fragments, scFv antibody fragments, linear antibodies, single domain antibodies such as sdAb (either VL or VH), camelid VHH domains, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The portion of the CAR composition of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-tumor effect" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically The term "xenogeneic" refers to a graft derived from an animal of a different species.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The phrase "disease associated with expression of CD19" includes, but is not limited to, a disease associated with expression of CD19 or condition associated with cells which express CD19 including, e.g., proliferative diseases such as a cancer or malignancy or a precancerous condition such as a myelodysplasia, a myelodysplastic syndrome or a preleukemia; or a noncancer related indication associated with cells which express CD19. In one aspect, a cancer associated with expression of CD19 is a hematolical cancer. In one aspect, the hematolical cancer is a leukemia or a lymphoma. In one aspect, a cancer associated with expression of CD19 includes cancers and malignancies including, but not limited to, e.g., one or more acute leukemias including but not limited to, e.g., B-cell acute Lymphoid Leukemia ("BALL"), T-cell acute Lymphoid Leukemia ("TALL"), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of CD19 comprise, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further diseases associated with expression of CD19 expression include, but not limited to, e.g., atypical and/or non-classical cancers, malignancies, precancerous conditions or proliferative diseases associated with expression of CD19. Non-cancer related indications associated with expression of CD19 include, but are not limited to, e.g., autoimmune disease, (e.g., lupus), inflammatory disorders (allergy and asthma) and transplantation.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation," refers to a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

The term "stimulatory molecule," refers to a molecule expressed by a T cell that provides the primary cytoplasmic signaling sequence(s) that regulate primary activation of the TCR complex in a stimulatory way for at least some aspect of the T cell signaling pathway. In one aspect, the primary signal is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS") and CD66d. In a specific CAR of the invention, the intracellular signaling domain in any one or more CARS of the invention comprises an intracellular signaling sequence, e.g., a primary signaling sequence of CD3-zeta. In a specific CAR of the invention, the primary signaling sequence of CD3-zeta is the sequence provided as SEQ ID NO:17, or the equivalent residues from a non-human species, e.g., mouse, rodent, monkey, ape and the like. In a specific CAR of the invention, the primary signaling sequence of CD3-zeta is the sequence as provided in SEQ ID NO:43, or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, and CD66d DAP10 and DAP12.

The term "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO:17. In one aspect, the "zeta stimulatory domain" or a "CD3-zeta stimulatory domain" is the sequence provided as SEQ ID NO:43.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an MHC class I molecule, BTLA and a Toll ligand receptor, as well as OX40, CD2, CD27, CD28, CDS, ICAM-1, LFA-1 (CD11a/CD18) and 4-1BB (CD137).

A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank accno. AAA62478.2, or the equivalent residues from a non-human species, e.g., mouse, rodent, monkey, ape and the like. In one aspect, the "4-1BB costimulatory domain" is the sequence provided as SEQ ID NO:16 or the equivalent residues from a non-human species, e.g., mouse, rodent, monkey, ape and the like.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The term "flexible polypeptide linker" or "linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)n, where n is a positive integer equal to or greater than 1. For example, n=1, n=2, n=3. n=4, n=5 and n=6, n=7, n=8, n=9 and n=10 (SEQ ID NO:105). In one embodiment, the flexible polypeptide linkers include, but are not limited to, $(Gly_4 Ser)_4$ (SEQ ID NO:106) or $(Gly_4 Ser)_3$ (SEQ ID NO:107). In another embodiment, the linkers include multiple repeats of $(Gly_2Ser)$, $(GlySer)$ or $(Gly_3Ser)$ (SEQ ID NO:108). Also included within the scope of the invention are linkers described in WO2012/138475, incorporated herein by reference).

As used herein, a 5' cap (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 109), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

The term "signal transduction pathway" refers to the biochemical relationship between a variety of signal transduction molecules that play a role in the transmission of a signal from one portion of a cell to another portion of a cell.

The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin's lymphoma, non-Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

DESCRIPTION

Provided herein are compositions of matter and methods of use for the treatment of a disease such as cancer using humanized anti-CD19 chimeric antigen receptors (CAR).

In one aspect, the invention provides a number of chimeric antigen receptors (CAR) comprising an antibody or antibody fragment engineered for enhanced binding to a CD19 protein. In one aspect, the invention provides a cell (e.g., T cell) engineered to express a CAR, wherein the CAR T cell ("CART") exhibits an antitumor property. In one aspect a cell is transformed with the CAR and the CAR is expressed on the cell surface. In some embodiments, the cell (e.g., T cell) is transduced with a viral vector encoding a CAR. In some embodiments, the viral vector is a retroviral vector. In some embodiments, the viral vector is a lentiviral vector. In some such embodiments, the cell may stably express the CAR. In another embodiment, the cell (e.g., T cell) is transfected with a nucleic acid, e.g., mRNA, cDNA, DNA, encoding a CAR. In some such embodiments, the cell may transiently express the CAR.

In one aspect, the anti-CD19 protein binding portion of the CAR is a scFv antibody fragment. In one aspect such antibody fragments are functional in that they retain the equivalent binding affinity, e.g., they bind the same antigen with comparable efficacy, as the IgG antibody from which it is derived. In one aspect such antibody fragments are functional in that they provide a biological response that can include, but is not limited to, activation of an immune response, inhibition of signal-transduction origination from its target antigen, inhibition of kinase activity, and the like, as will be understood by a skilled artisan. In one aspect, the anti-CD19 antigen binding domain of the CAR is a scFv antibody fragment that is humanized compared to the murine sequence of the scFv from which it is derived. In one aspect the parental murine scFv sequence is the CAR19 construct provided in PCT publication WO2012/079000 and provided herein as SEQ ID NO:58.

In some aspects, the antibodies of the invention are incorporated into a chimeric antigen receptor (CAR). In one aspect, the CAR comprises the polypeptide sequence provided as SEQ ID NO: 12 in PCT publication WO2012/079000, and provided herein as SEQ ID NO: 58, wherein the scFv domain is substituted by one or more sequences selected from SEQ ID NOS: 1-12. In one aspect, the scFv domains of SEQ ID NOS:1-12 are humanized variants of the scFv domain of SEQ ID NO:59, which is an scFv fragment of murine origin that specifically binds to human CD19. Humanization of this mouse scFv may be desired for the clinical setting, where the mouse-specific residues may induce a human-anti-mouse antigen (HAMA) response in patients who receive CART19 treatment, e.g., treatment with T cells transduced with the CAR19 construct.

In one aspect, the anti-CD19 binding domain, e.g., humanized scFv, portion of a CAR of the invention is encoded by a transgene whose sequence has been codon optimized for expression in a mammalian cell. In one aspect, entire CAR construct of the invention is encoded by a transgene whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

In one aspect, the humanized CAR19 comprises the scFv portion provided in SEQ ID NO:1. In one aspect, the humanized CAR19 comprises the scFv portion provided in SEQ ID NO:2. In one aspect, the humanized CAR19 comprises the scFv portion provided in SEQ ID NO:3. In one aspect, the humanized CAR19 comprises the scFv portion provided in SEQ ID NO:4. In one aspect, the humanized CAR19 comprises the scFv portion provided in SEQ ID NO:5. In one aspect, the humanized CAR19 comprises the scFv portion provided in SEQ ID NO:6. In one aspect, the humanized CAR19 comprises the scFv portion provided in SEQ ID NO:7. In one aspect, the humanized CAR19 comprises the scFv portion provided in SEQ ID NO:8. In one aspect, the humanized CAR19 comprises the scFv portion provided in SEQ ID NO:9. In one aspect, the humanized CAR19 comprises the scFv portion provided in SEQ ID NO:10. In one aspect, the humanized CAR19 comprises the scFv portion provided in SEQ ID NO:11. In one aspect, the humanized CAR19 comprises the scFv portion provided in SEQ ID NO:12.

In one aspect, the CARs of the invention combine an antigen binding domain of a specific antibody with an intracellular signaling molecule. For example, in some aspects, the intracellular signaling molecule includes, but is not limited to, CD3-zeta chain, 4-1BB and CD28 signaling modules and combinations thereof. In one aspect, the antigen binding domain binds to CD19. In one aspect, the CD19 CAR comprises a CAR selected from the sequence provided in one or more of SEQ ID NOS: 31-42. In one aspect, the CD19 CAR comprises the sequence provided in SEQ ID NO:31. In one aspect, the CD19 CAR comprises the sequence provided in SEQ ID NO:32. In one aspect, the CD19 CAR comprises the sequence provided in SEQ ID NO:33. In one aspect, the CD19 CAR comprises the sequence provided in SEQ ID NO:34. In one aspect, the CD19 CAR comprises the sequence provided in SEQ ID NO:35. In one aspect, the CD19 CAR comprises the sequence provided in SEQ ID NO:36. In one aspect, the CD19 CAR comprises the sequence provided in SEQ ID NO:37. In one aspect, the CD19 CAR comprises the sequence provided in SEQ ID NO:38. In one aspect, the CD19 CAR comprises the sequence provided in SEQ ID NO:39. In one aspect, the CD19 CAR comprises the sequence provided in SEQ ID NO:40. In one aspect, the CD19 CAR comprises the sequence provided in SEQ ID NO:41. In one aspect, the CD19 CAR comprises the sequence provided in SEQ ID NO:42.

Furthermore, the present invention provides CD19 CAR compositions and their use in medicaments or methods for treating, among other diseases, cancer or any malignancy or autoimmune diseases involving cells or tissues which express CD19.

In one aspect, the CAR of the invention can be used to eradicate CD19-expressing normal cells, thereby applicable for use as a cellular conditioning therapy prior to cell transplantation. In one aspect, the CD19-expressing normal cell is a CD19-expressing normal stem cell and the cell transplantation is a stem cell transplantation.

In one aspect, the invention provides a cell (e.g., T cell) engineered to express a chimeric antigen receptor (CAR), wherein the CAR T cell ("CART") exhibits an antitumor property. A preferred antigen is CD19. In one aspect, the antigen binding domain of the CAR comprises a partially humanized anti-CD19 antibody fragment. In one aspect, the antigen binding domain of the CAR comprises a partially humanized anti-CD19 antibody fragment comprising an scFv. Accordingly, the invention provides a CD19-CAR that comprises a humanized anti-CD19 binding domain and is engineered into a T cell and methods of their use for adoptive therapy.

In one aspect, the CD19-CAR comprises at least one intracellular domain selected from the group of a CD137 (4-1BB) signaling domain, a CD28 signaling domain, a CD3zeta signal domain, and any combination thereof. In one aspect, the CD19-CAR comprises at least one intracellular signaling domain is from one or more co-stimulatory molecule(s) other than a CD137 (4-1BB) or CD28.

Chimeric Antigen Receptor (CAR)

The present invention encompasses a recombinant DNA construct comprising sequences encoding a CAR, wherein the CAR comprises a humanized antibody fragment that binds specifically to CD19, e.g., human CD19, wherein the sequence of the antibody fragment is contiguous with and in the same reading frame as a nucleic acid sequence encoding an intracellular signaling domain. The intracellular signaling domain can comprise a costimulatory signaling domain and/or a primary signaling domain, e.g., a zeta chain. The costimulatory signaling domain refers to a portion of the CAR comprising at least a portion of the intracellular domain of a costimulatory molecule.

In specific aspects, a CAR construct of the invention comprises a scFv domain selected from the group consisting of SEQ ID NOS:1-12, wherein the scFv may be preceded by an optional leader sequence such as provided in SEQ ID NO: 13, and followed by an optional hinge sequence such as provided in SEQ ID NO:14 or SEQ ID NO:45 or SEQ ID NO:47 or SEQ ID NO:49, a transmembrane region such as provided in SEQ ID NO:15, an intracellular signalling domain that includes SEQ ID NO:16 or SEQ ID NO:51 and a CD3 zeta sequence that includes SEQ ID NO:17 or SEQ ID NO:43, wherein the domains are contiguous with and in the same reading frame to form a single fusion protein. Also included in the invention is a nucleotide sequence that encodes the polypeptide of each of the scFv fragments selected from the group consisting of SEQ IS NO:1, SEQ ID NO:2, SEQ ID NO:3, SEQ ID NO:4, SEQ ID NO:5, SEQ IS NO:6, SEQ ID NO:7, SEQ ID NO:8, SEQ ID NO:9, SEQ ID NO:10, SEQ ID NO:11 and SEQ ID NO:12. Also included in the invention is a nucleotide sequence that encodes the polypeptide of each of the scFv fragments selected from the group consisting of SEQ IS NO:1, SEQ ID NO:2, SEQ ID NO:3, SEQ ID NO:4, SEQ ID NO:5, SEQ IS NO:6, SEQ ID NO:7, SEQ ID NO:8, SEQ ID NO:9, SEQ ID NO:10, SEQ ID NO:11 and SEQ ID NO:12, and each of the domains of SEQ ID NOS: 13-17, plus the encoded CD19CAR fusion protein of the invention. In one aspect an exemplary CD19CAR constructs comprise an optional leader sequence, an extracellular antigen binding domain, a hinge, a transmembrane domain, and an intracellular stimulatory domain. In one aspect an exemplary CD19CAR construct comprises an optional leader sequence, an extracellular antigen binding domain, a hinge, a transmembrane domain, an intracellular costimulatory domain and an intracellular stimulatory domain. Specific CD19 CAR constructs containing humanized scFv domains of the invention are provided as SEQ ID NOS: 31-42.

Full-length CAR sequences are also provided herein as SEQ ID NOS: 31-42, as shown in Table 3.

An exemplary leader sequence is provided as SEQ ID NO: 13. An exemplary hinge/spacer sequence is provided as SEQ ID NO: 14 or SEQ ID NO:45 or SEQ ID NO:47 or SEQ ID NO:49. An exemplary transmembrane domain sequence is provided as SEQ ID NO:15. An exemplary sequence of the intracellular signaling domain of the 4-1BB protein is provided as SEQ ID NO: 16. An exemplary sequence of the intracellular signaling domain of CD27 is provided as SEQ ID NO:51. An exemplary CD3zeta domain sequence is provided as SEQ ID NO: 17 or SEQ ID NO:43.

In one aspect, the present invention encompasses a recombinant nucleic acid construct comprising a nucleic acid molecule encoding a CAR, wherein the nucleic acid molecule comprises the nucleic acid sequence encoding an anti-CD19 binding domain, e.g., described herein, that is contiguous with and in the same reading frame as a nucleic acid sequence encoding an intracellular signaling domain. In one aspect, the anti-CD19 binding domain is selected from one or more of SEQ ID NOS:1-12. In one aspect, the anti-CD19 binding domain is encoded by a nucleotide residues 64 to 813 of the sequence provided in one or more of SEQ ID NOS:61-72. In one aspect, the anti-CD19 binding domain is encoded by a nucleotide residues 64 to 813 of SEQ ID NO:61. In one aspect, the anti-CD19 binding domain is encoded by a nucleotide residues 64 to 813 of SEQ ID NO:62. In one aspect, the anti-CD19 binding domain is encoded by a nucleotide residues 64 to 813 of SEQ ID NO:63. In one aspect, the anti-CD19 binding domain is encoded by a nucleotide residues 64 to 813 of SEQ ID NO:64. In one aspect, the anti-CD19 binding domain is encoded by a nucleotide residues 64 to 813 of SEQ ID NO:65. In one aspect, the anti-CD19 binding domain is encoded by a nucleotide residues 64 to 813 of SEQ ID NO:66. In one aspect, the anti-CD19 binding domain is encoded by a nucleotide residues 64 to 813 of SEQ ID NO:67. In one aspect, the anti-CD19 binding domain is encoded by a nucleotide residues 64 to 813 of SEQ ID NO:68. In one aspect, the anti-CD19 binding domain is encoded by a nucleotide residues 64 to 813 of SEQ ID NO:69. In one aspect, the anti-CD19 binding domain is encoded by a nucleotide residues 64 to 813 of SEQ ID NO:70. In one aspect, the anti-CD19 binding domain is encoded by a nucleotide residues 64 to 813 of SEQ ID NO:71. In one aspect, the anti-CD19 binding domain is encoded by a nucleotide residues 64 to 813 of SEQ ID NO:72.

In one aspect, the present invention encompasses a recombinant nucleic acid construct comprising a transgene encoding a CAR, wherein the nucleic acid molecule comprises a nucleic acid sequence encoding an anti-CD19 binding domain selected from one or more of SEQ ID NOS:61-72, wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, e.g., CD3-zeta, CD28, 4-1BB, and the like. In some instances, the CAR can comprise any combination of CD3-zeta, CD28, 4-1BB, and the like. In one aspect the nucleic acid sequence of a CAR construct of the invention is selected from one or more of SEQ ID NOS: 85-96. In one aspect the nucleic acid sequence of a CAR construct is SEQ ID NO:85. In one aspect the nucleic acid sequence of a CAR construct is SEQ ID NO:86. In one aspect the nucleic acid sequence of a CAR construct is SEQ ID NO:87. In one aspect the nucleic acid sequence of a CAR construct is SEQ ID NO:88. In one aspect the nucleic acid sequence of a CAR construct is SEQ ID NO:89. In one aspect the nucleic acid sequence of a CAR construct is SEQ ID NO:90. In one aspect the nucleic acid sequence of a CAR construct is SEQ ID NO:91. In one aspect the nucleic acid sequence of a CAR construct is SEQ ID NO:92. In one aspect the nucleic acid sequence of a CAR construct is SEQ ID NO:93. In one aspect the nucleic acid sequence of a CAR construct is SEQ ID NO:94. In one aspect the nucleic acid sequence of a CAR construct is SEQ ID NO:95. In one aspect the nucleic acid sequence of a CAR construct is SEQ ID NO:96. In one aspect the nucleic acid sequence of a CAR construct is SEQ ID NO:97. In one aspect the nucleic acid sequence of a CAR construct is SEQ ID NO:98. In one aspect the nucleic acid sequence of a CAR construct is SEQ ID NO:99.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the nucleic acid of interest can be produced synthetically, rather than cloned.

The present invention includes retroviral and lentiviral vector constructs expressing a CAR that can be directly transduced into a cell.

The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO:118). RNA so produced can efficiently transfect different kinds of cells. In one embodiment, the template includes sequences for the CAR. In an embodiment, an RNA CAR vector is transduced into a T cell by electroporation.

Antigen Binding Domain

In one aspect, the CAR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in a CAR of the invention include those associated with viral, bacterial and parasitic infections, autoimmune disease and cancer cells.

In one aspect, the CAR-mediated T-cell response can be directed to an antigen of interest by way of engineering an antigen binding domain that specifically binds a desired antigen into the CAR.

In one aspect, the portion of the CAR comprising the antigen binding domain comprises an antigen binding domain that targets CD19. In one aspect, the antigen binding domain targets human CD19. In one aspect, the antigen binding domain of the CAR has the same or a similar binding specificity as the FMC63 scFv fragment described in Nicholson et al. Mol. Immun. 34 (16-17): 1157-1165 (1997).

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

Thus, in one aspect, the antigen binding domain comprises a humanized antibody or an antibody fragment. In one embodiment, the humanized anti-CD19 binding domain comprises one or more (e.g., all three) light chain complementary determining region 1 (LC CDR1), light chain complementary determining region 2 (LC CDR2), and light chain complementary determining region 3 (LC CDR3) of a humanized anti-CD19 binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized anti-CD19 binding domain described herein, e.g., a humanized anti-CD19 binding domain comprising one or more, e.g., all three, LC CDRs and one or more, e.g., all three, HC CDRs. In one embodiment, the humanized anti-CD19 binding domain comprises one or more (e.g., all three) heavy chain complementary determining region 1 (HC CDR1), heavy chain complementary determining region 2 (HC CDR2), and heavy chain complementary determining region 3 (HC CDR3) of a humanized anti-CD19 binding domain described herein, e.g., the humanized anti-CD19 binding domain has two variable heavy chain regions, each comprising a HC CDR1, a HC CDR2 and a HC CDR3 described herein. In one embodiment, the humanized anti-CD19 binding domain comprises a humanized light chain variable region described herein (e.g., in Table 3) and/or a humanized heavy chain variable region described herein (e.g., in Table 3). In one embodiment, the humanized anti-CD19 binding domain comprises a humanized heavy chain variable region described herein (e.g., in Table 3), e.g., at least two humanized heavy chain variable regions described herein (e.g., in Table 3). In one embodiment, the anti-CD19 binding domain is a scFv comprising a light chain and a heavy chain of an amino acid sequence of Table 3. In an embodiment, the anti-CD19 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 3, or a sequence with 95-99% identity with an amino acid sequence of Table 3; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 3, or a sequence with 95-99% identity to an amino acid sequence of Table 3. In one embodiment, the humanized anti-CD19 binding domain comprises a sequence selected from a group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, or a sequence with 95-99% identify thereof. In one embodiment, the nucleic acid sequence encoding the humanized anti-CD19 binding domain comprises a sequence selected from a group consisting of SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:70, SEQ ID NO:71 and SEQ ID NO:72, or a sequence with 95-99% identify thereof. In one embodiment, the humanized anti-CD19 binding domain is a scFv, and a light chain variable region comprising an amino acid sequence described herein, e.g., in Table 3, is attached to a heavy chain variable region comprising an amino acid sequence described herein, e.g., in Table 3, via a linker, e.g., a linker described herein. In one embodiment, the humanized anti-CD19 binding domain includes a (Gly$_4$-Ser)n linker, wherein n is 1, 2, 3, 4, 5, or 6, preferably 3 or 4 (SEQ ID NO:53). The light chain variable region and heavy chain variable region of a scFv can be, e.g., in any of the following orientations: light chain variable region-linker-heavy chain variable region or heavy chain variable region-linker-light chain variable region.

In one aspect, the antigen binding domain portion comprises one or more sequence selected from SEQ ID NOS: 1-12. In one aspect the humanized CAR is selected from one or more sequence selected from SEQ ID NOS: 31-42. In some aspects, a non-human antibody is humanized, where specific sequences or regions of the antibody are modified to increase similarity to an antibody naturally produced in a human or fragment thereof. In one aspect, the antigen binding domain is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody or antibody fragment has one or more amino acid residues remaining in it from a source which is nonhuman. These nonhuman amino acid residues are often referred to as "import" residues, which are typically taken from an "import" variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized antibodies and antibody fragments, substantially less than an intact human variable domain has been substituted by the corresponding sequence from a nonhuman species. Humanized antibodies are often human antibodies in which some CDR residues and possibly some framework (FR) residues are substituted by residues from analogous sites in rodent antibodies. Humanization of antibodies and antibody fragments can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (see, e.g., Nicholson et al. Mol. Immun. 34 (16-17): 1157-1165 (1997); Carter et al., Proc. Natl. Acad. Sci. USA, 89:4285 (1992); Presta et al., J. Immunol., 151:2623 (1993), the contents of which are incorporated herein by reference herein in their entirety). In some embodiments, the framework region, e.g., all four framework regions, of the heavy chain variable region are derived from a VH4_4-59 germline sequence. In one embodiment, the framework region can comprise, one, two, three, four or five modifications, e.g., substitutions, e.g., from the amino acid at the corresponding murine sequence (e.g., of SEQ ID NO:58). In one embodiment, the framework region, e.g., all four framework regions of the light chain variable region are derived from a VK3_1.25 germline sequence. In one embodiment, the framework region can comprise, one, two, three, four or five modifications, e.g., substitutions, e.g., from the amino acid at the corresponding murine sequence (e.g., of SEQ ID NO:58).

In some aspects, the portion of a CAR composition of the invention that comprises an antibody fragment is humanized with retention of high affinity for the target antigen and other favorable biological properties. According to one aspect of the invention, humanized antibodies and antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind the target antigen. In this way, FR residues can be selected and combined from the recipient and import sequences so that the desired antibody or antibody fragment characteristic, such as increased affinity for the target antigen, is achieved. In general, the CDR residues are directly and most substantially involved in influencing antigen binding.

A humanized antibody or antibody fragment may retain a similar antigenic specificity as the original antibody, e.g., in the present invention, the ability to bind human CD19. In some embodiments, a humanized antibody or antibody fragment may have improved affinity and/or specificity of binding to human CD19.

In one aspect, the anti-CD19 binding domain is characterized by particular functional features or properties of an antibody or antibody fragment. For example, in one aspect, the portion of a CAR composition of the invention that comprises an antigen binding domain specifically binds human CD19. In one aspect, the antigen binding domain has the same or a similar binding specificity to human CD19 as the FMC63 scFv described in Nicholson et al. Mol. Immun. 34 (16-17): 1157-1165 (1997). In one aspect, the invention relates to an antigen binding domain comprising an antibody or antibody fragment, wherein the antibody binding domain specifically binds to a CD19 protein or fragment thereof, wherein the antibody or antibody fragment comprises a variable light chain and/or a variable heavy chain that includes an amino acid sequence of SEQ ID NO: 1-12. In one aspect, the antigen binding domain comprises an amino acid sequence of an scFv selected from SEQ ID NOs: 1-12. In certain aspects, the scFv is contiguous with and in the same reading frame as a leader sequence. In one aspect the leader sequence is the polypeptide sequence provided as SEQ ID NO:13.

In one aspect, the anti-CD19 binding domain is a fragment, e.g., a single chain variable fragment (scFv). In one aspect, the anti-CD19 binding domain is a Fv, a Fab, a (Fab')2, or a bi-functional (e.g. bi-specific) hybrid antibody (e.g., Lanzavecchia et al., Eur. J. Immunol. 17, 105 (1987)). In one aspect, the antibodies and fragments thereof of the invention binds a CD19 protein with wild-type or enhanced affinity.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as ($Gly_4Ser$)n, where n is a positive integer equal to or greater than 1 (SEQ ID NO:18). In one embodiment, the linker can be ($Gly_4Ser$)$_4$ (SEQ ID NO:106) or ($Gly_4Ser$)$_3$ (SEQ ID NO:107). Variation in the linker length may retain or enhance activity, giving rise to superior efficacy in activity studies.

Stability and Mutations

The stability of an anti-CD19 binding domain, e.g., scFv molecules (e.g., soluble scFv) can be evaluated in reference to the biophysical properties (e.g., thermal stability) of a conventional control scFv molecule or a full length antibody. In one embodiment, the humanized scFv has a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a control binding molecule (e.g. a conventional scFv molecule) in the described assays.

The improved thermal stability of the anti-CD19 binding domain, e.g., scFv is subsequently conferred to the entire CART19 construct, leading to improved therapeutic properties of the CART19 construct. The thermal stability of the anti-CD19 binding domain, e.g., scFv can be improved by at least about 2° C. or 3° C. as compared to a conventional antibody. In one embodiment, the anti-CD19 binding domain, e.g., scFv has a 1° C. improved thermal stability as compared to a conventional antibody. In another embodiment, the anti-CD19 binding domain, e.g., scFv has a 2° C. improved thermal stability as compared to a conventional antibody. In another embodiment, the scFv has a 4, 5, 6, 7, 8, 9, 10, 11, 12, 13, 14, 15° C. improved thermal stability as compared to a conventional antibody. Comparisons can be made, for example, between the scFv molecules disclosed herein and scFv molecules or Fab fragments of an antibody from which the scFv VH and VL were derived. Thermal stability can be measured using methods known in the art. For example, in one embodiment, Tm can be measured. Methods for measuring Tm and other methods of determining protein stability are described in more detail below.

Mutations in scFv (arising through humanization or direct mutagenesis of the soluble scFv) alter the stability of the scFv and improve the overall stability of the scFv and the CART19 construct. Stability of the humanized scFv is compared against the murine scFv using measurements such as Tm, temperature denaturation and temperature aggregation.

The binding capacity of the mutant scFvs can be determined using assays described in the Examples.

In one embodiment, the anti-CD19 binding domain, e.g., scFv comprises at least one mutation arising from the humanization process such that the mutated scFv confers improved stability to the CART19 construct. In another embodiment, the anti-CD19 binding domain, e.g., scFv comprises at least 1, 2, 3, 4, 5, 6, 7, 8, 9, 10 mutations arising from the humanization process such that the mutated scFv confers improved stability to the CART19 construct.

Methods of Evaluating Protein Stability

The stability of an antigen binding domain may be assessed using, e.g., the methods described below. Such methods allow for the determination of multiple thermal unfolding transitions where the least stable domain either unfolds first or limits the overall stability threshold of a multidomain unit that unfolds cooperatively (e.g., a multidomain protein which exhibits a single unfolding transition). The least stable domain can be identified in a number of additional ways. Mutagenesis can be performed to probe which domain limits the overall stability. Additionally, protease resistance of a multidomain protein can be performed under conditions where the least stable domain is known to be intrinsically unfolded via DSC or other spectroscopic methods (Fontana, et al., (1997) Fold. Des., 2: R17-26; Dimasi et al. (2009) J. Mol. Biol. 393: 672-692). Once the least stable domain is identified, the sequence encoding this domain (or a portion thereof) may be employed as a test sequence in the methods.

a) Thermal Stability

The thermal stability of the compositions may be analyzed using a number of non-limiting biophysical or biochemical techniques known in the art. In certain embodiments, thermal stability is evaluated by analytical spectroscopy.

An exemplary analytical spectroscopy method is Differential Scanning calorimetry (DSC). DSC employs a calorimeter which is sensitive to the heat absorbances that accompany the unfolding of most proteins or protein domains (see, e.g. Sanchez-Ruiz, et al., Biochemistry, 27: 1648-52, 1988). To determine the thermal stability of a protein, a sample of the protein is inserted into the calorimeter and the temperature is raised until the Fab or scFv unfolds. The temperature at which the protein unfolds is indicative of overall protein stability.

Another exemplary analytical spectroscopy method is Circular Dichroism (CD) spectroscopy. CD spectrometry measures the optical activity of a composition as a function of increasing temperature. Circular dichroism (CD) spectroscopy measures differences in the absorption of left-handed polarized light versus right-handed polarized light which arise due to structural asymmetry. A disordered or unfolded structure results in a CD spectrum very different from that of an ordered or folded structure. The CD spectrum reflects the sensitivity of the proteins to the denaturing effects of increasing temperature and is therefore indicative of a protein's thermal stability (see van Mierlo and Steemsma, J. Biotechnol., 79(3):281-98, 2000).

Another exemplary analytical spectroscopy method for measuring thermal stability is Fluorescence Emission Spectroscopy (see van Mierlo and Steemsma, supra). Yet another exemplary analytical spectroscopy method for measuring thermal stability is Nuclear Magnetic Resonance (NMR) spectroscopy (see, e.g. van Mierlo and Steemsma, supra).

The thermal stability of a composition can be measured biochemically. An exemplary biochemical method for assessing thermal stability is a thermal challenge assay. In a "thermal challenge assay", a composition is subjected to a range of elevated temperatures for a set period of time. For example, in one embodiment, test scFv molecules or molecules comprising scFv molecules are subject to a range of increasing temperatures, e.g., for 1-1.5 hours. The activity of the protein is then assayed by a relevant biochemical assay. For example, if the protein is a binding protein (e.g. an scFv or scFv-containing polypeptide) the binding activity of the binding protein may be determined by a functional or quantitative ELISA.

Such an assay may be done in a high-throughput format and those disclosed in the Examples using *E. coli* and high throughput screening. A library of anti-CD19 binding domain, e.g., scFv variants may be created using methods known in the art. Anti-CD19 binding domain, e.g., scFv expression may be induced and the anti-CD19 binding domain, e.g., scFv may be subjected to thermal challenge. The challenged test samples may be assayed for binding and those anti-CD19 binding domain, e.g., scFvs which are stable may be scaled up and further characterized.

Thermal stability is evaluated by measuring the melting temperature (Tm) of a composition using any of the above techniques (e.g. analytical spectroscopy techniques). The melting temperature is the temperature at the midpoint of a thermal transition curve wherein 50% of molecules of a composition are in a folded state (See e.g., Dimasi et al. (2009) J. Mol Biol. 393: 672-692). In one embodiment, Tm values for an anti-CD19 binding domain, e.g., scFv are about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an IgG is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for a multivalent antibody is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C.

Thermal stability is also evaluated by measuring the specific heat or heat capacity (Cp) of a composition using an analytical calorimetric technique (e.g. DSC). The specific heat of a composition is the energy (e.g. in kcal/mol) is required to rise by 1° C., the temperature of 1 mol of water. As large Cp is a hallmark of a denatured or inactive protein composition. The change in heat capacity (ΔCp) of a composition is measured by determining the specific heat of a composition before and after its thermal transition. Thermal stability may also be evaluated by measuring or determining other parameters of thermodynamic stability including Gibbs free energy of unfolding (ΔG), enthalpy of unfolding (ΔH), or entropy of unfolding (ΔS). One or more of the above biochemical assays (e.g. a thermal challenge assay) are used to determine the temperature (i.e. the $T_C$ value) at which 50% of the composition retains its activity (e.g. binding activity).

In addition, mutations to the anti-CD19 binding domain, e.g., scFv alter the thermal stability of the anti-CD19 binding domain, e.g., scFv compared with the unmutated anti-CD19 binding domain, e.g., scFv. When the humanized anti-CD19 binding domain, e.g., scFv is incorporated into a CART19 construct, the anti-CD19 binding domain, e.g., humanized scFv confers thermal stability to the overall anti-CD19 CART construct. In one embodiment, the anti-CD19 binding domain, e.g., scFv comprises a single mutation that confers thermal stability to the anti-CD19 binding domain, e.g., scFv. In another embodiment, the anti-CD19 binding domain, e.g., scFv comprises multiple mutations that confer thermal stability to the anti-CD19 binding domain, e.g., scFv. In one embodiment, the multiple mutations in the anti-CD19 binding domain, e.g., scFv have an additive effect on thermal stability of the anti-CD19 binding domain, e.g., scFv.

b) % Aggregation

The stability of a composition can be determined by measuring its propensity to aggregate. Aggregation can be measured by a number of non-limiting biochemical or biophysical techniques. For example, the aggregation of a composition may be evaluated using chromatography, e.g. Size-Exclusion Chromatography (SEC). SEC separates molecules on the basis of size. A column is filled with semi-solid beads of a polymeric gel that will admit ions and small molecules into their interior but not large ones. When a protein composition is applied to the top of the column, the compact folded proteins (i.e. non-aggregated proteins) are distributed through a larger volume of solvent than is available to the large protein aggregates. Consequently, the large aggregates move more rapidly through the column, and in this way the mixture can be separated or fractionated into its components. Each fraction can be separately quantified (e.g. by light scattering) as it elutes from the gel. Accordingly, the % aggregation of a composition can be determined by comparing the concentration of a fraction with the total concentration of protein applied to the gel. Stable compositions elute from the column as essentially a single fraction and appear as essentially a single peak in the elution profile or chromatogram.

c) Binding Affinity

The stability of a composition can be assessed by determining its target binding affinity. A wide variety of methods for determining binding affinity are known in the art. An exemplary method for determining binding affinity employs surface plasmon resonance. Surface plasmon resonance is an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., i (1991) Biotechniques 11:620-627; Johnsson, B., et al. (1995) J. Mol. Recognit. 8:125-131; and Johnnson, B., et al. (1991) Anal. Biochem. 198:268-277.

In one aspect, the antigen binding domain of the CAR comprises an amino acid sequence that is homologous to an antigen binding domain amino acid sequence described herein, and the antigen binding domain retains the desired functional properties of the anti-CD19 antibody fragments described herein. In one specific aspect, the CAR composition of the invention comprises an antibody fragment. In a further aspect, that antibody fragment comprises an scFv.

In various aspects, the antigen binding domain of the CAR is engineered by modifying one or more amino acids within one or both variable regions (e.g., VH and/or VL), for example within one or more CDR regions and/or within one or more framework regions. In one specific aspect, the CAR composition of the invention comprises an antibody fragment. In a further aspect, that antibody fragment comprises an scFv.

It will be understood by one of ordinary skill in the art that the antibody or antibody fragment of the invention may further be modified such that they vary in amino acid sequence (e.g., from wild-type), but not in desired activity. For example, additional nucleotide substitutions leading to amino acid substitutions at "non-essential" amino acid residues may be made to the protein For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences, refers to two or more sequences that are the same. Two sequences are "substantially identical" if two sequences have a specified percentage of amino acid residues or nucleotides that are the same (e.g., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

In one aspect, the present invention contemplates modifications of the starting antibody or fragment (e.g., scFv) amino acid sequence that generate functionally equivalent molecules. For example, the VH or VL of an anti-CD19 binding domain, e.g., scFv, comprised in the CAR can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL framework region of the anti-CD19 binding domain, e.g., scFv. The present invention contemplates modifications of the entire CAR construct, e.g., modifications in one or more amino acid sequences of the various domains of the CAR construct in order to generate functionally equivalent molecules. The CAR construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting CAR construct.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the otherdomains of the CAR is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the CART cell surface. In a different aspect the amino acid sequence of the transmembrane domain may be modified or substituted so as to minimize interactions with the binding domains of the native binding partner present in the same CART.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain of particular use in this invention may include at least the transmembrane region(s) of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge, e.g., an IgG4 hinge, or a CD8a hinge. In one embodiment, the hinge or spacer comprises (e.g., consists of) the amino acid sequence of SEQ ID NO:14. In one aspect, the transmembrane domain comprises (e.g., consists of) a transmembrane domain of SEQ ID NO: 15.

In one aspect, the hinge or spacer comprises an IgG4 hinge. For example, in one embodiment, the hinge or spacer comprises a hinge of the amino acid sequence ESKYGPPCPPCPAPEFLGGPSVFLFPPKPKDTLMISRTPEVTCVVVDVSQEDPEVQFNW YVDGVEVHNAKTKPREEQFN-STYRVVSVLTVLHQDWLNGKEYKCKVSNKGLPSSIEK TISKAKGQPREPQVYTLPPSQEEMTKNQVSLT-CLVKGFYPSDIAVEWESNGQPENNYK TTPPVLDSDGSFFLY-SRLTVDKSRWQEGNVFSCSVMHEALHN-HYTQKSLSLSLGKM (SEQ ID NO:45). In some embodiments, the hinge or spacer comprises a hinge encoded by a nucleotide sequence of (SEQ ID NO: 46)
GAGAGCAAGTACGGCCCTCCCTGCCCCCCTTGCCCTGCCCCGAGTTCCT

GGGCGGACCCAGCGTGTTCCTGTTCCCCCCAAGCCCAAGGACACCCTGA

TGATCAGCCGGACCCCCGAGGTGACCTGTGTGGTGGTGGACGTGTCCCAG

GAGGACCCCGAGGTCCAGTTCAACTGGTACGTGGACGGCGTGGAGGTGCA

CAACGCCAAGACCAAGCCCCGGGAGGAGCAGTTCAATAGCACCTACCGGG

TGGTGTCCGTGCTGACCGTGCTGCACCAGGACTGGCTGAACGGCAAGGAA

TACAAGTGTAAGGTGTCCAACAAGGGCCTGCCCAGCAGCATCGAGAAAAC

CATCAGCAAGGCCAAGGGCCAGCCTCGGGAGCCCCAGGTGTACACCCTGC

CCCCTAGCCAAGAGGAGATGACCAAGAACCAGGTGTCCCTGACCTGCCTG

GTGAAGGGCTTCTACCCCAGCGACATCGCCGTGGAGTGGGAGAGCAACGG

CCAGCCCGAGAACAACTACAAGACCACCCCCCCTGTGCTGGACAGCGACG

GCAGCTTCTTCCTGTACAGCCGGCTGACCGTGGACAAGAGCCGGTGGCAG

GAGGGCAACGTCTTTAGCTGCTCCGTGATGCACGAGGCCCTGCACAACCA

CTACACCCAGAAGAGCCTGAGCCTGTCCCTGGGCAAGATG.

In one aspect, the hinge or spacer comprises an IgD hinge. For example, in one embodiment, the hinge or spacer comprises a hinge of the amino acid sequence RWPESPKAQASSVPTAQPQAEGSLAKATTAPATTRN-TGRGGEEKKKEKEKEEQEERET KTPECP-SHTQPLGVYLLTPAVQDLWLRDKATFTCFVVGSDLK-DAHLTWEVAGKVPTG GVEEGLLERHSNGSQSQHSRLTL-PRSLWNAGTSVTCTLNHPSLPPQRLMALREPAAQA PVKLSLNLLASSDPPEAASWLLCEVSGFSPPNILL-MWLEDQREVNTSGFAPARPPPQPG STTFWAWSVLRVPAPPSPQPATYTCVVSHEDSRTLL-NASRSLEVSYVTDH (SEQ ID NO:47). In some embodiments, the hinge or spacer comprises a hinge encoded by a nucleotide sequence of (SEQ ID NO: 48)
AGGTGGCCCGAAAGTCCCAAGGCCCAGGCATCTAGTGTTCCTACTGCACA

GCCCCAGGCAGAAGGCAGCCTAGCCAAAGCTACTACTGCACCTGCCACTA

CGCGCAATACTGGCCGTGGCGGGGAGGAGAAGAAAAAGGAGAAAGAGAAA

GAAGAACAGGAAGAGAGGGAGACCAAGACCCCTGAATGTCCATCCCATAC

CCAGCCGCTGGGCGTCTATCTCTTGACTCCCGCAGTACAGGACTTGTGGC

TTAGAGATAAGGCCACCTTTACATGTTTCGTCGTGGGCTCTGACCTGAAG

GATGCCCATTTGACTTGGGAGGTTGCCGGAAAGGTACCCACAGGGGGGT

TGAGGAAGGGTTGCTGGAGCGCCATTCCAATGGCTCTCAGAGCCAGCACT

CAAGACTCACCCTTCCGAGATCCCTGTGGAACGCCGGGACCTCTGTCACA

TGTACTCTAAATCATCCTAGCCTGCCCCCACAGCGTCTGATGGCCCTTAG

AGAGCCAGCCGCCCAGGCACCAGTTAAGCTTAGCCTGAATCTGCTCGCCA

GTAGTGATCCCCCAGAGGCCGCCAGCTGGCTCTTATGCGAAGTGTCCGGC

TTTAGCCCGCCCAACATCTTGCTCATGTGGCTGGAGGACCAGCGAGAAGT

GAACACCAGCGGCTTCGCTCCAGCCCGGCCCCCACCCCAGCCGGGTTCTA

CCACATTCTGGGCCTGGAGTGTCTTAAGGGTCCCAGCACCACCTAGCCCC

CAGCCAGCCACATACACCTGTGTTGTGTCCCATGAAGATAGCAGGACCCT

GCTAAATGCTTCTAGGAGTCTGGAGGTTTCCTACGTGACTGACCATT.

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in one aspect, the linker comprises the amino acid sequence of GGGGSGGGGS (SEQ ID NO:49). In some embodiments, the linker is encoded by a nucleotide sequence of (SEQ ID NO: 50)
GGTGGCGGAGGTTCTGGAGGTGGAGGTTCC.

Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, and CD66d. In one embodiment, a CAR of the invention comprises an intracellular signaling domain, e.g., a primary signaling domain of CD3-zeta.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

The intracellular signalling domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706).

The intracellular signaling sequences within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 16. In one aspect, the signaling domain of CD3-zeta is a signaling domain of SEQ ID NO: 17.

In one aspect, the intracellular signaling domain is designed to comprise the signaling domain of CD3-zeta and the signaling domain of CD27. In one aspect, the signaling domain of CD27 comprises an amino acid sequence of

```
                                        (SEQ ID NO: 51)
QRRKYRSNKGESPVEPAEPCRYSCPREEEGSTIPIQEDYRKPEPACSP.
```

In one aspect, the signalling domain of CD27 is encoded by a nucleic acid sequence of

```
                                        (SEQ ID NO: 52)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC.
```

In one aspect, the CAR-expressing cell described herein can further comprise a second CAR, e.g., a second CAR that includes a different antigen binding domain, e.g., to the same target (CD19) or a different target (e.g., CD123). In one embodiment, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In another aspect, the CAR-expressing cell described herein can further express another agent, e.g., an agent which enhances the activity of a CAR-expressing cell. For example, in one embodiment, the agent can be an agent which inhibits an inhibitory molecule. Inhibitory molecules, e.g., PD1, can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, LAG3, CTLA4, CD160, BTLA, LAIR1, TIM3, 2B4 and TIGIT, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1), can be fused to a transmembrane domain and intracellular signaling domains such as 41BB and CD3 zeta (also referred to herein as a PD1 CAR). In one embodiment, the PD1 CAR, when used incombinations with a CD19 CAR described herein, improves the persistence of the T cell. In one embodiment, the CAR is a PD1 CAR comprising the extracellular domain of PD1 indicated as underlined in SEQ ID NO: 121. In one embodiment, the PD1 CAR comprises the amino acid sequence of SEQ ID NO:121.

(SEQ ID NO: 121)
Malpvtalllplalllhaarp<u>pqwfldspdrpwnpptfspallvvteqdn</u>

<u>atftcsfsntsesfvlnwyrmspsnqtdklaafpedrsqpgqdcrfrvtq</u>

<u>lpnqrdfhmsvvrarrndsqtylcqaislapkaqikeslraelrvterra</u>

<u>evptahpspsprpagqfqtlv</u>ttpaprpptpaptiasqplslrpeacrp aaggavhtrgldfacdiyiwaplagtcgvlllslvitlyckrgrkkllyi fkqpfmrpvqttqeedgcscrfpeeeeggcelrvkfsrsadapaykqgqn qlynelnlgrreeydvldkrrgrdpemggkprrknpqeglynelqkdkma eayseigmkgerrgkghdglyqglstatkdtydalhmqalppr.

In one embodiment, the PD1 CAR comprises the amino acid sequence provided below (SEQ ID NO:119).

(SEQ ID NO: 119)
pgwfldspdrpwnpptfspallvvtegdnatftcsfsntsesfvlnwyrm spsnqtdklaafpedrsqpgqdcrfrvtqlpnqrdfhmsvvrarrndsqt ylcqaislapkaqikeslraelrvterraevptahpspsprpagqfqtlv tttpaprpptpaptiasqplslrpeacrpaaggavhtrgldfacdiyiwa plagtcgvlllslvitlyckrgrkkllyifkqpfmrpvqttqeedgcscr fpeeeeggcelrvkfsrsadapaykqgqnqlynelnlgrreeydvldkrr grdpemggkprrknpqeglynelqkdkmaeayseigmkgerrgkghdgl yqglstatkdtydalhmqalppr.

In one embodiment, the agent comprises a nucleic acid sequence encoding the PD1 CAR, e.g., the PD1 CAR described herein. In one embodiment, the nucleic acid sequence for the PD1 CAR is shown below, with the PD1 ECD underlined below in SEQ ID NO: 120

(SEQ ID NO: 120)
atggccctccctgtcactgccctgcttctcccctcgcactcctgctcca cgccgctagacc<u>acccggatggtttctggactctccggatcgcccgtgga</u>

<u>atcccccaaccttctcaccggcactcttggttgtgactgagggcgataat</u>

<u>gcgaccttcacgtgctcgttctccaacacctccgaatcattcgtgctgaa</u>

<u>ctggtaccgcatgagcccgtcaaaccagaccgacaagctcgccgcgtttc</u>

<u>cggaagatcggtcgcaaccgggacaggattgtcggttccgcgtgactcaa</u>

<u>ctgccgaatggcagagacttccacatgagcgtggtccgcgctaggcgaaa</u>

<u>cgactccgggacctacctgtgcgga</u>gccatctcgctggcgcctaaggccc aaatcaaagagagcttgagggccgaactgagagtgaccgagcgcagagct gaggtgccaactgcacatccatcccatcgcctcggcctgcggggcagtt tcagaccctggtcacgaccactccggcgccgcgcccaccgactccggccc caactatcgcgagccagcccctgtcgctgaggccggaagcatgccgccct gccgccggaggtgctgtgcatacccggggattggacttcgcatgcgacat ctacatttgggctcctctcgccggaacttgtggcgtgctccttctgtccc tggtcatcaccctgtactgcaagcggggtcggaaaaagcttctgtacatt ttcaagcagcccttcatgaggcccgtgcaaaccacccaggaggaggacgg ttgctcctgccggttccccgaagaggaagaaggaggttgcgagctgcgcg tgaagttctcccggagcgccgacgcccccgcctataagcagggccagaac -continued

```
cagctgtacaacgaactgaacctgggacggcgggaagagtacgatgtgct ggacaagcggcgcggccgggacccccgaaatgggcgggaagcctagaagaa agaaccctcaggaaggcctgtataacgagctgcagaaggacaagatggcc gaggcctactccgaaattgggatgaagggagagccggcggaggggaaaggg gcacgacggcctgtaccaaggactgtccaccgccaccaaggacacatacg atgccctgcacatgcaggcccttcccctcgc.
```

In another aspect, the present invention provides a population of CAR-expressing cells, e.g., CART cells. In some embodiments, the population of CAR-expressing cells comprises a mixture of cells expressing different CARs. For example, in one embodiment, the population of CART cells can include a first cell expressing a CAR having an anti-CD19 binding domain described herein, and a second cell expressing a CAR having a different anti-CD19 binding domain, e.g., an anti-CD19 binding domain described herein that differs from the anti-CD19 binding domain in the CAR expressed by the first cell. As another example, the population of CAR-expressing cells can include a first cell expressing a CAR that includes an anti-CD19 binding domain, e.g., as described herein, and a second cell expressing a CAR that includes an antigen binding domain to a target other than CD19 (e.g., CD123). In one embodiment, the population of CAR-expressing cells includes, e.g., a first cell expressing a CAR that includes a primary intracellular signaling domain, and a second cell expressing a CAR that includes a secondary signaling domain.

In another aspect, the present invention provides a population of cells wherein at least one cell in the population expresses a CAR having an anti-CD19 domain described herein, and a second cell expressing another agent, e.g., an agent which enhances the activity of a CAR-expressing cell. For example, in one embodiment, the agent can be an agent which inhibits an inhibitory molecule. Inhibitory molecules, e.g., can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, CTLA4, TIM3, LAG3, VISTA, BTLA, TIGIT, LAIR1, CD160, 2B4 and TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO:118). RNA so produced can efficiently transfect different kinds of cells. In one aspect, the template includes sequences for the CAR.

In one aspect the anti-CD19 CAR is encoded by a messenger RNA (mRNA). In one aspect the mRNA encoding the anti-CD19 CAR is introduced into a T cell for production of a CART cell.

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 110) (size can be 50-5000 T (SEQ ID NO: 111)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (SEQ ID NO: 112).

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides (SEQ ID NO: 113) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Nucleic Acid Constructs Encoding a CAR

The present invention also provides nucleic acid molecules encoding one or more CAR constructs described herein. In one aspect, the nucleic acid molecule is provided as a messenger RNA transcript. In one aspect, the nucleic acid molecule is provided as a DNA construct.

Accordingly, in one aspect, the invention pertains to an isolated nucleic acid molecule encoding a chimeric antigen receptor (CAR), wherein the CAR comprises an anti-CD19 binding domain (e.g., a humanized anti-CD19 binding domain), a transmembrane domain, and an intracellular signaling domain comprising a stimulatory domain, e.g., a costimulatory signaling domain and/or a primary signaling domain, e.g., zeta chain. In one embodiment, the anti-CD19 binding domain is an anti-CD19 binding domain described herein, e.g., an anti-CD19 binding domain which comprises a sequence selected from a group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, or a sequence with 95-99% identify thereof. In one embodiment, the transmembrane domain is transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO: 15, or a sequence with 95-99% identity thereof. In one embodiment, the anti-CD19 binding domain is connected to the transmembrane domain by a hinge region, e.g., a hinge described herein. In one embodiment, the hinge region comprises SEQ ID NO:14 or SEQ ID NO:45 or SEQ ID NO:47 or SEQ ID NO:49, or a sequence with 95-99% identity thereof. In one embodiment, the isolated nucleic acid molecule further comprises a sequence encoding a costimulatory domain. In one embodiment, the costimulatory domain is a functional signaling domain of a protein selected from the group consisting of OX40, CD27, CD28, CDS, ICAM-1, LFA-1 (CD11a/CD18), ICOS (CD278), and 4-1BB (CD137). In one embodiment, the costimulatory domain comprises a sequence of SEQ ID NO:16, or a sequence with 95-99% identity thereof. In one embodiment, the intracellular signaling domain comprises a functional signaling domain of 4-1BB and a functional signaling domain of CD3 zeta. In one embodiment, the intracellular signaling domain comprises the sequence of SEQ ID NO: 16 or SEQ ID NO:51, or a sequence with 95-99% identity thereof, and the sequence of SEQ ID NO: 17 or SEQ ID NO:43, or a sequence with 95-99% identity thereof, wherein the sequences comprising the intracellular signaling domain are expressed in the same frame and as a single polypeptide chain.

In another aspect, the invention pertains to an isolated nucleic acid molecule encoding a CAR construct comprising a leader sequence of SEQ ID NO: 13, a scFv domain having a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, (or a sequence with 95-99% identify thereof), a hinge region of SEQ ID NO:14 or SEQ ID NO:45 or SEQ ID NO:47 or SEQ ID NO:49 (or a sequence with 95-99% identity thereof), a transmembrane domain having a sequence of SEQ ID NO: 15 (or a sequence with 95-99% identity thereof), a 4-1BB costimulatory domain having a sequence of SEQ ID NO:16 or a CD27 costimulatory domain having a sequence of SEQ ID NO:51 (or a sequence with 95-99% identity thereof), and a CD3 zeta stimulatory domain having a sequence of SEQ ID NO:17 or SEQ ID NO:43 (or a sequence with 95-99% identity thereof).

In another aspect, the invention pertains to an isolated polypeptide molecule encoded by the nucleic acid molecule. In one embodiment, the isolated polypeptide molecule comprises a sequence selected from the group consisting of SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41 and SEQ ID NO:42 or a sequence with 95-99% identify thereof.

In another aspect, the invention pertains to a nucleic acid molecule encoding a chimeric antigen receptor (CAR) molecule that comprises an anti-CD19 binding domain, a transmembrane domain, and an intracellular signaling domain comprising a stimulatory domain, and wherein said anti-CD19 binding domain comprises a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, or a sequence with 95-99% identify thereof.

In one embodiment, the encoded CAR molecule further comprises a sequence encoding a costimulatory domain. In one embodiment, the costimulatory domain is a functional signaling domain of a protein selected from the group consisting of OX40, CD27, CD28, CDS, ICAM-1, LFA-1 (CD11a/CD18) and 4-1BB (CD137). In one embodiment, the costimulatory domain comprises a sequence of SEQ ID NO:16. In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO:15. In one embodiment, the intracellular signaling domain comprises a functional signaling domain of 4-1BB and a functional signaling domain of zeta. In one embodiment, the intracellular signaling domain comprises the sequence of SEQ ID NO: 16 and the sequence of SEQ ID NO: 17, wherein the sequences comprising the intracellular signaling domain are expressed in the same frame and as a single polypeptide chain. In one embodiment, the anti-CD19 binding domain is connected to the transmembrane domain by a hinge region. In one embodiment, the hinge region comprises SEQ ID NO:14. In one embodiment, the hinge region comprises SEQ ID NO:45 or SEQ ID NO:47 or SEQ ID NO:49.

In another aspect, the invention pertains to an encoded CAR molecule comprising a leader sequence of SEQ ID NO: 13, a scFv domain having a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12, or a sequence with 95-99% identify thereof, a hinge region of SEQ ID NO:14 or SEQ ID NO:45 or SEQ ID NO:47 or SEQ ID NO:49, a transmembrane domain having a sequence of SEQ ID NO: 15, a 4-1BB costimulatory domain having a sequence of SEQ ID NO:16 or a CD27 costimulatory domain having a sequence of SEQ ID NO:51, and a CD3 zeta stimulatory domain having a sequence of SEQ ID NO:17 or SEQ ID NO:43. In one embodiment, the encoded CAR molecule comprises a sequence selected from a group consisting of SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41 and SEQ ID NO:42, or a sequence with 95-99% identify thereof.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, crisper, CAS9, and zinc finger nucleases. See below June et al. 2009 Nature Reviews Immunology 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter that is capable of expressing a CAR transgene in a mammalian T cell is the EF1α promoter. The native EF1α promoter drives expression of the alpha subunit of the elongation factor-1 complex, which is responsible for the enzymatic delivery of aminoacyl tRNAs to the ribosome. The EF1α promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009). In one aspect, the EF1a promoter comprises the sequence provided as SEQ ID NO:100.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into a host cell is calcium phosphate transfection Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a CAR encoding nucleic acid molecule. In one aspect, a CAR vector can be directly transduced into a cell, e.g., a T cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells. In one aspect, the mammalian T cell is a human T cell.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present invention, any number of T cell lines available in the art, may be used. In certain aspects of the present invention, T cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In one aspect, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in one aspect, T cells are isolated by incubation with anti-CD3/anti-CD28 (e.g., 3×28)-conjugated beads, such as DYNABEADS® M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/ml is used. In one aspect, a concentration of 1 billion cells/ml is used. In a further aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is 5×10e6/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle:cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects of the present invention, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one aspect of the present invention, the mixture may be cultured for several hours (about 3 hours) to about 14 days or any hourly integer value in between. In one aspect, the mixture may be cultured for 21 days. In one aspect of the invention the beads and the T cells are cultured together for about eight days. In one aspect, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a CD19 CAR is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a CD19 CAR are described in further detail below Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of CD4+ and CD8+ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of CARP T cells following antigen stimulation can be measured by flow cytometry. For example, a mixture of CD4+ and CD8+ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the CD4+ and/or CD8+ T cell subsets by flow cytometry. See, e.g., Milone et al., Molecular Therapy 17(8): 1453-1464 (2009). Alternatively, a mixture of CD4+ and CD8+ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated with either CD19+ K562 cells (K562-CD19), wild-type K562 cells (K562 wild type) or K562 cells expressing hCD32 and 4-1BBL in the presence of antiCD3 and anti-CD28 antibody (K562-BBL-3/28) following washing. Exogenous IL-2 is added to the cultures every other day at 100 IU/ml. GFP+ T cells are enumerated by flow cytometry using bead-based counting. See, e.g., Milone et al., Molecular Therapy 17(8): 1453-1464 (2009).

Sustained CAR+ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter following stimulation with αCD3/αCD28 coated magnetic beads on day 0, and transduction with the indicated CAR on day 1.

Animal models can also be used to measure a CART activity. For example, xenograft model using human CD19-specific CARP T cells to treat a primary human pre-B ALL in immunodeficient mice can be used. See, e.g., Milone et al., Molecular Therapy 17(8): 1453-1464 (2009). Very briefly, after establishment of ALL, mice are randomized as to treatment groups. Different numbers of αCD19-ζ and αCD19-BB-ζ engineered T cells are coinjected at a 1:1 ratio into NOD-SCID-$\gamma^{-/-}$ mice bearing B-ALL. The number of copies of αCD19-ζ and αCD19-BB-ζ vector in spleen DNA from mice is evaluated at various times following T cell injection. Animals are assessed for leukemia at weekly intervals. Peripheral blood CD19+B-ALL blast cell counts are measured in mice that are injected with αCD19-ζ CAR+ T cells or mock-transduced T cells. Survival curves for the groups are compared using the log-rank test. In addition, absolute peripheral blood CD4+ and CD8+ T cell counts 4 weeks following T cell injection in NOD-SCID-$\gamma^{-/-}$ mice can also be analyzed. Mice are injected with leukemic cells and 3 weeks later are injected with T cells engineered to express CAR by a bicistronic lentiviral vector that encodes the CAR linked to eGFP. T cells are normalized to 45-50% input GFP T cells by mixing with mock-transduced cells prior to injection, and confirmed by flow cytometry. Animals are assessed for leukemia at 1-week intervals. Survival curves for the CARP T cell groups are compared using the log-rank test.

Dose dependent CAR treatment response can be evaluated. See, e.g., Milone et al., Molecular Therapy 17(8): 1453-1464 (2009). For example, peripheral blood is obtained 35-70 days after establishing leukemia in mice injected on day 21 with CAR T cells, an equivalent number of mock-transduced T cells, or no T cells. Mice from each group are randomly bled for determination of peripheral blood CD19+ ALL blast counts and then killed on days 35 and 49. The remaining animals are evaluated on days 57 and 70.

Assessment of cell proliferation and cytokine production has been previously described, e.g., at Milone et al., Molecular Therapy 17(8): 1453-1464 (2009). Briefly, assessment of CAR-mediated proliferation is performed in microtiter plates by mixing washed T cells with K562 cells expressing CD19 (K19) or CD32 and CD137 (KT32-BBL) for a final T-cell:K562 ratio of 2:1. K562 cells are irradiated with gamma-radiation prior to use. Anti-CD3 (clone OKT3) and anti-CD28 (clone 9.3) monoclonal antibodies are added to cultures with KT32-BBL cells to serve as a positive control for stimulating T-cell proliferation since these signals support long-term $CD8^+$ T cell expansion ex vivo. T cells are enumerated in cultures using CountBright™ fluorescent beads (Invitrogen, Carlsbad, Calif.) and flow cytometry as described by the manufacturer. CARP T cells are identified by GFP expression using T cells that are engineered with eGFP-2A linked CAR-expressing lentiviral vectors. For CAR+ T cells not expressing GFP, the CAR+ T cells are detected with biotinylated recombinant CD19 protein and a secondary avidin-PE conjugate. CD4+ and $CD8^+$ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, Calif.) according the manufacturer's instructions. Fluorescence is assessed using a FACScalibur flow cytometer, and data is analyzed according to the manufacturer's instructions.

Cytotoxicity can be assessed by a standard 51Cr-release assay. See, e.g., Milone et al., Molecular Therapy 17(8): 1453-1464 (2009). Briefly, target cells (K562 lines and primary pro-B-ALL cells) are loaded with 51Cr (as NaCrO4, New England Nuclear, Boston, Mass.) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released 51Cr is then measured using a gamma particle counter (Packard Instrument Co., Waltham, Mass.). Each condition is performed in at least triplicate, and the percentage of lysis is calculated using the formula: % Lysis=(ER−SR)/(TR−SR), where ER represents the average 51Cr released for each experimental condition.

Imaging technologies can be used to evaluate specific trafficking and proliferation of CARs in tumor-bearing animal models. Such assays have been described, for example, in Barrett et al., Human Gene Therapy 22:1575-1586 (2011). Briefly, NOD/SCID/$\gamma c^{-/-}$ (NSG) mice are injected IV with Nalm-6 cells followed 7 days later with T cells 4 hour after electroporation with the CAR constructs. The T cells are stably transfected with a lentiviral construct to express firefly luciferase, and mice are imaged for bioluminescence. Alternatively, therapeutic efficacy and specificity of a single injection of CARP T cells in Nalm-6 xenograft model can be measured as the following: NSG mice are injected with Nalm-6 transduced to stably express firefly luciferase, followed by a single tail-vein injection of T cells electroporated with CD19 CAR 7 days later. Animals are imaged at various time points post injection. For example, photon-density heat maps of firefly luciferasepositive leukemia in representative mice at day 5 (2 days before treatment) and day 8 (24 hr post CARP PBLs) can be generated.

Other assays, including those described in the Example section herein as well as those that are known in the art can also be used to evaluate the CD19 CAR constructs of the invention.

Therapeutic Application
CD19 Associated Diseases and/or Disorders

In one aspect, the invention provides methods for treating a disease associated with CD19 expression. In one aspect, the invention provides methods for treating a disease wherein part of the tumor is negative for CD19 and part of the tumor is positive for CD19. For example, the CAR of the invention is useful for treating subjects that have undergone treatment for a disease associated with elevated expression of CD19, wherein the subject that has undergone treatment for elevated levels of CD19 exhibits a disease associated with elevated levels of CD19.

In one aspect, the invention pertains to a vector comprising CD19 CAR operably linked to promoter for expression in mammalian T cells. In one aspect, the invention provides a recombinant T cell expressing the CD19 CAR for use in treating CD19-expressing tumors, wherein the recombinant T cell expressing the CD19 CAR is termed a CD19 CART. In one aspect, the CD19 CART of the invention is capable of contacting a tumor cell with at least one CD19 CAR of the invention expressed on its surface such that the CART targets the tumor cell and growth of the tumor is inhibited.

In one aspect, the invention pertains to a method of inhibiting growth of a CD19-expressing tumor cell, comprising contacting the tumor cell with a CD19 CAR T cell of the present invention such that the CART is activated in response to the antigen and targets the cancer cell, wherein the growth of the tumor is inhibited.

In one aspect, the invention pertains to a method of treating cancer in a subject. The method comprises administering to the subject a CD19 CAR T cell of the present invention such that the cancer is treated in the subject. An example of a cancer that is treatable by the CD19 CAR T cell of the invention is a cancer associated with expression of CD19. In one aspect, the cancer associated with expression of CD19 is a hematological cancer. In one aspect, the hematolical cancer is a leukemia or a lymphoma. In one aspect, a cancer associated with expression of CD19 includes cancers and malignancies including, but not limited to, e.g., one or more acute leukemias including but not limited to, e.g., B-cell acute Lymphoid Leukemia ("BALL"), T-cell acute Lymphoid Leukemia ("TALL"), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of CD19 include, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with CD19 expression include, but not limited to, e.g., atypical and/or non-classical cancers, malignancies, precancerous conditions or proliferative diseases associated with expression of CD19.

In some embodiments, a cancer that can be treated with a CD19 CAR, e.g., described herein, is multiple myeloma. Multiple myeloma is a cancer of the blood, characterized by accumulation of a plasma cell clone in the bone marrow.

Current therapies for multiple myeloma include, but are not limited to, treatment with lenalidomide, which is an analog of thalidomide. Lenalidomide has activities which include anti-tumor activity, angiogenesis inhibition, and immunomodulation. Generally, myeloma cells are thought to be negative for CD19 expression by flow cytometry. The present invention encompasses the recognition that a small percent of myeloma tumor cells express CD19, as demonstrated in Example 6. Thus, in some embodiments, a C19 CAR, e.g., as described herein, may be used to target myeloma cells. In some embodiments, CD19 CAR therapy can be used in combination with one or more additional therapies, e.g., lenalidomide treatment.

The invention includes a type of cellular therapy where T cells are genetically modified to express a chimeric antigen receptor (CAR) and the CAR T cell is infused to a recipient in need thereof. The infused cell is able to kill tumor cells in the recipient. Unlike antibody therapies, CAR-modified T cells are able to replicate in vivo resulting in long-term persistence that can lead to sustained tumor control. In various aspects, the T cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

The invention also includes a type of cellular therapy where T cells are modified, e.g., by in vitro transcribed RNA, to transiently express a chimeric antigen receptor (CAR) and the CAR T cell is infused to a recipient in need thereof. The infused cell is able to kill tumor cells in the recipient. Thus, in various aspects, the T cells administered to the patient, is present for less than one month, e.g., three weeks, two weeks, one week, after administration of the T cell to the patient.

Without wishing to be bound by any particular theory, the anti-tumor immunity response elicited by the CAR-modified T cells may be an active or a passive immune response, or alternatively may be due to a direct vs indirect immune response. In one aspect, the CAR transduced T cells exhibit specific proinflammatory cytokine secretion and potent cytolytic activity in response to human cancer cells expressing the CD19, resist soluble CD19 inhibition, mediate bystander killing and mediate regression of an established human tumor. For example, antigen-less tumor cells within a heterogeneous field of CD19-expressing tumor may be susceptible to indirect destruction by CD19-redirected T cells that has previously reacted against adjacent antigen-positive cancer cells.

In one aspect, the fully-human CAR-modified T cells of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of diseases, disorders and conditions associated with expression of CD19. In certain aspects, the cells of the invention are used in the treatment of patients at risk for developing diseases, disorders and conditions associated with expression of CD19. Thus, the present invention provides methods for the treatment or prevention of diseases, disorders and conditions associated with expression of CD19 comprising administering to a subject in need thereof, a therapeutically effective amount of the CAR-modified T cells of the invention.

In one aspect the CART cells of the inventions may be used to treat a proliferative disease such as a cancer or malignancy or is a precancerous condition such as a myelodysplasia, a myelodysplastic syndrome or a preleukemia. In one aspect, the cancer is a hematolical cancer. In one aspect, the hematolical cancer is a leukemia or a lymphoma. In one aspect, the CART cells of the invention may be used to treat cancers and malignancies such as, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with CD19 expression include, but not limited to, e.g., atypical and/or non-classical cancers, malignancies, precancerous conditions or proliferative diseases expressing CD19. Non-cancer related indications associated with expression of CD19 include, but are not limited to, e.g., autoimmune disease, (e.g., lupus), inflammatory disorders (allergy and asthma) and transplantation.

The CAR-modified T cells of the present invention may be administered either alone, or as a pharmaceutical composition in combination with diluents and/or with other components such as IL-2 or other cytokines or cell populations.

Hematologic Cancer

Hematological cancer conditions are the types of cancer such as leukemia and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

The present invention provides for compositions and methods for treating cancer. In one aspect, the cancer is a hematologic cancer including but not limited to hematolical cancer is a leukemia or a lymphoma. In one aspect, the CART cells of the invention may be used to treat cancers and malignancies such as, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with CD19 expression includes, but not limited to, e.g., atypical and/or nonclassical cancers, malignancies, precancerous conditions or proliferative diseases expressing CD19.

The present invention also provides methods for inhibiting the proliferation or reducing a CD19-expressing cell population, the methods comprising contacting a population of cells comprising a CD19-expressing cell with an anti-CD19 CART cell of the invention that binds to the CD19-expressing cell. In a specific aspect, the present invention provides methods for inhibiting the proliferation or reducing the population of cancer cells expressing CD19, the methods comprising contacting the CD19-expressing cancer cell population with an anti-CD19 CART cell of the invention that binds to the CD19-expressing cell. In one aspect, the present invention provides methods for inhibiting the proliferation or reducing the population of cancer cells expressing CD19, the methods comprising contacting the CD19-expressing cancer cell population with an anti-CD19 CART cell of the invention that binds to the CD19-expressing cell. In certain aspects, the anti-CD19 CART cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with CD19-expressing cells relative to a negative control. In one aspect, the subject is a human.

The present invention also provides methods for preventing, treating and/or managing a disease associated with CD19-expressing cells (e.g., a hematologic cancer or atypical cancer expressing CD19), the methods comprising administering to a subject in need an anti-CD19 CART cell of the invention that binds to the CD19-expressing cell. In one aspect, the subject is a human. Non-limiting examples of disorders associated with CD19-expressing cells include autoimmune disorders (such as lupus), inflammatory disorders (such as allergies and asthma) and cancers (such as hematological cancers or atypical cancers expressing CD19).

The present invention also provides methods for preventing, treating and/or managing a disease associated with CD19-expressing cells, the methods comprising administering to a subject in need an anti-CD19 CART cell of the invention that binds to the CD19-expressing cell. In one aspect, the subject is a human.

The present invention provides methods for preventing relapse of cancer associated with CD19-expressing cells, the methods comprising administering to a subject in need thereof an anti-CD19 CART cell of the invention that binds to the CD19-expressing cell. In one aspect, the methods comprise administering to the subject in need thereof an effective amount of an anti-CD19 CART cell described herein that binds to the CD19-expressing cell in combination with an effective amount of another therapy.

Combination Therapies

A CAR-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

In further aspects, a CAR-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In one embodiment, a CAR-expressing cell described herein can be used in combination with a chemotherapeutic agent. Exemplary chemotherapeutic agents include an anthracycline (e.g., doxorubicin (e.g., liposomal doxorubicin)). a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzumab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary mTOR inhibitors include, e.g., temsirolimus; ridaforolimus (formally known as deferolimus, (1R,2R,4S)-4-[(2R)-2 [(1R,9S,12S,15R,16E,18R,19R,21R,23S,24E, 26E,28Z,30S,32S,35R)-1,18-dihydroxy-19,30-dimethoxy-15,17,21,23,29,35-hexamethyl-2,3,10,14,20-pentaoxo-11, 36-dioxa-4-azatricyclo[30.3.1.0$^{4,9}$]hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126, CAS 936487-67-1), and XL765.

Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, a CAR expressing cell described herein is administered to a subject in combination with an mTOR inhibitor, e.g., an mTOR inhibitor described herein, e.g., a rapalog such as everolimus. In one embodiment, the mTOR inhibitor is administered prior to the CAR-expressing cell. For example, in one embodiment, the mTOR inhibitor can be administered prior to apheresis of the cells. In one embodiment, the subject has CLL.

In one embodiment, a CAR expressing cell described herein is administered to a subject in combination with a GITR agonist, e.g., a GITR agonist described herein. In one embodiment, the GITR agonist is administered prior to the CAR-expressing cell. For example, in one embodiment, the GITR agonist can be administered prior to apheresis of the cells. In one embodiment, the subject has CLL.

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present invention may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. Accordingly, the methods described herein can comprise administering a CAR-expressing cell described herein to a subject and further administering an agent to manage elevated levels of a soluble factor resulting from treatment with a CAR-expressing cell. In one embodiment, the soluble factor elevated in the subject is one or more of IFN-γ, TNFα, IL-2 and IL-6. Therefore, an agent administered to treat this side effect can be an agent that neutralizes one or more of these soluble factors. Such agents include, but are not limited to a steroid, an inhibitor of TNFα, and an inhibitor of IL-6. An example of a TNFα inhibitor is entanercept. An example of an IL-6 inhibitor is Tocilizumab (toc).

In one embodiment, the subject can be administered an agent which enhances the activity of a CAR-expressing cell. For example, in one embodiment, the agent can be an agent which inhibits an inhibitory molecule. Inhibitory molecules, e.g., Programmed Death 1 (PD1), can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, can be used to inhibit expression of an inhibitory molecule in the CAR-expressing cell. In an embodiment the inhibitor is an shRNA. In an embodiment, the inhibitory molecule is inhibited within a CAR-expressing cell. In these embodiments, a dsRNA molecule that inhibits expression of the inhibitory molecule is linked to the nucleic acid that encodes a component, e.g., all of the components, of the CAR. In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206).). In an embodiment, the agent is an antibody or antibody fragment that binds to TIM3. In an embodiment, the agent is an antibody or antibody fragment that binds to LAG3.

PD1 is an inhibitory member of the CD28 family of receptors that also includes CD28, CTLA-4, ICOS, and BTLA. PD1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al.

2004 Clin Cancer Res 10:5094). Immune suppression can be reversed by inhibiting the local interaction of PD1 with PD-L1. Antibodies, antibody fragments, and other inhibitors of PD1, PD-L1 and PD-L2 are available in the art and may be used combination with a CD19 CAR described herein. For example, nivolumab (also referred to as BMS-936558 or MDX1106; Bristol-Myers Squibb) is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. Pidilizumab (CT-011; Cure Tech) is a humanized IgG1k monoclonal antibody that binds to PD1Pidilizumab and other humanized anti-PD1 monoclonal antibodies are disclosed in WO2009/101611. Lambrolizumab (also referred to as MK03475; Merck) is a humanized IgG4 monoclonal antibody that binds to PD1. Lambrolizumab and other humanized anti-PD1 antibodies are disclosed in U.S. Pat. No. 8,354,509 and WO2009/114335. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S. Publication No.: 20120039906. Other anti-PD-L1 binding agents include YW243.55.S70 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD1 and B7-H1. Other anti-PD1 antibodies include AMP 514 (Amplimmune), among others, e.g., anti-PD1 antibodies disclosed in U.S. Pat. No. 8,609,089, US 2010028330, and/or US 20120114649.

In some embodiments, the agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an antracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the CAR. In another embodiment, the fusion protein is expressed by a cell, e.g., a T cell that does not express an anti-CD19 CAR.

In one embodiment, the agent which enhances activity of a CAR-expressing cell described herein is miR-17-92.

Pharmaceutical Compositions and Treatments

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In one aspect, the T cell compositions of the present invention are administered by i.v. injection. The compositions of T cells may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more CAR constructs of the invention may be introduced, thereby creating a CAR T cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR T cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one embodiment, the CAR is introduced into T cells, e.g., using in vitro transcription, and the subject (e.g., human) receives an initial administration of CAR T cells of the invention, and one or more subsequent administrations of the CAR T cells of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR T cells of the invention are administered to the subject (e.g., human) per week, e.g., 2, 3, or 4 administrations of the CAR T cells of the invention are administered per week. In one embodiment, the subject (e.g., human subject) receives more than one administration of the CAR T cells per week (e.g., 2, 3 or 4 administrations per week) (also referred to herein as a cycle), followed by a week of no CAR T cells administrations, and then one or more additional administration of the CAR T cells (e.g., more than one administration of the CAR T cells per week) is administered to the subject. In another embodiment, the subject (e.g., human subject) receives more than one cycle of CAR T cells, and the time between each cycle is less than 10, 9, 8, 7, 6, 5, 4, or 3 days. In one embodiment, the CAR T cells are administered every other day for 3 administrations per week. In one embodiment, the CAR T cells of the invention are administered for at least two, three, four, five, six, seven, eight or more weeks.

In one aspect, CD19 CARTs are generated using lentiviral viral vectors, such as lentivirus. CARTs generated that way will have stable CAR expression.

In one aspect, CARTs transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the T cell by electroporation.

A potential issue that can arise in patients being treated using transiently expressing CAR T cells (particularly with murine scFv bearing CARTs) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CART infusion breaks should not last more than ten to fourteen days.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: Humanization of Murine Anti-CD19 Antibody

Humanization of murine CD19 antibody is desired for the clinical setting, where the mouse-specific residues may induce a human-anti-mouse antigen (HAMA) response in patients who receive CART19 treatment, i.e., treatment with T cells transduced with the CAR19 construct. VH and VL sequences of hybridoma derived murine CD19 antibody were extracted from published literature (Nicholson et al, 1997, supra). Humanization was accomplished by grafting CDR regions from murine CD19 antibody onto human germline acceptor frameworks VH4_4-59 and VK3_L25 (vBASE database). In addition to the CDR regions, five framework residues, i.e. VH #71, #73, #78 and VL #71 #87, thought to support the structural integrity of the CDR regions were retained from the murine sequence. Further, the human J elements JH4 and JK2 were used for the heavy and light chain, respectively. The resulting amino acid sequences of the humanized antibody were designated FMC63_VL_hz and FMC63_VH_hz1, respectively, and are shown below in Table 1. The residue numbering follows Kabat (Kabat E. A. et al, 1991, supra). For CDR definitions, both Kabat as well as Chothia et al, 1987 supra) were used. Residues coming from mouse CD19 are shown in bold/italic. Positions #60/61/62 boxed indicate potential post-translational modification (PTM) site in CDR H2, also termed HCDR2.

TABLE 1

Amino acid sequences of humanized CD19 variable domains (SEQ ID NOs: 114-117, respectively, in order of appearance).

| Kabat # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35a | 35b | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Chothia CDR | | | | | | | | | | | | | | | | | | | | | | | | | CDR H1 | | | | | | | | | | | | | | | | | | | | | |
| Kabat CDR | | | | | | | | | | | | | | | | | | | | | | | | | | | | | | | CDR H1 | | | | | | | | | | | | | | |
| FMC63_VH.hz1 | Q | V | Q | L | Q | E | S | G | P | G | L | V | K | P | S | E | T | L | S | L | T | C | T | V | S | G | V | S | L | P | D | Y | G | V | S | | | W | I | R | Q | P | P | G | K | G |
| FMC63_VH.hz2 | Q | V | Q | L | Q | E | S | G | P | G | L | V | K | P | S | E | T | L | S | L | T | C | T | V | S | G | V | S | L | P | D | Y | G | V | S | | | W | I | R | Q | P | P | G | K | G |
| FMC63_VH.hz3 | Q | V | Q | L | Q | E | S | G | P | G | L | V | K | P | S | E | T | L | S | L | T | C | T | V | S | G | V | S | L | P | D | Y | G | V | S | | | W | I | R | Q | P | P | G | K | G |

| Kabat # | 45 | 46 | 47 | 48 | 49 | 50 | 51 | 52 | 52a | 52b | 52c | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|---|---|---|---|---|---|
| Chothia CDR | | | | | | CDR H2 | | | | | | | | | | | | | | | | | | |
| Kabat CDR | | | | | | CDR H2 | | | | | | | | | | | | | | | | | | |
| FMC63_VH.hz1 | L | E | W | I | G | V | I | W | | | | G | S | E | T | T | Y | Y | V | N | S | L | K | S |
| FMC63_VH.hz2 | L | E | W | I | G | V | I | W | | | | G | S | E | T | T | Y | Y | S | S | S | L | K | S |
| FMC63_VH.hz3 | L | E | W | I | G | V | I | W | | | | G | S | E | T | T | Y | Y | Q | S | S | L | K | S |

| Kabat # | 66 | 67 | 68 | 69 | 70 | 71 | 72 | 73 | 74 | 75 | 76 | 77 | 78 | 79 | 80 | 81 | 82 | 82a | 82b | 82c | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| FMC63_VH.hz1 | R | V | T | I | S | K | D | N | S | K | N | Q | V | S | L | K | L | S | S | V | T | A | A | D | T | A | V | Y | Y | C | A | K |
| FMC63_VH.hz2 | R | V | T | I | S | K | D | N | S | K | N | Q | V | S | L | K | L | S | S | V | T | A | A | D | T | A | V | Y | Y | C | A | K |
| FMC63_VH.hz3 | R | V | T | I | S | K | D | N | S | K | N | Q | V | S | L | K | L | S | S | V | T | A | A | D | T | A | V | Y | Y | C | A | K |

| Kabat # | 95 | 96 | 97 | 98 | 99 | 100 | 100a | 100b | 100c | 100d | * | * | * | * | * | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|
| Chothia CDR | CDR H3 | | | | | | | | | | | | | | | | | | | | | | | | | | | |
| Kabat CDR | CDR H3 | | | | | | | | | | | | | | | | | | | | | | | | | | | |
| FMC63_VH.hz1 | H | Y | Y | Y | G | G | S | Y | A | M | | | | | | D | Y | W | G | Q | G | T | L | V | T | V | S | S |
| FMC63_VH.hz2 | H | Y | Y | Y | G | G | S | Y | A | M | | | | | | D | Y | W | G | Q | G | T | L | V | T | V | S | S |
| FMC63_VH.hz3 | H | Y | Y | Y | G | G | S | Y | A | M | | | | | | D | Y | W | G | Q | G | T | L | V | T | V | S | S |

| Kabat # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 27e | 27f | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Chothia CDR | | | | | | | | | | | | | | | | | | | | | | | | | CDR L1 | | | | | | | | | | | | | | | | | | | | | | |
| Kabat CDR | | | | | | | | | | | | | | | | | | | | | | | | | CDR L1 | | | | | | | | | | | | | | | | | | | | | | |
| FMC63 VL hz1 | E | I | V | M | T | Q | S | P | A | T | L | S | L | S | P | G | E | R | A | T | L | S | C | R | A | S | Q | | | | | | | D | I | S | K | Y | L | N | W | Y | Q | Q | K | P |

| Kabat # | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Chothia CDR | | | | | | | | | CDRL2 | | | | | | | | | | | | | | | | | | | | | | | | | | | | | | | | | | | | |
| Kabat CDR | | | | | | | | | | CDR L2 | | | | | | | | | | | | | | | | | | | | | | | | | | | | | | | | | | | |
| FMC63 VL hz1 | G | Q | A | P | R | L | L | I | Y | H | T | S | R | L | H | S | | | | G | I | P | A | R | F | S | G | S | G | S | G | T | D | Y | T | L | T | I | S | S | L | Q | P | E | D |

| Kabat # | 86 | 87 | 88 | 89 | 90 | 91 | 92 | 93 | 94 | 95 | 95a | 95b | 95c | 95d | 95e | 95f | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|
| Chothia CDR | | | CDR L3 | | | | | | | | | | | | | | | | | | | | | | | | | |
| Kabat CDR | | | CDR L3 | | | | | | | | | | | | | | | | | | | | | | | | | |
| FMC63 VL hz1 | F | A | V | Y | F | C | Q | Q | G | N | T | L | P | | | | Y | T | F | C | Q | G | T | K | L | E | I | K |

These humanized CD19 IgGs were used to generate soluble scFvs to test for expression and scFvs for the full CART CD19 constructs (See Examples below). Of interest was that during humanization, position 62 in the CDRH2 region prefers to be a serine residue rather than the alanine present in the murine CDRH2. The murine sequence lacks a post-translational modification (PTM), and has asparagine-serine-alanine at positions 60/61/62, respectively in CDRH2. This generates potential PTM motifs (indicated as the boxed cite in CDRH2) during the course of humanization. Whether the PTM site generated during humanization process was actually a "true" PTM site or merely a theoretical one was tested. It was hypothesized that the amino acid motif asparagine followed by serine (NS) may be susceptible to post-translational deamidation but not something that was readily apparent. It was also hypothesized that asparagine followed by any amino acid except proline and then followed by serine (N×S, x≠P) may be susceptible to post-translational N-glycosylation. To test this hypothesis, two IgG variants, were generated in which the asparagine at position 60 (known to be a glycosylation site) was mutated to serine, or glutamine and designated FMC63_VH_hz2 (N60S) and FMC63_VH_hz2 (N60Q), respectively. These constructs were generated in order to eliminate the potential post-translational modification site (PTM) and test for retained activity (See Example 2 below).

Cloning:

DNA sequences coding for mouse and humanized VL and VH domains were obtained, and the codons for the constructs were optimized for expression in cells from *Homo sapiens*.

Sequences coding for VL and VH domain were subcloned from the cloning vectors into expression vectors suitable for secretion in mammalian cells. The heavy and light chains were cloned into individual expression vectors to allow co-transfection. Elements of the expression vector include a promoter (Cytomegalovirus (CMV) enhancer-promoter), a signal sequence to facilitate secretion, a polyadenylation signal and transcription terminator (Bovine Growth Hormone (BGH) gene), an element allowing episomal replication and replication in prokaryotes (e.g. SV40 origin and ColE1 or others known in the art) and elements to allow selection (ampicillin resistance gene and zeocin marker).

Expression:

Chimera and humanized IgG candidates were expressed in HEK293F mammalian cells at 1 ml scale. Cleared supernatants were used for FACS binding studies. More precisely, HEK293F cells were diluted to 5E5 cells/ml in FreeStyle medium supplemented with Pen/Strep and 1 ml transferred into 24 round bottom deep well plate. 0.5 µg of light and 0.5 µg of heavy chain mammalian expression plasmids were diluted in the same medium together with 4 µl of FuGENE HD (Roche REF 04709705001). After 15 min RT incubation, DNA/Fugene mix was added drop-wise to the cells and placed in a 5% $CO_2$ incubator at 250 rpm, 37° C. for five days. Supernatant were then separated from the cells by centrifugation. To measure IgG content, aliquots of 200 µL were placed in the wells of 96-well microtiter plates. All samples and standards were measured in duplicate using Protein A Dip and read biosensors (Fortebio Cat No 18-5010). The plate was placed in an Octet instrument (ForteBio) and allowed to equilibrate to 27° C. in the thermostated chamber. Data were processed automatically using the Octet User Software version 3.0 and concentration determined by comparing to an IgG standard curve.

Binding Analysis by FACS:

Humanized and chimera antibodies were evaluated with a flow cytometry binding assay using cell line 300.19-hsCD19FL. This cell line was generated by transfecting the mouse preB cell line 300.19 with a vector (hCD19 FL/pEF4-myc-His A) encoding the full length human CD19 encoding sequence and natural promoter as well as a Zeocin resistance gene. In brief, 300.19 cells were electroporated with the linearized plasmid and then cells expressing high levels of hsCD19 were identified using an APC-conjugated anti-human CD19 Ab (clone HIB19 from BD 555415) and subsequently sorted using a FACS Aria flow cytometer. The sorted hsCD19+ cells were cultured and confirmed to stably express high levels of hsCD19.

The binding assay could be performed directly with the serum free culture media containing the expressed IgG. All evaluated IgGs were normalized to the same concentration (85 nM), before to be diluted by a 3 fold serial dilution down to 1.4 pM. Then, in a 96-well plate, aliquots of $5 \times 10^5$ cells/well were incubated for 30 min at 4° C. with diluted IgGs. Cells were washed twice with FACS buffer (0.5% BSA in PBS) before addition of the detection antibody, an APC conjugated goat anti-hu IgG, Fc fragment specific (Dianova #109-136-098), diluted 1:1000 in FACS buffer. Cells were incubated a further 30 min at 4° C., then washed twice in FACS buffer and assayed using FACS Calibur (BD Bioscience). Binding curves plotting (median of fluorescence intensity versus IgG concentration) and $EC_{50}$ determination were performed with GraphPad Prism™ 3.0 software with nonlinear regression analysis, sigmoidal dose response (variable slope).

The FACS analyses show that apparent binding for all evaluated IgGs can vary widely, with some constructs exhibiting a 5 to 10 fold shift in EC50 as an IgG versus a scFv. Based on $EC_{50}$ values, lead candidates are chosen that have a binding affinity within a factor of 2 or better compared to the chimeric reference.

Example 2: Characterization of Anti-CD19 Soluble scFv Fragments Derived from Humanized CD19 IgG Antibodies Soluble scFv fragments were generated from the humanized CD19 IgGs described in Example 1 using standard molecule biology techniques. These soluble scFvs were used in characterization studies to examine the stability, cell surface expression, and binding properties of the scFvs. Additionally, experiments were also conducted to investigate the impact of the potential PTM introduced during the humanization process.

scFv Expression and Purification

For transfection of each scFv construct, around 3e8 293F cells were transfected with 100 µg of plasmid using PEI as the transfection reagent at the ratio of 3:1 (PEI:DNA). The cells were grown in 100 ml EXPi293 Expression media (Invitrogen) in a shaker flask at 37° C., 125 rpm, 8% $CO_2$. The culture was harvested after six days and used for protein purification.

293F cells were harvested by spinning down at 3500 g for 20 minutes. The supernatant was collected and filtered through VacuCap90 PF Filter Unit (w/0.8/0.2 µm Super Membrane, PALL). Around 400 µl 400 ul of Ni-NTA agarose beads (Qiagen) were added to the supernatant. The mixture was rotated and incubated for 4 hrs at 4° C. It was loaded onto a purification column and washed with washing buffer with 20 mM Histidine. The protein was eluted with 500 µl elution buffer with 300 mM Histidine. The samples were dialyzed against PBS buffer at 4 C overnight. Protein samples were quantified using nanodrop 2000c.

scFv Conformation and Colloidal Stability Analysis

Thermostability of the scFv was determined by DSF:mix 10-20 μl of protein sample with the dye Sypro Orange (Invitrogen Cat #S6650) of a final dilution at 1:1000, in a total volume of 25 μl in PBS, run BioRad CFX1000 (25 C for 2 min, then increment 0.5° C. for 30 second, 25 to 95° C.).

For analytical SEC experiment, around 15-20 μg of scFv protein sample in 20 μl PBS was injected onto TSKgel Super SW2000 at 0.3 ml/min flow rate on n Agilent 1100 series.

EC50 by FACS Binding

Mouse cell line 300.CD19 were grown in RPMI 1640 with 0.5 mg/ml Zeocin. Around 5e5 cells/per well were transferred to the BD Falcon 96 well plate. The cells were spin down at 900 rpm (Sorval Legend XT centrifuge) for 3 minutes. The supernatant were removed. Anti-CD19 scFv protein samples were diluted in DPBS with 5% FBS. The samples were added into the wells, mixed well with the cells and incubated for 1 hour. The cells were washed twice in the DPBS with 5% FBS. The cells were incubated with antipoly His PE (R&D) for 1 hour, washed twice before FACS analysis (LSRII from BD Biosciences).

Kinetic Analysis by Proteon

Kinetics were determined using Bio-Rad Proteon. Immobilization was performed using standard amine coupling on a GLC sensor chip. The scFv samples were diluted to 0.03 mg/mL in acetate pH 4.5 and applied to the chip at a flow rate of 30 μL/min for 300 seconds. The CD19 ligand was then serial diluted in PBS-Tween and injected at a flow rate of 50 μL/min for 120 seconds with a dissociation time of 480 seconds. The chip surface was regenerated with glycine pH 2.5. Data was fitted using a 1:1 Langmuir model.

Surface Expression of CART19 Constructs and Staining by FACS

HEK293F suspension cells transiently transfected with different anti-hCD19 CARTs were harvested 2 days after the transfection. Around 1e6 cells were placed into each well of a V-shape 96 well plate (Greiner Bio-One, Germany) and washed three times with 0.2 ml FACS buffer (1×PBS containing 4% bovine serum albumin (BSA) (BSA fraction V, Roche Diagnostics, Indianapolis, Ind.). Cells were resuspended in 0.2 ml of the FCAS buffer with either 0.2 μg of biotinylated protein L (GenScript, Piscataway, N.J.) or 100 nM of hCD19(AA 1-291)-hIgG1 Fc (Generated in NIBRI) and incubated at 4° C. for 30 minutes. Cells were then washed with 0.2 ml of FACS buffer three times, and incubated with 1 μl Streptavidin Alexa Fluor 488 (Life Technologies, Grand Island, N.Y.) in 0.2 ml of FACS buffer for samples with protein L, or 2 μl of PE anti-human Fc ϒ (Jackson ImmunoResearch Laboratories, West Grove, Pa.) in 0.2 ml of FACS buffer for samples with hCD19-hIgG1 Fc for 30 minutes at 4° C. in the dark. After washing with 0.2 ml of FACS buffer three times, cells were analyzed on a LSRII (BD Biosciences, San Jose, Calif.) machine using the FACSDiva software (BD Biosciences, San Jose, Calif.). Immunofluorescence staining was analyzed as the relative log fluorescence of live cells, and the percentage of the Alexa Fluor 488 positive or PE positive cells were measured.

Analysis of Potential PMTs Generated During the Humanization Process

Of interest was that during humanization, position 62 in the CDRH2 region prefers to be a serine residue rather than the alanine present in the murine CDRH2 as described in Example 1. Whether the PTM site generated during humanization process was actually a "true" PTM site or merely a theoretical one was tested. Two IgG variants were generated in which the asparagine at position 60 (known to be a glycosylation site) was mutated to serine, or glutamine and designated FMC63_VH_hz2 (N60S) and FMC63_VH_hz2 (N60Q), respectively. These constructs were generated in order to eliminate the potential post-translational modification site (PTM) and test for retained activity.

Results

Anti-CD19 humanized scFvs and mouse scFv were expressed in 293F cells and purified through His tag. The expression and yield of all humanized scFvs was much higher than the original mouse scFv (data not shown).

To confirm identity and assess integrity, the scFV constructs are analyzed with or without incubation with N-glycanase F (PNGaseF) followed by both high-performance liquid chromatography mass spectrometry (HPLC-MS) (See FIG. 3) and SDS-PAGE (data not shown). PNGaseF is an enzyme specific for the removal of N-linked glycan structures from the consensus sequence N-X-S/T/C where X is any amino acid except proline. Briefly, the samples are diluted in water to 0.1 μg/μL and either left untreated or incubated with PNGaseF at a 1:2 (w/w) PNGaseF:scFV ratio for 3 hours at 37° C.

SDS-PAGE analysis is performed using a NuPAGE 4-12% Bis-Tris gel from Novex. Approximately 2 μg scFV are loaded into each lane and the electrophoresis is conducted at 200 V constant for 40 minutes. Following electrophoresis, the gel is stained using PhastGel Blue R 250 stain (Amersham Pharmacia) and destained with 10% acetic acid, 30% methanol.

HPLC-MS analysis is performed on the Water's Acquity UPLC system coupled to a Xevo-Tof mass spectrometer. Approximately 1 μg of each sample is loaded onto a R 1/10 2.1×100 mm 10 μm POROS column (Applied Biosciences) set to 60° C. at a flow rate of 0.5 mL/min. Mobile phases are composed of 0.1% formic acid (A) and 0.1% formic acid, 75% isopropanol, 25% acetonitrile (B). Protein is eluted from the column with a reverse phase gradient from 25%-90% B in 12 minutes. The acquisition is performed using electrospray positive scan at the m/z range of 600-4000 Da with a source cone voltage ramp 20-50V. The resulting spectra are deconvoluted using MaxEnt1.

Figure 3:
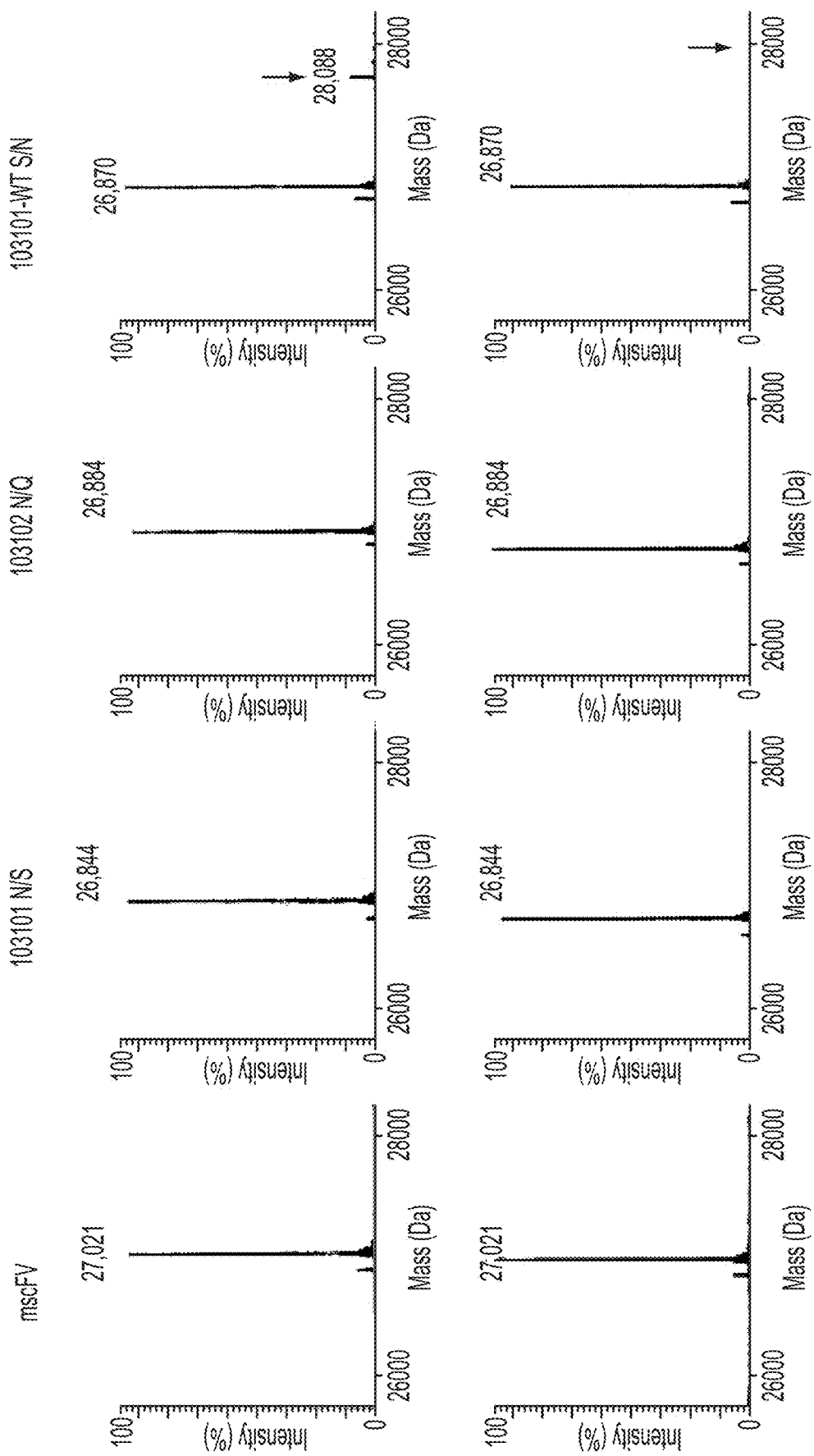
FIG. 3 is a graphic representation of the deconvoluted HPLC mass spectra for scFvs of the invention, where the top row depicts untreated scFv and the bottom row depicts the cognate deglycosylated scFv.

The glycosylation site was introduced during the process of humanization. The non-PTM variants (VH: N60S or N60Q) were without this additional form. The construct was the only one with a consensus site of N-linked glycosylation in HC CDR2. From the SDS-PAGE analysis, the untreated samples migrated as single bands consistent with the approximate molecular weights of the sequences for all constructs except 103101-WT (S/N) for which doublet is observed. This construct is the only one with a consensus site of N-linked glycosylation in H-CDR2. When treated with PNGaseF, the higher molecular weight band of the doublet is no longer present suggesting partial occupancy of the site. Similarly, the observed molecular weights from the deconvoluted mass spectra are consistent with those predicted from the amino acid sequences. However, while the other constructs demonstrated a single primary molecular species, 103101-WT (S/N) also had a population 1217 Daltons higher than that predicted from the sequence which is no longer present after treatment with PNGaseF. This is consistent with the presence of a single predominant N-linked glycoform, likely oligomannose 5 based upon mass. The presence of the glycosylated form was confirmed by the MS analysis as shown in FIG. 3.

Figure 4:
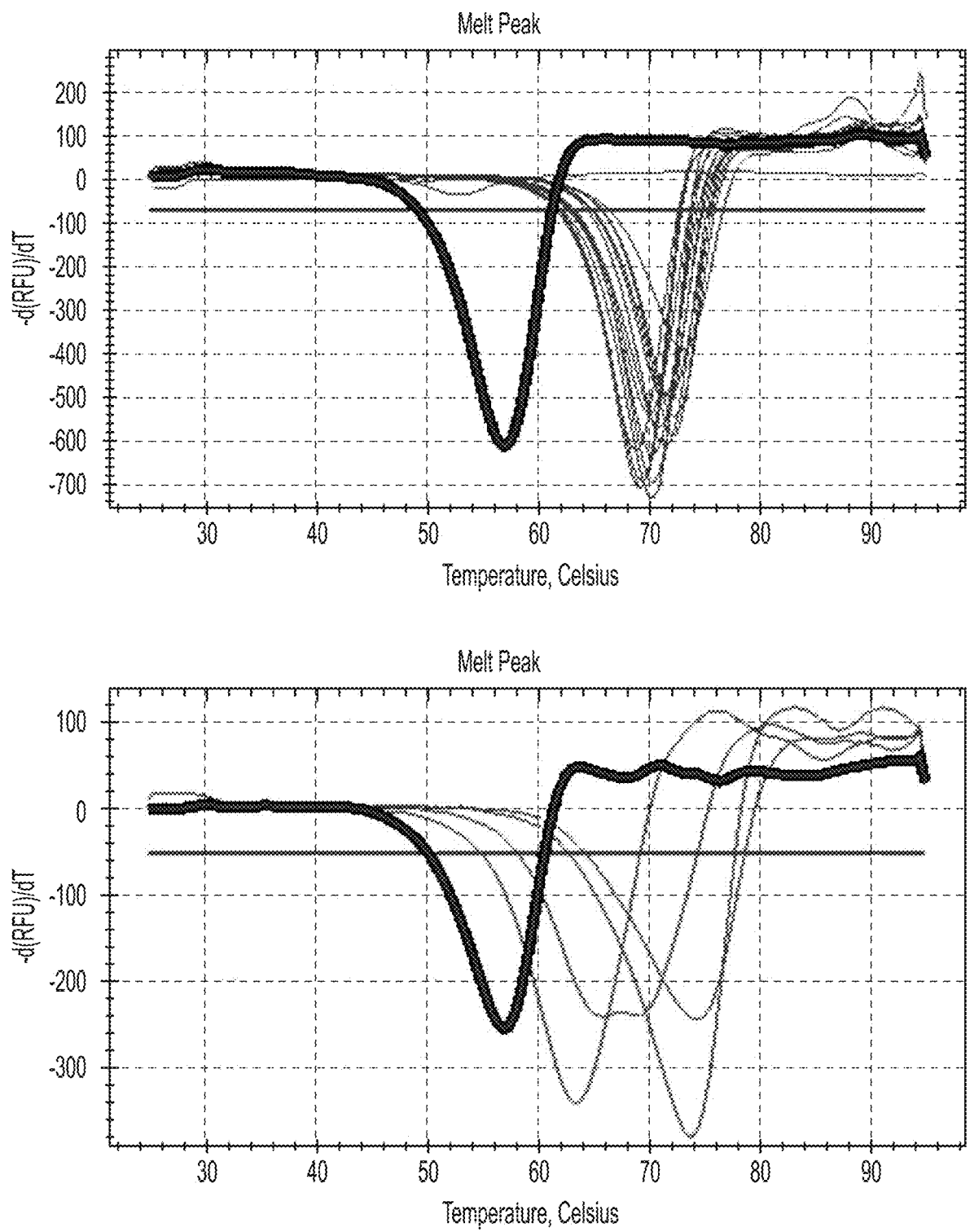
FIG. 4 is a graphic representation of the conformation stability as measured by Differential Scanning Fluorimetry. The Tm of mouse scFv was 57° C. (thick line). All humanized scFv variants show higher Tm at around 70° C. as compared to the parental mouse scFv. The residues introduced by humanization have improved the Tm by more than 10° C.

The conformation stability was measured by Differential Scanning Fluorimetry (DSF). As shown in FIG. 4, the Tm of mouse scFv was 57° C., while the human variants showed higher Tm at around 70° C. The Tm for all the humanized scFv is much better than the murine scFv, clearly showing that all the humanized scFv are more stable than the murine scFv. This stability will likely translate to the CART19 construct, likely leading to improved therapeutic properties.

The activity of the purified scFv was measure by binding to hCD19 expression cells as well as by binding to hCD19 antigen using SPR based detection method. Mouse cell line 300 was used to determine the binding of scFvs. The $EC_{50}$ of mouse scFv for hCD19 was around 06-1.6 nM. The humanized variants showed $EC_{50}$ of the same range in the low or sub nM $EC_{50}$s range.

Example 3: CD19 CAR Constructs

ScFv to be used in the final CAR construct were derived from the humanized IgG described in Example 1. The order in which the VL and VH domains appear in the scFv was varied (i.e., VL-VH, or VH-VL orientation), and where either three or four copies of the "G45" (SEQ ID NO:18) subunit, in which each subunit comprises the sequence GGGGS (SEQ ID NO:18) (e.g., (G4S)$_3$ (SEQ ID NO:107) or (G4S)$_4$ (SEQ ID NO:106)), connect the variable domains to create the entirety of the scFv domain, as shown in Table 2.

TABLE 2

Humanized CD19 scFv constructs showing VH and VL orientation and linker length ("3G4S" is disclosed as SEQ ID NO: 107 and "4G4S" is disclosed as SEQ ID NO: 106).

| construct ID | Length aa | annotation | Vh change |
|---|---|---|---|
| mscFvCTL019 | 486 | VL-VH, 3G4S | |
| 104879 | 491 | VL-VH, 4G4S | N/S |
| 104880 | 491 | VL-VH, 4G4S | N/Q |
| 104881 | 491 | VH-VL, 4G4S | N/S |
| 104882 | 491 | VH-VL, 4G4S | N/Q |
| 104875 | 486 | VL-VH, 3G4S | N/S |
| 104876 | 486 | VL-VH, 3G4S | N/Q |
| 104877 | 486 | VH-VL, 3G4S | N/S |
| 104878 | 486 | VH-VL, 3G4S | N/Q |
| 105974 | 491 | VL-VH, 4G4S | S/N |
| 105975 | 491 | VH-VL, 4G4S | S/N |
| 105976 | 486 | VL-VH, 3G4S | S/N |
| 105977 | 486 | VH-VL, 3G4S | S/N |

The sequences of the humanized scFv fragments (SEQ ID NOS: 1-12) are provided below in Table 3. Full CAR constructs were generated using SEQ ID NOs: 1-12 with additional sequences, SEQ ID NOs: 13-17, shown below, to generate full CAR constructs with SEQ ID NOs: 31-42.

leader (amino acid sequence)
(SEQ ID NO: 13)
MALPVTALLLPLALLLHAARP leader (nucleic acid sequence)
(SEQ ID NO: 54)
ATGGCCCTGCCTGTGACAGCCCTGCTGCTGCCTCTGGCTCTGCTGCTGCA

TGCCGCTAGACCC

CD8 hinge (amino acid sequence)
(SEQ ID NO: 14)
TTTPAPRPPTPAPTIASQPLSLRPEACRPAAGGAVHTRGLDFACD CD8 hinge (nucleic acid sequence)
(SEQ ID NO: 55)
ACCACGACGCCAGCGCCGCGACCACCAACACCGGCGCCCACCATCGCGTC

GCAGCCCCTGTCCCTGCGCCCAGAGGCGTGCCGGCCAGCGGCGGGGGGCG

CAGTGCACACGAGGGGGCTGGACTTCGCCTGTGAT

CD8 transmembrane (amino acid sequence)
(SEQ ID NO: 15)
IYIWAPLAGTCGVLLLSLVITLYC transmembrane (nucleic acid sequence)
(SEQ ID NO: 56)
ATCTACATCTGGGCGCCCTTGGCCGGGACTTGTGGGGTCCTTCTCCTGTC

ACTGGTTATCACCCTTTACTGC 4-1BB Intracellular domain (amino acid sequence)
(SEQ ID NO: 16)
KRGRKKLLYIFKQPFMRPVQTTQEEDGCSCRFPEEEEGGCEL 4-1BB Intracellular domain (nucleic acid sequence)
(SEQ ID NO: 60)
AAACGGGGCAGAAAGAAACTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTG

CD3 zeta domain (amino acid sequence)
(SEQ ID NO: 17)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

CD3 zeta (nucleic acid sequence)
(SEQ ID NO: 101)
AGAGTGAAGTTCAGCAGGAGCGCAGACGCCCCCGCGTACAAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC

CD3 zeta domain (amino acid sequence;
NCBI Reference Sequence NM_000734.3)
(SEQ ID NO: 43)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

CD3 zeta (nucleic acid sequence;
NCBI Reference Sequence NM_000734.3);
(SEQ ID NO: 44)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC

IgG4 Hinge (amino acid sequence)
(SEQ ID NO: 102)
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGKM

IgG4 Hinge (nucleotide sequence)
(SEQ ID NO: 103)
GAGAGCAAGTACGGCCCTCCCTGCCCCCCTTGCCCTGCCCCCGAGTTCCT

GGGCGGACCCAGCGTGTTCCTGTTCCCCCCCAAGCCCAAGGACACCCTGA

TGATCAGCCGGACCCCCGAGGTGACCTGTGTGGTGGTGGACGTGTCCCAG

GAGGACCCCGAGGTCCAGTTCAACTGGTACGTGGACGGCGTGGAGGTGCA

CAACGCCAAGACCAAGCCCCGGGAGGAGCAGTTCAATAGCACCTACCGGG

TGGTGTCCGTGCTGACCGTGCTGCACCAGGACTGGCTGAACGGCAAGGAA

TACAAGTGTAAGGTGTCCAACAAGGGCCTGCCCAGCAGCATCGAGAAAAC

CATCAGCAAGGCCAAGGGCCAGCCTCGGGAGCCCCAGGTGTACACCCTGC

CCCCTAGCCAAGAGGAGATGACCAAGAACCAGGTGTCCCTGACCTGCCTG

GTGAAGGGCTTCTACCCCAGCGACATCGCCGTGGAGTGGGAGAGCAACGG

CCAGCCCGAGAACAACTACAAGACCACCCCCCCTGTGCTGGACAGCGACG

GCAGCTTCTTCCTGTACAGCCGGCTGACCGTGGACAAGAGCCGGTGGCAG

GAGGGCAACGTCTTTAGCTGCTCCGTGATGCACGAGGCCCTGCACAACCA

CTACACCCAGAAGAGCCTGAGCCTGTCCCTGGGCAAGATG

These clones all contained a Q/K residue change in the signal domain of the co-stimulatory domain derived from 4-1BB.

TABLE 3

Humanized CD19 CAR Constructs

| Name | SEQ ID | Sequence |
|---|---|---|
| CAR 1 | | |
| CAR1 scFv domain | 1 | EIVMTQSPATLSLSPGERATLSCRASQDISKYLNWYQQKPGQAPRLLIYHT SRLHSGIPARFSGSGSGTDYTLTISSLQPEDFAVYFCQQGNTLPYTFGQGT KLEIKGGGGSGGGGSGGGGSQVQLQESGPGLVKPSETLSLTCTVSGVSLPD YGVSWIRQPPGKGLEWIGVIWGSETTYYSSSLKSRVTISKDNSKNQVSLKL SSVTAADTAVYYCAKHYYYGGSYAMDYWGQGTLVTSS |
| 103101 CAR1 Soluble scFv-nt | 61 | atggccctccctgtcaccgccctgctgcttccgctggctcttctgctccacgccgc tcggcccgaaattgtgatgacccagtcacccgccactcttagcctttcacccggtg agcgcgcaaccctgtcttgcagagcctcccaagacatctcaaaatacctttaattgg tatcaacagaagcccggacaggctcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacaccctgccctacacctttggacagggcaccaagctcgagattaaaggtggagg tggcagcggaggaggtgggtccggcggtggaggaagccaggtccaactccaagaaa gcggacccgggtcttgtgaagccatcagaaactctttcactgacttgtactgtgagc ggagtgtctctccccgattacgggtgtcttggatcagacagccaccggggaaggg tctggaatggattggagtgatttggggctctgagactacttactactcttcatccc tcaagtcacgcgtcaccatctcaaaggacaactctaagaatcaggtgtcactgaaa ctgtcatctgtgaccgcagccgacaccgccgtgtactattgcgctaagcattacta ttatggcgggagctacgcaatggattactggggacagggtactctggtcaccgtgt ccagccaccaccatcatcaccatcaccat |
| 103101 CAR1 Soluble scFv-aa | 73 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikggggsggggsggggsqvqlqesgpglvkpsetlsltctvs gvslpdygvswirqppgkglewigviwgsettyyssslksrvtiskdnsknqvslk lssvtaadtavyycakhyyyggsyamdywgqgtlvtvsshhhhhhhh |
| 104875 CAR 1-Full-nt | 85 | atggccctccctgtcaccgccctgctgcttccgctggctcttctgctccacgccgc tcggcccgaaattgtgatgacccagtcacccgccactcttagcctttcacccggtg agcgcgcaaccctgtcttgcagagcctcccaagacatctcaaaatacctttaattgg tatcaacagaagcccggacaggctcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacaccctgccctacacctttggacagggcaccaagctcgagattaaaggtggagg tggcagcggaggaggtgggtccggcggtggaggaagccaggtccaactccaagaaa gcggacccgggtcttgtgaagccatcagaaactctttcactgacttgtactgtgagc ggagtgtctctccccgattacgggtgtcttggatcagacagccaccggggaaggg tctggaatggattggagtgatttggggctctgagactacttactactcttcatccc tcaagtcacgcgtcaccatctcaaaggacaactctaagaatcaggtgtcactgaaa ctgtcatctgtgaccgcagccgacaccgccgtgtactattgcgctaagcattacta ttatggcgggagctacgcaatggattactggggacagggtactctggtcaccgtgt ccagcaccactaccccagcaccgaggccaccacccccggctcctaccatgcctcc cagcctctgtccctgcgtccggaggcatgtagaccgcagctggtggggccgtgca tacccggggtcttgacttcgcctgcgatatctacatttgggcccctctggctggta cttgcggggtcctgctgctttcactcgtgatcactcttactgtaagcgcggtcgg aagaagctgctgtacatctttaagcaaccttcatgaggcctgtgcagactactca agaggaggacggctgttcatgccggttcccagaggaggaggaggaaggcggctgcgaac |

TABLE 3-continued

Humanized CD19 CAR Constructs

| Name | SEQ ID | Sequence |
|---|---|---|
| | | tgcgcgtgaaattcagccgcagcgcagatgctccagcctacaagcaggggcagaac<br>cagctctacaacgaactcaatcttggtcggagagaggagtacgacgtgctggacaa<br>gcggagaggacgggacccagaaatgggcgggaagccgcgcagaaagaatccccaag<br>agggcctgtacaacgagctccaaaaggataagatggcagaagcctatagcgagatt<br>ggtatgaaggggaaccagaagaggcaaaggccacgacggactgtaccagggact<br>cagcaccgccaccaaggacacctatgacgctcttcacatgcaggccctgccgcctc<br>gg |
| 104875<br>CAR 1-<br>Full-aa | 31 | MALPVTALLLPLALLLHAARPeivmtqspatlslspgeratlscrasqdiskylnw<br>yqqkpgqaprlliyhtsrlhsgiparfsgsgsgtdytltisslqpedfavyfcqqg<br>ntlpytfgqgtkleikggggsggggsggggsqvqlqesgpglvkpsetlsltctvs<br>gvslpdygvswirqppgkglewigviwgsettyyssslksrvtiskdnsknqvslk<br>lssvtaadtavyycakhyyyggsyamdywgqgtlvtvssttttpaprpptpaptias<br>qplslrpeacrpaaggavhtrgldfacdiyiwaplagtcgvlllslvitlyckrgr<br>kkllyifkqpfmrpvqttqeedgcscrfpeeeeggcelrvkfsrsadapaykqgqn<br>qlynelnlgrreeydvldkrrgrdpemggkprrknpqeglynelqkdkmaeaysei<br>gmkgerrrgkghdglyqglstatkdtydalhmqalppr |

CAR 2

| Name | SEQ ID | Sequence |
|---|---|---|
| CAR2 scFv<br>domain | 2 | eivmtqspatlslspgeratlscrasqdiskylnwyqqkpgqaprlliyhtsrlhs<br>giparfsgsgsgtdytltisslqpedfavyfcqqgntlpytfgqgtkleikggggs<br>ggggsggggsqvqlqesgpglvkpsetlsltctvsgvslpdygvswirqppgkgle<br>wigviwgsettyyqsslksrvtiskdnsknqvslklssvtaadtavyycakhyyyg<br>gsyamdywgqgtlvtvss |
| 103102<br>CAR2-<br>Soluble<br>scFv-nt | 62 | atggccctccctgtcaccgccctgctgcttccgctggctcttctgctccacgccgc<br>tcggcccgaaattgtgatgacccagtcacccgccactcttagcctttcacccggtg<br>agcgcgcaaccctgtcttgcagagcctcccaagacatctcaaatacccttaattgg<br>tatcaacagaagcccggacaggctcctcgccttctgatctaccacaccagccggct<br>ccattctggaatccctgccaggttcagcggtagcggatctgggaccgactacaccc<br>tcactatcagctcactgcagccagaggacttcgctgtctatttctgtcagcaaggg<br>aacacctgccctacacctttggacagggcaccaagctcgagattaaaggtggagg<br>tggcagcggaggaggtgggtccggcggtggaggaagccaggtccaactccaagaaa<br>gcggaccgggtcttgtgaagccatcagaaactctttcactgacttgtactgtgagc<br>ggagtgtctctccccgattacggggtgtcttggatcagacagccaccggggaaggg<br>tctggaatggattggagtgatttgggggctctgagactacttactaccaatcatccc<br>tcaagtcacgcgtcaccatctcaaaggacaactctaagaatcaggtgtcactgaaa<br>ctgtcatctgtgaccgcagccgacaccgccgtgtactattgcgctaagcattacta<br>ttatggcgggagctacgcaatggattactggggacagggtactctggtcaccgtgt<br>ccagccaccaccatcatcaccatcaccat |
| 103102<br>CAR2-<br>Soluble<br>scFv-aa | 74 | MALPVTALLLPLALLLHAARPeivmtqspatlslspgeratlscrasqdiskylnw<br>yqqkpgqaprlliyhtsrlhsgiparfsgsgsgtdytltisslqpedfavyfcqqg<br>ntlpytfgqgtkleikggggsggggsggggsqvqlqesgpglvkpsetlsltctvs<br>gvslpdygvswirqppgkglewigviwgsettyyqsslksrvtiskdnsknqvslk<br>lssvtaadtavyycakhyyyggsyamdywgqgtlvtvsshhhhhhhh |
| 104876<br>CAR 2-<br>Full-nt | 86 | atggccctccctgtcaccgccctgctgcttccgctggctcttctgctccacgccgc<br>tcggcccgaaattgtgatgacccagtcacccgccactcttagcctttcacccggtg<br>agcgcgcaaccctgtcttgcagagcctcccaagacatctcaaatacccttaattgg<br>tatcaacagaagcccggacaggctcctcgccttctgatctaccacaccagccggct<br>ccattctggaatccctgccaggttcagcggtagcggatctgggaccgactacaccc<br>tcactatcagctcactgcagccagaggacttcgctgtctatttctgtcagcaaggg<br>aacacctgccctacacctttggacagggcaccaagctcgagattaaaggtggagg<br>tggcagcggaggaggtgggtccggcggtggaggaagccaggtccaactccaagaaa<br>gcggaccgggtcttgtgaagccatcagaaactctttcactgacttgtactgtgagc<br>ggagtgtctctccccgattacggggtgtcttggatcagacagccaccggggaaggg<br>tctggaatggattggagtgatttgggggctctgagactacttactaccaatcatccc<br>tcaagtcacgcgtcaccatctcaaaggacaactctaagaatcaggtgtcactgaaa<br>ctgtcatctgtgaccgcagccgacaccgccgtgtactattgcgctaagcattacta<br>ttatggcgggagctacgcaatggattactggggacagggtactctggtcaccgtgt<br>ccagccaccactacccagcaccgaggcacccaccccggctcctaccatcgcctcc<br>cagcctctgtccctgcgtccggaggcatgtagacccgcagctggtggggccgtgca<br>tacccggggtcttgacttcgcctgcgatatctacatttgggcccctctggctggta<br>cttgcggggcctgctgctttcactcgtgatcactctttactgtaagcgcggtcgg<br>aagaagctgctgtacatctttaagcaacccttcatgaggcctgtgcagactactca<br>agaggaggacggctgttcatgccggttcccagaggaggaggaaggcggctgcgaac<br>tgcgcgtgaaattcagccgcagcgcagatgctccagcctacaagcaggggcagaac<br>cagctctacaacgaactcaatcttggtcggagagaggagtacgacgtgctggacaa<br>gcggagaggacgggacccagaaatgggcgggaagccgcgcagaaagaatccccaag<br>agggcctgtacaacgagctccaaaaggataagatggcagaagcctatagcgagatt<br>ggtatgaaggggaaccagaagaggcaaaggccacgacggactgtaccagggact<br>cagcaccgccaccaaggacacctatgacgctcttcacatgcaggccctgccgcctc<br>gg |

TABLE 3-continued

Humanized CD19 CAR Constructs

| Name | SEQ ID | Sequence |
|---|---|---|
| 104876 CAR 2- Full-aa | 32 | MALPVTALLLPLALLLHAARPeivmtqspatlslspgeratlscrasqdiskylynw yqqkpgqaprlliyhtsrlhsgiparfsgsgsgtdytltisslqpedfavyfcqqg ntlpytfgqgtkleikgggsgggsgggsqvqlqesgpglvkpsetlsltctvs gvslpdygvswirqppgkglewigviwgsettyyqsslksrvtiskdnsknqvslk lssvtaadtavyycakhyyyggsyamdywgqgtlvtvssttttpaprppptpaptias qplslrpeacrpaaggavhtrgldfacdiyiwaplagtcgvlllslvitlyckrgr kkllyifkqpfmrpvqttqeedgcscrfpeeeeggcelrvkfsrsadapaykqgqn qlynelnlgrreeydvldkrrgrdpemggkprrknpqeglynelqkdkmaeaysei gmkgerrrgkghdglyqglstatkdtydalhmqalppr |

CAR 3

| Name | SEQ ID | Sequence |
|---|---|---|
| CAR3 scFv domain | 3 | qvqlqesgpglvkpsetlsltctvsgvslpdygvswirqppgkglewigviwgset tyyssslksrvtiskdnsknqvslklssvtaadtavyycakhyyyggsyamdywgq gtlvtvssggggsggggsggggseivmtqspatlslspgeratlscrasqdiskyl nwyqqkpgqaprlliyhtsrlhsgiparfsgsgsgtdytltisslqpedfavyfcq qgntlpytfgqgtkleik |
| 103104 CAR 3- Soluble scFv-nt | 63 | atggctctgccgtgaccgcactcctcctgccactggctctgctgcttcacgccgc tcgcccacaagtccagcttcaagaatcagggcctggtctggtgaagccatctgaga ctctgtccctcacttgcaccgtgagcggagtgtccctcccagactacggagtgagc tggattagacagcctcccggaaagggactggagtggatcggagtgatttggggtag cgaaaccacttactattcatcttccctgaagtcacgggtcaccatttcaaaggata actcaaagaatcaagtgagcctcaagctctcatcagtcaccgccgctgacaccgcc gtgtattactgtgccaagcattactactatggagggtcctacgccatggactactg gggccagggaactctggtcactgtgtcatctggtggaggaggtagcggaggaggcg ggagcggtggaggtggctccgaaatcgtgatgacccagagccctgcaaccctgtcc ctttctcccggggaacgggctaccctttcttgtcgggcatcacaagatatctcaaa atacctcaattggtatcaacagaagccgggacaggcccctaggcttcttatctacc acacctctcgcctgcatagcgggattcccgcacgctttagcgggtctggaagcggg accgactacactctgaccatctcatctctccagcccgaggacttcgccgtctactt ctgccagcagggtaacaccctgccgtacaccttcggccagggcaccaagcttgaga tcaaacatcaccaccatcatcaccatcac |
| 103104 CAR 3- Soluble scFv-aa | 75 | MALPVTALLLPLALLLHAARPqvqlqesgpglvkpsetlsltctvsgvslpdygvs wirqppgkglewigviwgsettyyssslksrvtiskdnsknqvslklssvtaadta vyycakhyyyggsyamdywgqgtlvtvssggggsggggsggggseivmtqspatls lspgeratlscrasqdiskylnwyqqkpgqaprlliyhtsrlhsgiparfsgsgsg tdytltisslqpedfavyfcqqgntlpytfgqgtkleikhhhhhhhh |
| 104877 CAR 3- Full-nt | 87 | atggctctgccgtgaccgcactcctcctgccactggctctgctgcttcacgccgc tcgcccacaagtccagcttcaagaatcagggcctggtctggtgaagccatctgaga ctctgtccctcacttgcaccgtgagcggagtgtccctcccagactacggagtgagc tggattagacagcctcccggaaagggactggagtggatcggagtgatttggggtag cgaaaccacttactattcatcttccctgaagtcacgggtcaccatttcaaaggata actcaaagaatcaagtgagcctcaagctctcatcagtcaccgccgctgacaccgcc gtgtattactgtgccaagcattactactatggagggtcctacgccatggactactg gggccagggaactctggtcactgtgtcatctggtggaggaggtagcggaggaggcg ggagcggtggaggtggctccgaaatcgtgatgacccagagccctgcaaccctgtcc ctttctcccggggaacgggctaccctttcttgtcgggcatcacaagatatctcaaa atacctcaattggtatcaacagaagccgggacaggcccctaggcttcttatctacc acacctctcgcctgcatagcgggattcccgcacgctttagcgggtctggaagcggg accgactacactctgaccatctcatctctccagcccgaggacttcgccgtctactt ctgccagcagggtaacaccctgccgtacaccttcggccagggcaccaagcttgaga tcaaaaccactactcccgctccaaggccacccaccccctgccccgaccatcgcctct cagccgctttcctgcgtccggaggcatgtagacccgcagctggtggggccgtgca tacccggggtcttgacttcgcctgcgatatctacatttgggcccctctggctggta cttgcggggtcctgctgctttcactcgtgatcactctttactgtaagcgcggtcgg aagaagctgctgtacatctttaagcaacccttcatgaggcctgtgcagactactca agaggaggacggctgttcatgccggttcccagaggaggaggaaggcggctgcgaac tgcgcgtgaaattcagccgcagcgcagatgctccagcctacaagcaggggcagaac cagctctacaacgaactcaatcttggtcggagagaggagtacgacgtgctggacaa gcggagaggacgggacccagaaatgggcgggaagccgcgcagaaagaatccccaag agggcctgtacaacgagctccaaaaggataagatggcagaagcctatagcgagatt ggtatgaaggggaacgcagaagaggcaaaggccacgacggactgtaccagggact cagcaccgccaccaaggacacctatgacgctcttcacatgcaggccctgccgcctc gg |

TABLE 3-continued

Humanized CD19 CAR Constructs

| Name | SEQ ID | Sequence |
|---|---|---|
| 104877 CAR 3- Full-aa | 33 | MALPVTALLLPLALLLHAARPqvqlqesgpglvkpsetlsltctvsgvslpdygvs wirqppgkglewigviwgsettyyssslksrvtiskdnsknqvslklssvtaadta vyycakhyyyggsyamdywgqgtlvtvssggggsggggsggggseivmtqspatls lspgeratlscrasqdiskylnwyqqkpgqaprlliyhtsrlhsgiparfsgsgsg tdytltisslqpedfavyfcqqgntlpytfgqgtkleiktttpaprppptpaptias qplslrpeacrpaaggavhtrgldfacdiyiwaplagtcgvlllslvitlyckrgr kkllyifkqpfmrpvqttqeedgcscrfpeeeeggcelrvkfsrsadapaykqgqn qlynelnlgrreeydvldkrrgrdpemggkprrknpqeglynelqkdkmaeaysei gmkgerrrgkghdglyqglstatkdtydalhmqalppr |

CAR 4

| Name | SEQ ID | Sequence |
|---|---|---|
| CAR4 scFv domain | 4 | qvqlqesgpglvkpsetlsltctvsgvslpdygvswirqppgkglewigviwgset tyyqsslksrvtiskdnsknqvslklssvtaadtavyycakhyyyggsyamdywgq gtlvtvssggggsggggsggggseivmtqspatlslspgeratlscrasqdiskyl nwyqqkpgqaprlliyhtsrlhsgiparfsgsgsgtdytltisslqpedfavyfcq qgntlpytfgqgtkleik |
| 103106 CAR4- Soluble scFv-nt | 64 | atggctctgccgtgaccgcactcctcctgccactggctctgctgcttcacgccgc tcgcccacaagtccagcttcaagaatcagggcctggtctggtgaagccatctgaga ctctgtccctcacttgcaccgtgagcggagtgtccctcccagactacggagtgagc tggattagacagcctcccggaaagggactggagtggatcggagtgatttggggtag cgaaaccacttactatcaatcttcctgaagtcacgggtcaccatttcaaaggata actcaaagaatcaagtgagcctcaagctctcatcagtcaccgccgctgacaccgcc gtgtattactgtgccaagcattactactatgagggtcctacgccatggactactg gggccagggaactctggtcactgtgtcatctggtggaggaggtagcggaggaggcg ggagcggtggaggtggctccgaaatcgtgatgacccagagccctgcaaccctgtcc ctttctcccggggaacgggctacccttcttgtcgggcatcacaagatatctcaaa atacctcaattggtatcaacagaagccgggacaggcccctaggcttcttatctacc acacctctcgcctgcatagcgggattcccgcacgctttagcgggtctggaagcggg accgactacactctgaccatctcatctctccagcccgaggacttcgccgtctactt ctgccagcagggtaacaccctgccgtacaccttcggccagggcaccaagcttgaga tcaaacatcaccaccatcatcaccatcac |
| 103106 CAR4- Soluble scFv-aa | 76 | MALPVTALLLPLALLLHAARPqvqlqesgpglvkpsetlsltctvsgvslpdygvs wirqppgkglewigviwgsettyyqsslksrvtiskdnsknqvslklssvtaadta vyycakhyyyggsyamdywgqgtlvtvssggggsggggsggggseivmtqspatls lspgeratlscrasqdiskylnwyqqkpgqaprlliyhtsrlhsgiparfsgsgsg tdytltisslqpedfavyfcqqgntlpytfgqgtkleikhhhhhhhh |
| 104878 CAR 4- Full-nt | 88 | atggctctgccgtgaccgcactcctcctgccactggctctgctgcttcacgccgc tcgcccacaagtccagcttcaagaatcagggcctggtctggtgaagccatctgaga ctctgtccctcacttgcaccgtgagcggagtgtccctcccagactacggagtgagc tggattagacagcctcccggaaagggactggagtggatcggagtgatttggggtag cgaaaccacttactatcaatcttcctgaagtcacgggtcaccatttcaaaggata actcaaagaatcaagtgagcctcaagctctcatcagtcaccgccgctgacaccgcc gtgtattactgtgccaagcattactactatgagggtcctacgccatggactactg gggccagggaactctggtcactgtgtcatctggtggaggaggtagcggaggaggcg ggagcggtggaggtggctccgaaatcgtgatgacccagagccctgcaaccctgtcc ctttctcccggggaacgggctacccttcttgtcgggcatcacaagatatctcaaa atacctcaattggtatcaacagaagccgggacaggcccctaggcttcttatctacc acacctctcgcctgcatagcgggattcccgcacgctttagcgggtctggaagcggg accgactacactctgaccatctcatctctccagcccgaggacttcgccgtctactt ctgccagcagggtaacaccctgccgtacaccttcggccagggcaccaagcttgaga tcaaaaccactactcccgctccaaggccacccaccccctgccccgaccatcgcctct cagccgcttccctgcgtccggaggcatgtagacccgcagctggtggggccgtgca tacccggggtcttgacttcgcctgcgatatctacatttgggcccctctggctggta cttgcggggtcctgctgctttcactcgtgatcactctttactgtaagcgcggtcgg aagaagctgctgtacatctttaagcaaccttcatgaggcctgtgcagactactca agaggaggacggctgttcatgccggttcccagaggaggaggaaggcggctgcgaac tgcgcgtgaaattcagccgcagcgcagatgctccagcctacaagcaggggcagaac cagctctacaacgaactcaatcttggtcggagagaggagtacgacgtgctggacaa gcggagaggacgggacccagaaatgggcgggaagccgcgcagaaagaatccccaag agggcctgtacaacgagctccaaaaggataagatggcagaagcctatagcgagatt ggtatgaaaggggaacgcagaagaggcaaaggccacgacggactgtaccagggact cagcaccgccaccaaggacacctatgacgctcttcacatgcaggccctgccgcctc gg |

TABLE 3-continued

Humanized CD19 CAR Constructs

| Name | SEQ ID | Sequence |
|---|---|---|
| 104878 CAR 4- Full-aa | 34 | MALPVTALLLPLALLLHAARPqvqlqesgpglvkpsetlsltctvsgvslpdygvs wirqppgkglewigviwgsettyyqsslksrvtiskdnsknqvslklssvtaadta vyycakhyyyggsyamdywgqgtlvtvssggggsggggsggggseivmtqspatls lspgeratlscrasqdiskylnwyqqkpgqaprlliyhtsrlhsgiparfsgsgsg tdytltisslqpedfavyfcqqgntlpytfgqgtkleiktttpaprpptpaptias qplslrpeacrpaaggavhtrgldfacdiyiwaplagtcgvlllslvitlyckrgr kkllyifkqpfmrpvqttqeedgcscrfpeeeeggcelrvkfsrsadapaykqgqn qlynelnlgrreeydvldkrrgrdpemggkprrknpqeglynelqkdkmaeaysei gmkgerrrgkghdglyqglstatkdtydalhmqalppr |

CAR 5

| Name | SEQ ID | Sequence |
|---|---|---|
| CAR5 scFv domain | 5 | eivmtqspatlslspgeratlscrasqdiskylnwyqqkpgqaprlliyhtsrlhs giparfsgsgsgtdytltisslqpedfavyfcqqgntlpytfgqgtkleikggggs ggggsggggsggggsqvqlqesgpglvkpsetlsltctvsgvslpdygvswirqpp gkglewigviwgsettyyssslksrvtiskdnsknqvslklssvtaadtavyycak hyyyggsyamdywgqgtlvtvss |
| 99789 CAR5- Soluble scFv-nt | 65 | atggccctcccagtgaccgctctgctgctgcctctcgcacttcttctccatgccgc tcggcctgagatcgtcatgacccaaagccccgctaccctgtccctgtcaccggcg agagggcaaccctttcatgcagggccagccaggacatttctaagtacctcaactgg tatcagcagaagccagggcaggctcctcgcctgctgatctaccacaccagccgcct ccacagcggtatccccgccagattttccgggagcgggtctggaaccgactacaccc tcaccatctcttctctgcagcccgaggatttcgccgtctatttctgccagcaggg aatactctgccgtacaccttcggtcaaggtaccaagctggaaatcaagggaggcgg aggatcaggcggtggcggaagcggaggaggtggctccggaggaggaggttcccaag tgcagcttcaagaatcaggacccggacttgtgaagccatcagaaaccctctccctg acttgtaccgtgtccggtgtgagcctccccgactacggagtctcttggattcgcca gcctccggggaagggtcttgaatggattggggtgatttggggatcagagactactt actactcttcatcacttaagtcacgggtcaccatcagcaaagataatagcaagaac caagtgtcacttaagctgtcatctgtgaccgccgctgacaccgccgtgtactattg tgccaaacattactattacggagggtcttatgctatggactactggggacagggga ccctggtgactgtctctagccatcaccatcaccatcatcac |
| 99789 CAR5- Soluble scFv-aa | 77 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikggggsggggsggggsggggsqvqlqesgpglvkpsetlsl tctvsgvslpdygvswirqppgkglewigviwgsettyyssslksrvtiskdnskn qvslklssvtaadtavyycakhyyyggsyamdywgqgtlvtvsshhhhhhhh |
| 104879 CAR 5- Full-nt | 89 | atggccctccctgtcaccgccctgctgcttccgctggctcttctgctccacgccgc tcggcccgaaattgtgatgacccagtcacccgccactcttagcctttcaccggtg agcgcgcaaccctgtcttgcagagcctcccaagacatctcaaatacctaattgg tatcaacagaagcccggacaggctcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacaccctgccctacacctttggacagggcaccaagctcgagattaaaggtggagg tggcagcggaggaggtgggtccggcggtggaggaagcggcggaggcgggagccagg tccaactccaagaaagcggaccgggtcttgtgaagccatcagaaactctttcactg acttgtactgtgagcggagtgtctctccccgattacggggtgtcttggatcagaca gccaccggggaagggtctggaatggattggagtgatttgggggctctgagactactt actactcttcatccctaagtcacgcgtcaccatctcaaaggacaactctaagaat caggtgtcactgaaactgtcatctgtgaccgcagccgacaccgccgtgtactattg cgctaagcattactattatggcgggagctacgcaatggattactggggacagggta ctctggtcaccgtgtccagcaccactaccccagcaccgaggccacccaccccggct cctaccatcgcctcccagcctctgtccctgcgtccggaggcatgtagacccgcagc tggtgggccgtgcataccggggtcttgacttcgcctgcgatatctacatttggg cccctctggctggtacttgcggggtcctgctgcttcactcgtgatcactctttac tgtaagcgcggtcggaagaagctgctgtacatcttaagcaacccttcatgaggcc tgtgcagactactcaagaggaggacggctgttcatgccggttcccagaggaggagg aaggcggctgcgaactgcgcgtgaaattcagccgcagcgcagatgctccagcctac aagcaggggcagaaccagctctacaacgaactcaatcttggtcggagagaggagta cgacgtgctggacaagcggagaggacgggacccagaaatgggcgggaagccgcgca gaaagaatccccaagagggcctgtacaacgagctccaaaaggataagatggcagaa gcctatagcgagattggtatgaaagggaacgcagaagaggcaaaggccacgacgg actgtaccagggactcagcaccgccaccaaggacacctatgacgctcttcacatgc aggccctgccgcctcgg |

TABLE 3-continued

Humanized CD19 CAR Constructs

| Name | SEQ ID | Sequence |
|---|---|---|
| 104879 CAR 5- Full-aa | 35 | MALPVTALLLPLALLLHAARPeivmtqspatlslspgeratlscrasqdiskylynw yqqkpgqaprlliyhtsrlhsgiparfsgsgsgtdytltisslqpedfavyfcqqg ntlpytfgqgtkleikggggsggggsggggsggggsqvqlqesgpglvkpsetlsl tctvsgvslpdygvswirqppgkglewigviwgsettyyssslksrvtiskdnskn qvslklssvtaadtavyycakhyyyggsyamdywgqgtlvtvsstttpaprpptpa ptiasqplslrpeacrpaaggavhtrgldfacdiyiwaplagtcgvlllslvitly ckrgrkkllyifkqpfmrpvqttqeedgcscrfpeeeeggcelrvkfsrsadapay kqgqnqlynelnlgrreeydvldkrrgrdpemggkprrknpqeglynelqkdkmae ayseigmkgerrrgkghdglyqglstatkdtydalhmqalppr |

CAR 6

| CAR6 scFv domain | 6 | eivmtqspatlslspgeratlscrasqdiskylnwyqqkpgqaprlliyhtsrlhs giparfsgsgsgtdytltisslqpedfavyfcqqgntlpytfgqgtkleikggggs ggggsggggsggggsqvqlqesgpglvkpsetlsltctvsgvslpdygvswirqpp gkglewigviwgsettyyqsslksrvtiskdnsknqvslklssvtaadtavyycak hyyyggsyamdywgqgtlvtvss |
| 99790 CAR6- Soluble scFv-nt | 66 | atggccctcccagtgaccgctctgctgctgcctctcgcactt cttctccatgccgc tcggcctgagatcgtcatgacccaaagccccgctaccctgtccctgtcaccggcg agagggcaaccctttcatgcagggccagccaggacatttctaagtacctcaactgg tatcagcagaagccagggcaggctcctcgcctgctgatctaccacaccagccgcct ccacagcggtatccccgccagattttcgggagcgggtctggaaccgactacaccc tcaccatctcttctctgcagcccgaggatttcgccgtctatttctgccagcagggg aatactctgccgtacaccttcggtcaaggtaccaagctggaaatcaagggaggcgg aggatcaggcggtggcggaagcggaggaggtggctccggaggaggaggttcccaag tgcagcttcaagaatcaggacccggacttgtgaagccatcagaaaccctctccctg acttgtaccgtgtccggtgtgagcctccccgactacggagtctcttggattcgcca gcctccggggaagggtcttgaatggattggggtgatttgggatcagagactactt actaccagtcatcacttaagtcacgggtcaccatcagcaaagataatagcaagaac caagtgtcacttaagctgtcatctgtgaccgccgctgacaccgccgtgtactattg tgccaaacattactattacggagggtcttatgctatggactactggggacaggga ccctggtgactgtctctagccatcaccatcaccaccatcatcac |
| 99790 CAR6- Soluble scFv-aa | 78 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikggggsggggsggggsggggsqvqlqesgpglvkpsetlsl tctvsgvslpdygvswirqppgkglewigviwgsettyyqsslksrvtiskdnskn qvslklssvtaadtavyycakhyyyggsyamdywgqgtlvtvsshhhhhhhh |
| 104880 CAR6- Full-nt | 90 | atggccctccctgtcaccgccctgctgctccgctggctcttctgctccacgccgc tcggcccgaaattgtgatgacccagtcacccgccactcttagcctttcaccggtg agcgcgcaaccctgtcttcagagcctcccaagacatctcaaatacct taattgg tatcaacagaagcccggacaggctcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacaccctgccctacacctttggacagggcaccaagctcgagattaaaggtggagg tggcagcggaggaggtgggccggcggtggaggaagcggaggcggagggagccagg tccaactccaagaaagcggaccgggtcttgtgaagccatcagaaactctttcactg acttgtactgtgagcggagtgtctctccccgattacggggtgtcttggatcagaca gccaccggggaagggtctggaatggattggagtgatttgggctctgagactactt actaccaatcatccctcaagtcacgcgtcaccatctcaaaggacaactctaagaat caggtgtcactgaaactgtcatctgtgaccgcagccgacaccgccgtgtactattg cgctaagcattactattatggcgggagctacgcaatggattactggggacagggta ctctggtcaccgtgtccagcaccactaccccagcaccgaggccaccccaccccggct cctaccatcgcctcccagcctctgtccctgcgtccgaggcatgtagacccgcagc tggtgggccgtgcatacccggggtcttgacttcgcctgcgatatctacatttggg cccctctggctggtacttgcggggtcctgctgctttcactcgtgatcactctttac tgtaagcgcggtcggaagaagctgctgtacatctttaagcaacccttcatgaggcc tgtgcagactactcaagaggaggacggctgttcatgccggttcccagaggaggagg aaggcggctgcgaactgcgcgtgaaattcagccgcagcgcagatgctccagcctac aagcaggggcagaaccagctctacaacgaactcaatcttggtcggagagaggagta cgacgtgctggacaagcggagaggacgggacccagaaatgggcgggaagccgcgca gaaagaatcccaagagggcctgtacaacgagctccaaaaggataagatggcagaa gcctatagcgagattggtatgaaagggaacgcagaagaggcaaaggccacgacgg actgtaccagggactcagcaccgccaccaaggacacctatgacgctcttcacatgc aggccctgccgcctcgg |

TABLE 3-continued

Humanized CD19 CAR Constructs

| Name | SEQ ID | Sequence |
|---|---|---|
| 104880 CAR6-Full-aa | 36 | MALPVTALLLPLALLLHAARPeivmtqspatlslspgeratlscrasqdiskylynw yqqkpgqaprlliyhtsrlhsgiparfsgsgsgtdytltisslqpedfavyfcqqg ntlpytfgqgtkleikgggsgggsgggsgggsgggsqvqlqesgpglvkpsetlsl tctvsgvslpdygvswirqppgkglewigviwgsettyyqsslksrvtiskdnskn qvslklssvtaadtavyycakhyyyggsyamdywgqgtlvtvsstttpaprpptpa ptiasqplslrpeacrpaaggavhtrgldfacdiyiwaplagtcgvlllslvitly ckrgrkkllyifkqpfmrpvqttqeedgcscrfpeeeeggcelrvkfsrsadapay kqgqnqlynelnlgrreeydvldkrrgrdpemggkprrknpqeglynelqkdkmae ayseigmkgerrrgkghdglyqglstatkdtydalhmqalppr |

CAR 7

| CAR7 scFv domain | 7 | qvqlqesgpglvkpsetlsltctvsgvslpdygvswirqppgkglewigviwgset tyyssslksrvtiskdnsknqvslklssvtaadtavyycakhyyyggsyamdywgq gtlvtvssggggsggggsggggsggggseivmtqspatlslspgeratlscrasqd iskylnwyqqkpgqaprlliyhtsrlhsgiparfsgsgsgtdytltisslqpedfa vyfcqqgntlpytfgqgtkleik |
| 100796 CAR7-Soluble scFv-nt | 67 | atggcactgcctgtcactgccctcctgctgcctctggccctcctcctgcatgccgc caggccccaagtccagctgcaagagtcaggacccggactggtgaagccgtctgaga ctctctcactgacttgtaccgtcagcggcgtgtccctccccgactacggagtgtca tggatccgccaacctcccgggaaagggcttgaatggattggtgtcatctggggttc tgaaaccacctactactcatcttcctgaagtccagggtgaccatcagcaaggata attccaagaaccaggtcagccttaagctgtcatctgtgaccgctgctgacaccgcc gtgtattactgcgccaagcactactattacggaggaagctacgctatggactattg gggacagggcactctcgtgactgtgagcagcggcggtggagggtctggaggtggag gatccggtggtggtgggtcaggcgaggagggagcgagattgtgatgactcagtca ccagccacccttctctttcacccggcgagagagcaaccctgagctgtagagccag ccaggacatttctaagtacctcaactggtatcagcaaaaaccggggcaggccctc gcctcctgatctaccatacctcacgccttcactctggtatccccgctcggtttagc ggatcaggatctggtaccgactacactctgaccatttccagcctgcagcagaaga tttcgcagtgtatttctgccagcagggcaatacccttccttacaccttcggtcagg gaaccaagctcgaaatcaagcaccatcaccatcatcaccaccat |
| 100796 CAR7-Soluble scFv-aa | 79 | MALPVTALLLPLALLLHAARPqvqlqesgpglvkpsetlsltctvsgvslpdygvs wirqppgkglewigviwgsettyysslksrvtiskdnsknqvslklssvtaadta vyycakhyyyggsyamdywgqgtlvtvssggggsggggsggggsggggseivmtqs patlslspgeratlscrasqdiskylnwyqqkpgqaprlliyhtsrlhsgiparfs gsgsgtdytltisslqpedfavyfcqqgntlpytfgqgtkleikhhhhhhhh |
| 104881 CAR 7 Full-nt | 91 | atggctctgcccgtgaccgcactcctcctgccactggctctgctgcttcacgccgc tcgcccacaagtccagcttcaagaatcagggcctggtctggtgaagccatctgaga ctctgtccctcacttgcaccgtgagcggagtgtccctcccagactacggagtgagc tggattagacagcctcccggaaagggactggagtggatcggagtgatttggggtag cgaaaccacttactattcatcttcctgaagtcacgggtcacctttcaaaggata actcaaagaatcaagtgagcctcaagtctctcatcagtcaccgccgctgacaccgcc gtgtattactgtgccaagcattactactatggagggtcctacgccatggactactg gggccagggaactctggtcactgtgtcatctggtggaggaggtagcggaggaggcg ggagcggtggaggtggctccgaggtggcggaagcgaaatcgtgatgacccagagc cctgcaaccctgtccctttctccggggaacgggctaccctttcttgtcgggcatc acaagatatctcaaaatacctcaattggtatcaacagaagccgggacaggcccta ggcttcttatctaccacacctctcgcctgcatagcgggattcccgcacgctttagc gggtctggaagcgggaccgactacactctgaccatctcatctctccagcccgagga cttcgccgtctacttctgccagcagggtaacacctgccgtacaccttcggcagg gcaccaagcttgagatcaaaaccactactcccgctccaaggcaccccaccccctgcc ccgaccatcgcctctcagccgctttcctgcgtccggaggcatgtagacccgcagc tggtggggccgtgcataccggggtcttgacttcgcctgcgatatctacatttggg cccctctggctggtacttgcggggtcctgctgctttcactcgtgatcactctttac tgtaagcgcggtcggaagaagctgctgtacatctttaagcaacccttcatgaggcc tgtgcagactactcaagaggaggacggctgttcatgccggttcccagaggaggagg aaggcggctgcgaactgcgcgtgaaattcagccgcagcgcagatgctccagcctac aagcaggggcagaaccagctctacaacgaactcaatcttggtcggagagaggagta cgacgtgctggacaagcggagaggacgggacccagaaatgggcgggaagccgcgca gaaagaatcccaagagggcctgtacaacgagctccaaaaggataagatggcagaa gcctatagcgagattggtatgaaaggggaacgcagaagaggcaaaggccacgacgg actgtaccagggactcagcaccgccaccaaggacacctatgacgctcttcacatgc aggccctgccgcctcgg |

TABLE 3-continued

Humanized CD19 CAR Constructs

| Name | SEQ ID | Sequence |
|---|---|---|
| 104881 CAR 7 Full-aa | 37 | MALPVTALLLPLALLLHAARPqvqlqesgpglvkpsetlsltctvsgvslpdygvs wirqppgkglewigviwgsettyyssslksrvtiskdnsknqvslklssvtaadta vyycakhyyyggsyamdywgqgtlvtvssggggsggggsggggsggggseivmtqs patlslspgeratlscrasqdiskylnwyqqkpgqaprlliyhtsrlhsgiparfs gsgsgtdytltisslqpedfavyfcqqgntlpytfgqgtkleikttpaprpptpa ptiasqplslrpeacrpaaggavhtrgldfacdiyiwaplagtcgvlllslvitly ckrgrkkllyifkqpfmrpvqttqeedgcscrfpeeeeggcelrvkfsrsadapay kqgqnqlynelnlgrreeydvldkrrgrdpemggkpprrknpqeglynelqkdkmae ayseigmkgerrrgkghdglyqglstatkdtydalhmqalppr |

CAR 8

| Name | SEQ ID | Sequence |
|---|---|---|
| CAR8 scFv domain | 8 | qvqlqesgpglvkpsetlsltctvsgvslpdygvswirqppgkglewigviwgset tyyqsslksrvtiskdnsknqvslklssvtaadtavyycakhyyyggsyamdywgq gtlvtvssggggsggggsggggsggggseivmtqspatlslspgeratlscrasqd iskylnwyqqkpgqaprlliyhtsrlhsgiparfsgsgsgtdytltisslqpedfa vyfcqqgntlpytfgqgtkleik |
| 100798 CAR8-Soluble scFv-nt | 68 | atggcactgcctgtcactgccctcctgctgcctctggccctcctcctgcatgccgc caggccccaagtccagctgcaagagtcaggacccggactggtgaagccgtctgaga ctctctcactgacttgtaccgtcagcggcgtgtcctccccgactacggagtgtca tggatccgccaacctcccgggaaagggcttgaatggattggtgtcatctggggttc tgaaaccacctactaccagtcttcctgaagtccagggtgaccatcagcaaggata attccaagaaccaggtcagccttaagctgtcatctgtgaccgctgctgacaccgcc gtgtattactgcgccaagcactactattacgaggaagctacgctatggactattg gggacagggcactctcgtgactgtgagcagcggcggtggaggtctggaggtggag gatccggtggtggtgggtcaggcggaggagggagcgagattgtgatgactcagtca ccagccacccttctctttcacccggcgagagagcaaccctgagctgtagagccag ccaggacatttctaagtacctcaactggtatcagcaaaaaccggggcaggcccctc gcctcctgatctaccatacctcacgccttcactctggtatccccgctcggtttagc ggatcaggatctggtaccgactacactctgaccatttccagcctgcagcagaaga tttcgcagtgtatttctgccagcagggcaatacccttccttacaccttcggtcagg gaaccaagctcgaaatcaagcaccatcaccatcatcatcaccac |
| 100798 CAR8-Soluble scFv-aa | 80 | MALPVTALLLPLALLLHAARPqvqlqesgpglvkpsetlsltctvsgvslpdygvs wirqppgkglewigviwgsettyyqsslksrvtiskdnsknqvslklssvtaadta vyycakhyyyggsyamdywgqgtlvtvssggggsggggsggggsggggseivmtqs patlslspgeratlscrasqdiskylnwyqqkpgqaprlliyhtsrlhsgiparfs gsgsgtdytltisslqpedfavyfcqqgntlpytfgqgtkleikhhhhhhhh |
| 104882 CAR 8-Full-nt | 92 | atggctctgcccgtgaccgcactcctcctgccactggctctgctgcttcacgccgc tcgcccacaagtccagcttcaagaatcagggcctggtctggtgaagccatctgaga ctctgtccctcacttgcaccgtgagcggagtgtccctcccagactacggagtgagc tggattagacagcctcccggaaagggactggagtggatcggagtgatttggggtag cgaaaccacttactatcaatcttcctgaagtcacgggtcacctttcaaaggata actcaaagaatcaagtgagcctcaagctctcatcagtcaccgccgctgacaccgcc gtgtattactgtgccaagcattactactatgagggtcctacgccatggactactg gggccagggaactctggtcactgtgtcatctggtggaggaggtagcggaggaggcg ggagcggtggaggtggctccgaggcggtgggtcagaaatcgtgatgacccagagc cctgcaaccctgtcccttctcccggggaacgggctacccttcttgtcgggcatc acaagatatctcaaaatacctcaattggtatcaacagaagccgggacaggcccta ggcttcttatctaccacacctctcgcctgcatagcgggattcccgcacgctttagc gggtctggaagcgggaccgactacactctgaccatctcatctctccagcccgagga cttcgccgtctacttctgccagcagggtaacaccctgccgtacaccttcggccagg gcaccaagcttgagatcaaaaccactactcccgctccaaggcaccaccccctgcc ccgaccatcgcctctcagccgctttcctgcgtccggaggcatgtagacccgcagc tggtggggccgtgcataccggggtcttgacttcgcctgcgatatctacatttggg cccctctggctggtacttgcgggcctgctgctttcactcgtgatcactctttac tgtaagcgcggtcggaagaagctgctgtacatcttaagcaaccctcatgaggcc tgtgcagactactcaagaggaggacggctgttcatgccggttcccagaggaggagg aaggcggctgcgaactgcgcgtgaaattcagccgcagcgcagatgctccagcctac aagcaggggcagaaccagctctacaacgaactcaatcttggtcggagagaggagta cgacgtgctggacaagcggagaggacgggacccagaaatgggcgggaagccgcgca gaaagaatcccaagagggcctgtacaacgagctccaaaggataagatggcagaa gcctatagcgagattggtatgaaagggaacgcagaagaggcaaggccacgacgg actgtaccagggactcagcaccgccaccaaggacacctatgacgctcttcacatgc aggccctgccgcctcgg |

TABLE 3-continued

Humanized CD19 CAR Constructs

| Name | SEQ ID | Sequence |
|---|---|---|
| 104882 CAR 8- Full-aa | 38 | MALPVTALLLPLALLLHAARPqvqlqesgpglvkpsetlsltctvsgvslpdygvs wirqppgkglewigviwgsettyyqsslksrvtiskdnsknqvslklssvtaadta vyycakhyyyggsyamdywgqgtlvtvssggggsggggsggggsggggseivmtqs patlslspgeratlscrasqdiskylnwyqqkpgqaprlliyhtsrlhsgiparfs gsgsgtdytltisslqpedfavyfcqqgntlpytfgqgtkleikttt paprpptpa ptiasqplslrpeacrpaaggavhtrgldfacdiyiwaplagtcgvlllslvitly ckrgrkkllyifkqpfmrpvqttqeedgcscrfpeeeeggcelrvkfsrsadapay kqgqnqlynelnlgrreeydvldkrrgrdpemggkprrknpqeglynelqkdkmae ayseigmkgerrrgkghdglyqglstatkdtydalhmqalppr |

CAR 9

| CAR9 scFv domain | 9 | eivmtqspatlslspgeratlscrasqdiskylnwyqqkpgqaprlliyhtsrlhs giparfsgsgsgtdytltisslqpedfavyfcqqgntlpytfgqgtkleikggggs ggggsggggsggggsqvqlqesgpglvkpsetlsltctvsgvslpdygvswirqpp gkglewigviwgsettyynsslksrvtiskdnsknqvslklssvtaadtavyycak hyyyggsyamdywgqgtlvtvss |
| 99789 CAR9- Soluble scFv-nt | 69 | atggccctcccagtgaccgctctgctgctgcctctcgcacttcttctccatgccgc tcggcctgagatcgtcatgacccaaagccccgctaccctgtccctgtcaccggcg agagggcaaccctttcatgcagggccagccaggacatttctaagtacctcaactgg tatcagcagaagccagggcaggctcctcgcctgctgatctaccacaccagccgcct ccacagcggtatccccgccagattttccgggagcgggtctggaaccgactacaccc tcaccatctcttctctgcagcccgaggatttcgccgtctatttctgccagcagggg aatactctgccgtacaccttcggtcaaggtaccaagctggaaatcaagggaggcgg aggatcaggcggtggcggaagcggaggaggtggctccggaggaggaggttcccaag tgcagcttcaagaatcaggacccgacttgtgaagccatcagaaaccctctccctg acttgtaccgtgtccggtgtgagcctccccgactacggagtctcttggattcgcca gcctccggggaagggtcttgaatggattggggtgatttggggatcagagactactt actacaattcatcacttaagtcacgggtcaccatcagcaaagataatagcaagaac caagtgtcacttaagctgtcatctgtgaccgccgctgacaccgccgtgtactattg tgccaaacattactattacggagggtcttatgctatggactactggggacagggga ccctggtgactgtctctagccatcaccatcaccatcatcac |
| 99789 CAR9- Soluble scFv-aa | 81 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikggggsggggsggggsggggsqvqlqesgpglvkpsetlsl tctvsgvslpdygvswirqppgklewigviwgsettyynsslksrvtiskdnskn qvslklssvtaadtavyycakhyyyggsyamdywgqgtlvtvsshhhhhhhh |
| 105974 CAR 9- Full-nt | 93 | atggccctccctgtcaccgccctgctgctccgctggctcttctgctccacgccgc tcggcccgaaattgtgatgacccagtcacccgccactcttagcctttcaccggtg agcgcgcaaccctgtcttgcagagcctcccaagacatctcaaatacctcaattgg tatcaacagaagcccggacaggctcctcgccttctgatctaccacaccagccggct ccattctggaatccctgccaggttcagcggtagcggatctgggaccgactacaccc tcactatcagctcactgcagccagaggactttcgctgtctatttctgtcagcaaggg aacaccctgccctacacctttggacagggcaccaagctcgagattaaaggtggagg tggcagcggaggaggtgggtccggcggtggaggaagcggaggcggtgggagccagg tccaactccaagaaagcggaccgggtcttgtgaagccatcagaaactctttcactg acttgtactgtgagcggagtgtctctccccgattacggggtgtcttggatcagaca gccaccggggaagggtctggaatggattggagtgatttgggggctctgagactactt actacaactcatccctcaagtcacgcgtcaccatctcaaggacaactctaagaat caggtgtcactgaaactgtcatctgtgaccgcagccgacaccgccgtgtactattg cgctaagcattactattatggcgggagctacgcaatggattactggggacagggta ctctggtcaccgtgtccagcaccactaccccagcaccgaggccacccaccccggct cctaccatcgcctcccagcctctgtccctgcgtccggaggcatgtagacccgcagc tggtggggccgtgcatacccggggtcttgacttcgcctgcgatatctacatttggg cccctctggctggtacttgcggggtcctgctgctttcactcgtgatcactctttac tgtaagcgcggtcggaagaagctgctgtacatcttcaagcaacccttcatgaggcc tgtgcagactactcaagaggaggacggctgttcatgccggttcccagaggaggagg aaggcggctgcgaactgcgcgtgaaattcagccgcagcgcagatgctccagcctac aagcaggggcagaaccagctctacaacgaactcaatcttggtcggagagaggagta cgacgtgctggacaagcggagaggacgggacccagaaatgggcgggaagccgcgca gaaagaatcccccaagagggcctgtacaacgagctccaaaaggataagatggcagaa gcctatagcgagattggtatgaagggaacgcagaagaggcaaaggccacgacgg actgtaccagggactcagcaccgccaccaaggacacctatgacgctcttcacatgc aggccctgccgcctcgg |

TABLE 3-continued

Humanized CD19 CAR Constructs

| Name | SEQ ID | Sequence |
| --- | --- | --- |
| 105974 CAR 9- Full-aa | 39 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikgggsggggsggggsggggsqvqlqesgpglvkpsetlsl tctvsgvslpdygvswirqppgkglewigviwgsettyynsslksrvtiskdnskn qvslklssvtaadtavyycakhyyyggsyamdywgqgtlvtvsstttpaprpptpa ptiasqplslrpeacrpaaggavhtrgldfacdiyiwaplagtcgvlllslvitly ckrgrkkllyifkqpfmrpvqttqeedgcscrfpeeeeggcelrvkfsrsadapay kqgqnqlynelnlgrreeydvldkrrgrdpemggkprrknpqeglynelqkdkmae ayseigmkgerrrgkghdglyqglstatkdtydalhmqalppr |

CAR10

| CAR10 scFv domain | 10 | qvqlqesgpglvkpsetlsltctvsgvslpdygvswirqppgkglewigviwgset tyynsslksrvtiskdnsknqvslklssvtaadtavyycakhyyyggsyamdywgq gtlvtvssggggsggggsggggsggggseivmtqspatlslspgeratlscrasqd iskylnwyqqkpgqaprlliyhtsrlhsgiparfsgsgsgtdytltisslqpedfa vyfcqqgntlpytfgqgtkleik |
| --- | --- | --- |
| 100796 CAR10- Soluble scFv-nt | 70 | atggcactgcctgtcactgccctcctgctgcctctggccctccttctgcatgccgc caggcccaagtccagctgcaagagtcaggacccggactggtgaagccgtctgaga ctctctcactgacttgtaccgtcagcggcgtgtcccctcccgactacggagtgtca tggatccgccaacctcccgggaaagggcttgaatggattggtgtcatctggggttc tgaaaccacctactacaactcttccctgaagtccagggtgaccatcagcaaggata attccaagaaccaggtcagccttaagctgtcatctgtgaccgctgctgacaccgcc gtgtattactgcgccaagcactactattacggaggaagctacgctatggactattg gggacagggcactctcgtgactgtgagcagcggcggtggagggtctggaggtggag gatccggtggtggtgggtcaggcggagggagcgagattgtgatgactcagtca ccagccaccctttctctttcaccggcgagagagcaaccctgagctgtagagccag ccaggacatttctaagtacctcaactggtatcagcaaaaaccggggcaggcccctc gcctcctgatctaccatacctcacgccttcactctggtatccccgctcggtttagc ggatcaggatctggtaccgactacactctgaccatttccagcctgcagcagaaga tttcgcagtgtatttctgccagcagggcaatacccttccttacaccttcggtcagg gaaccaagctcgaaatcaagcaccatcaccatcatcaccaccat |
| 100796 CAR10- Soluble scFv-aa | 82 | MALPVTALLLPLALLLHAARPqvqlqesgpglvkpsetlsltctvsgvslpdygvs wirqppgkglewigviwgsettyynsslksrvtiskdnsknqvslklssvtaadta vyycakhyyyggsyamdywgqgtlvtvssggggsggggsggggsggggseivmtqs patlslspgeratlscrasqdiskylnwyqqkpgqaprlliyhtsrlhsgiparfs gsgsgtdytltisslqpedfavyfcqqgntlpytfgqgtkleikhhhhhhhh |
| 105975 CAR 10 Full-nt | 94 | atggccctccctgtcaccgccctgctgcttccgctggctcttctgctccacgccgc tcggcccgaaattgtgatgacccagtcacccgccactcttagcctttcaccggtg agcgcgcaaccctgtcttgcagagcctcccaagacatctcaaataccttaattgg tatcaacagaagcccggacaggctcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacaccctgccctacacctttggacagggcaccaagctcgagattaaaggtggagg tggcagcggaggaggtgggtccggcggtggaggaagcggaggcggtgggagccagg tccaactccaagaaagcggaccgggtcttgtgaagccatcagaaactctttcactg acttgtactgtgagcggagtgtctctcccgattacggggtgtcttggatcagaca gccaccggggaagggtctggaatggattggagtgatttgggctctgagactactt actacaactcatccctcaagtcacgcgtcaccatctcaaggacaactctaagaat caggtgtcactgaaactgtcatctgtgaccgcagccgacaccgccgtgtactattg cgctaagcattactattatggcgggagctacgcaatggattactgggacagggta ctctggtcaccgtgtccagcaccactaccccagcaccgaggccacccacccccggct cctaccatcgcctcccagcctctgtccctgcgtccggaggcatgtagacccgcagc tggtgggccgtgcatacccggggtcttgacttcgcctgcgatatctacatttggg cccctctggctggtacttgcggggtcctgctgctttcactcgtgatcactctttac tgtaagcgcggtcggaagaagctgctgtacatcttcaagcaacccttcatgaggcc tgtgcagactactcaagaggaggacggctgttcatgccggttcccagaggaggagg aaggcggctgcgaactgcgcgtgaaattcagccgcagcgcagatgctccagcctac aagcaggggcagaaccagctctacaacgaactcaatcttggtcggagagaggagta cgacgtgctggacaagcggagaggacgggacccagaaatgggcgggaagccgcgca gaaagaatcccaagagggcctgtacaacgagctccaaaaggataagatggcagaa gcctatagcgagattggtatgaaagggaacgcagaagaggcaaaggccacgacgg actgtaccagggactcagcaccgccaccaaggacacctatgacgctcttcacatgc aggccctgccgcctcgg |

TABLE 3-continued

Humanized CD19 CAR Constructs

| Name | SEQ ID | Sequence |
|---|---|---|
| 105975 CAR 10 Full-aa | 40 | MALPVTALLLPLALLLHAARPEIVMTQSPATLSLSPGERATLSCRASQDISKYLNW YQQKPGQAPRLLIYHTSRLHSGIPARFSGSGSGTDYTLTISSLQPEDFAVYFCQQG NTLPYTFGQGTKLEIKGGGGSGGGGSGGGGSGGGGSQVQLQESGPGLVKPSETLSL TCTVSGVSLPDYGVSWIRQPPGKGLEWIGVIWGSETTYYNSSLKSRVTISKDNSKN QVSLKLSSVTAADTAVYYCAKHYYYGGSYAMDYWGQGTLVTVSSTTTPAPRPPTPA PTIASQPLSLRPEACRPAAGGAVHTRGLDFACDIYIWAPLAGTCGVLLLSLVITLY CKRGRKKLLYIFKQPFMRPVQTTQEEDGCSCRFPEEEEGGCELRVKFSRSADAPAY KQGQNQLYNELNLGRREEYDVLDKRRGRDPEMGGKPRRKNPQEGLYNELQKDKMAE AYSEIGMKGERRRGKGHDGLYQGLSTATKDTYDALHMQALPPR |

CAR11

| CAR11 scFv domain | 11 | eivmtqspatlslspgeratlscrasqdiskylnwyqqkpgqaprlliyhtsrlhs giparfsgsgsgtdytltisslqpedfavyfcqqgntlpytfgqgtkleikggggs ggggsggggsqvqlqesgpglvkpsetlsltctvsgvslpdygvswirqppgkgle wigviwgsettyynsslksrvtiskdnsknqvslklssvtaadtavyycakhyyyg gsyamdywgqgtlvtvss |
| 103101 CAR11-Soluble scFv-nt | 71 | Atggccctccctgtcaccgccctgctgcttccgctggctcttctgctccacgccgc tcggcccgaaattgtgatgacccagtcacccgccactcttagcctttcaccggtg agcgcgcaaccctgtcttgcagagcctcccaagacatctcaaaataccttaattgg tatcaacagaagcccggacaggctcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacaccctgccctacacctttggacagggcaccaagctcgagattaaaggtggagg tggcagcggaggaggtgggtccggcggtgaggaagccaggtccaactccaagaaa gcggacccgggtcttgtgaagccatcagaaactctttcactgacttgtactgtgagc ggagtgtctctccccgattacggggtgtcttggatcagacagccaccggggaaggg tctggaatggattggagtgatttggggctctgagactacttactacaattcatccc tcaagtcacgcgtcaccatctcaaaggacaactctaagaatcaggtgtcactgaaa ctgtcatctgtgaccgcagccgacaccgccgtgtactattgcgctaagcattacta ttatggcgggagctacgcaatggattactggggacagggtactctggtcaccgtgt ccagccaccaccatcatcaccatcaccat |
| 103101 CAR11-Soluble scFv-aa | 83 | MALPVTALLLPLALLLHAARPeivmtqspatlslspgeratlscrasqdiskylnw yqqkpgqaprlliyhtsrlhsgiparfsgsgsgtdytltisslqpedfavyfcqqg ntlpytfgqgtkleikggggsggggsggggsqvqlqesgpglvkpsetlsltctvs gvslpdygvswirqppgkglewigviwgsettyynsslksrvtiskdnsknqvslk lssvtaadtavyycakhyyyggsyamdywgqgtlvtvsshhhhhhhh |
| 105976 CAR 11 Full-nt | 95 | atggctctgcccgtgaccgcactcctcctgccactggctctgctgcttcacgccgc tcgcccacaagtccagcttcaagaatcagggcctggtctggtgaagccatctgaga ctctgtccctcacttgcaccgtgagcggagtgtccctcccagactacggagtgagc tggattagacagcctcccggaaagggactggagtggatcggagtgatttggggtag cgaaaccacttactataactcttccctgaagtcacgggtcaccttcaaaggata actcaaagaatcaagtgagcctcaagctctcatcagtcaccgccgctgacaccgcc gtgtattactgtgccaagcattactactatggagggtcctacgccatggactactg gggccagggaactctggtcactgtgtcatctggtggaggaggtagcggaggaggcg ggagcggtggaggtggctccggaggtggcggaagcgaaatcgtgatgacccagagc cctgcaacccctgtcccttctccggggaacgggctaccctttcttgtcgggcatc acaagatatctcaaaatacctcaattggtatcaacagaagcccggacaggccccta ggcttcttatctaccacacctctcgcctgcatagcgggattcccgcacgctttagc gggtctggaagcgggaccgactacactctgaccatctcatctctccagcccgagga cttcgccgtctacttctgccagcagggtaacaccctgccgtacaccttcggccagg gcaccaagcttgagatcaaaaccactactcccgctccaaggccacccaccccctgcc ccgaccatcgcctctcagccgctttcctgcgtccggaggcatgtagacccgcagc tggtggggccgtgcatacccggggtcttgacttcgcctgcgatatctacatttggg cccctctggctggtacttgcggggtcctgctgctttcactcgtgatcactctttac tgtaagcgcggtcggaagaagctgctgtacatcttaagcaacccttcatgaggcc tgtgcagactactcaagaggaggacggctgttcatgccggttcccagaggaggagg aaggcggctgcgaactgcgcgtgaaattcagccgcagcgcagatgctccagcctac aagcaggggcagaaccagctctacaacgaactcaatctgggtcggagagaggagta cgacgtgctggacaagcggagaggacgggacccagaaatgggcgggaagccgcgca gaaagaatcccaagagggcctgtacaacgagctccaaaaggataagatggcagaa gcctatagcgagattggtatgaaagggaacgcagaagaggcaaaggccacgacgg actgtaccagggactcagcaccgccaccaaggacacctatgacgctcttcacatgc aggccctgccgcctcgg |

TABLE 3-continued

Humanized CD19 CAR Constructs

| Name | SEQ ID | Sequence |
|---|---|---|
| 105976 CAR 11 Full-aa | 41 | MALPVTALLLPLALLLHAARPQVQLQESGPGLVKPSETLSLTCTVSGVSLPDYGVS WIRQPPGKGLEWIGVIWGSETTYYNSSLKSRVTISKDNSKNQVSLKLSSVTAADTA VYYCAKHYYYGGSYAMDYWGQGTLVTVSSGGGGSGGGGSGGGGSGGGGSEIVMTQS PATLSLSPGERATLSCRASQDISKYLNWYQQKPGQAPRLLIYHTSRLHSGIPARFS GSGSGTDYTLTISSLQPEDFAVYFCQQGNTLPYTFGQGTKLEIKTTTPAPRPPTPA PTIASQPLSLRPEACRPAAGGAVHTRGLDFACDIYIWAPLAGTCGVLLLSLVITLY CKRGRKKLLYIFKQPFMRPVQTTQEEDGCSCRFPEEEEGGCELRVKFSRSADAPAY KQGQNQLYNELNLGRREEYDVLDKRRGRDPEMGGKPRRKNPQEGLYNELQKDKMAE AYSEIGMKGERRRGKGHDGLYQGLSTATKDTYDALHMQALPPR |

CAR12

| CAR12 scFv domain | 12 | qvqlqesgpglvkpsetlsltctvsgvslpdygvswirqppgkglewigviwgset tyynsslksrvtiskdnsknqvslklssvtaadtavyycakhyyyggsyamdywgq gtlvtvssggggsggggsggggseivmtqspatlslspgeratlscrasqdiskyl nwyqqkpgqaprlliyhtsrlhsgiparfsgsgsgtdytltisslqpedfavyfcq qgntlpytfgqgtkleik |
| 103104 CAR12- Soluble scFv-nt | 72 | atggctctgccgtgaccgcactcctcctgccactggctctgctgcttcacgccgc tcgcccacaagtccagcttcaagaatcagggcctggtctggtgaagccatctgaga ctctgtccctcacttgcaccgtgagcggagtgtcctcccagactacggagtgagc tggattagacagcctcccggaaagggactggagtggatcggagtgatttggggtag cgaaaccacttactataactcttccctgaagtcacgggtcaccatttcaaaggata actcaaagaatcaagtgagcctcaagctctcatcagtcaccgccgctgacaccgcc gtgtattactgtgccaagcattactactatggagggtcctacgccatggactactg gggccagggaactctggtcactgtgtcatctggtggaggaggtagcggaggaggcg ggagcggtggaggtggctccgaaatcgtgatgacccagagccctgcaaccctgtcc ctttctcccggggaacgggctaccctttcttgtcgggcatcacaagatatctcaaa ataccctcaattggtatcaacagaagccgggacaggcccctaggcttcttatctac acacctctcgcctgcatagcgggattcccgcacgctttagcgggtctggaagcggg accgactacactctgaccatctcatctctccagcccgaggacttcgccgtctactt ctgccagcagggtaacaccctgccgtacaccttcggccagggcaccaagcttgaga tcaaacatcaccaccatcatcaccatcac |
| 103104 CAR12- Soluble scFv-aa | 84 | MALPVTALLLPLALLLHAARPqvqlqesgpglvkpsetlsltctvsgvslpdygvs wirqppgkglewigviwgsettyynsslksrvtiskdnsknqvslklssvtaadta vyycakhyyyggsyamdywgqgtlvtvssggggsggggsggggseivmtqspatls lspgeratlscrasqdiskylnwyqqkpgqaprlliyhtsrlhsgiparfsgsgsg tdytltisslqpedfavyfcqqgntlpytfgqgtkleikhhhhhhhh |
| 105977 CAR 12- Full-nt | 96 | atggccctccctgtcaccgccctgctgctccgctggctcttctgctccacgccgc tcggcccgaaattgtgatgacccagtcacccgccactcttagcctttcaccggtg agcgcgcaaccctgtcttgcagagcctcccaagacatctcaaatacctaattgg tatcaacagaagcccggacaggctcctcgccttctgatctaccacaccagccggct ccattctggaatccctgccaggttcagcggtagcggatctgggaccgactacaccc tcactatcagctcactgcagccagaggacttcgctgtctatttctgtcagcaaggg aacaccctgccctacacctttggacagggcaccaagctcgagattaaaggtggagg tggcagcggaggaggtgggtccggcggtggaggaagccaggtccaactccaagaaa gcggaccgggtcttgtgaagccatcagaaactcttcactgacttgtactgtgagc ggagtgtctctccccgattacggggtgtcttggatcagacagccaccggggaaggg tctggaatggattggagtgatttgggctctgagactacttactacaactcatccc tcaagtcacgcgtcaccatctcaaaggacaactctaagaatcaggtgtcactgaaa ctgtcatctgtgaccgcagccgacaccgccgtgtactattgcgctaagcattacta ttatggcgggagctacgcaatggattactggggacagggtcctggtcaccgtgt ccagcaccactaccccagcaccgaggccaccccacccgggctcctaccatcgcctcc cagcctctgtccctgcgtccggaggcatgtagacccgcagctggtgggccgtgca tacccggggtcttgacttcgcctgcgatatctacatttgggcccctctggctggta cttgcggggtcctgctgctttcactcgtgatcactctttactgtaagcgcggtcgg aagaagctgctgtacatctttaagcaacccttcatgaggcctgtgcagactactca agaggaggacggctgttcatgccggttcccagaggaggaggaaggcggctgcgaac tgcgcgtgaaattcagccgcagcgcagatgctccagcctacaagcaggggcagaac cagctctacaacgaactcaatcttggtcggagagaggagtacgacgtgctggacaa gcggagaggacgggacccagaaatgggcgggaagccgcgcagaaagaatccccaag agggcctgtacaacgagctccaaaaggataagatggcagaagcctatagcgagatt ggtatgaaggggaacgcagaagaggcaaaggccacgacggactgtaccagggact cagcaccgccaccaaggacacctatgacgctcttcacatgcaggccctgccgcctc gg |

TABLE 3-continued

Humanized CD19 CAR Constructs

| Name | SEQ ID | Sequence |
|---|---|---|
| 105977 CAR 12-Full-aa | 42 | MALPVTALLLPLALLLHAARPEIVMTQSPATLSLSPGERATLSCRASQDISKYLNW YQQKPGQAPRLLIYHTSRLHSGIPARFSGSGSGTDYTLTISSLQPEDFAVYFCQQG NTLPYTFGQGTKLEIKGGGGSGGGGSGGGGSQVQLQESGPGLVKPSETLSLTCTVS GVSLPDYGVSWIRQPPGKGLEWIGVIWGSETTYYNSSLKSRVTISKDNSKNQVSLK LSSVTAADTAVYYCAKHYYYGGSYAMDYWGQGTLVTVSSTTTPAPRPPTPAPTIAS QPLSLRPEACRPAAGGAVHTRGLDFACDIYIWAPLAGTCGVLLLSLVITLYCKRGR KKLLYIFKQPFMRPVQTTQEEDGCSCRFPEEEEGGCELRVKFSRSADAPAYKQGQN QLYNELNLGRREEYDVLDKRRGRDPEMGGKPRRKNPQEGLYNELQKDKMAEAYSEI GMKGERRRGKGHDGLYQGLSTATKDTYDALHMQALPPR |

CTL019

| | | |
|---|---|---|
| CTL019-Soluble scFv-Histag-nt | 97 | atggccctgcccgtcaccgctctgctgctgcccccttgctctgcttcttcatgcagc aaggccggacatccagatgacccaaaccacctcatccctctctgcctctcttggag acagggtgaccatttcttgtcgcgccagccaggacattcaagtatctgaactgg tatcagcagaagccggacggaaccgtgaagctcctgatctaccatacctctcgcct gcatagcggcgtgccctcacgcttctctggaagcggatcaggaaccgattattctc tcactatttcaaatcttgagcaggaagatattgccacctattctgccagcagggt aataccctgccctacaccttcggaggagggaccaagctcgaaatcaccggtggagg aggcggcggtggagggtctggtggaggtggttctgaggtgaagctgcaagaat caggcctggacttgtggcccttcacagtccctgagcgtgacttgcaccgtgtcc ggagtctccctgcccgactacggagtgtcatggatcagacaacctccacggaaagg actggaatggctcggtgtcatctggggtagcgaaactacttactacaattcagccc tcaaaagcaggctgactattatcaaggacaacagcaagtcccaagtcttcttaag atgaactcactccagactgacgacaccgcaatctactattgtgctaagcactacta ctacggaggatcctacgctatggattactggggacaaggtacttccgtcactgtct cttcacaccatcatcaccatcaccatcac |
| CTL019-Soluble scFv-Histag-aa | 98 | MALPVTALLLPLALLLHAARPdiqmtqttsslsaslgdrvtiscrasqdiskylnw yqqkpdgtvklliyhtsrlhsgvpsrfsgsgsgtdysltisnleqediatyfcqqg ntlpytfgggtkleitggggsggggsggggsevklqesgpglvapsqslsvtctvs gvslpdygvswirqpprkglewlgviwgsettyynsalksrltiikdnsksqvflk mnslqtddtaiyycakhyyyggsyamdywgqgtsvtvsshhhhhhhh |
| CTL019 Full-nt | 99 | atggccttaccagtgaccgccttgctcctgccgctggccttgctgctgccacgccgc caggccggacatccagatgacacagactacatcctccctgtctgcctctctggag acagagtcaccatcagttgcagggcaagtcaggacattagtaaatatttaaattgg tatcagcagaaaccagatggaactgttaaactcctgatctaccatacatcaagatt acactcaggagtcccatcaaggttcagtggcagtgggtctggaacagattattctc tcaccattagcaacctggagcaagaagatattgccacttacttttgccaacaggt aatacgcttccgtacacgttcggaggggggaccaagctggagatcacaggtggcgg tggctcgggcggtggtgggtcgggtggcggcggatctgaggtgaaactgcaggagt caggacctggcctggtggcgccctcacagagcctgtccgtcacatgcactgtctca gggggtctcattacccgactatggtgtaagctggattcgccagcctccacgaaaggg tctggagtggctgggagtaatatggggtagtgaaaccacatactataattcagctc tcaaatccagactgaccatcatcaaggacaactccaagagccaagttttcttaaaa atgaacagtctgcaaactgatgacacagcccatttactactgtgccaaacattatta ctacggtggtagctatgctatggactactggggccaaggaacctcagtcaccgtct cctcaaccacgacgccagcgccgcgaccaccaacaccggcgcccaccatcgcgtcg cagccccgtccctgcgcccagaggcgtgccggccagcggcggggggcgcagtgca cacgaggggctggacttcgcctgtgatatctacatctgggcgccccttggccggga cttgtggggtccttctcctgtcactggttatcacccttactgcaaacggggcaga aagaaactcctgtatatattcaaacaaccatttatgagaccagtacaaactactca agaggaagatggctgtagctgccgatttccagaagaagaagaaggaggatgtgaac tgagagtgaagttcagcaggagcgcagacgcccccgcgtacaagcagggccagaac cagctctctataacgagctcaatctaggacgaagaggagtacgatgttttggacaa gagacgtggccgggacccccgagatgggggggaaagccgagaaggaagaaccctcagg aaggcctgtacaatgaactgcagaaagataagatggcggaggcctacagtgagatt gggatgaaaggcgagcgccggaggggcaaggggcacgatggcctttaccagggtct cagtacagccaccaaggacacctacgacgcccttcacatgcaggccctgccccctc gc |
| CTL019 Full-aa | 58 | MALPVTALLLPLALLLHAARPdiqmtqttsslsaslgdrvtiscrasqdiskylnw yqqkpdgtvklliyhtsrlhsgvpsrfsgsgsgtdysltisnleqediatyfcqqg ntlpytfgggtkleitggggsggggsggggsevklqesgpglvapsqslsvtctvs gvslpdygvswirqpprkglewlgviwgsettyynsalksrltiikdnsksqvflk mnslqtddtaiyycakhyyyggsyamdywgqgtsvtvsstttpaprpptpaptias qplslrpeacrpaaggavhtrgldfacdiyiwaplagtcgvlllslvitlyckrgr kkllyifkqpfmrpvqttqeedgcscrfpeeeeggcelrvkfsrsadapaykqgqn qlynelnlgrreeydvldkrrgrdpemggkprrknpqeglynelqkdkmaeaysei gmkgerrrgkghdglyqglstatkdtydalhmqalppr |

TABLE 3-continued

Humanized CD19 CAR Constructs

| Name | SEQ ID | Sequence |
|---|---|---|
| CTL019 scFv domain | 59 | diqmtqttsslsaslgdrvtiscrasqdiskylnwyqqkpdgtvklliyhtsrlhs gvpsrfsgsgsgtdysltisnleqediatyfcqqgntlpytfgggtkleitggggs ggggsggggsevklqesgpglvapsqslsvtctvsgvslpdygvswirqpprkgle wlgviwgsettyynsalksrltiikdnsksqvflkmnslqtddtaiyycakhyyyg gsyamdywgqgtsvtvss |

The sequences of humanized CDR sequences of the scFv domains are shown in Table 4 for the heavy chain variable domains and in Table 5 for the light chain variable domains. "ID" stands for the respective SEQ ID NO for each CDR.

TABLE 4

Heavy Chain Variable Domain CDRs (Kabat)

| Candidate | FW | HCDR1 | ID | HCDR2 | ID | HCDR3 | ID |
|---|---|---|---|---|---|---|---|
| murine_CART19 | | GVSLPDYGVS | 19 | VIWGSETTYYNSALKS | 20 | HYYYGGSYAMDY | 24 |
| humanized_CART19 a | VH4 | GVSLPDYGVS | 19 | VIWGSETTYYSSSLKS | 21 | HYYYGGSYAMDY | 24 |
| humanized_CART19 b | VH4 | GVSLPDYGVS | 19 | VIWGSETTYYQSSLKS | 22 | HYYYGGSYAMDY | 24 |
| humanized_CART19 c | VH4 | GVSLPDYGVS | 19 | VIWGSETTYYNSSLKS | 23 | HYYYGGSYAMDY | 24 |

TABLE 5

Light Chain Variable Domain CDRs

| Candidate | FW | LCDR1 | ID | LCDR2 | ID | LCDR3 | ID |
|---|---|---|---|---|---|---|---|
| murine_CART19 | | RASQDISKYLN | 25 | HTSRLHS | 26 | QQGNTLPYT | 27 |
| humanized_CART19 a | VK3 | RASQDISKYLN | 25 | HTSRLHS | 26 | QQGNTLPYT | 27 |
| humanized_CART19 b | VK3 | RASQDISKYLN | 25 | HTSRLHS | 26 | QQGNTLPYT | 27 |
| humanized_CART19 c | VK3 | RASQDISKYLN | 25 | HTSRLHS | 26 | QQGNTLPYT | 27 |

Table 6 is an identification key correlating the CD19 constructs numerical names to the specific orientation of the light and heavy chains of the scFv, the number of linker units (i.e., (G4S)$_3$ (SEQ ID NO:107) or (G4S)$_4$ (SEQ ID NO:106)), separating the heavy and light chains, and the distinguishing amino acid sequences in the heavy chain CDR2.

TABLE 6

CD19 CAR designations.

| Clone ID/CAR# | Alt. Clone ID | Chain Orientation | Linkers | Site of Heavy CDR2 mutation | SEQ ID NO |
|---|---|---|---|---|---|
| 104875 (CAR1) | C2136 | L2H | 3x | YSSSL | 28 |
| 104876 (CAR2) | C2137 | L2H | 3x | YQSSL | 29 |
| 104877 (CAR3) | C2138 | H2L | 3x | YSSSL | 28 |
| 104878 (CAR4) | C2139 | H2L | 3x | YQSSL | 29 |
| 104879 (CAR5) | C2140 | L2H | 4x | YSSSL | 28 |
| 104880 (CAR6) | C2141 | L2H | 4x | YQSSL | 29 |
| 104881 (CAR7) | C2142 | H2L | 4x | YSSSL | 28 |
| 104882 (CAR8) | C2143 | H2L | 4x | YQSSL | 29 |
| 105974 (CAR9) | C2144 | L2H | 4x | YNSSL | 30 |

TABLE 6-continued

CD19 CAR designations.

| Clone ID/CAR# | Alt. Clone ID | Chain Orientation | Linkers | Site of Heavy CDR2 mutation | SEQ ID NO |
|---|---|---|---|---|---|
| 105975 (CAR10) | C2145 | H2L | 4x | YNSSL | 30 |
| 105976 (CAR11) | C2146 | L2H | 3x | YNSSL | 30 |
| 105977 (CAR12) | C2147 | H2L | 3x | YNSSL | 30 |
| CTL019 | muCART19 | L2H | 3x | YNSAL | 57 |

The CAR scFv fragments were then cloned into lentiviral vectors to create a full length CAR construct in a single coding frame, and using the EF1 alpha promoter for expression (SEQ ID NO: 100).

EF1 alpha promoter (SEQ ID NO: 100)
CGTGAGGCTCCGGTGCCCGTCAGTGGGCAGAGCGCACATCGCCCACAGTC

CCCGAGAAGTTGGGGGGAGGGGTCGGCAATTGAACCGGTGCCTAGAGAAG

GTGGCGCGGGGTAAACTGGGAAAGTGATGTCGTGTACTGGCTCCGCCTTT

TTCCCGAGGGTGGGGAGAACCGTATATAAGTGCAGTAGTCGCCGTGAAC

GTTCTTTTTCGCAACGGGTTTGCCGCCAGAACACAGGTAAGTGCCGTGTG

TGGTTCCCGCGGGCCTGGCCTCTTTACGGGTTATGGCCCTTGCGTGCCTT

GAATTACTTCCACCTGGCTGCAGTACGTGATTCTTGATCCCGAGCTTCGG

GTTGGAAGTGGGTGGGAGAGTTCGAGGCCTTGCGCTTAAGGAGCCCCTTC

GCCTCGTGCTTGAGTTGAGGCCTGGCCTGGGCGCTGGGGCCGCCGCGTGC

GAATCTGGTGGCACCTTCGCGCCTGTCTCGCTGCTTTCGATAAGTCTCTA

GCCATTTAAATTTTTGATGACCTGCTGCGACGCTTTTTTTCTGGCAAGA

TAGTCTTGTAAATGCGGGCCAAGATCTGCACACTGGTATTTCGGTTTTTG

GGGCCGCGGGCGGCGACGGGGCCCGTGCGTCCCAGCGCACATGTTCGGCG

AGGCGGGGCCTGCGAGCGCGGCCACCGAGAATCGGACGGGGGTAGTCTCA

AGCTGGCCGGCCTGCTCTGGTGCCTGGCCTCGCGCCGCCGTGTATCGCCC

CGCCCTGGGCGGCAAGGCTGGCCCGGTCGGCACCAGTTGCGTGAGCGGAA

AGATGGCCGCTTCCCGGCCCTGCTGCAGGGAGCTCAAAATGGAGGACGCG

GCGCTCGGGAGAGCGGGCGGGTGAGTCACCCACACAAAGGAAAAGGGCCT

TTCCGTCCTCAGCCGTCGCTTCATGTGACTCCACGGAGTACCGGGCGCCG

TCCAGGCACCTCGATTAGTTCTCGAGCTTTTGGAGTACGTCGTCTTTAGG

TTGGGGGAGGGGTTTTATGCGATGGAGTTTCCCCACACTGAGTGGGTGG

AGACTGAAGTTAGGCCAGCTTGGCACTTGATGTAATTCTCCTTGGAATTT

GCCCTTTTTGAGTTTGGATCTTGGTTCATTCTCAAGCCTCAGACAGTGGT

TCAAAGTTTTTTTCTTCCATTTCAGGTGTCGTGA.

Analysis of the humanized CAR constructs was conducted as described in Example 4.

Example 4: Analysis of Humanized CD19 Constructs in CART

To evaluate the feasibility of targeting CD19 via a CAR technology, the single chain variable fragments for an anti-CD19 antibody is cloned into a lentiviral CAR expression vector with the CD3zeta chain and the 4-1BB costimulatory molecule in four different configurations and the optimal construct is selected based on the quantity and quality of the effector T cell response of CD19 CAR transduced T cells ("CART19" or "CART19 T cells") in response to CD19+ targets. Effector T cell responses include, but are not limited to, cellular expansion, proliferation, doubling, cytokine production and target cell killing or cytolytic activity (degranulation).

Materials and Methods

Generation of Redirected Humanized CART19 T Cells

The humanized CART19 lentiviral transfer vectors are used to produce the genomic material packaged into the VSVg psuedotyped lentiviral particles. Lentiviral transfer vector DNA is mixed with the three packaging components of VSVg, gag/pol and rev in combination with lipofectamine reagent to transfect them together in to 293T cells. After 24 and 48 hr, the media is collected, filtered and concentrated by ultracentrifugation. The resulting viral preparation is stored at −80 C. The number of transducing units is determined by titration on SupT1 cells. Redirected CART19 T cells are produced by activating fresh naïve T cells by engaging with CD3x28 beads for 24 hrs and then adding the appropriate number of transducing units to obtain the desired percentage of transduced T cells. These modified T cells are allowed to expand until they become rested and come down in size at which point they are cryopreserved for later analysis. The cell numbers and sizes are measured using a coulter multisizer III. Before cryopreserving, percentage of cells transduced (expressing the CART19 on the cell surface) and their relative fluorescence intensity of that expression are determined by flow cytometric analysis on an LSRII. From the histogram plots, the relative expression levels of the CARs can be examined by comparing percentage transduced with their relative fluorescent intensity.

Evaluating Cytolytic Activity, Proliferation Capabilities and Cytokine Secretion of Humanized CART19 Redirected T Cells.

To evaluate the functional abilities of humanized CAR19 T cells to kill, proliferate and secrete cytokines, the cells are thawed and allowed to recover overnight. In addition to the humanized CART19, the murine CART19 was used for comparative purposes while SS1-BBz was used as non-targeting expressed CAR for background CAR/T cell effect. The "control" gold standard (GS) CART19 was used in all assays to compare assay variation. Importantly, the GS CART19 are cells produced in research grade (i.e., not clinical grade) manufacturing conditions and include the addition of IL-2 to the growth culture. This likely impacts the overall viability and functionality of these cells and should not be evaluated as a direct comparison to the research grade production of the other transduced T cell populations. The T cell killing was directed towards K562, a chronic myelogenous leukemia cell line expressing or not expressing CD19 or Pt14, B cells isolated from CLL patients. For this flow based cytotoxicity assay, the target cells are stained with CSFE to quantitate their presence. The target cells were stained for CD19 expression to confirm similar target antigens levels. The cytolytic activities of CAR19 T cells are measured at a titration of effector:target cell ratios of 10:1, 3:1, 1:1, 0.3:1 and 0:1 where effectors were defined as T cells expressing the anti-CD19 chimeric receptor. Assays were initiated by mixing an appropriate number of T cells with a constant number of targets cells. After 16 hrs, total volume of each mixture was removed and each well washed combining appropriately. The T cells were stained for CD2 and all cells stained with live/dead marker 7AAD. After the final wash, the pelleted cells were re-suspended in a specific volume with a predetermined number of counting beads. Cell staining data was collected by LSRII flow cytometry and analyzed with FloJo software using beads to quantitate results.

For measuring cell proliferation and cytokine production of humanized CAR19 T cells, cells are thawed and allowed to recover overnight. In addition to the humanized CART19, the murine CART19 was used for comparative purposes while SS1-BBz was used as a non-targeting expressed CAR for background CAR/T cell effect. The "control" gold standard (GS) CART19 was used in all assays to compare assay variation. The T cells were directed either towards K562, a chronic myelogenous leukemia cell line expressing or not expressing CD19 or Pt14, B cells isolated from CLL patients. In addition, CD3x28 beads were used to evaluate the potential of T cells to respond to the endogenous immunological signals. To analyze proliferation, T cells were stained with CSFE. The proliferation is the dilution of the CSFE stain reflecting the separation of the parental markings now into two daughter cells. The assay tests only an effector:target ratios of 1:1 and 1:0 where effectors were defined as T cells expressing the anti-CD19 chimeric receptor. The assay is done in duplicate and 24 hrs after mixing of the cells, 50% of the media is removed/replaced for cytokine analysis using the Luminex 10-plex panel of human cytokines detection. After 5 days, T cells were stained for CAR expression, phenotyped as either CD4 or CD8 cells and stained for live/dead with 7AAD. After the final wash, the pelleted cells were re-suspended in a specific volume with a predetermined number of BD counting beads. Cell staining data was collected by LSRII flow cytometry and analyzed with FloJo software using beads to quantitate results. Total cell counts were determined by number of cells counted relative to a specific number of beads multiplied by the fraction of beads yet to be counted.

To evaluate the potential for the humanized CART19 cells to function similarly to the currently successful murine CART19, we wanted to assess in vitro their ability to kill targeted cells, to proliferate in response to the targeted antigen and to show signs of persistence. By packaging each of the humanized CART19 lentiviral constructs and titering them on SupT1 cells, we are able to determine the amount of virus to normalize transductions to be around 50%. This allows for more direct comparisons of activity starting with similar average intergration sites per cell.

The therapeutic CAR19 T cells are generated by starting with the blood from a normal apheresed donor whose naïve T cells are obtained by negative selection for T cells, CD4+ and CD8+ lymphocytes. These cells are activated by CD3x 28 beads in 10% RPMI at 37 C, 5% $CO_2$.

After 24 hrs, the T cells are blasting and the normalized amount of virus is added. The T cells begin to divide into a logarithmic growth pattern which is monitored by measuring the cell counts per ml and cell size. As the T cells begin to rest down, the logarithmic growth wanes and the cell size shrinks. The combination of slowing growth rate and T cell size approaching ~300 fl determines the state for T cells to be cryopreserved or restimulated.

There is a very similar trend of T cells resting down as seen by size. The almost overlapping pattern between the humanized CART cells with the current murine CART19 and UTD population indicates no unusual effect of the humanized CAR19 on the normal T cell expansion following activation. As a control, SS1-BBz is used to define unwanted antigen independent CAR activity. The expansion profile in total cell numbers shows the differences in the actual numbers in the individual expansions are likely due mainly to different starting number of cells. By normalizing starting T cell numbers, a tight cluster is seen for all the CART19 cells. In addition, the unwanted effect of antigen independent CAR activation is detected in the line running lower and away from the group.

The level of surface expression for each of these CAR19 expressing cells was determined. The titered virus normalized for transduction show comparable expression levels correlating with transduction efficiency, percent cells transduced. Some CARs had their titers extrapolated from earlier packagings, and though their percentages transduced are lower, their MFI are also reduced as expected. The results indicate that there is no detectable negative effect of the humanized CAR19 on the cells ability to expand normally when compared to the UTD and murine CAR19 T cells.

The ability of the humanized CART19 cells to selectively discern a cell surface specific epitope expressed on cells and destroy them is analyzed. Wild type K562 cells do not express CD19 but can be transduced to express CD19. Comparing these killing curves, titrating the amount of effector cells shows that those cells expressing CD19 are destroyed. Redirected T cells from the same donor and modified with either humanized CART19 cells or current clinical murine CART19 cells indicate no difference in their ability to kill. The killing curves show that a very similar killing capacity is found among humanized CART19 cells targeting CD19+ CLL cells from patient 14. Interestingly, there is a decrease in overall cytolytic activity, in particularly GS CART19, suggesting these cells may possess specific inhibitory properties. The similar level of CD19 expressed on the targets cells indicates the expression level is not the reason for differences in cell killing.

The necessary property of the humanized CART19 cells to proliferate after seeing target cells is found in all constructs after being stimulated by the control CD3x28 beads and the CD19 expressing targets. Targeting Pt14 CLL cells appear to indicate a slightly greater proliferation rate with scFvs with a light to heavy chain orientation with no bias seen when having a 3x or 4xGGGGS linkage (SEQ ID NOS 107 and 106, respectively). The proliferative results reflect the total number of cells accumulated over the 5 days, indicating that the humanized CART19s, 2146, 2144, 2136, 2141 and 2137 drive a more proliferative signal to the T cells. Impressively, this was detected in the humanized CART19 cells targeting Pt14 CLL cells.

Overall, the humanized CART19 constructs exhibit very similar characteristics to the current murine CART19 in cytolytic activity, proliferative response and cytokine secretion to antigen specific targets. The potential of humanized CART19 cells, (2146, 2144, 2136, 2141 and 2137), to drive a more proliferative signal to the T cells upon target activation would seem to be an extra benefit of these new constructs to potentially enhance therapeutic response.

Results

Using both degranulation and cytokine production assays, it is demonstrated that the engineered CART19 T cells specifically target CD19+ cells.

ND317 cells transduced with humanized CD19CAR constructs (a.k.a. "huCART19") of the invention were analyzed. There was a tight similarity in size of the T cells during their expansions after CD3×28 activation and transduction with the humanized CART19 candidates relative to the murine CART19 and unmodified (UTD) T cells.

Experiments showed little difference in the number of T cells that accumulated during their expansions after CD3×28 activation and transduction with the different humanized CART19 candidates relative to the murine CART19 and unmodified (UTD) T cells.

Cell surface expressions of humanized CART19 are comparable and their expression level very similar to murine CART19. The overlay of histograms plotting the cell surface expression staining pattern of each humanized CART19 transduced T cells and the mean fluorescent intensity (MFI) calculated from these profiles correlates well with the percentage of cells transduced.

Furthermore the humanized CART19 have similar specific cytotoxic activities in targeting CD19 expressing target cells and comparable to murine CART19. Plots from 16 hr-flow-based killing assays using titrating Effector to Target (E:T) ratios with effector humanized CART19 cells targeting CSFE labeled K562cc (FIG. 1A. non-expressing CD19 controls), K562.CD19 (FIG. 1B, K562 cells transduced to express CD19) or Pt14 (FIG. 1C, B cells from CLL patient). The cytolytic activities of all the humanized CART19 cells are similar and comparable to the murine CART19. The differences in the cytolytic activity between different targets is similar and comparable indicating the murine CART19's activity is preserved in the humanized form of CART19.

Figure 5:
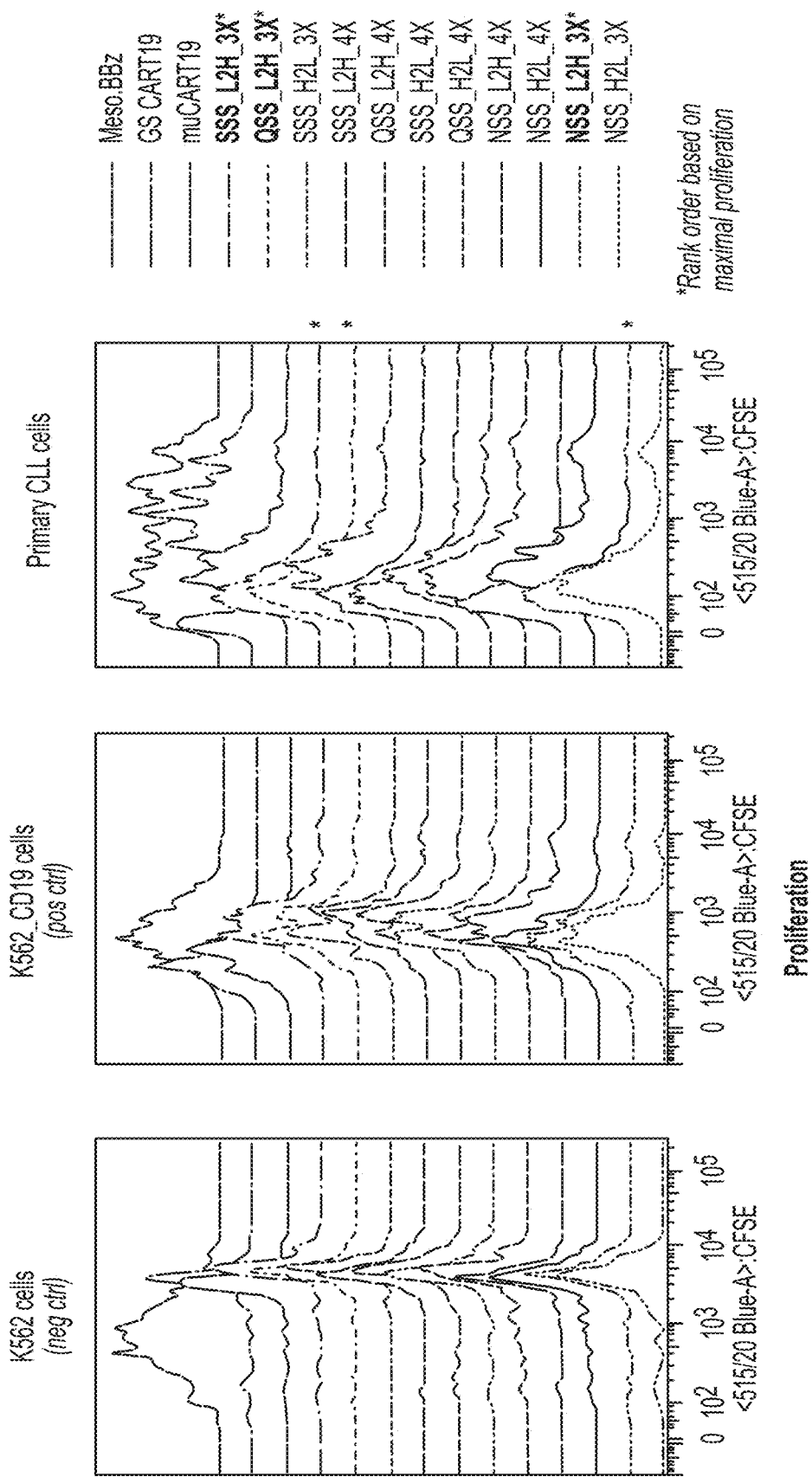
FIG. 5 is a graphic representation of CD19 CAR transduced T cell proliferation, wherein the CART19 cells are directed either towards (a) a chronic myelogenous leukemia ("CML") cell line that is negative for the expression of CD19, and hence used as a negative control; (b) recombinant K562 cells positive for expression of CD19, and hence used as a positive control; or (c) to Pt14 B cells isolated from a CLL patient and which expresses CD19 on the cell surface.
Figure 6A:
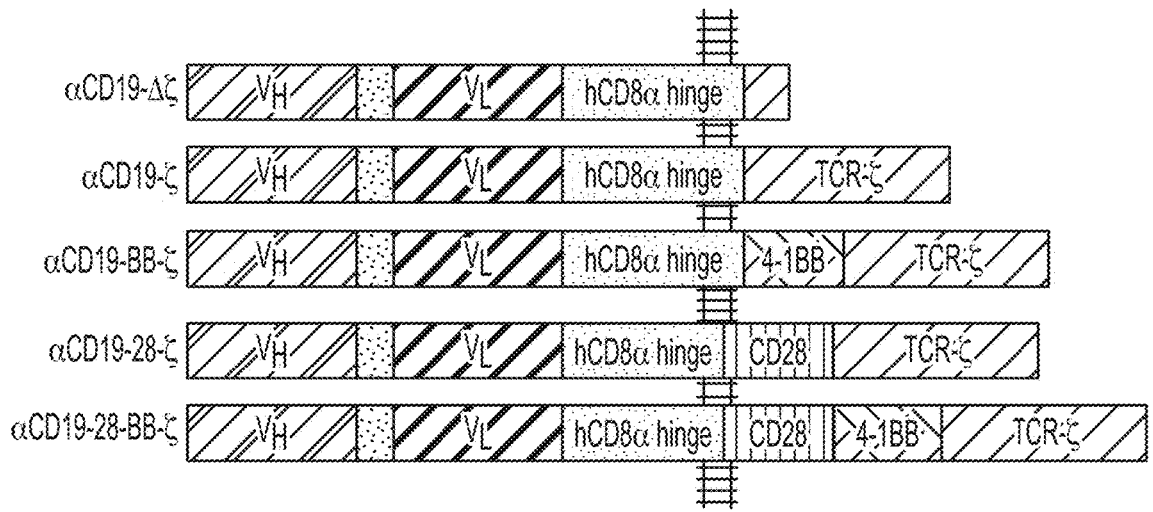
FIGS. 6A and 6B are schematics of representative CARs.
Figure 6B:
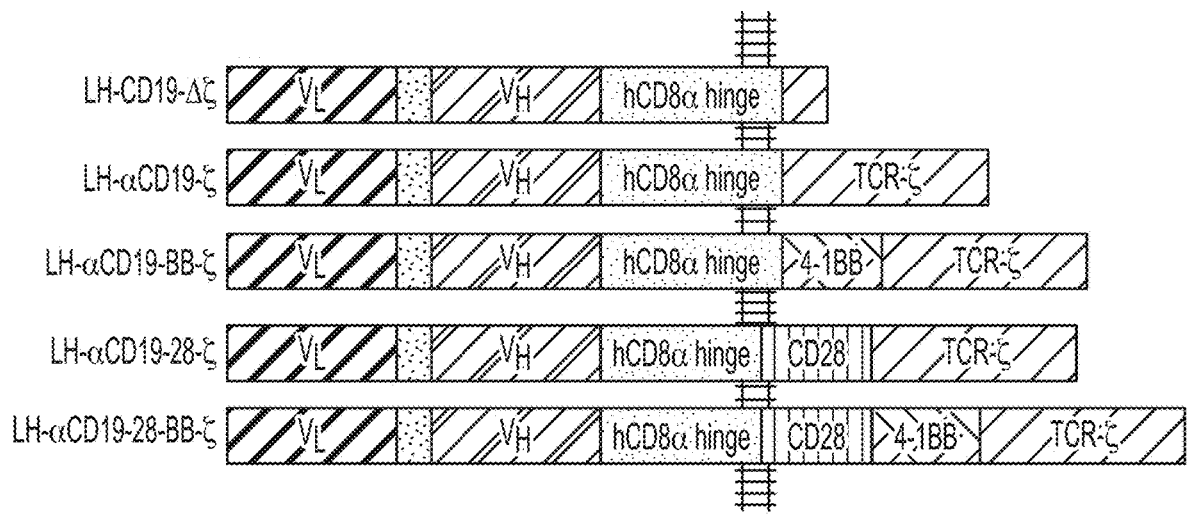

Histogram overlays of CFSE marked humanized CART19 cells 6 days after being mixed with target cells show their proliferative capacity (FIG. 5). The proliferative response delivered from the CAR19 is a necessary response after engagement with and killing of target cells to develop a positive clinical response. The dilution of SS1-BBz CSFE staining, an indicator of dividing daughter cells diluting out the parental cell's stain, is a result of unrested T cells maintaining divisions in a targeting independent mechanism.

Figure 2B:
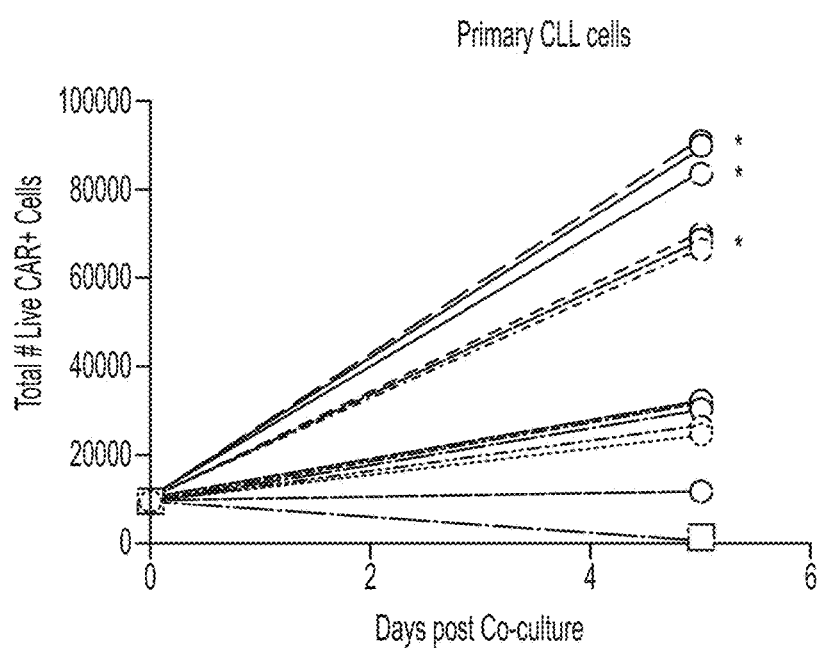

The cell populations overall ability to proliferate is evaluated with CD3×28 beads which mimics the endogenous engagement of the TCR and the co-stimulator CD28. Data indicates each cell population has a comparable proliferation potential. All humanized and murine CART19 cells proliferate strongly and comparably upon engagement with K562 cells expressing CD19. Humanized CART19 cells also responded well to B cells obtained from a CLL patient though some seem to respond slightly less. As shown in FIGS. 2A and 2B, the humanized CART19 cells 2136, 2137, 2140, 2141, 2144 and 2146 can be seen to have a slightly more robust proliferation as evidenced by the greater dilution of CSFE staining. These constructs all have the same variable chain orientation of light to heavy, indicating that this is the orientation of choice. A closer look at the amino acid changes in the heavy CDR2 site (Table 1) reveals that each of the three variations YSSSL, YQSSL and YNSSL (SEQ ID NOS:28, 29 and 30, respectively) are represented in the constructs that appeared to have the more robust proliferations after seeing targets. In addition, these observed constructs have both the G4S linker containing 3 copies of the subunit (3G4S) (SEQ ID NO: 107) and the G4S linker containing 4 copies of the subunit (4G4S) (SEQ ID NO: 106), indicating the linker size did not influence function.

From the proliferative expansions described above, the total cell numbers after 5 days post tumor engagement is determined. The cells show a decline in numbers than were initially seeded, indicating activation is required to maintain survival. An endogenous activation control is analyzed to show that the total cell count at the end of 6 days was similar. Humanized CART19 cells targeting K562 cells expressing CD19 show that the two murine CART19 cells both end up with the higher cell numbers, with 2146 slightly above all the other constructs with similar values. Total cell numbers were also analyzed 6 days after exposure to B cells from Patient 14 (pt14), and interestingly shows that the previously selected out humanized CART19 constructs 2146, 2144, 2136, 2141 and 2137, all of which have the light to heavy chain orientation and represent the three amino acid variations YSSSL, YQSSL and YNSSL (SEQ ID NOS: 28, 29 and 30, respectively), resulted in higher total cell numbers, higher than the murine CART19s. This unexpected differentiation between the various humanized anti-CD19CAR clones may translate to better clinical efficacy of CART cells transduced with these constructs.

Background levels of cytokine produced from humanized CART19 cells after exposure to the control K562 cells not expressing CD19 were analyzed. 24 hr supernatants were analyzed using a luminex 30-plex panel. The potential cytokine profile from stimulation of the endogenous immune system with the CD3×28 beads indicate each of the cell populations have a comparable cytokine profile.

Data also shows that the humanized CART19 and murine CART19 produce similar cytokine profiles at similar levels when responding to the same targets. The cytokine profile was lower but similar when targeting the Pt14 target cells.

Example 5: Humanized CD19 CAR T Cell Treatment in an In Vivo ALL Model

Primary human ALL cells can be grown in immune compromised mice without having to culture them in vitro. These mice can be used to test the efficacy of chimeric antigen receptor (CAR) T cells in a model that represents the patient population that will be found in the clinic. The model used here, HALLX5447, was passaged twice in NOD.Cg-Prkdc$^{scid}$Il2rg$^{tm1 Wjl}$/SzJ (NSG) mice, prior to use in studies testing the efficacy of CAR T cells.

Murine CD19 CAR T cells have previously been shown to target and kill leukemia cells in an NSG mouse model of primary human ALL. The CD19 scFv (single chain Fc variable fragment) has been humanized and the present example compares the ability of T cells expressing a humanized CD19 CAR (CAR 2) to eliminate ALL tumor cells in vivo to that of the murine CD19 CAR T cells. Here, the efficacy of these cells has been directly compared in mice with established primary human ALL, as assayed by peripheral blood FACS analysis of human CD19$^+$ cells. Following an implant of 1.5×10$^6$ primary ALL cells intravenously, a disease burden of 2.5-4% CD19$^+$ human cells in the blood was achieved by 2 weeks post-tumor implantation. This CD19 percentage is of total cells in the blood of the mice. 100% of human cells in the mice prior to treatment with CAR T cells are tumor cells. Percentages above 2% CD19$^+$ human cells in the peripheral blood are considered to be established human ALL disease in this model. The leukemia-bearing mice were treated with the CAR T cells once the leukemia is established in the mice, approximately two to three weeks after tumor implantation. Mice in each group were treated with 5×10$^6$ total human T cells. The transduction efficiencies of the donor human T cells with the CAR expressing lentivirus were between 40-60%. Following treatment with the T cells, mice were bled weekly for analysis of the percentage of CD19$^+$ human cells in the blood as a biomarker for disease progression.

Materials and Methods:

Primary Human ALL Cells:

Primary cells were not cultured in vitro prior to implantation. These cells were harvested from a patient with ALL and then transferred into mice for establishment and expansion. After the tumor cells were expanded in the mice, the bone marrow and splenocytes were harvested and viably frozen in separate batches for re-implantation. The cells were frozen in 90% DMSO and 10% FBS at a minimum concentration of $5 \times 10^6$ cells per milliliter. For re-implantation, the frozen ALL cells were thawed and then injected intravenously in to NSG mice, in order to generate mice with ALL that will be used to compare the anti-tumor efficacy of the humanized CD19 CAR T cells and the murine CD19 CAR T cells.

Mice:

6 week old NSG (NOD.Cg-Prkdc$^{scid}$Il2rg$^{tm1 Wjl}$/SzJ) mice were received from the Jackson Laboratory (stock number 005557). Animals were allowed to acclimate to the Novartis NIBRI animal facility for at least 3 days prior to experimentation. Animals were handled in accordance with Novartis ACUC regulations and guidelines.

Tumor Implantation:

In vivo serially passaged primary human ALL cells, model HALLX5447, were thawed in a 37° C. water bath. The cells were then transferred to a 15 ml conical tube and washed twice with cold sterile PBS. The primary ALL cells were then counted and resuspended at a concentration of $15 \times 10^6$ cells per milliliter of PBS. The cells were placed on ice and immediately (within one hour) implanted in the mice. The ALL cells were injected intravenously via the tail vein in a 100 μl volume, for a total of $1.5 \times 10^6$ cells per mouse.

CAR T Cell Dosing:

Mice were administered $5 \times 10^6$ T cells 16 days after tumor implantation. Cells were partially thawed in a 37 degree Celsius water bath and then completely thawed by the addition of 1 ml of cold sterile PBS to the tube containing the cells. The thawed cells were transferred to a 15 ml falcon tube and adjusted to a final volume of 10 mls with PBS. The cells were washed twice at 1000 rpm for 10 minutes each time and then counted on a hemocytometer. T cells were then resuspended at a concentration of $50 \times 10^6$ cells per ml of cold PBS and kept on ice until the mice were dosed. The mice were injected intravenously via the tail vein with 100 μl of the CAR T cells for a dose of $5 \times 10^6$ T cells per mouse. Five mice per group were treated either with 100 μl of PBS alone (PBS), untransduced T cells (Mock), murine CD19 CAR T cells (muCTL019), or humanized CD19 CAR T cells (huCTL019). The untransduced T cells, muCTL019 T cells, and huCTL019 T cells were all prepared from the same human donor in parallel.

Animal Monitoring:

The health status of the mice was monitored daily, including twice weekly body weight measurements. The percent change in body weight was calculated as $(BW_{current} - BW_{initial})/(BW_{initial}) \times 100\%$. Tumor burden was monitored weekly by peripheral blood FACS analysis. Mice were bled weekly via the tail vein into EDTA coated tubes that were kept on ice. 10-20 μl of blood was plated from the tubes into 96 well plates on ice. Red blood cells were lysed with ACK red blood cell lysis buffer (Life Technologies, catalog number A10492-01) and then washed twice with cold PBS. The cells were incubated with an Fc blocking mix of human and mouse Fc block (Miltenyi Biotec, catalog numbers 130-059-901 and 130-092-575) for 30 minutes and then incubated with an anti-human CD19 antibody for 30 minutes. The cells were fixed with a 2% paraformaldehyde solution for 20 minutes, washed and stored in PBS+2% FBS overnight prior to analysis on a BD Canto or Fortessa, followed by further analysis using the FlowJo FACS analysis software. The cells were analyzed to determine the percent of human CD19$^+$ cells in the blood of the human HALLX5447 ALL tumor-bearing NSG mice. CD19 percentages in the blood are reported as the mean±standard error of the mean (SEM).

Percent treatment/control (T/C) values were calculated using the following formula:

$$\% T/C = 100 \times \Delta T/\Delta C \text{ if } \Delta T \geq 0;$$

$$\% \text{Regression} = 100 \times \Delta T/T_{initial} \text{ if } \Delta T < 0;$$

where T=mean peripheral blood CD19 percentage of the drug-treated group on the final day of the study; $T_{initial}$=peripheral blood CD19 percentage of the drug-treated group on initial day of dosing; ΔT=mean peripheral blood CD19 percentage of the drug-treated group on the final day of the study−mean peripheral blood CD19 percentage of the drug treated group on the initial day of dosing; C=mean peripheral blood CD19 percentage of the control group on the final day of the study; and ΔC=mean peripheral blood CD19 percentage of the control group on the final day of the study−mean peripheral blood CD19 percentage of the control group on the initial day of dosing.

T/C values in the range of 100% to 42% are interpreted to have no or minimal anti-tumor activity; T/C values that are ≤42% and >10% are interpreted to have anti-tumor activity or tumor growth inhibition. T/C values≤10% or regression values≥−10% are interpreted to be tumor stasis. Regression values<−10% are reported as regression.

Results:

The anti-tumor activity of murine and humanized CD19 CAR T cells were evaluated and directly compared in a primary model of human ALL. Following tumor implantation on day 0, mice were randomized into treatment groups and treated with $5 \times 10^6$ T cells intravenously on day 16. ALL disease burden and animal health were monitored until animals achieved endpoint. The mice in all the groups were euthanized on day 65 post-tumor implantation when disease burden in the control groups was above 80% human CD19$^+$ cells in the peripheral blood.

Figure 7:
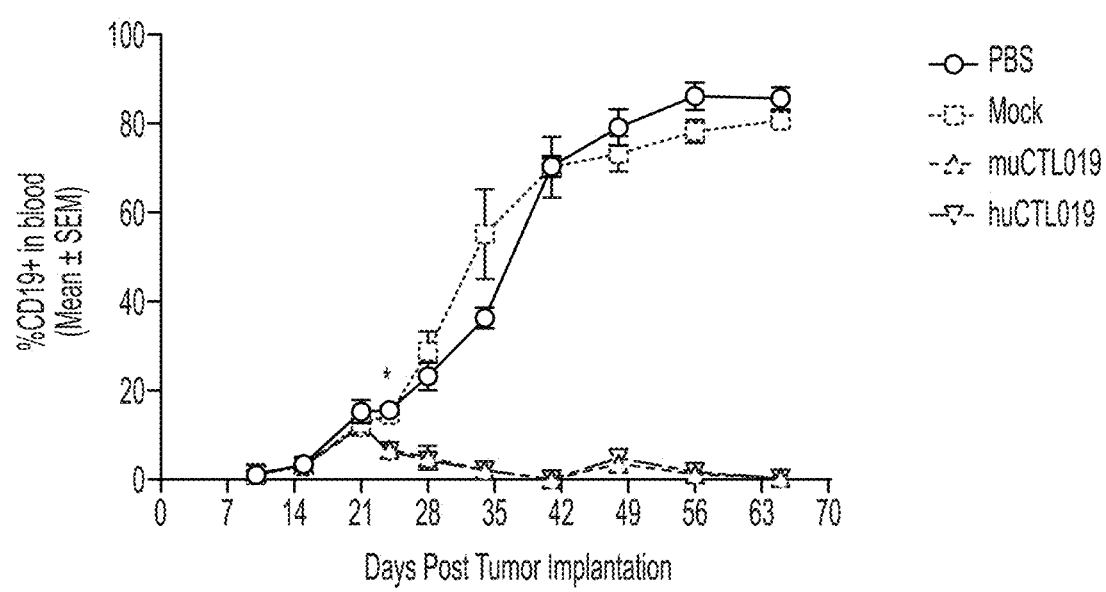
FIG. 7 depicts HALLX5447 primary ALL disease progression in NSG mice after treatment with CD19 transduced CAR T cells. The growth of primary human ALL cells in NSG mice after treatment with CAR T cells specific for CD19 demonstrated control of disease progression. Mean percentage of CD19+ human ALL cells was an indicator of disease burden in the peripheral blood in NSG mice to day 65 post tumor implant. Black circles: mice treated with 100 ul of PBS via the tail vein; red squares: mice treated with mock transduced T cells; blue triangles: mice treated with murine CD19 CAR transduced T cells; and inverted purple triangles: mice treated with humanized CD19 CAR transduced T cells. Significance calculated by ANOVA; * denotes P<0.01.

A clear difference in disease burden was seen between the control groups and the groups treated with either the murine or the humanized CD19 CAR T cells with P<0.01 from day 24 after tumor implantation, and continuing to the end of the study at day 65. The murine and human CD19 CAR T cells demonstrate a similar ability to control human HALLX5447 ALL tumor cell growth in NSG mice. Both groups showed a peak peripheral blood disease level of 12-15% human CD19$^+$ cells at day 21 post HALLX5447 implantation. 42 days after tumor cell implantation, no human CD19$^+$ cells were detectable in the huCTL019 group, while the percentage of human CD19$^+$ cells in the muCTL019 group dropped to about 1%. Both the murine and the humanized CD19 CAR T cells resulted in a comparable ability to control the expansion of primary human ALL cells in this model (P>0.05). The % T/C values for the mock transduced T cell group was 94.40%, demonstrating that the mock transduced T cells had no anti-tumor activity. The percent regression of the muCTL019 group was −89.75% and the huCTL019 group was −90.46%, demonstrating that both of these treatments were able to cause a regression of the HALLX5447 tumor model. The peripheral blood human CD19$^+$ cell percentages as a measure of the disease burden in these mice is shown in FIG. 7. The PBS treatment group, which did not receive any T cells, demonstrated baseline primary ALL tumor growth kinetics in intravenously implanted NSG mice. The Mock treatment group received untransduced T cells that underwent the same in vitro expansion process as the CAR T cells. These cells serve as a T cell control to show the non-specific response of the T cells in this tumor model. Both the PBS and Mock transduced T cell treatment groups demonstrated continuous tumor progression throughout the experiment. Both the murine and the humanized CD19 CAR T cells control the progression of disease within one week of the $5\times10^6$ T cell injections and demonstrate a similar ability to sustain disease control over the course of this 65 day study.

The anti-tumor activity of murine and humanized CD19 CAR transduced T cells was assessed in an efficacy study in NSG mice bearing a primary human ALL model, HALLX5447. This study demonstrated that both the murine and humanized CD19 CAR T cells (muCTL019 and huCTL019) are capable of mounting an anti-tumor response in a primary model of human ALL. In addition, this response, as assayed by peripheral blood disease burden is the same for the muCTL019 and huCTL019 cells. Both the murine and humanized CD19 CAR T cells control primary ALL growth within a week of the mice being dosed with the T cells. Initially after treatment, the disease burden continued to increase before decreasing to virtually undetectable levels. One treatment with either the murine or humanized CAR T cells resulted in a sustained anti-tumor response over the course of the 65 day disease progression in control treated mice. The humanized CD19 CAR T cells demonstrated a similar ability to mount an efficacious anti-CD19 tumor response and control ALL disease burden as was seen with the murine CD19 CAR T cells.

Example 6: CD19 CAR T Cells for Use in Treating Multiple Myeloma

Even with current regimens of chemotherapy, targeted therapies, and autologous stem cell transplant, myeloma is considered an incurable disease. The present example describes treating multiple myeloma (MM) with autologous T cells directed to CD19 with a chimeric antigen receptor (lentivirus/CD19:4-1BB:CD3zeta; also known as "CART19" or CTL019). This example demonstrates that CD19-directed CAR therapies have the potential to establish deep, long-term durable remissions based on targeting the myeloma stem cell and/or tumor cells that express very low (undetectable by most methods) levels of CD19.

In treating a patient with an aggressive secondary plasma cell leukemia, we found that CART19 administered two days after a salvage autologous stem cell transplant resulted in rapid clearance of plasma cell leukemia and a very good partial response in a patient who had progressed through multiple lines of chemotherapy. This patient was transfusion-dependent for months prior to the treatment; at two months after the treatment, she has recovered her blood counts (with normal-range platelet counts and white blood cell counts) and has not required transfusions since she was discharged from the hospital from her treatment.

Because myeloma cells do not naturally express CD19, the finding that CART19 treatment induced a rapid and significant tumor response in this tumor was surprising. Without wishing to be bound by a particular theory, it was reasoned that CART19 could be used to treat myeloma because: (1) while myeloma cells are traditionally thought to be negative for CD19 expression by flow cytometry, there are data indicating that myeloma cells may express very low levels of CD19, such that expression is detectable by RNA but not by flow cytometry or immunohistochemistry; and (2) the concept of targeting the clonotypic B cell, which is thought to be the cancerous stem cell that gives rise to multiple myeloma, and is particularly resistant to chemotherapy. There is a clonal relationship between B cells and myeloma tumor cells, but traditional myeloma therapy is aimed at the malignant plasma cells rather than B cells. CART19 for treating myeloma therefore targets a different cell population than most myeloma therapies.

Figure 8:
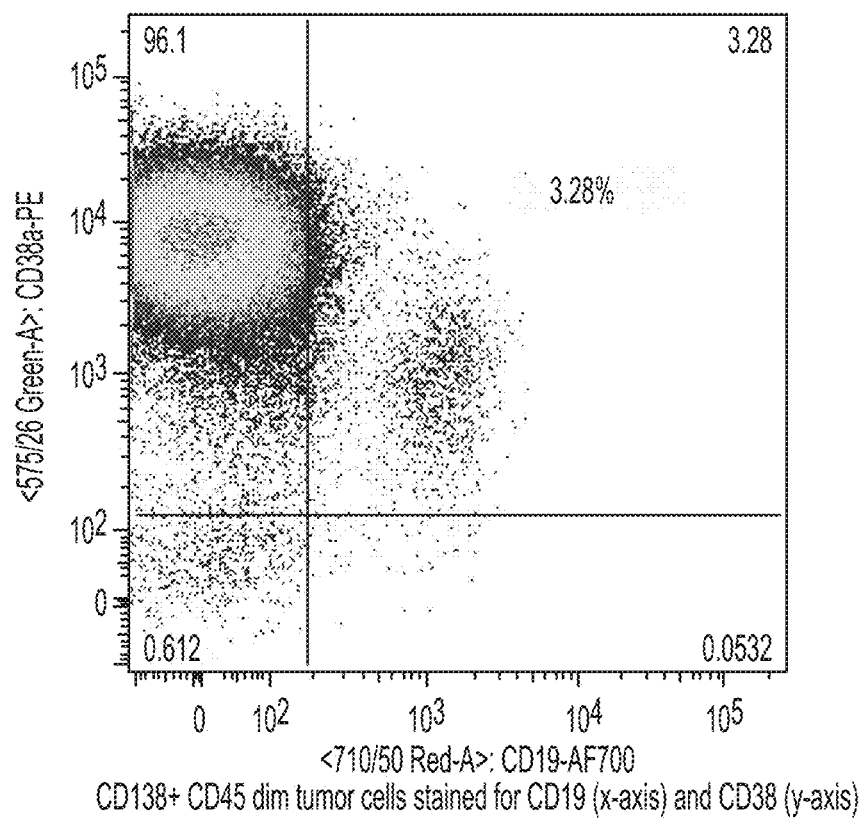
FIG. 8 depicts CD19 expression in a patient's tumor cells. $CD138^+$ $CD45^{dim}$ tumor cells were stained for CD19 (x-axis) and CD38 (y-axis).

In our single patient experience, the patient had circulating plasma cells, and we were able to test her tumor cells for the expression of CD19. Approximately 1-2% of her tumor cells expressed the CD19 antigen. (FIG. 8). Thus, it was reasoned that CART19 may have a direct effect on a very small population of her tumor cells; a very good partial response, though would not have been predicted based on targeting only the very small population of CD19+ tumor cells.

In this case, CART19 was administered following autologous stem cell transplant rescue after high-dose melphalan. Although this is a standard therapy in myeloma, it is not curative. Furthermore, this patient had previously undergone tandem autologous stem cell transplants and relapsed early (<6 months) after transplant. Without wishing to be bound by a particular theory, use of CART19 cells as described in the present example may have a non-overlapping mechanism in the treatment of myeloma when combined with a salvage autologous stem cell transplant.

Ten additional multiple myeloma patients will be treated with CART19 in a Phase I trial.
Dose Rationale and Risks/Benefits We have chosen to use flat dosing via the intravenous route of administration for this protocol. The primary objective of this protocol was to test the safety and feasibility of administering CART-19 cells to patients with multiple myeloma. The primary toxicities that were anticipated are (I) cytokine release when the CARs encounter their surrogate CD 19 antigen on malignant or normal B cells; (2) depletion of normal B cells, similar to rituximab therapy; (3) steroid-responsive skin and gastrointestinal syndromes resembling graft-versus-host disease as has been seen previously when expanded/costimulated autologous T-cells have been coupled with ASCT for MM. A theoretical concern was whether transformation or uncontrolled proliferation of the CART-19 T cells might occur in response to high levels of CD 19. This was less a concern in this application compared to another study of CLL patients, as the burden of clonotypic B-cells in MM is expected to be far lower than the burden of malignant B-cells in the refractory CLL patients treated on that study.
Dose Rationale With the first 3 patients, we have observed clinical activity at doses ranging from $1.4\times10^7$ to $1.1\times10^9$ CART-19 cells. This observation demonstrates, at least in the first 3 patients treated, that there is not an obvious dose response relationship. A complete response was observed in patients administered with two log fold difference in dose. Thus, unlike standard drugs that are metabolized, CAR T cells can have a wide dose response range. This is most likely because the CAR T cells are able to proliferate extensively in the patients. We therefore set a dose range of $1-5\times10^8$ CART-19 cells for infusion. In this single-patient study offered on a compassionate use basis, the patient was offered up to $5\times10^8$ CART19 cells, with no lower dose limit. For the ten patient trial, patients will be offered $1-5\times10^7$ CART-19 cells.

General Design

This was single patient-study offered on a compassionate use basis; it was modeled after a Phase I study to determine if the infusion of autologous T cells transduced to express CART-19 is safe. The primary goals of the study were to determine the safety, tolerability and engraftment potential of CART-19 T cells in patients undergoing salvage ASCT after early relapse following first ASCT. The protocol consists of an open label pilot study.

At entry subjects will undergo a bone marrow biopsy and routine laboratory and imaging assessment of their MM. Eligible subjects will undergo steady-state apheresis to obtain large numbers of peripheral blood mononuclear cells (PBMC) for CART-19 manufacturing. The T cells will be purified from the PBMC, transduced with TCRζ/4-1BB lentiviral vector, expanded in vitro and then frozen for future administration. The number of patients who have inadequate T cell collections, expansion or manufacturing compared to the number of patients who have T cells successfully manufactured will be recorded; feasibility of product manufacturing is not expected to be problematic in this patient population.

Subjects will generally have had adequate peripheral blood stem cells remaining stored from the mobilization/collection performed in preparation for their first ASCT to conduct two additional ASCT. Those who do not will undergo a second mobilization/collection procedure either before or after their steady-state apheresis with a regimen according to the treating physician's preference. Approximately two weeks after the initial leukapheresis, subjects will be admitted to the hospital and receive high-dose melphalan (day −2) followed by infusion of autologous stem cells two days later (day 0), and all subjects will receive infusion of CART-19 cells four days later (day +2). Up to 10 patients will be enrolled.

All subjects will have blood tests to assess safety, and engraftment and persistence of the CART-19 cells at regular intervals through week 4 of the study. At day +42 and day +100, subjects will undergo bone marrow aspirates/biopsies to assess the bone marrow plasma cell burden and trafficking of CART-19 cells to the bone marrow. A formal response assessment will be made at day 100 according to International Myeloma Working Group (IMWG) criteria136, and TTP will be monitored according to routine clinical practice for patients with multiple myeloma. The main efficacy outcome measured in this study will be a comparison of TTP after a patient's initial ASCT to TTP after the ASCT on this study.

As the primary endpoint of this study is safety and feasibility of infusion of CART-19 cells with ASCT, the study will employ an early stopping rule. Briefly, if less than 2 severe, unexpected adverse events occur among the first five subjects treated, the study will then accrue an additional five subjects towards a target enrollment of 10. We will observe treated subjects for 40 days after CART-19 infusion (i.e., through the first official response assessment at day 42) before enrolling a subsequent subject until five subjects have been enrolled and so observed. For treatment of the second group of five patients, no waiting period will be required between subjects.

Following the 6 months of intensive follow-up, subjects will be evaluated at least quarterly for two years with a medical history, physical examination, and blood tests. Following this evaluation, subjects will enter a roll-over study for annual follow-up by phone and questionnaire for up to additional thirteen years to assess for the diagnosis of long-term health problems, such as development of new malignancy.

Primary Study Endpoints

This pilot trial is designed to test the safety and feasibility of the autologous T cells transduced with the CD19 TCRζ/4-1BB in patients undergoing salvage ASCT for MM following early relapse after first ASCT.

Primary safety and feasibility endpoints include:

Occurrence of study-related adverse events, defined as NCJ CTC 2: grade 3 signs/symptoms, laboratory toxicities and clinical events that are possibly, likely or definitely related to study treatment at any time from the infusion until week 24. This will include infusional toxicity and any toxicity possibly related to the CART-19 cells including but not limited to:

a. Fevers
b. Rash
c. Neutropenia, thrombocytopenia, anemia, marrow aplasia
d. Hepatic dysfunction
e. Pulmonary infiltrates or other pulmonary toxicity
f. GVHD-like syndromes affecting gastrointestinal tract or skin.

Feasibility to manufacture CART-19 cells from patient apheresis products. The number of manufactured products that do not meet release criteria for vector transduction efficiency, T cell purity, viability, sterility and tumor contamination will be determined.

The depth and duration of response following autologous stem cell transplant with CART19 will be compared to the depth and duration of response that each patient initially achieved following standard autologous stem cell transplant.

Subject Selection and Withdrawal

Inclusion Criteria

Subjects must have undergone a prior ASCT for MM and have progressed within 365 days of stem cell infusion. Subjects who have undergone two prior ASCTs as part of a planned tandem ASCT consolidation regimen are eligible. Progression will be defined according to IMWG criteria for progressive disease or, for patients who attained CR or sCR after initial ASCT, criteria for relapse from CR (Durie et al. Leukemia 2006; 20(9):1467-1473). N.B.: There is no requirement that patients must enroll within 365 days of prior ASCT, and patients may be treated with other agents, including experimental agents, following relapse/progression after prior ASCT before enrollment on this study.

Subjects must have signed written, informed consent.

Subjects must have adequate vital organ function to receive high-dose melphalan as defined by the following criteria, measured within 12 weeks prior to the date of melphalan infusion: a. Senun creatinine ≤2.5 or estimated creatinine clearance ≥30 ml/min and not dialysis-dependent. b. SGOT≤3× the upper limit of normal and total bilirubin ≤2.0 mg/dl (except for patients in whom hyperbilirubinemia is attributed to Gilbert's syndrome). c. Left ventricular ejection fraction (LVEF)≥45% or, if LVEF is <45%, a formal evaluation by a cardiologist identifying no clinically significant cardiovascular function impairment. LVEF assessment must have been performed within six weeks of enrollment. d. Adequate pulmonary function with FEV1, FVC, TLC, DLCO (after appropriate adjustment for lung volume and hemoglobin concentration) ≥40% of predicted values. Pulmonary function testing must have been performed within six weeks of enrollment.

Subjects must have an ECOG performance status of 0-2, unless a higher performance status is due solely to bone pain.

Exclusion Criteria Subjects must not:
Have any active and uncontrolled infection.
Have active hepatitis B, hepatitis C, or HIV infection.
Any uncontrolled medical disorder that would preclude participation as outlined.

Treatment Regimen

Therapy for Relapsed/Progressive Multiple Myeloma

Patients may receive, prior to enrollment, therapy for relapsed/progressive multiple myeloma according to the preference of their treating physicians. Therapy may continue upon enrollment.

Patients must stop all therapy for two weeks prior to apheresis and for two weeks prior to high-dose melphalan. If more than two weeks are expected to lapse between apheresis and high-dose melphalan, patients may resume therapy after apheresis at the discretion of their treating physicians.

High-Dose Melphalan (Day −2)

Patients will be admitted to the hospital on day −3 or −2 and will undergo examination by the attending physician and routine laboratory tests, which will include monitoring parameters for tumor lysis syndrome, prior to commencement of the treatment protocol. Blood for MM monitoring laboratory tests (SPEP, quantitative immunoglobulins, and serum free light chain analysis), will be drawn prior to initiation of therapy if such tests had not been drawn within 7 days of admission.

High-dose therapy will consist of melphalan at a dose of 200 mg/m$^2$ administered intravenously over approximately 20 minutes on day −2. The dose of melphalan will be reduced to 140 mg/m$^2$ for patients >70 years of age or for patients of any age whom, at the discretion of the treating physician, may not tolerate a dose of 200 mg/m$^2$ All patients will receive standard anti-emetic prophylaxis, which may include dexamethasone, and standard antibiotic prophylaxis.

Stem-Cell Re-Infusion (Day 0)

Stem cell infusion will take place on day 0, at least 18 hours after the administration of the high-dose melphalan. Stem cells will be infused intravenously over approximately 20-60 minutes following premedication according to standard institutional practice. At least 2×10$^6$ CD34+ progenitors/kg body weight should be infused. In addition, at least 1×10$^6$ CD34+ progenitors/kg body weight should be available as a back-up stem-cell product to be infused in the event of delayed engraftment or late graft failure. G-CSF should be administered SQ beginning on day +5, dosed according to standard institutional practice. Other supportive care measures such as transfusion support will be done in accordance with standard institutional guidelines.

CART19 Cell Infusion (Day +2)

A single dose of CART-19 transduced T cells will be given consisting of up to 5×10$^7$ CART-19 cells. There is no minimal acceptable dose for infusion of cells transduced with the CD19 TCRζ4-1BB vector in this single-patient protocol. CART-19 cells will be given as a single dose by rapid i.v. infusion on day +2 after stem cell infusion.

Maintenance Lenalidomide

Subjects who received and tolerated maintenance lenalidomide after their first ASCT will re-initiate lenalidomide maintenance therapy at approximately day +100, assuming there are no contraindications in the judgment of the treating physician.

Preparation and Administration of Study Drug

The CART-19 T cells are prepared in the CVPF and are not released from the CVPF until FDA approved release criteria for the infused cells (e.g., cell dose, cell purity, sterility, average copy number of vectors/cell, etc.) are met. Upon release, the cells are taken to the bedside for administration.

Cell thawing. The frozen cells will be transported in dry ice to the subject's bedside. The cells will be thawed at the bedside using a water bath maintained at 36° C. to 38° C. The bag will be gently massaged until the cells have just thawed. There should be no frozen clumps left in the container. If the CART-19 cell product appears to have a damaged or the bag to be leaking, or otherwise appears to be compromised, it should not be infused and should be returned to the CVPF as specified below.

Premedication. Side effects following T cell infusions include transient fever, chills, and/or nausea; see Cruz et al. for review (Cytotherapy 2010; 12(6):743-749). It is recommended that the subject be pre-medicated with acetaminophen and diphenhydramine hydrochloride prior to the infusion of CART-19 cells. These medications may be repeated every six hours as needed. A course of non-steroidal anti-inflammatory medication may be prescribed if the patient continues to have fever not relieved by acetaminophen. It is recommended that patients not receive systemic corticosteroids such as hydrocortisone, prednisone, methylprednisolone or dexamethasone at any time, except in the case of a life-threatening emergency, since this may have an adverse effect on T cells. If corticosteroids are required for an acute infusional reaction, an initial dose of hydrocortisone 100 mg is recommended.

Febrile reaction. In the unlikely event that the subject develops sepsis or systemic bacteremia following CAR T cell infusion, appropriate cultures and medical management should be initiated. If a contaminated CART-19 T cell product is suspected, the product can be retested for sterility using archived samples that are stored in the CVPF.

Administration. The infusion will take place in an isolated room in Rhoads, using precautions for immunosuppressed patients. The transduced T cells will be administered by rapid intravenous infusion at a flow rate of approximately 10 mL to 20 ml per minute through an 18-gauge latex free Y-type blood set with a 3-way stopcock. The duration of the infusion will be approximately 2-20 minutes. Each infusion bag will have affixed to it a label containing the following: "FOR AUTOLOGOUS USE ONLY." In addition the label will have at least two unique identifiers such as the subject's initials, birth date, and study number. Prior to the infusion, two individuals will independently verify all this information in the presence of the subject and so confirm that the information is correctly matched to the participant.

Emergency medical equipment (i.e., emergency trolley) will be available during the infusion in case the subject has an allergic response, or severe hypotensive crisis, or any other reaction to the infusion. Vital signs (temperature, respiration rate, pulse, and blood pressure) will be taken before and after infusion, then every 15 minutes for at least one hour and until these signs are satisfactory and stable. The subject will be asked not to leave until the physician considers it is safe for him or her to do so.

Packaging

Infusion will be comprised of a single dose of 1-5×10$^8$ CAT19-transduced cells, with a minimal acceptable dose of 1×10$^7$ CART-19 cells for infusion. Each bag will contain an aliquot (volume dependent upon dose) of cryomedia containing the following infusible grade reagents (% v/v): 31.25% plasmalyte-A, 31.25% dextrose (5%), 0.45% NaCl, up to 7.5% DMSO, 1% dextran 40, 5% human serum albumin.

Apheresis

A large volume (12-15 liters or 4-6 blood volumes) apheresis procedure is carried out at the apheresis center. PBMC are obtained for CART-19 during this procedure. From a single leukapheresis, the intention is to harvest at least $50 \times 10^9$ white blood cells to manufacture CART-19 T cells. Baseline blood leukocytes for FDA look-back requirements and for research are also obtained and cryopreserved. The cell product is expected to be ready for release approximately 2-4 weeks later. Flow cytometry lymphocyte subset quantitation, including CD19 and CD20 B cell determination. Baseline assessment is made for human anti-VSV-G and anti-murine antibody (HAMA). If a subject has previously had an adequate apheresis collection banked according to current Good Manufacturing Practices at the Clinical Cell and Vaccine Production Facility these cells may be used as the source of cells for CART-19 manufacturing. Using a banked apheresis product would avert the expense, time, and risk to the subject of undergoing an additional apheresis collection.

Cytoreductive Chemotherapy

The lymphodepleting chemotherapy will be high-dose melphalan as described herein.

CART-19 Infusion

Infusion will begin on day +2 after stem-cell reinfusion.

On day +2 prior to the first infusion, patients will have a CBC with differential, and assessment of CD3, CD4 and CD8 counts since chemotherapy is given in part to induce lymphopenia.

The first dose will be administered using a single dose. The cells are thawed at the patient's bedside. The thawed cells will be given at as rapid an infusion rate as tolerated such that the duration of the infusion will be approximately 10-15 minutes. In order to facilitate mixing, the cells will be administered simultaneously using a Y-adapter. Subjects will be infused and premedicated as described herein. Subjects' vital signs will be assessed and pulse oxymetry done prior to dosing, at the end of the infusion, and every 15 minutes thereafter for 1 hour and until these are stable and satisfactory. A blood sample for determination of a baseline CART-19 level is obtained any time prior to the first infusion and 20 minutes to 4 hours after each infusion (and sent to TCSL).

Patients experiencing toxicities related to high-dose melphalan will have their infusion schedule delayed until these toxicities have resolved. The specific toxicities warranting delay of T cell infusions include: 1) Pulmonary: Requirement for supplemental oxygen to keep saturation greater than 95% or presence of radiographic abnormalities on chest x-ray that are progressive; 2) Cardiac: New cardiac arrhythmia not controlled with medical management 3) Hypotension requiring vasopressor support. 4) Active Infection: Positive blood cultures for bacteria, fungus, or virus within 48-hours of T cell infusion.

Management of Toxicity

Uncontrolled T cell proliferation. Toxicity associated with allogeneic or autologous T cell infusions has been managed with a course of pharmacologic immunosuppression. T body associated toxicity has been reported to respond to systemic corticosteroids. If uncontrolled T cell proliferation occurs (grade 3 or 4 toxicity related to CART-19 cells), subjects may be treated with corticosteroids. Subjects will be treated with pulse methylprednisolone (2 mg/kg i.v. divided q8 hr×2 days), followed by a rapid taper.

In addition, based on the observations of subjects treated on another protocol, there is some concern for macrophage activation syndrome (MAS), though the CD 19+ tumor burden is expected to be much lower in patients with myeloma than in patients with CLL. Treatment and timing of treatment of this toxicity will be at the discretion of the patient's physician and the study investigator. Suggested management might include: if the subject has a fever greater than 101° F. that lasts more than 2 consecutive days and there is no evidence of infection (negative blood cultures, CXR or other source), tocilizumab 4 mg/kg can be considered. The addition of corticosteroids and anti-TNF therapy can be considered at the physician's discretion.

B cell depletion. It is possible that B cell depletion and hypogammaglobulinemia will occur. This is common with anti-CD20 directed therapies. In the event of clinically significant hypogammaglobulinemia (i.e. systemic infections), subjects will be given intravenous immunoglobulin (IVIG) by established clinical dosing guidelines to restore normal levels of serum immunoglobulin levels, as has been done with Rituximab.

Primary graft failure. Primary graft failure (i.e., non-engraftment) may be more common after second ASCT compared to first ASCT. Eligibility criteria stipulate that sufficient stem cells must be available for rescue reinfusion at the discretion of the treating physician in the event of primary graft failure.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. An isolated chimeric antigen receptor (CAR) molecule comprising a single chain antibody or single chain antibody fragment which comprises an anti-CD19 binding domain, a transmembrane domain, and an intracellular signaling domain comprising a primary intracellular signaling domain and a costimulatory domain, wherein:
  (i) the anti-CD19 binding domain comprises a light chain complementary determining region 1 (LC CDR1) of SEQ ID NO: 25, a light chain complementary determining region 2 (LC CDR2) of SEQ ID NO: 26, and a light chain complementary determining region 3 (LC CDR3) of SEQ ID NO: 27, and a heavy chain complementary determining region 1 (HC CDR1) of SEQ ID NO: 19, a heavy chain complementary determining region 2 (HC CDR2) of SEQ ID NO: 21, 22, or 23, and a heavy chain complementary determining region 3 (HC CDR3) of SEQ ID NO: 24;
  (ii) the primary intracellular signaling domain comprises a native intracellular signaling domain of CD3-zeta, or a variant thereof having at least one modification but not more than 20 modifications of the amino acid sequence of SEQ ID NO: 43; and
  (iii) the costimulatory domain comprises a functional signaling domain of a protein selected from the group consisting of OX40, CD2, CD27, CD28, ICAM-1, LFA-1, 4-1BB, and ICOS.

2. The isolated CAR molecule of claim 1, wherein the anti-CD19 binding domain is a scFv.

3. The isolated CAR molecule of claim 1, wherein the anti-CD19 binding domain comprises a light chain variable region listed in any of SEQ ID NOs: 1-12 and a heavy chain variable region listed in any of SEQ ID NOs: 1-12.

4. The isolated CAR molecule of claim 1, wherein the anti-CD19 binding domain comprises: a light chain variable region comprising an amino acid sequence having at least one, two or three modifications but not more than 30, 20 or 10 modifications of an amino acid sequence of a light chain variable region listed in any of SEQ ID NOs: 1-12, or an amino acid sequence with at least 95% identity to an amino acid sequence of a light chain variable region listed in any of SEQ ID NOs: 1-12.

5. The isolated CAR molecule of claim 1, wherein the anti-CD19 binding domain comprises a heavy chain variable region comprising an amino acid sequence having at least one, two or three modifications but not more than 30, 20 or 10 modifications of an amino acid sequence of a heavy chain variable region listed in any of SEQ ID NOs: 1-12, or an amino acid sequence with at least 95% identity to an amino acid sequence of a heavy chain variable region listed in any of SEQ ID NOs: 1-12.

6. The isolated CAR molecule of claim 1, wherein the anti-CD19 binding domain comprises a sequence selected from the group consisting of SEQ ID NO:1, SEQ ID NO:2, SEQ ID NO:3, SEQ ID NO: 4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12, or an amino acid sequence with at least 95% identity thereto.

7. The isolated CAR molecule of claim 1, wherein the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154.

8. The isolated CAR molecule of claim 1, wherein the transmembrane domain comprises:
  (i) the amino acid sequence of SEQ ID NO: 15; or
  (ii) an amino acid sequence having at least one, two or three modifications but not more than 20, 10 or 5 modifications of the amino acid sequence of SEQ ID NO: 15, or an amino acid sequence with at least 95% identity to the amino acid sequence of SEQ ID NO: 15.

9. The isolated CAR molecule of claim 7, wherein the anti-CD19 binding domain is connected to the transmembrane domain by a hinge region.

10. The isolated CAR molecule of claim 9, wherein the hinge region comprises the amino acid sequence of SEQ ID NO:14 or SEQ ID NO:102, or an amino acid sequence with at least 95% identity thereto.

11. The isolated CAR molecule of claim 1, wherein the costimulatory domain comprises:
  (i) the amino acid sequence of SEQ ID NO: 16; or
  (ii) an amino acid sequence having at least one, two or three modifications but not more than 20, 10 or 5 modifications of the amino acid sequence of SEQ ID NO: 16, or an amino acid sequence with at least 95% identity to the amino acid sequence of SEQ ID NO: 16.

12. The isolated CAR molecule of claim 1, wherein the intracellular signaling domain comprises a functional signaling domain of 4-1BB and/or a functional signaling domain of CD3 zeta.

13. The isolated CAR molecule of claim 1, wherein the intracellular signaling domain comprises:
  (i) the amino acid sequence of SEQ ID NO: 16 and/or the amino acid sequence of SEQ ID NO:17;
  (ii) the amino acid sequence of SEQ ID NO:16 and/or the amino acid sequence of SEQ ID NO:43;
  (iii) an amino acid sequence having at least one, two or three modifications but not more than 20, 10 or 5 modifications of the amino acid sequence of SEQ ID NO:16 and/or the amino acid sequence of SEQ ID NO:17 or SEQ ID NO:43, or an amino acid sequence with at least 95% identity to the amino acid sequence of SEQ ID NO:16 and/or the amino acid sequence of SEQ ID NO:17 or SEQ ID NO:43; or
  (iv) the amino acid sequence of SEQ ID NO: 16 and the amino acid sequence of SEQ ID NO: 17 or SEQ ID NO:43, wherein the sequences comprising the intracellular signaling domain are expressed in the same frame and as a single polypeptide chain.

14. The isolated CAR molecule of claim 1, further comprising a leader sequence.

15. The isolated CAR molecule of claim 14, wherein the leader sequence comprises the amino acid sequence of SEQ ID NO: 13, or an amino acid sequence with at least 95% identity to the amino acid sequence of SEQ ID NO:13.

16. An anti-CD19 binding domain comprising a light chain complementary determining region 1 (LC CDR1) of SEQ ID NO: 25, a light chain complementary determining region 2 (LC CDR2) of SEQ ID NO: 26, and a light chain complementary determining region 3 (LC CDR3) of SEQ ID NO: 27, and a heavy chain complementary determining region 1 (HC CDR1) of SEQ ID NO: 19, a heavy chain complementary determining region 2 (HC CDR2) of SEQ ID NO: 21, 22, or 23, and a heavy chain complementary determining region 3 (HC CDR3) of SEQ ID NO: 24.

17. The anti-CD19 binding domain of claim 16, wherein the anti-CD19 binding domain comprises a light chain variable region and a heavy chain variable region of the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12.

18. The anti-CD19 binding domain of claim 16, wherein the anti-CD19 binding domain comprises: a light chain variable region comprising an amino acid sequence having at least one, two or three modifications but not more than 30, 20 or 10 modifications of an amino acid sequence of a light chain variable region provided in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12 or an amino acid sequence with at least 95% identity to an amino acid sequence of a light chain variable region provided in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12; and/or a heavy chain variable region comprising an amino acid sequence having at least one, two or three modifications but not more than 30, 20 or 10 modifications of an amino acid sequence of a heavy chain variable region provided in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12, or an amino acid sequence with at least 95% identity to an amino acid sequence of a heavy chain variable region provided in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12.

19. The isolated CAR molecule of claim 1, wherein the HC CDR2 comprises the amino acid sequence of SEQ ID NO: 21.

20. The isolated CAR molecule of claim 1, wherein the HC CDR2 comprises the amino acid sequence of SEQ ID NO: 22.

21. The isolated CAR molecule of claim 1, wherein the HC CDR2 comprises the amino acid sequence of SEQ ID NO: 23.

22. The isolated CAR molecule of claim 1, comprising the amino acid sequence of any of SEQ ID NOs: 31-42, or an amino acid sequence with at least 95% identity thereto, without the leader sequence of SEQ ID NO: 13.

23. The isolated CAR molecule of claim 1, comprising the amino acid sequence of SEQ ID NO: 32, without the leader sequence of SEQ ID NO: 13.

24. The isolated CAR molecule of claim 1, comprising, from N-terminus to C-terminus:
 an anti-CD19 binding domain comprising the amino acid sequence of SEQ ID NO: 2,
 a transmembrane domain comprising the amino acid sequence of SEQ ID NO: 15,
 a costimulatory domain comprising the amino acid sequence of SEQ ID NO: 16, and
 a primary intracellular signaling domain comprising the amino acid sequence of SEQ ID NO: 17.

25. An isolated chimeric antigen receptor (CAR) molecule comprising, from N-terminus to C-terminus:
 an anti-CD19 binding domain comprising the amino acid sequence of SEQ ID NO: 2,
 a transmembrane domain comprising the amino acid sequence of SEQ ID NO: 15,
 a costimulatory domain comprising the amino acid sequence of SEQ ID NO: 16, and
 a primary intracellular signaling domain comprising the amino acid sequence of SEQ ID NO: 43.

26. An isolated chimeric antigen receptor (CAR) molecule comprising a single chain antibody or single chain antibody fragment which comprises an anti-CD19 binding domain, a transmembrane domain, and an intracellular signaling domain comprising a primary intracellular signaling domain and a costimulatory domain, wherein:
 (i) the anti-CD19 binding domain comprises a light chain complementary determining region 1 (LC CDR1) of SEQ ID NO: 25, a light chain complementary determining region 2 (LC CDR2) of SEQ ID NO: 26, and a light chain complementary determining region 3 (LC CDR3) of SEQ ID NO: 27, and a heavy chain complementary determining region 1 (HC CDR1) of SEQ ID NO: 19, a heavy chain complementary determining region 2 (HC CDR2) of SEQ ID NO: 21, 22, or 23, and a heavy chain complementary determining region 3 (HC CDR3) of SEQ ID NO: 24;
 (ii) the primary intracellular signaling domain comprises a native intracellular signaling domain of FcR gamma, or a functional fragment thereof; and
 (iii) the costimulatory domain comprises a functional signaling domain of a protein selected from the group consisting of OX40, CD2, CD27, CD28, ICAM-1, LFA-1, 4-1BB, and ICOS.

* * * * *

SEQUENCE LISTING

<160> NUMBER OF SEQ ID NOS: 121

<210> SEQ ID NO 1
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

-continued

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Ser Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser

<210> SEQ ID NO 2
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gln Val Gln Leu Gln Glu
                115                 120                 125

Ser Gly Pro Gly Leu Val Lys Pro Ser Glu Thr Leu Ser Leu Thr Cys
        130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Gln Ser Ser Leu Lys Ser Arg Val Thr Ile Ser
                180                 185                 190

Lys Asp Asn Ser Lys Asn Gln Val Ser Leu Lys Leu Ser Ser Val Thr
                195                 200                 205

Ala Ala Asp Thr Ala Val Tyr Tyr Cys Ala Lys His Tyr Tyr Tyr Gly
        210                 215                 220

Gly Ser Tyr Ala Met Asp Tyr Trp Gly Gln Gly Thr Leu Val Thr Val
225                 230                 235                 240

Ser Ser

<210> SEQ ID NO 3
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
                20                  25                  30

Gly Val Ser Trp Ile Arg Gln Pro Pro Gly Lys Gly Leu Glu Trp Ile
            35                  40                  45

Gly Val Ile Trp Gly Ser Glu Thr Thr Tyr Tyr Ser Ser Ser Leu Lys
        50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Leu Val Thr Val Ser Ser Gly Gly Gly Gly Ser Gly Gly Gly
            115                 120                 125

Gly Ser Gly Gly Gly Gly Ser Glu Ile Val Met Thr Gln Ser Pro Ala
        130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
                180                 185                 190

Ile Pro Ala Arg Phe Ser Gly Ser Gly Ser Gly Thr Asp Tyr Thr Leu
            195                 200                 205

Thr Ile Ser Ser Leu Gln Pro Glu Asp Phe Ala Val Tyr Phe Cys Gln

```
                210                 215                 220
Gln Gly Asn Thr Leu Pro Tyr Thr Phe Gly Gln Gly Thr Lys Leu Glu
225                 230                 235                 240

Ile Lys

<210> SEQ ID NO 4
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys

<210> SEQ ID NO 5
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Glu Ile Val Met Thr Gln Ser Pro Ala Thr Leu Ser Leu Ser Pro Gly
```

```
                    1               5                  10                 15
            Glu Arg Ala Thr Leu Ser Cys Arg Ala Ser Gln Asp Ile Ser Lys Tyr
                            20                  25                  30

Leu Asn Trp Tyr Gln Gln Lys Pro Gly Gln Ala Pro Arg Leu Leu Ile
                            35                  40                  45

Tyr His Thr Ser Arg Leu His Ser Gly Ile Pro Ala Arg Phe Ser Gly
                            50                  55                  60

Ser Gly Ser Gly Thr Asp Tyr Thr Leu Thr Ile Ser Ser Leu Gln Pro
             65                  70                  75                  80

Glu Asp Phe Ala Val Tyr Phe Cys Gln Gln Gly Asn Thr Leu Pro Tyr
                                85                  90                  95

Thr Phe Gly Gln Gly Thr Lys Leu Glu Ile Lys Gly Gly Gly Gly Ser
                            100                 105                 110

Gly Gly Gly Gly Ser Gly Gly Gly Gly Ser Gly Gly Gly Gly Ser Gln
                            115                 120                 125

Val Gln Leu Gln Glu Ser Gly Pro Gly Leu Val Lys Pro Ser Glu Thr
            130                 135                 140

Leu Ser Leu Thr Cys Thr Val Ser Gly Val Ser Leu Pro Asp Tyr Gly
            145                 150                 155                 160

Val Ser Trp Ile Arg Gln Pro Pro Gly Lys Gly Leu Glu Trp Ile Gly
                            165                 170                 175

Val Ile Trp Gly Ser Glu Thr Thr Tyr Tyr Ser Ser Ser Leu Lys Ser
                            180                 185                 190

Arg Val Thr Ile Ser Lys Asp Asn Ser Lys Asn Gln Val Ser Leu Lys
                            195                 200                 205

Leu Ser Ser Val Thr Ala Ala Asp Thr Ala Val Tyr Tyr Cys Ala Lys
                            210                 215                 220

His Tyr Tyr Tyr Gly Gly Ser Tyr Ala Met Asp Tyr Trp Gly Gln Gly
            225                 230                 235                 240

Thr Leu Val Thr Val Ser Ser
                            245

<210> SEQ ID NO 6
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Glu Ile Val Met Thr Gln Ser Pro Ala Thr Leu Ser Leu Ser Pro Gly
             1               5                  10                  15

Glu Arg Ala Thr Leu Ser Cys Arg Ala Ser Gln Asp Ile Ser Lys Tyr
                            20                  25                  30

Leu Asn Trp Tyr Gln Gln Lys Pro Gly Gln Ala Pro Arg Leu Leu Ile
                            35                  40                  45

Tyr His Thr Ser Arg Leu His Ser Gly Ile Pro Ala Arg Phe Ser Gly
                            50                  55                  60

Ser Gly Ser Gly Thr Asp Tyr Thr Leu Thr Ile Ser Ser Leu Gln Pro
             65                  70                  75                  80

Glu Asp Phe Ala Val Tyr Phe Cys Gln Gln Gly Asn Thr Leu Pro Tyr
                                85                  90                  95

Thr Phe Gly Gln Gly Thr Lys Leu Glu Ile Lys Gly Gly Gly Gly Ser
                            100                 105                 110
```

Gly Gly Gly Gly Ser Gly Gly Gly Ser Gly Gly Gly Ser Gln
            115                 120                 125

Val Gln Leu Gln Glu Ser Gly Pro Gly Leu Val Lys Pro Ser Glu Thr
            130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
            165                 170                 175

Val Ile Trp Gly Ser Glu Thr Thr Tyr Tyr Gln Ser Ser Leu Lys Ser
            180                 185                 190

Arg Val Thr Ile Ser Lys Asp Asn Ser Lys Asn Gln Val Ser Leu Lys
            195                 200                 205

Leu Ser Ser Val Thr Ala Ala Asp Thr Ala Val Tyr Tyr Cys Ala Lys
210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
            245

<210> SEQ ID NO 7
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245

<210> SEQ ID NO 8
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
            245

<210> SEQ ID NO 9
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Asn Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Gly Gly Ser Tyr Ala Met Asp Tyr Trp Gly Gln Gly
225                 230                 235                 240

Thr Leu Val Thr Val Ser Ser
                245
```

<210> SEQ ID NO 10
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 10

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95
```

```
Lys His Tyr Tyr Tyr Gly Gly Ser Tyr Ala Met Asp Tyr Trp Gly Gln
                100                 105                 110

Gly Thr Leu Val Thr Val Ser Gly Gly Gly Ser Gly Gly Gly
        115                 120                 125

Gly Ser Gly Gly Gly Ser Gly Gly Gly Ser Glu Ile Val Met
130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
                180                 185                 190

Arg Leu His Ser Gly Ile Pro Ala Arg Phe Ser Gly Ser Gly Ser Gly
                195                 200                 205

Thr Asp Tyr Thr Leu Thr Ile Ser Ser Leu Gln Pro Glu Asp Phe Ala
                210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245

<210> SEQ ID NO 11
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Asn Ser Ser Leu Lys Ser Arg Val Thr Ile Ser
            180                 185                 190
```

```
Lys Asp Asn Ser Lys Asn Gln Val Ser Leu Lys Leu Ser Val Thr
            195                 200                 205

Ala Ala Asp Thr Ala Val Tyr Tyr Cys Ala Lys His Tyr Tyr Gly
    210                 215                 220

Gly Ser Tyr Ala Met Asp Tyr Trp Gly Gln Gly Thr Leu Val Thr Val
225                 230                 235                 240

Ser Ser

<210> SEQ ID NO 12
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Glu Ile Val Met Thr Gln Ser Pro Ala
130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys

<210> SEQ ID NO 13
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 13

Met Ala Leu Pro Val Thr Ala Leu Leu Pro Leu Ala Leu Leu Leu
1               5                   10                  15

His Ala Ala Arg Pro
            20

<210> SEQ ID NO 14
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 15
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 16
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 17
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 17

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 18
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Gly Gly Gly Ser
1               5

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly Val Ser Leu Pro Asp Tyr Gly Val Ser
1               5                   10

<210> SEQ ID NO 20
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Val Ile Trp Gly Ser Glu Thr Thr Tyr Tyr Asn Ser Ala Leu Lys Ser
1               5                   10                  15

<210> SEQ ID NO 21
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21
```

-continued

Val Ile Trp Gly Ser Glu Thr Thr Tyr Tyr Ser Ser Ser Leu Lys Ser
1               5                   10                  15

<210> SEQ ID NO 22
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Val Ile Trp Gly Ser Glu Thr Thr Tyr Tyr Gln Ser Ser Leu Lys Ser
1               5                   10                  15

<210> SEQ ID NO 23
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Val Ile Trp Gly Ser Glu Thr Thr Tyr Tyr Asn Ser Ser Leu Lys Ser
1               5                   10                  15

<210> SEQ ID NO 24
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

His Tyr Tyr Tyr Gly Gly Ser Tyr Ala Met Asp Tyr
1               5                   10

<210> SEQ ID NO 25
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Arg Ala Ser Gln Asp Ile Ser Lys Tyr Leu Asn
1               5                   10

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

His Thr Ser Arg Leu His Ser
1               5

-continued

<210> SEQ ID NO 27
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gln Gln Gly Asn Thr Leu Pro Tyr Thr
1               5

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Tyr Ser Ser Ser Leu
1               5

<210> SEQ ID NO 29
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Tyr Gln Ser Ser Leu
1               5

<210> SEQ ID NO 30
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Tyr Asn Ser Ser Leu
1               5

<210> SEQ ID NO 31
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln

```
            35                  40                  45
Asp Ile Ser Lys Tyr Leu Asn Trp Tyr Gln Gln Lys Pro Gly Gln Ala
             50                  55                  60
Pro Arg Leu Leu Ile Tyr His Thr Ser Arg Leu His Ser Gly Ile Pro
 65                  70                  75                  80
Ala Arg Phe Ser Gly Ser Gly Ser Gly Thr Asp Tyr Thr Leu Thr Ile
                 85                  90                  95
Ser Ser Leu Gln Pro Glu Asp Phe Ala Val Tyr Phe Cys Gln Gln Gly
            100                 105                 110
Asn Thr Leu Pro Tyr Thr Phe Gly Gln Gly Thr Lys Leu Glu Ile Lys
            115                 120                 125
Gly Gly Gly Gly Ser Gly Gly Gly Gly Ser Gly Gly Gly Gly Ser Gln
            130                 135                 140
Val Gln Leu Gln Glu Ser Gly Pro Gly Leu Val Lys Pro Ser Glu Thr
145                 150                 155                 160
Leu Ser Leu Thr Cys Thr Val Ser Gly Val Ser Leu Pro Asp Tyr Gly
                165                 170                 175
Val Ser Trp Ile Arg Gln Pro Pro Gly Lys Gly Leu Glu Trp Ile Gly
                180                 185                 190
Val Ile Trp Gly Ser Glu Thr Thr Tyr Tyr Ser Ser Ser Leu Lys Ser
                195                 200                 205
Arg Val Thr Ile Ser Lys Asp Asn Ser Lys Asn Gln Val Ser Leu Lys
210                 215                 220
Leu Ser Ser Val Thr Ala Ala Asp Thr Ala Val Tyr Tyr Cys Ala Lys
225                 230                 235                 240
His Tyr Tyr Tyr Gly Gly Ser Tyr Ala Met Asp Tyr Trp Gly Gln Gly
                245                 250                 255
Thr Leu Val Thr Val Ser Ser Thr Thr Thr Pro Ala Pro Arg Pro Pro
                260                 265                 270
Thr Pro Ala Pro Thr Ile Ala Ser Gln Pro Leu Ser Leu Arg Pro Glu
            275                 280                 285
Ala Cys Arg Pro Ala Ala Gly Gly Ala Val His Thr Arg Gly Leu Asp
            290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Lys Arg Gly Arg
                325                 330                 335
Lys Lys Leu Leu Tyr Ile Phe Lys Gln Pro Phe Met Arg Pro Val Gln
                340                 345                 350
Thr Thr Gln Glu Glu Asp Gly Cys Ser Cys Arg Phe Pro Glu Glu Glu
            355                 360                 365
Glu Gly Gly Cys Glu Leu Arg Val Lys Phe Ser Arg Ser Ala Asp Ala
            370                 375                 380
Pro Ala Tyr Lys Gln Gly Gln Asn Gln Leu Tyr Asn Glu Leu Asn Leu
385                 390                 395                 400
Gly Arg Arg Glu Glu Tyr Asp Val Leu Asp Lys Arg Arg Gly Arg Asp
                405                 410                 415
Pro Glu Met Gly Gly Lys Pro Arg Arg Lys Asn Pro Gln Glu Gly Leu
                420                 425                 430
Tyr Asn Glu Leu Gln Lys Asp Lys Met Ala Glu Ala Tyr Ser Glu Ile
            435                 440                 445
Gly Met Lys Gly Glu Arg Arg Arg Gly Lys Gly His Asp Gly Leu Tyr
            450                 455                 460
```

-continued

```
Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 32
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Gln Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320
```

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 33
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Ser Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr

```
                180                 185                 190
Gln Gln Lys Pro Gly Gln Ala Pro Arg Leu Leu Ile Tyr His Thr Ser
            195                 200                 205

Arg Leu His Ser Gly Ile Pro Ala Arg Phe Ser Gly Ser Gly Ser Gly
        210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
                245                 250                 255

Gly Thr Lys Leu Glu Ile Lys Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 34
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45
```

-continued

Ser Leu Pro Asp Tyr Gly Val Ser Trp Ile Arg Gln Pro Gly Lys
    50                  55                  60

Gly Leu Glu Trp Ile Gly Val Ile Trp Gly Ser Glu Thr Thr Tyr
 65              70                  75                  80

Gln Ser Ser Leu Lys Ser Arg Val Thr Ile Ser Lys Asp Asn Ser Lys
                 85                  90                  95

Asn Gln Val Ser Leu Lys Leu Ser Ser Val Thr Ala Ala Asp Thr Ala
                100                 105                 110

Val Tyr Tyr Cys Ala Lys His Tyr Tyr Gly Gly Ser Tyr Ala Met
            115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
            180                 185                 190

Gln Gln Lys Pro Gly Gln Ala Pro Arg Leu Leu Ile Tyr His Thr Ser
            195                 200                 205

Arg Leu His Ser Gly Ile Pro Ala Arg Phe Ser Gly Ser Gly Ser Gly
    210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
            245                 250                 255

Gly Thr Lys Leu Glu Ile Lys Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 35
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Asp Ile Ser Lys Tyr Leu Asn Trp Tyr Gln Gln Lys Pro Gly Gln Ala
50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Gly Ser Gly
            130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Ser
        195                 200                 205

Ser Ser Leu Lys Ser Arg Val Thr Ile Ser Lys Asp Asn Ser Lys Asn
    210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
                245                 250                 255

Tyr Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr

```
            325                 330                 335
Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
            355                 360                 365

Phe Pro Glu Glu Glu Glu Gly Cys Glu Leu Arg Val Lys Phe Ser
            370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
                450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 36
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gly
    130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190
```

```
Leu Glu Trp Ile Gly Val Ile Trp Gly Ser Glu Thr Thr Tyr Tyr Gln
            195                 200                 205

Ser Ser Leu Lys Ser Arg Val Thr Ile Ser Lys Asp Asn Ser Lys Asn
        210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Gly Gly Ser Tyr Ala Met Asp
            245                 250                 255

Tyr Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
            290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
            325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
            355                 360                 365

Phe Pro Glu Glu Glu Glu Gly Gly Cys Glu Leu Arg Val Lys Phe Ser
            370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
            405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
            485                 490

<210> SEQ ID NO 37
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45
```

-continued

```
Ser Leu Pro Asp Tyr Gly Val Ser Trp Ile Arg Gln Pro Pro Gly Lys
 50                  55                  60
Gly Leu Glu Trp Ile Gly Val Ile Trp Gly Ser Glu Thr Thr Tyr Tyr
 65                  70                  75                  80
Ser Ser Ser Leu Lys Ser Arg Val Thr Ile Ser Lys Asp Asn Ser Lys
                 85                  90                  95
Asn Gln Val Ser Leu Lys Leu Ser Ser Val Thr Ala Ala Asp Thr Ala
            100                 105                 110
Val Tyr Tyr Cys Ala Lys His Tyr Tyr Gly Gly Ser Tyr Ala Met
        115                 120                 125
Asp Tyr Trp Gly Gln Gly Thr Leu Val Thr Val Ser Ser Gly Gly Gly
130                 135                 140
Gly Ser Gly Gly Gly Gly Ser Gly Gly Gly Gly Ser Gly Gly Gly Gly
145                 150                 155                 160
Ser Glu Ile Val Met Thr Gln Ser Pro Ala Thr Leu Ser Leu Ser Pro
                165                 170                 175
Gly Glu Arg Ala Thr Leu Ser Cys Arg Ala Ser Gln Asp Ile Ser Lys
            180                 185                 190
Tyr Leu Asn Trp Tyr Gln Gln Lys Pro Gly Gln Ala Pro Arg Leu Leu
        195                 200                 205
Ile Tyr His Thr Ser Arg Leu His Ser Gly Ile Pro Ala Arg Phe Ser
210                 215                 220
Gly Ser Gly Ser Gly Thr Asp Tyr Thr Leu Thr Ile Ser Ser Leu Gln
225                 230                 235                 240
Pro Glu Asp Phe Ala Val Tyr Phe Cys Gln Gln Gly Asn Thr Leu Pro
                245                 250                 255
Tyr Thr Phe Gly Gln Gly Thr Lys Leu Glu Ile Lys Thr Thr Thr Pro
            260                 265                 270
Ala Pro Arg Pro Pro Thr Pro Ala Pro Thr Ile Ala Ser Gln Pro Leu
        275                 280                 285
Ser Leu Arg Pro Glu Ala Cys Arg Pro Ala Ala Gly Gly Ala Val His
290                 295                 300
Thr Arg Gly Leu Asp Phe Ala Cys Asp Ile Tyr Ile Trp Ala Pro Leu
305                 310                 315                 320
Ala Gly Thr Cys Gly Val Leu Leu Leu Ser Leu Val Ile Thr Leu Tyr
                325                 330                 335
Cys Lys Arg Gly Arg Lys Lys Leu Leu Tyr Ile Phe Lys Gln Pro Phe
            340                 345                 350
Met Arg Pro Val Gln Thr Thr Gln Glu Glu Asp Gly Cys Ser Cys Arg
        355                 360                 365
Phe Pro Glu Glu Glu Glu Gly Gly Cys Glu Leu Arg Val Lys Phe Ser
370                 375                 380
Arg Ser Ala Asp Ala Pro Ala Tyr Lys Gln Gly Gln Asn Gln Leu Tyr
385                 390                 395                 400
Asn Glu Leu Asn Leu Gly Arg Arg Glu Glu Tyr Asp Val Leu Asp Lys
                405                 410                 415
Arg Arg Gly Arg Asp Pro Glu Met Gly Gly Lys Pro Arg Arg Lys Asn
            420                 425                 430
Pro Gln Glu Gly Leu Tyr Asn Glu Leu Gln Lys Asp Lys Met Ala Glu
        435                 440                 445
Ala Tyr Ser Glu Ile Gly Met Lys Gly Glu Arg Arg Arg Gly Lys Gly
450                 455                 460
His Asp Gly Leu Tyr Gln Gly Leu Ser Thr Ala Thr Lys Asp Thr Tyr
```

```
                465                 470                 475                 480

Asp Ala Leu His Met Gln Ala Leu Pro Pro Arg
                485                 490

<210> SEQ ID NO 38
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Gln Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335
```

```
Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
            355                 360                 365

Phe Pro Glu Glu Glu Glu Gly Gly Cys Glu Leu Arg Val Lys Phe Ser
            370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
                450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 39
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Asp Ile Ser Lys Tyr Leu Asn Trp Tyr Gln Gln Lys Pro Gly Gln Ala
50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Gly Ser Gly
    130                 135                 140

Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190
```

```
Leu Glu Trp Ile Gly Val Ile Trp Gly Ser Glu Thr Thr Tyr Tyr Asn
            195                 200                 205

Ser Ser Leu Lys Ser Arg Val Thr Ile Ser Lys Asp Asn Ser Lys Asn
        210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Gly Gly Ser Tyr Ala Met Asp
                245                 250                 255

Tyr Trp Gly Gln Gly Thr Leu Val Thr Val Ser Ser Thr Thr Pro
                260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
        290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
        370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
        450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 40
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
                35                  40                  45

Asp Ile Ser Lys Tyr Leu Asn Trp Tyr Gln Gln Lys Pro Gly Gln Ala
```

```
                50                  55                  60
Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
                100                 105                 110

Asn Thr Leu Pro Tyr Thr Phe Gly Gln Gly Thr Lys Leu Glu Ile Lys
                115                 120                 125

Gly Gly Gly Gly Ser Gly Gly Gly Ser Gly Gly Gly Ser Gly
130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
                180                 185                 190

Leu Glu Trp Ile Gly Val Ile Trp Gly Ser Glu Thr Thr Tyr Tyr Asn
                195                 200                 205

Ser Ser Leu Lys Ser Arg Val Thr Ile Ser Lys Asp Asn Ser Lys Asn
                210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Gly Ser Tyr Ala Met Asp
                245                 250                 255

Tyr Trp Gly Gln Gly Thr Leu Val Thr Val Ser Ser Thr Thr Thr Pro
                260                 265                 270

Ala Pro Arg Pro Pro Thr Pro Ala Pro Thr Ile Ala Ser Gln Pro Leu
                275                 280                 285

Ser Leu Arg Pro Glu Ala Cys Arg Pro Ala Ala Gly Gly Ala Val His
                290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
                355                 360                 365

Phe Pro Glu Glu Glu Glu Gly Gly Cys Glu Leu Arg Val Lys Phe Ser
                370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
                435                 440                 445

Ala Tyr Ser Glu Ile Gly Met Lys Gly Glu Arg Arg Arg Gly Lys Gly
                450                 455                 460

His Asp Gly Leu Tyr Gln Gly Leu Ser Thr Ala Thr Lys Asp Thr Tyr
465                 470                 475                 480
```

-continued

Asp Ala Leu His Met Gln Ala Leu Pro Pro Arg
                485                 490

<210> SEQ ID NO 41
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Asn Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Gly Gly Ser Tyr Ala Met
            115                 120                 125

Asp Tyr Trp Gly Gln Gly Thr Leu Val Thr Val Ser Ser Gly Gly Gly
        130                 135                 140

Gly Ser Gly Gly Gly Gly Ser Gly Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

-continued

```
Cys Lys Arg Gly Arg Lys Lys Leu Leu Tyr Ile Phe Lys Gln Pro Phe
            340                 345                 350

Met Arg Pro Val Gln Thr Thr Gln Glu Asp Gly Cys Ser Cys Arg
        355                 360                 365

Phe Pro Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 42
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Asn Ser Ser Leu Lys Ser
```

```
        195                 200                 205
Arg Val Thr Ile Ser Lys Asp Asn Ser Lys Asn Gln Val Ser Leu Lys
210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
                260                 265                 270

Thr Pro Ala Pro Thr Ile Ala Ser Gln Pro Leu Ser Leu Arg Pro Glu
                275                 280                 285

Ala Cys Arg Pro Ala Ala Gly Gly Ala Val His Thr Arg Gly Leu Asp
                290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
                355                 360                 365

Glu Gly Gly Cys Glu Leu Arg Val Lys Phe Ser Arg Ser Ala Asp Ala
370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Gly Arg Asp
                405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 43
<211> LENGTH: 112
<212> TYPE: PRT
<213> ORGANISM: Homo sapiens

<400> SEQUENCE: 43

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
                35                  40                  45

Pro Arg Arg Lys Asn Pro Gln Glu Gly Leu Tyr Asn Glu Leu Gln Lys
                50                  55                  60

Asp Lys Met Ala Glu Ala Tyr Ser Glu Ile Gly Met Lys Gly Glu Arg
65              70                  75                  80
```

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 44
<211> LENGTH: 336
<212> TYPE: DNA
<213> ORGANISM: Homo sapiens

<400> SEQUENCE: 44
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga aagataagat ggcggaggcc tacagtgaga ttgggatgaa aggcgagcgc     240 cggagggggca aggggcacga tggcctttac cagggtctca gtacagccac caaggacacc     300
tacgacgccc ttcacatgca ggccctgccc cctcgc                              336

<210> SEQ ID NO 45
<211> LENGTH: 230
<212> TYPE: PRT
<213> ORGANISM: Homo sapiens

<400> SEQUENCE: 45

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230

<210> SEQ ID NO 46
<211> LENGTH: 690
<212> TYPE: DNA
<213> ORGANISM: Homo sapiens

<400> SEQUENCE: 46

```
gagagcaagt acggccctcc ctgcccccct tgccctgccc ccgagttcct gggcggaccc      60
agcgtgttcc tgttcccccc caagcccaag gacaccctga tgatcagccg gaccccgag     120
gtgacctgtg tggtggtgga cgtgtcccag gaggacccg aggtccagtt caactggtac     180
gtggacggcg tggaggtgca caacgccaag accaagcccc gggaggagca gttcaatagc     240
acctaccggg tggtgtccgt gctgaccgtg ctgcaccagg actggctgaa cggcaaggaa     300
tacaagtgta aggtgtccaa caagggcctg cccagcagca tcgagaaaac catcagcaag     360
gccaagggcc agcctcggga gccccaggtg tacaccctgc ccctagcca agaggagatg     420
accaagaacc aggtgtccct gacctgcctg gtgaagggct tctaccccag cgacatcgcc     480
gtggagtggg agagcaacgg ccagcccgag aacaactaca agaccacccc ccctgtgctg     540
gacagcgacg gcagcttctt cctgtacagc cggctgaccg tggacaagag ccggtggcag     600
gagggcaacg tctttagctg ctccgtgatg cacgaggccc tgcacaacca ctacacccag     660
aagagcctga gcctgtccct gggcaagatg                                      690
```

<210> SEQ ID NO 47
<211> LENGTH: 282
<212> TYPE: PRT
<213> ORGANISM: Homo sapiens

<400> SEQUENCE: 47

```
Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205
```

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
                260                 265                 270

Ser Leu Glu Val Ser Tyr Val Thr Asp His
                275                 280

<210> SEQ ID NO 48
<211> LENGTH: 847
<212> TYPE: DNA
<213> ORGANISM: Homo sapiens

<400> SEQUENCE: 48

```
aggtggcccg aaagtcccaa ggcccaggca tctagtgttc ctactgcaca gccccaggca      60
gaaggcagcc tagccaaagc tactactgca cctgccacta cgcgcaatac tggccgtggc     120
ggggaggaga agaaaaagga gaaagagaaa gaagaacagg aagagaggga gaccaagacc     180
cctgaatgtc catcccatac ccagccgctg ggcgtctatc tcttgactcc cgcagtacag     240
gacttgtggc ttagagataa ggccaccttt acatgtttcg tcgtgggctc tgacctgaag     300
gatgcccatt tgacttggga ggttgccgga aaggtaccca caggggggt tgaggaaggg     360
ttgctggagc gccattccaa tggctctcag agccagcact caagactcac ccttccgaga     420
tccctgtgga acgccgggac ctctgtcaca tgtactctaa atcatcctag cctgccccca     480
cagcgtctga tggcccttag agagccagcc gcccaggcac cagttaagct tagcctgaat     540
ctgctcgcca gtagtgatcc cccagaggcc gccagctggc tcttatgcga agtgtccggc     600
tttagcccgc ccaacatctt gctcatgtgg ctggaggacc agcgagaagt gaacaccagc     660
ggcttcgctc cagcccggcc cccaccccag ccgggttcta ccacattctg ggcctggagt     720
gtcttaaggg tcccagcacc acctagcccc cagccagcca catacacctg tgttgtgtcc     780
catgaagata gcaggaccct gctaaatgct tctaggagtc tggaggtttc ctacgtgact     840
gaccatt                                                               847
```

<210> SEQ ID NO 49
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Gly Gly Gly Ser Gly Gly Gly Gly Ser
1               5                   10

<210> SEQ ID NO 50
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

```
Gly Gly Thr Gly Gly Cys Gly Gly Ala Gly Gly Thr Thr Cys Thr Gly
1               5                   10                  15

Gly Ala Gly Gly Thr Gly Gly Ala Gly Gly Thr Thr Cys Cys
                20                  25                  30
```

<210> SEQ ID NO 51
<211> LENGTH: 48
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

```
Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
                20                  25                  30

Ile Pro Ile Gln Glu Asp Tyr Arg Lys Pro Glu Pro Ala Cys Ser Pro
            35                  40                  45
```

<210> SEQ ID NO 52
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123
```

<210> SEQ ID NO 53
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (6)..(30)
<223> OTHER INFORMATION: /replace=" "
<220> FEATURE:
<221> NAME/KEY: MISC_FEATURE
<222> LOCATION: (6)..(30)
<223> OTHER INFORMATION: /note="Variant residues given in the sequence
      have no preference with respect to those in the annotations for
      variant positions"
<220> FEATURE:
<221> NAME/KEY: MISC_FEATURE
<222> LOCATION: (1)..(30)
<223> OTHER INFORMATION: /note="This sequence may encompass 1-6
      "Gly Gly Gly Gly Ser" repeating units"
<220> FEATURE:
<221> NAME/KEY: MISC_FEATURE
<222> LOCATION: (1)..(30)
<223> OTHER INFORMATION: /note="See specification as filed for detailed
      description of substitutions and preferred embodiments"

<400> SEQUENCE: 53

Gly Gly Gly Gly Ser Gly Gly Gly Gly Ser Gly Gly Gly Gly Ser Gly

```
1               5                   10                  15
Gly Gly Gly Ser Gly Gly Gly Gly Ser Gly Gly Gly Gly Ser
            20                  25                  30
```

<210> SEQ ID NO 54
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54

```
atggccctgc ctgtgacagc cctgctgctg cctctggctc tgctgctgca tgccgctaga      60
ccc                                                                   63
```

<210> SEQ ID NO 55
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55

```
accacgacgc cagcgccgcg accaccaaca ccggcgccca ccatcgcgtc gcagcccctg      60
tccctgcgcc agaggcgtg ccggccagcg gcggggggcg cagtgcacac gaggggctg      120 gacttcgcct gtgat                                                      135
```

<210> SEQ ID NO 56
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56

```
atctacatct gggcgccctt ggccgggact tgtggggtcc ttctcctgtc actggttatc      60
accctttact gc                                                         72
```

<210> SEQ ID NO 57
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

```
Tyr Asn Ser Ala Leu
1               5
```

<210> SEQ ID NO 58
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

```
Met Ala Leu Pro Val Thr Ala Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
```

```
                        405                 410                 415
Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 59
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 60
<211> LENGTH: 126
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 60
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126

<210> SEQ ID NO 61
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 61
atggccctcc ctgtcaccgc cctgctgctt ccgctggctc ttctgctcca cgccgctcgg    60
cccgaaattg tgatgaccca gtcacccgcc actcttagcc tttcacccgg tgagcgcgca   120
accctgtctt gcagagcctc ccaagacatc tcaaaatacc ttaattggta tcaacagaag   180
cccggacagg ctcctcgcct tctgatctac cacaccagcc ggctccattc tggaatccct   240
gccaggttca gcggtagcgg atctgggacc gactacaccc tcactatcag ctcactgcag   300
ccagaggact cgctgtgtcta tttctgtcag caagggaaca cctgccctca cctttgga    360 cagggcacca agctcgagat taaaggtgga ggtggcagcg gaggaggtgg gtccggcggt   420
ggaggaagcc aggtccaact ccaagaaagc ggaccgggtc ttgtgaagcc atcagaaact   480
cttctactga cttgtactgt gagcggagtg tctctcccg attacggggt gtcttggatc   540
agacagccac cggggaaggg tctggaatgg attggagtga tttggggctc tgagactact   600
tactactctt catccctcaa gtcacgcgtc accatctcaa aggacaactc taagaatcag   660
gtgtcactga aactgtcatc tgtgaccgca gccgacaccg ccgtgtacta ttgcgctaag   720
cattactatt atggcgggag ctacgcaatg gattactggg gacagggtac tctggtcacc   780
gtgtccagcc accaccatca tcaccatcac cat                                813

<210> SEQ ID NO 62
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62
atggccctcc ctgtcaccgc cctgctgctt ccgctggctc ttctgctcca cgccgctcgg    60
cccgaaattg tgatgaccca gtcacccgcc actcttagcc tttcacccgg tgagcgcgca   120
accctgtctt gcagagcctc ccaagacatc tcaaaatacc ttaattggta tcaacagaag   180
cccggacagg ctcctcgcct tctgatctac cacaccagcc ggctccattc tggaatccct   240
gccaggttca gcggtagcgg atctgggacc gactacaccc tcactatcag ctcactgcag   300
ccagaggact cgctgtgtcta tttctgtcag caagggaaca cctgccctca cctttgga    360
```

| | |
|---|---:|
| cagggcacca agctcgagat taaaggtgga ggtggcagcg gaggaggtgg gtccggcggt | 420 |
| ggaggaagcc aggtccaact ccaagaaagc ggaccgggtc ttgtgaagcc atcagaaact | 480 |
| cttcactga cttgtactgt gagcggagtg tctctcccg attacggggt gtcttggatc | 540 |
| agacagccac cggggaaggg tctggaatgg attggagtga tttggggctc tgagactact | 600 |
| tactaccaat catccctcaa gtcacgcgtc accatctcaa aggacaactc taagaatcag | 660 |
| gtgtcactga aactgtcatc tgtgaccgca gccgacaccg ccgtgtacta ttgcgctaag | 720 |
| cattactatt atggcgggag ctacgcaatg gattactggg gacagggtac tctggtcacc | 780 |
| gtgtccagcc accaccatca tcaccatcac cat | 813 |

```
<210> SEQ ID NO 63
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 63
```

| | |
|---|---:|
| atggctctgc ccgtgaccgc actcctcctg ccactggctc tgctgcttca cgccgctcgc | 60 |
| ccacaagtcc agcttcaaga atcagggcct ggtctggtga agccatctga gactctgtcc | 120 |
| ctcacttgca ccgtgagcgg agtgtccctc ccagactacg gagtgagctg gattagacag | 180 |
| cctcccggaa agggactgga gtggatcgga gtgatttggg gtagcgaaac cacttactat | 240 |
| tcatcttccc tgaagtcacg ggtcaccatt tcaaaggata actcaaagaa tcaagtgagc | 300 |
| ctcaagctct catcagtcac cgccgctgac accgccgtgt attactgtgc caagcattac | 360 |
| tactatggag gtcctacgc catggactac tggggccagg gaactctggt cactgtgtca | 420 |
| tctggtggag gaggtagcgg aggaggcggg agcggtggag gtggctccga aatcgtgatg | 480 |
| acccagagcc ctgcaaccct gtcccttct cccggggaac gggctaccct ttcttgtcgg | 540 |
| gcatcacaag atatctcaaa atacctcaat tggtatcaac agaagccggg acaggcccct | 600 |
| aggcttctta tctaccacac ctctcgcctg catagcggga ttcccgcacg ctttagcggg | 660 |
| tctggaagcg ggaccgacta cactctgacc atctcatctc tccagcccga ggacttcgcc | 720 |
| gtctacttct gccagcaggg taacaccctg ccgtacacct tcggccaggg caccaagctt | 780 |
| gagatcaaac atcaccacca tcatcaccat cac | 813 |

```
<210> SEQ ID NO 64
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64
```

| | |
|---|---:|
| atggctctgc ccgtgaccgc actcctcctg ccactggctc tgctgcttca cgccgctcgc | 60 |
| ccacaagtcc agcttcaaga atcagggcct ggtctggtga agccatctga gactctgtcc | 120 |
| ctcacttgca ccgtgagcgg agtgtccctc ccagactacg gagtgagctg gattagacag | 180 |
| cctcccggaa agggactgga gtggatcgga gtgatttggg gtagcgaaac cacttactat | 240 |
| caatcttccc tgaagtcacg ggtcaccatt tcaaaggata actcaaagaa tcaagtgagc | 300 |
| ctcaagctct catcagtcac cgccgctgac accgccgtgt attactgtgc caagcattac | 360 |

```
tactatggag ggtcctacgc catggactac tggggccagg gaactctggt cactgtgtca    420
tctggtggag gaggtagcgg aggaggcggg agcggtggag gtggctccga aatcgtgatg    480
acccagagcc ctgcaaccct gtcccttcct cccggggaac gggctaccct ttcttgtcgg    540
gcatcacaag atatctcaaa atacctcaat tggtatcaac agaagccggg acaggccccc    600
aggcttctta tctaccacac ctctcgcctg catagcggga ttcccgcacg ctttagcggg    660
tctggaagcg ggaccgacta cactctgacc atctcatctc tccagcccga ggacttcgcc    720
gtctacttct gccagcaggg taacaccctg ccgtacacct tcggccaggg caccaagctt    780
gagatcaaac atcaccacca tcatcaccat cac                                 813
```

<210> SEQ ID NO 65
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65

```
atggccctcc cagtgaccgc tctgctgctg cctctcgcac ttcttctcca tgccgctcgg     60
cctgagatcg tcatgaccca aagccccgct accctgtccc tgtcacccgg cgagagggca    120
accctttcat gcagggccag ccaggacatt tctaagtacc tcaactggta tcagcagaag    180
ccagggcagg ctcctcgcct gctgatctac acaccagcc gcctccacag cggtatcccc     240
gccagatttt ccgggagcgg gtctggaacc gactacaccc tcaccatctc ttctctgcag    300
cccgaggatt tcgccgtcta tttctgccag caggggaata tctgccgta cacccttcggt    360 caaggtacca agctggaaat caaggaggc ggaggatcag gcggtggcgg aagcggagga    420
ggtggctccg gaggaggagg ttcccaagtg cagcttcaag aatcaggacc cggacttgtg    480
aagccatcag aaaccctctc cctgacttgt accgtgtccg gtgtgagcct ccccgactac    540
ggagtctctt ggattcgcca gcctccgggg aagggtcttg aatggattgg ggtgatttgg    600
ggatcagaga ctacttacta ctcttcatca cttaagtcac gggtcaccat cagcaaagat    660
aatagcaaga accaagtgtc acttaagctg tcatctgtga ccgccgctga caccgccgtg    720
tactattgtg ccaaacatta ctattacgga gggtcttatg ctatggacta ctggggacag    780
gggaccctgg tgactgtctc tagccatcac catcaccacc atcatcac                828
```

<210> SEQ ID NO 66
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 66

```
atggccctcc cagtgaccgc tctgctgctg cctctcgcac ttcttctcca tgccgctcgg     60
cctgagatcg tcatgaccca aagccccgct accctgtccc tgtcacccgg cgagagggca    120
accctttcat gcagggccag ccaggacatt tctaagtacc tcaactggta tcagcagaag    180
ccagggcagg ctcctcgcct gctgatctac acaccagcc gcctccacag cggtatcccc     240
gccagatttt ccgggagcgg gtctggaacc gactacaccc tcaccatctc ttctctgcag    300
```

| | |
|---|---|
| cccgaggatt tcgccgtcta tttctgccag caggggaata ctctgccgta caccttcggt | 360 |
| caaggtacca agctggaaat caagggaggc ggaggatcag gcggtggcgg aagcggagga | 420 |
| ggtggctccg gaggaggagg ttcccaagtg cagcttcaag aatcaggacc cggacttgtg | 480 |
| aagccatcag aaaccctctc cctgacttgt accgtgtccg gtgtgagcct ccccgactac | 540 |
| ggagtctctt ggattcgcca gcctccgggg aagggtcttg aatggattgg ggtgatttgg | 600 |
| ggatcagaga ctacttacta ccagtcatca cttaagtcac gggtcaccat cagcaaagat | 660 |
| aatagcaaga accaagtgtc acttaagctg tcatctgtga ccgccgctga caccgccgtg | 720 |
| tactattgtg ccaaacatta ctattacgga gggtcttatg ctatggacta ctggggacag | 780 |
| gggaccctgg tgactgtctc tagccatcac catcaccacc atcatcac | 828 |

<210> SEQ ID NO 67
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67

| | |
|---|---|
| atggcactgc ctgtcactgc cctcctgctg cctctggccc tccttctgca tgccgccagg | 60 |
| ccccaagtcc agctgcaaga gtcaggaccc ggactggtga agccgtctga gactctctca | 120 |
| ctgacttgta ccgtcagcgg cgtgtccctc cccgactacg gagtgtcatg gatccgccaa | 180 |
| cctcccggga aagggcttga atggattggt gtcatctggg gttctgaaac cacctactac | 240 |
| tcatcttccc tgaagtccag ggtgaccatc agcaaggata ttccaagaa ccaggtcagc | 300 |
| cttaagctgt catctgtgac cgctgctgac accgccgtgt attactgcgc caagcactac | 360 |
| tattacggag gaagctacgc tatggactat ggggacaggg cactctcgt gactgtgagc | 420 |
| agcggcggtg gagggtctgg aggtggagga tccgtggtg gtgggtcagg cggaggaggg | 480 |
| agcgagattg tgatgactca gtcaccagcc acccttctc tttcacccgg cgagagagca | 540 |
| accctgagct gtagagccag ccaggacatt tctaagtacc tcaactggta tcagcaaaaa | 600 |
| ccggggcagg cccctcgcct cctgatctac catacctcac gccttcactc tggtatcccc | 660 |
| gctcggttta gcggatcagg atctggtacc gactacactc tgaccatttc agcctgcag | 720 |
| ccagaagatt tcgcagtgta tttctgccag caggcaata ccttccta caccttcggt | 780 |
| cagggaacca agctcgaaat caagcaccat caccatcatc accaccat | 828 |

<210> SEQ ID NO 68
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68

| | |
|---|---|
| atggcactgc ctgtcactgc cctcctgctg cctctggccc tccttctgca tgccgccagg | 60 |
| ccccaagtcc agctgcaaga gtcaggaccc ggactggtga agccgtctga gactctctca | 120 |
| ctgacttgta ccgtcagcgg cgtgtccctc cccgactacg gagtgtcatg gatccgccaa | 180 |
| cctcccggga aagggcttga atggattggt gtcatctggg gttctgaaac cacctactac | 240 |
| cagtcttccc tgaagtccag ggtgaccatc agcaaggata ttccaagaa ccaggtcagc | 300 |

```
cttaagctgt catctgtgac cgctgctgac accgccgtgt attactgcgc caagcactac    360
tattacggag gaagctacgc tatggactat tggggacagg gcactctcgt gactgtgagc    420
agcggcggtg gagggtctgg aggtggagga tccggtggtg gtgggtcagg cggaggaggg    480
agcgagattg tgatgactca gtcaccagcc ccctttctc tttcacccgg cgagagagca    540
accctgagct gtagagccag ccaggacatt tctaagtacc tcaactggta tcagcaaaaa    600
ccggggcagg cccctcgcct cctgatctac catacctcac gccttcactc tggtatcccc    660
gctcggttta gcggatcagg atctggtacc gactacactc tgaccatttc agcctgcag    720 ccagaagatt tcgcagtgta tttctgccag cagggcaata cccttcctta caccttcggt    780
cagggaacca agctcgaaat caagcaccat caccatcatc atcaccac               828
```

```
<210> SEQ ID NO 69
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69
atggccctcc cagtgaccgc tctgctgctg cctctcgcac ttcttctcca tgccgctcgg     60
cctgagatcg tcatgaccca agccccgct accctgtccc tgtcacccgg cgagagggca    120 acccttcat gcagggccag ccaggacatt tctaagtacc tcaactggta tcagcagaag    180
ccagggcagg ctcctcgcct gctgatctac cacaccagcc gcctccacag cggtatcccc    240
gccagatttt ccgggagcgg gtctggaacc gactacaccc tcaccatctc ttctctgcag    300
cccgaggatt tcgccgtcta tttctgccag cagggggaata ctctgccgta caccttcggt    360
caaggtacca agctggaaat caaggggaggc ggaggatcag gcggtggcgg aagcggagga    420
ggtggctccg gaggaggagg ttcccaagtg cagcttcaag aatcaggacc cggacttgtg    480
aagccatcag aaaccctctc cctgacttgt accgtgtccg gtgtgagcct ccccgactac    540
ggagtctctt ggattcgcca gcctccgggg aagggtcttg aatggattgg ggtgatttgg    600
ggatcagaga ctacttacta caattcatca cttaagtcac gggtcaccat cagcaaagat    660
aatagcaaga accaagtgtc acttaagctg tcatctgtga ccgccgctga caccgccgtg    720
tactattgtg ccaaacatta ctattacgga gggtcttatg ctatggacta ctggggacag    780
gggaccctgg tgactgtctc tagccatcac catcaccacc atcatcac               828
```

```
<210> SEQ ID NO 70
<211> LENGTH: 828
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70
atggcactgc ctgtcactgc cctcctgctg cctctggccc tccttctgca tgccgccagg     60
ccccaagtcc agctgcaaga gtcaggaccc ggactggtga agccgtctga gactctctca    120
ctgacttgta ccgtcagcgg cgtgtccctc cccgactacg gagtgtcatg gatccgccaa    180
cctcccggga aagggcttga atggattggt gtcatctggg gttctgaaac cacctactac    240
```

| | |
|---|---|
| aactcttccc tgaagtccag ggtgaccatc agcaaggata attccaagaa ccaggtcagc | 300 |
| cttaagctgt catctgtgac cgctgctgac accgccgtgt attactgcgc caagcactac | 360 |
| tattacggag gaagctacgc tatggactat tggggacagg gcactctcgt gactgtgagc | 420 |
| agcggcggtg gagggtctgg aggtggagga tccggtggtg gtgggtcagg cggaggaggg | 480 |
| agcgagattg tgatgactca gtcaccagcc acccttctc tttcacccgg cgagagagca | 540 |
| accctgagct gtagagccag ccaggacatt tctaagtacc tcaactggta tcagcaaaaa | 600 |
| ccggggcagg cccctcgcct cctgatctac catacctcac gccttcactc tggtatcccc | 660 |
| gctcggttta gcggatcagg atctggtacc gactacactc tgaccatttc agcctgcag | 720 |
| ccagaagatt tcgcagtgta tttctgccag cagggcaata cccttcctta caccttcggt | 780 |
| cagggaacca agctcgaaat caagcaccat caccatcatc accaccat | 828 |

<210> SEQ ID NO 71
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71

| | |
|---|---|
| atggccctcc ctgtcaccgc cctgctgctt ccgctggctc ttctgctcca cgccgctcgg | 60 |
| cccgaaattg tgatgaccca gtcacccgcc actcttagcc tttcacccgg tgagcgcgca | 120 |
| accctgtctt gcagagcctc ccaagacatc tcaaaatacc ttaattggta tcaacagaag | 180 |
| cccggacagg ctcctcgcct tctgatctac cacaccagcc ggctccattc tggaatccct | 240 |
| gccaggttca gcgtagcgg atctgggacc gactacaccc tcactatcag ctcactgcag | 300 |
| ccagaggact cgctgtctta tttctgtcag caagggaaca ccctgcccta cacctttgga | 360 |
| cagggcacca agctcgagat aaaggtgga ggtggcagcg gaggaggtgg gtccggcggt | 420 |
| ggaggaagcc aggtccaact ccaagaaagc ggaccgggtc ttgtgaagcc atcagaaact | 480 |
| ctttcactga cttgtactgt gagcggagtg tctctccccg attacggggt gtcttggatc | 540 |
| agacagccac cggggaaggg tctggaatgg attggagtga tttggggctc tgagactact | 600 |
| tactacaatt catccctcaa gtcacgcgtc accatctcaa aggacaactc taagaatcag | 660 |
| gtgtcactga aactgtcatc tgtgaccgca gccgacaccg ccgtgtacta ttgcgctaag | 720 |
| cattactatt atggcgggag ctacgcaatg gattactggg gacagggtac tctggtcacc | 780 |
| gtgtccagcc accaccatca tcaccatcac cat | 813 |

<210> SEQ ID NO 72
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72

| | |
|---|---|
| atggctctgc ccgtgaccgc actcctcctg ccactggctc tgctgcttca cgccgctcgc | 60 |
| ccacaagtcc agcttcaaga atcagggcct ggtctggtga agccatctga gactctgtcc | 120 |
| ctcacttgca ccgtgagcgg agtgtccctc ccagactacg gagtgagctg gattagacag | 180 |
| cctcccggaa agggactgga gtggatcgga gtgatttggg gtagcgaaac cacttactat | 240 |

```
aactcttccc tgaagtcacg ggtcaccatt tcaaaggata actcaaagaa tcaagtgagc    300
ctcaagctct catcagtcac cgccgctgac accgccgtgt attactgtgc caagcattac    360
tactatggag ggtcctacgc catggactac tggggccagg gaactctggt cactgtgtca    420
tctggtggag gaggtagcgg aggaggcggg agcggtggag gtggctccga aatcgtgatg    480
acccagagcc ctgcaaccct gtccctttct cccggggaac gggctaccct ttcttgtcgg    540
gcatcacaag atatctcaaa ataccctcaat tggtatcaac agaagccggg acaggcccct    600
aggcttctta tctaccacac ctctcgcctg catagcggga ttcccgcacg ctttagcggg    660
tctggaagcg ggaccgacta cactctgacc atctcatctc tccagcccga ggacttcgcc    720
gtctacttct gccagcaggg taacaccctg ccgtacacct tcggccaggg caccaagctt    780
gagatcaaac atcaccacca tcatcaccat cac                                  813
```

<210> SEQ ID NO 73
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 73

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
```

```
                    245                 250                 255
Thr Leu Val Thr Val Ser Ser His His His His His His His
                260                 265                 270

<210> SEQ ID NO 74
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Asp Ile Ser Lys Tyr Leu Asn Trp Tyr Gln Gln Lys Pro Gly Gln Ala
        50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Gly Ser Gln
130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Gln Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser His His His His His His His
            260                 265                 270

<210> SEQ ID NO 75
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75
```

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Thr Val Ser Gly Val
            35                  40                  45

Ser Leu Pro Asp Tyr Gly Val Ser Trp Ile Arg Gln Pro Pro Gly Lys
        50                  55                  60

Gly Leu Glu Trp Ile Gly Val Ile Trp Gly Ser Glu Thr Thr Tyr Tyr
65                  70                  75                  80

Ser Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
                100                 105                 110

Val Tyr Tyr Cys Ala Lys His Tyr Tyr Gly Gly Ser Tyr Ala Met
                115                 120                 125

Asp Tyr Trp Gly Gln Gly Thr Leu Val Thr Val Ser Ser Gly Gly Gly
        130                 135                 140

Gly Ser Gly Gly Gly Ser Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
                180                 185                 190

Gln Gln Lys Pro Gly Gln Ala Pro Arg Leu Leu Ile Tyr His Thr Ser
                195                 200                 205

Arg Leu His Ser Gly Ile Pro Ala Arg Phe Ser Gly Ser Gly Ser Gly
210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
                245                 250                 255

Gly Thr Lys Leu Glu Ile Lys His His His His His His
                260                 265                 270
```

<210> SEQ ID NO 76
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Thr Val Ser Gly Val
            35                  40                  45

Ser Leu Pro Asp Tyr Gly Val Ser Trp Ile Arg Gln Pro Pro Gly Lys
        50                  55                  60

Gly Leu Glu Trp Ile Gly Val Ile Trp Gly Ser Glu Thr Thr Tyr Tyr
65                  70                  75                  80
```

```
Gln Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Gly Gly Ser Tyr Ala Met
        115                 120                 125

Asp Tyr Trp Gly Gln Gly Thr Leu Val Thr Val Ser Ser Gly Gly Gly
        130                 135                 140

Gly Ser Gly Gly Gly Gly Ser Gly Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
                180                 185                 190

Gln Gln Lys Pro Gly Gln Ala Pro Arg Leu Leu Ile Tyr His Thr Ser
            195                 200                 205

Arg Leu His Ser Gly Ile Pro Ala Arg Phe Ser Gly Ser Gly Ser Gly
        210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
                245                 250                 255

Gly Thr Lys Leu Glu Ile Lys His His His His His His
                260                 265                 270

<210> SEQ ID NO 77
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Gly Ser Gly
        130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
```

```
                    165                 170                 175

Leu Pro Asp Tyr Gly Val Ser Trp Ile Arg Gln Pro Gly Lys Gly
            180                 185                 190

Leu Glu Trp Ile Gly Val Ile Trp Gly Ser Glu Thr Thr Tyr Tyr Ser
        195                 200                 205

Ser Ser Leu Lys Ser Arg Val Thr Ile Ser Lys Asp Asn Ser Lys Asn
        210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Gly Gly Ser Tyr Ala Met Asp
                245                 250                 255

Tyr Trp Gly Gln Gly Thr Leu Val Thr Val Ser Ser His His His
            260                 265                 270

His His His His
        275

<210> SEQ ID NO 78
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Gly Ser Gly
        130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Gln
        195                 200                 205

Ser Ser Leu Lys Ser Arg Val Thr Ile Ser Lys Asp Asn Ser Lys Asn
        210                 215                 220

Gln Val Ser Leu Lys Leu Ser Ser Val Thr Ala Ala Asp Thr Ala Val
225                 230                 235                 240
```

```
Tyr Tyr Cys Ala Lys His Tyr Tyr Gly Gly Ser Tyr Ala Met Asp
                245                 250                 255

Tyr Trp Gly Gln Gly Thr Leu Val Thr Val Ser Ser His His His
            260                 265                 270

His His His His
        275

<210> SEQ ID NO 79
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Met Ala Leu Pro Val Thr Ala Leu Leu Leu Pro Leu Ala Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Ser Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Ser Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys His His His His
            260                 265                 270

His His His His
        275

<210> SEQ ID NO 80
<211> LENGTH: 276
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80
```

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Gln Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Ser Gly Gly Gly Ser Gly Gly Gly Gly
145                 150                 155                 160

Ser Glu Ile Val Met Thr Gln Ser Pro Ala Thr Leu Ser Leu Ser Pro
                165                 170                 175

Gly Glu Arg Ala Thr Leu Ser Cys Arg Ala Ser Gln Asp Ile Ser Lys
            180                 185                 190

Tyr Leu Asn Trp Tyr Gln Gln Lys Pro Gly Gln Ala Pro Arg Leu Leu
        195                 200                 205

Ile Tyr His Thr Ser Arg Leu His Ser Gly Ile Pro Ala Arg Phe Ser
    210                 215                 220

Gly Ser Gly Ser Gly Thr Asp Tyr Thr Leu Thr Ile Ser Ser Leu Gln
225                 230                 235                 240

Pro Glu Asp Phe Ala Val Tyr Phe Cys Gln Gln Gly Asn Thr Leu Pro
                245                 250                 255

Tyr Thr Phe Gly Gln Gly Thr Lys Leu Glu Ile Lys His His His His
            260                 265                 270

His His His His
        275

```
<210> SEQ ID NO 81
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81
```

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu

```
            20                  25                  30
Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Ser Gly Gly Gly Ser
            130                 135                 140

Gly Gly Gly Ser Gln Val Gln Leu Gln Glu Ser Gly Pro Gly Leu Val
145                 150                 155                 160

Lys Pro Ser Glu Thr Leu Ser Leu Thr Cys Thr Val Ser Gly Val Ser
                165                 170                 175

Leu Pro Asp Tyr Gly Val Ser Trp Ile Arg Gln Pro Pro Gly Lys Gly
            180                 185                 190

Leu Glu Trp Ile Gly Val Ile Trp Gly Ser Glu Thr Thr Tyr Tyr Asn
        195                 200                 205

Ser Ser Leu Lys Ser Arg Val Thr Ile Ser Lys Asp Asn Ser Lys Asn
210                 215                 220

Gln Val Ser Leu Lys Leu Ser Ser Val Thr Ala Ala Asp Thr Ala Val
225                 230                 235                 240

Tyr Tyr Cys Ala Lys His Tyr Tyr Tyr Gly Ser Tyr Ala Met Asp
                245                 250                 255

Tyr Trp Gly Gln Gly Thr Leu Val Thr Val Ser Ser His His His
            260                 265                 270

His His His His
        275
```

<210> SEQ ID NO 82
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Asn Ser Ser Leu Lys Ser Arg Val Thr Ile Ser Lys Asp Asn Ser Lys
                85                  90                  95
```

```
Asn Gln Val Ser Leu Lys Leu Ser Ser Val Thr Ala Ala Asp Thr Ala
            100                 105                 110
Val Tyr Tyr Cys Ala Lys His Tyr Tyr Gly Gly Ser Tyr Ala Met
            115                 120                 125
Asp Tyr Trp Gly Gln Gly Thr Leu Val Thr Val Ser Ser Gly Gly Gly
            130                 135                 140
Gly Ser Gly Gly Gly Ser Gly Gly Gly Ser Gly Gly Gly Gly
145                 150                 155                 160
Ser Glu Ile Val Met Thr Gln Ser Pro Ala Thr Leu Ser Leu Ser Pro
                    165                 170                 175
Gly Glu Arg Ala Thr Leu Ser Cys Arg Ala Ser Gln Asp Ile Ser Lys
            180                 185                 190
Tyr Leu Asn Trp Tyr Gln Gln Lys Pro Gly Gln Ala Pro Arg Leu Leu
            195                 200                 205
Ile Tyr His Thr Ser Arg Leu His Ser Gly Ile Pro Ala Arg Phe Ser
210                 215                 220
Gly Ser Gly Ser Gly Thr Asp Tyr Thr Leu Thr Ile Ser Ser Leu Gln
225                 230                 235                 240
Pro Glu Asp Phe Ala Val Tyr Phe Cys Gln Gln Gly Asn Thr Leu Pro
            245                 250                 255
Tyr Thr Phe Gly Gln Gly Thr Lys Leu Glu Ile Lys His His His His
            260                 265                 270
His His His His
    275

<210> SEQ ID NO 83
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Met Ala Leu Pro Val Thr Ala Leu Leu Leu Pro Leu Ala Leu Leu Leu
1               5                   10                  15
His Ala Ala Arg Pro Glu Ile Val Met Thr Gln Ser Pro Ala Thr Leu
            20                  25                  30
Ser Leu Ser Pro Gly Glu Arg Ala Thr Leu Ser Cys Arg Ala Ser Gln
        35                  40                  45
Asp Ile Ser Lys Tyr Leu Asn Trp Tyr Gln Gln Lys Pro Gly Gln Ala
    50                  55                  60
Pro Arg Leu Leu Ile Tyr His Thr Ser Arg Leu His Ser Gly Ile Pro
65                  70                  75                  80
Ala Arg Phe Ser Gly Ser Gly Ser Gly Thr Asp Tyr Thr Leu Thr Ile
                85                  90                  95
Ser Ser Leu Gln Pro Glu Asp Phe Ala Val Tyr Phe Cys Gln Gln Gly
            100                 105                 110
Asn Thr Leu Pro Tyr Thr Phe Gly Gln Gly Thr Lys Leu Glu Ile Lys
        115                 120                 125
Gly Gly Gly Gly Ser Gly Gly Gly Gly Ser Gly Gly Gly Gly Ser Gln
    130                 135                 140
Val Gln Leu Gln Glu Ser Gly Pro Gly Leu Val Lys Pro Ser Glu Thr
145                 150                 155                 160
```

```
Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Asn Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser His His His His His His His
                260                 265                 270
```

<210> SEQ ID NO 84
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 84

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Val
        35                  40                  45

Ser Leu Pro Asp Tyr Gly Val Ser Trp Ile Arg Gln Pro Pro Gly Lys
    50                  55                  60

Gly Leu Glu Trp Ile Gly Val Ile Trp Gly Ser Glu Thr Thr Tyr Tyr
65                  70                  75                  80

Asn Ser Ser Leu Lys Ser Arg Val Thr Ile Ser Lys Asp Asn Ser Lys
                85                  90                  95

Asn Gln Val Ser Leu Lys Leu Ser Ser Val Thr Ala Ala Asp Thr Ala
            100                 105                 110

Val Tyr Tyr Cys Ala Lys His Tyr Tyr Tyr Gly Gly Ser Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Glu Ile Val Met
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Asp Ile Ser Lys Tyr Leu Asn Trp Tyr
            180                 185                 190

Gln Gln Lys Pro Gly Gln Ala Pro Arg Leu Leu Ile Tyr His Thr Ser
        195                 200                 205

Arg Leu His Ser Gly Ile Pro Ala Arg Phe Ser Gly Ser Gly Ser Gly
    210                 215                 220

Thr Asp Tyr Thr Leu Thr Ile Ser Ser Leu Gln Pro Glu Asp Phe Ala
225                 230                 235                 240

Val Tyr Phe Cys Gln Gln Gly Asn Thr Leu Pro Tyr Thr Phe Gly Gln
```

```
                245                 250                 255
Gly Thr Lys Leu Glu Ile Lys His His His His His His His
            260                 265                 270

<210> SEQ ID NO 85
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
atggccctcc ctgtcaccgc cctgctgctt ccgctggctc ttctgctcca cgccgctcgg      60
cccgaaattg tgatgaccca gtcacccgcc actcttagcc tttcacccgg tgagcgcgca     120
accctgtctt gcagagcctc ccaagacatc tcaaaatacc ttaattggta tcaacagaag     180
cccggacagg ctcctcgcct tctgatctac cacaccagcc ggctccattc tggaatccct     240
gccaggttca gcggtagcgg atctgggacc gactacaccc tcactatcag ctcactgcag     300
ccagaggact cgctgtctta tttctgtcag caagggaaca ccctgcccta cacctttgga     360
cagggcacca agctcgagat taaggtggag gtggcagcg aggaggtgg gtccggcggt     420 ggaggaagcc aggtccaact ccaagaaagc ggacccggtc ttgtgaagcc atcagaaact     480
ctttcactga cttgtactgt gagcggagtg tctctccccg attacggggt gtcttggatc     540
agacagccac cggggaaggg tctggaatgg attggagtga tttggggctc tgagactact     600
tactactctt catccctcaa gtcacgcgtc accatctcaa aggacaactc taagaatcag     660
gtgtcactga aactgtcatc tgtgaccgca gccgacaccg ccgtgtacta ttgcgctaag     720
cattactatt atggcgggag ctacgcaatg gattactggg gacagggtac tctggtcacc     780
gtgtccagca ccactacccc agcaccgagg ccacccaccc cggctcctac catcgcctcc     840
cagcctctgt ccctgcgtcc ggaggcatgt agacccgcag ctggtgggc cgtgcatacc     900 cggggtcttg acttcgcctg cgatatctac atttgggccc ctctggctgg tacttgcggg     960
gtcctgctgc tttcactcgt gatcactctt tactgtaagc gcggtcggaa gaagctgctg    1020
tacatcttta gcaaccctt catgaggcct gtgcagacta ctcaagagga ggacggctgt    1080
tcatgccggt tcccagagga ggaggaaggc ggctgcgaac tgcgcgtgaa attcagccgc    1140
agcgcagatg ctccagccta caagcagggg cagaaccagc tctacaacga actcaatctt    1200
ggtcggagag aggagtacga cgtgctggac aagcggagag acgggacccc agaaatgggc    1260
gggaagccgc gcagaaagaa tccccaagag ggcctgtaca acgagctcca aaaggataag    1320
atggcagaag cctatagcga gattggtatg aaagggaac gcagaagagg caaaggccac    1380
gacggactgt accagggact cagcaccgcc accaaggaca cctatgacgc tcttcacatg    1440
caggccctgc cgcctcgg                                                   1458

<210> SEQ ID NO 86
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 86
```

| | |
|---|---|
| atggccctcc ctgtcaccgc cctgctgctt ccgctggctc ttctgctcca cgccgctcgg | 60 |
| cccgaaattg tgatgaccca gtcacccgcc actcttagcc tttcacccgg tgagcgcgca | 120 |
| accctgtctt gcagagcctc ccaagacatc tcaaaatacc ttaattggta tcaacagaag | 180 |
| cccggacagg ctcctcgcct tctgatctac acaccagcc ggctccattc tggaatccct | 240 |
| gccaggttca gcggtagcgg atctgggacc gactacaccc tcactatcag ctcactgcag | 300 |
| ccagaggact cgctgtcta tttctgtcag caagggaaca ccctgcccta cacctttgga | 360 |
| cagggcacca agctcgagat taaaggtgga ggtggcagcg gaggaggtgg gtccggcggt | 420 |
| ggaggaagcc aggtccaact ccaagaaagc ggacccggtc ttgtgaagcc atcagaaact | 480 |
| cttcactga cttgtactgt gagcggagtg tctctcccg attacggggt gtcttggatc | 540 |
| agacagccac cggggaaggg tctggaatgg attggagtga tttggggctc tgagactact | 600 |
| tactaccaat catccctcaa gtcacgcgtc accatctcaa aggacaactc taagaatcag | 660 |
| gtgtcactga aactgtcatc tgtgaccgca gccgacaccg ccgtgtacta ttgcgctaag | 720 |
| cattactatt atggcgggag ctacgcaatg gattactggg acagggtac tctggtcacc | 780 |
| gtgtccagca ccactacccc agcaccgagg ccacccaccc cggctcctac catcgcctcc | 840 |
| cagcctctgt ccctgcgtcc ggaggcatgt agacccgcag ctggtggggc cgtgcatacc | 900 |
| cggggtcttg acttcgcctg cgatatctac atttgggccc ctctggctgg tacttgcggg | 960 |
| gtcctgctgc tttcactcgt gatcactctt tactgtaagc gcggtcggaa gaagctgctg | 1020 |
| tacatcttta gcaaccctt catgaggcct gtgcagacta ctcaagagga ggacggctgt | 1080 |
| tcatgccggt tccagagga ggaggaaggc ggctgcgaac tgcgcgtgaa attcagccgc | 1140 |
| agcgcagatg ctccagccta caagcagggg cagaaccagc tctacaacga actcaatctt | 1200 |
| ggtcggagag aggagtacga cgtgctggac aagcggagag gacgggaccc agaaatgggc | 1260 |
| gggaagccgc gcagaaagaa tccccaagag ggcctgtaca cgagctcca aaaggataag | 1320 |
| atggcagaag cctatagcga gattggtatg aaaggggaac gcagaagagg caaaggccac | 1380 |
| gacggactgt accagggact cagcaccgcc accaaggaca cctatgacgc tcttcacatg | 1440 |
| caggccctgc cgcctcgg | 1458 |

<210> SEQ ID NO 87
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 87

| | |
|---|---|
| atggctctgc ccgtgaccgc actcctcctg ccactggctc tgctgcttca cgccgctcgc | 60 |
| ccacaagtcc agcttcaaga atcagggcct ggtctggtga agccatctga gactctgtcc | 120 |
| ctcacttgca ccgtgagcgg agtgtccctc ccagactacg gagtgagctg gattagacag | 180 |
| cctcccggaa agggactgga gtggatcgga gtgatttggg gtagcgaaac cacttactat | 240 |
| tcatcttccc tgaagtcacg ggtcaccatt tcaaaggata actcaaagaa tcaagtgagc | 300 |
| ctcaagctct catcagtcac cgccgctgac accgccgtgt attactgtgc caagcattac | 360 |
| tactatggag gtcctacgc catggactac tggggccagg gaactctggt cactgtgtca | 420 |
| tctggtggag gaggtagcgg aggaggcggg agcggtggag gtggctccga atcgtgatg | 480 |
| acccagagcc ctgcaaccct gtccctttct cccggggaac gggctaccct tcttgtcgg | 540 |

```
gcatcacaag atatctcaaa atacctcaat tggtatcaac agaagccggg acaggcccct      600
aggcttctta tctaccacac ctctcgcctg catagcggga ttcccgcacg ctttagcggg      660
tctggaagcg ggaccgacta cactctgacc atctcatctc tccagcccga ggacttcgcc      720
gtctacttct gccagcaggg taacaccctg ccgtacacct tcggccaggg caccaagctt      780
gagatcaaaa ccactactcc cgctccaagg ccacccaccc ctgccccgac catcgcctct      840
cagccgcttt ccctgcgtcc ggaggcatgt agacccgcag ctggtggggc cgtgcatacc      900
cggggtcttg acttcgcctg cgatatctac atttgggccc ctctggctgg tacttgcggg      960
gtcctgctgc tttcactcgt gatcactctt tactgtaagc gcggtcggaa gaagctgctg     1020
tacatcttta agcaacccctt catgaggcct gtgcagacta ctcaagagga ggacggctgt     1080
tcatgccggt tcccagagga ggaggaaggc ggctgcgaac tgcgcgtgaa attcagccgc     1140
agcgcagatg ctccagccta caagcagggg cagaaccagc tctacaacga actcaatctt     1200
ggtcggagag aggagtacga cgtgctggac aagcggagag acgggaccc agaaatgggc     1260 gggaagccgc gcagaaagaa tccccaagag ggcctgtaca cgagctcca aaaggataag     1320 atggcagaag cctatagcga gattggtatg aaaggggaac gcagaagagg caaaggccac     1380
gacggactgt accagggact cagcaccgcc accaaggaca cctatgacgc tcttcacatg     1440
caggccctgc cgcctcgg                                                   1458

<210> SEQ ID NO 88
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 88
atggctctgc ccgtgaccgc actcctcctg ccactggctc tgctgcttca cgccgctcgc       60
ccacaagtcc agcttcaaga atcagggcct ggtctggtga agccatctga gactctgtcc      120
ctcacttgca ccgtgagcgg agtgtccctc ccagactacg gagtgagctg gattagacag      180
cctcccggaa agggactgga gtggatcgga gtgatttggg gtagcgaaac cacttactat      240
caatcttccc tgaagtcacg ggtcaccatt tcaaaggata actcaaagaa tcaagtgagc      300
ctcaagctct catcagtcac cgccgctgac accgccgtgt attactgtgc caagcattac      360
tactatggag gtcctacgc catggactac tggggccagg gaactctggt cactgtgtca      420
tctggtggag gaggtagcgg aggaggcggg agcggtggag gtggctccga aatcgtgatg      480
acccagagcc ctgcaacccct gtccctttct cccggggaac gggctaccct ttcttgtcgg      540
gcatcacaag atatctcaaa atacctcaat tggtatcaac agaagccggg acaggcccct      600
aggcttctta tctaccacac ctctcgcctg catagcggga ttcccgcacg ctttagcggg      660
tctggaagcg ggaccgacta cactctgacc atctcatctc tccagcccga ggacttcgcc      720
gtctacttct gccagcaggg taacaccctg ccgtacacct tcggccaggg caccaagctt      780
gagatcaaaa ccactactcc cgctccaagg ccacccaccc ctgccccgac catcgcctct      840
cagccgcttt ccctgcgtcc ggaggcatgt agacccgcag ctggtggggc cgtgcatacc      900
cggggtcttg acttcgcctg cgatatctac atttgggccc ctctggctgg tacttgcggg      960
gtcctgctgc tttcactcgt gatcactctt tactgtaagc gcggtcggaa gaagctgctg     1020
```

| | |
|---|---|
| tacatcttta agcaaccctt catgaggcct gtgcagacta ctcaagagga ggacggctgt | 1080 |
| tcatgccggt tcccagagga ggaggaaggc ggctgcgaac tgcgcgtgaa attcagccgc | 1140 |
| agcgcagatg ctccagccta caagcagggg cagaaccagc tctacaacga actcaatctt | 1200 |
| ggtcggagag aggagtacga cgtgctggac aagcggagag acgggaccc agaaatgggc | 1260 |
| gggaagccgc gcagaaagaa tccccaagag ggcctgtaca cgagctcca aaggataag | 1320 |
| atggcagaag cctatagcga gattggtatg aaaggggaac gcagaagagg caaaggccac | 1380 |
| gacggactgt accagggact cagcaccgcc accaaggaca cctatgacgc tcttcacatg | 1440 |
| caggccctgc cgcctcgg | 1458 |

<210> SEQ ID NO 89
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 89

| | |
|---|---|
| atggccctcc ctgtcaccgc cctgctgctt ccgctggctc ttctgctcca cgccgctcgg | 60 |
| cccgaaattg tgatgaccca gtcacccgcc actcttagcc tttcacccgg tgagcgcgca | 120 |
| accctgtctt gcagagcctc ccaagacatc tcaaaatacc ttaattggta tcaacagaag | 180 |
| cccggacagg ctcctcgcct tctgatctac cacaccagcc ggctccattc tggaatccct | 240 |
| gccaggttca gcgtagcgg atctgggacc gactacaccc tcactatcag ctcactgcag | 300 |
| ccagaggact cgctgtctca tttctgtcag caagggaaca ccctgcccta cacctttgga | 360 |
| cagggcacca gctcgagat aaaggtgga ggtggcagcg gaggaggtgg gtccggcggt | 420 |
| ggaggaagcg gcggaggcgg gagccaggtc caactccaag aaagcggacc gggtcttgtg | 480 |
| aagccatcag aaactctttc actgacttgt actgtgagcg gagtgtctct ccccgattac | 540 |
| ggggtgtctt ggatcagaca gccaccgggg aagggtctgg aatggattgg agtgatttgg | 600 |
| ggctctgaga ctacttacta ctcttcatcc ctcaagtcac gcgtcaccat ctcaaaggac | 660 |
| aactctaaga tcaggtgtc actgaaactg tcatctgtga ccgcagccga caccgccgtg | 720 |
| tactattgcg ctaagcatta ctattatggc ggggagctacg caatggatta ctggggacag | 780 |
| ggtactctgg tcaccgtgtc cagcaccact accccagcac cgaggccacc caccccggct | 840 |
| cctaccatcg cctcccagcc tctgtccctg cgtccgagg catgtagacc cgcagctggt | 900 |
| ggggccgtgc ataccccggg tcttgacttc gcctgcgata tctacatttg ggccctctg | 960 |
| gctggtactt gcgggtcct gctgctttca ctcgtgatca ctcttactg taagcgcggt | 1020 |
| cggaagaagc tgctgtacat ctttaagcaa cccttcatga ggcctgtgca gactactcaa | 1080 |
| gaggaggacg gctgttcatg ccggttccca gaggaggagg aaggcggctg cgaactgcgc | 1140 |
| gtgaaattca gccgcagcgc agatgctcca gcctacaagc aggggcagaa ccagctctac | 1200 |
| aacgaactca atcttggtcg gagagaggag tacgacgtgc tggacaagcg gagaggacgg | 1260 |
| gacccagaaa tgggcgggaa gccgcgcaga aagaatcccc aagagggcct gtacaacgag | 1320 |
| ctccaaaagg ataagatggc agaagcctat agcgagattg gtatgaaagg ggaacgcaga | 1380 |
| agaggcaaag ccacgacgg actgtaccag ggactcagca ccgccaccaa ggacacctat | 1440 |
| gacgctcttc acatgcaggc cctgccgcct cgg | 1473 |

<210> SEQ ID NO 90
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 90

```
atggccctcc ctgtcaccgc cctgctgctt ccgctggctc ttctgctcca cgccgctcgg    60
cccgaaattg tgatgaccca gtcacccgcc actcttagcc tttcacccgg tgagcgcgca   120
accctgtctt gcagagcctc caagacatc tcaaaatacc ttaattggta tcaacagaag    180
cccggacagg ctcctcgcct tctgatctac cacaccagcc ggctccattc tggaatccct   240
gccaggttca gcgtagcgg atctgggacc gactacaccc tcactatcag ctcactgcag    300
ccagaggact cgctgtcta tttctgtcag caagggaaca ccctgcccta cacctttgga   360
cagggcacca gctcgagat taaaggtgga ggtggcagcg gaggaggtgg gtccggcggt    420
ggaggaagcg gaggcggagg gagccaggtc caactccaag aaagcggacc gggtcttgtg   480
aagccatcag aaactctttc actgacttgt actgtgagcg gagtgtctct ccccgattac   540
ggggtgtctt ggatcagaca gccaccgggg aagggtctgg aatggattgg agtgatttgg   600
ggctctgaga ctacttacta ccaatcatcc ctcaagtcac gcgtcaccat ctcaaaggac   660
aactctaaga tcaggtgtc actgaaactg tcatctgtga ccgcagccga caccgccgtg   720
tactattgcg ctaagcatta ctattatggc gggagctacg caatggatta ctggggacag   780
ggtactctgg tcaccgtgtc cagcaccact accccagcac cgaggccacc caccccggct   840
cctaccatcg cctcccagcc tctgtccctg cgtccggagg catgtagacc cgcagctggt   900
ggggccgtgc atacccgggg tcttgacttc gcctgcgata tctacatttg gccccctctg   960
gctggtactt gcggggtcct gctgctttca ctcgtgatca ctctttactg taagcgcggt  1020
cggaagaagc tgctgtacat ctttaagcaa cccttcatga ggcctgtgca gactactcaa  1080
gaggaggacg gctgttcatg ccggttccca gaggaggagg aaggcggctg cgaactgcgc  1140
gtgaaattca gccgcagcgc agatgctcca gcctacaagc aggggcagaa ccagctctac  1200
aacgaactca atcttggtcg gagagaggag tacgacgtgc tggacaagcg agaggacgg   1260
gacccagaaa tgggcgggaa gccgcgcaga aagaatcccc aagagggcct gtacaacgag  1320
ctccaaaagg ataagatggc agaagcctat agcgagattg gtatgaaagg ggaacgcaga  1380
agaggcaaag gccacgacgg actgtaccag ggactcagca ccgccaccaa ggacacctat  1440
gacgctcttc acatgcaggc cctgccgcct cgg                                1473
```

<210> SEQ ID NO 91
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 91

```
atggctctgc ccgtgaccgc actcctcctg ccactggctc tgctgcttca cgccgctcgc    60
ccacaagtcc agcttcaaga atcagggcct ggtctggtga agccatctga gactctgtcc   120
ctcacttgca ccgtgagcgg agtgtccctc ccagactacg gagtgagctg gattagacag   180
```

```
cctcccggaa agggactgga gtggatcgga gtgatttggg gtagcgaaac cacttactat    240
tcatcttccc tgaagtcacg ggtcaccatt tcaaaggata actcaaagaa tcaagtgagc    300
ctcaagctct catcagtcac cgccgctgac accgccgtgt attactgtgc caagcattac    360
tactatggag ggtcctacgc catggactac tggggccagg gaactctggt cactgtgtca    420
tctggtggag gaggtagcgg aggaggcggg agcggtggag gtggctccgg aggtggcgga    480
agcgaaatcg tgatgaccca gagccctgca accctgtccc tttctcccgg gaacgggct     540 accctttctt gtcgggcatc acaagatatc tcaaaatacc tcaattggta tcaacagaag    600
ccgggacagg cccctaggct tcttatctac cacacctctc gcctgcatag cgggattccc    660
gcacgcttta gcgggtctgg aagcgggacc gactacactc tgaccatctc atctctccag    720
cccgaggact tcgccgtcta cttctgccag caggtaaaca ccctgccgta caccttcggc    780
cagggcacca agcttgagat caaaaccact actcccgctc caaggccacc cacccctgcc    840
ccgaccatcg cctctcagcc gctttccctg cgtccggagg catgtagacc cgcagctggt    900
ggggccgtgc atacccgggg tcttgacttc gcctgcgata tctacatttg ggcccctctg    960
gctggtactt gcggggtcct gctgctttca ctcgtgatca ctcttactg taagcgcggt    1020 cggaagaagc tgctgtacat cttttaagcaa cccttcatga ggcctgtgca gactactcaa   1080
gaggaggacg gctgttcatg ccggttccca gaggaggagg aaggcggctg cgaactgcgc    1140
gtgaaattca gccgcagcgc agatgctcca gcctacaagg aggggcagaa ccagctctac    1200
aacgaactca atcttggtcg gagagaggag tacgacgtgc tggacaagcg gagaggacgg    1260
gacccagaaa tgggcgggaa gccgcgcaga aagaatcccc aagagggcct gtacaacgag    1320
ctccaaaagg ataagatggc agaagcctat agcgagattg gtatgaaagg ggaacgcaga    1380
agaggcaaag gccacgacgg actgtaccag ggactcagca ccgccaccaa ggacacctat    1440
gacgctcttc acatgcaggc cctgccgcct cgg                                 1473
```

<210> SEQ ID NO 92
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 92

```
atggctctgc ccgtgaccgc actcctcctg ccactggctc tgctgcttca cgccgctcgc     60
ccacaagtcc agcttcaaga atcagggcct ggtctggtga agccatctga gactctgtcc    120
ctcacttgca ccgtgagcgg agtgtccctc ccagactacg gagtgagctg gattagacag    180
cctcccggaa agggactgga gtggatcgga gtgatttggg gtagcgaaac cacttactat    240
caatcttccc tgaagtcacg ggtcaccatt tcaaaggata actcaaagaa tcaagtgagc    300
ctcaagctct catcagtcac cgccgctgac accgccgtgt attactgtgc caagcattac    360
tactatggag ggtcctacgc catggactac tggggccagg gaactctggt cactgtgtca    420
tctggtggag gaggtagcgg aggaggcggg agcggtggag gtggctccgg aggcggtggg    480
tcagaaatcg tgatgaccca gagccctgca accctgtccc tttctcccgg ggaacgggct    540
accctttctt gtcgggcatc acaagatatc tcaaaatacc tcaattggta tcaacagaag    600
ccgggacagg cccctaggct tcttatctac cacacctctc gcctgcatag cgggattccc    660
gcacgcttta gcgggtctgg aagcgggacc gactacactc tgaccatctc atctctccag    720
```

```
cccgaggact tcgccgtcta cttctgccag cagggtaaca ccctgccgta caccttcggc    780
cagggcacca agcttgagat caaaaccact actcccgctc caaggccacc caccccctgcc   840 ccgaccatcg cctctcagcc gctttccctg cgtccggagg catgtagacc cgcagctggt    900
ggggccgtgc atacccgggg tcttgacttc gcctgcgata tctacatttg gcccctctg    960 gctggtactt gcggggtcct gctgctttca ctcgtgatca ctctttactg taagcgcggt   1020
cggaagaagc tgctgtacat ctttaagcaa cccttcatga ggcctgtgca gactactcaa   1080
gaggaggacg gctgttcatg ccggttccca gaggaggagg aaggcggctg cgaactgcgc   1140
gtgaaattca gccgcagcgc agatgctcca gcctacaagc aggggcagaa ccagctctac   1200
aacgaactca atcttggtcg gagagaggag tacgacgtgc tggacaagcg gagaggacgg   1260
gacccagaaa tgggcgggaa gccgcgcaga aagaatcccc aagagggcct gtacaacgag   1320
ctccaaaagg ataagatggc agaagcctat agcgagattg gtatgaaagg ggaacgcaga   1380
agaggcaaag gccacgacgg actgtaccag ggactcagca ccgccaccaa ggacacctat   1440
gacgctcttc acatgcaggc cctgccgcct cgg                                1473
```

<210> SEQ ID NO 93
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
atggccctcc ctgtcaccgc cctgctgctt ccgctggctc ttctgctcca cgccgctcgg     60
cccgaaattg tgatgaccca gtcacccgcc actcttagcc tttcacccgg tgagcgcgca    120
accctgtctt gcagagcctc ccaagacatc tcaaaatacc ttaattggta tcaacagaag    180
cccggacagg ctcctcgcct tctgatctac cacaccagcc ggctccattc tggaatccct    240
gccaggttca gcggtagcgg atctgggacc gactacaccc tcactatcag ctcactgcag    300
ccagaggact tcgctgtcta tttctgtcag caagggaaca ccctgcccta cacctttgga    360
cagggcacca agctcgagat taaaggtgga ggtggcagcg gaggaggtgg gtccggcggt    420
ggaggaagcg gaggcggtgg gagccaggtc caactccaag aaagcggacc gggtcttgtg    480
aagccatcag aaactctttc actgacttgt actgtgagcg gagtgtctct ccccgattac    540
ggggtgtctt ggatcagaca gccaccgggg aagggtctgg aatggattgg agtgatttgg    600
ggctctgaga ctacttacta caactcatcc ctcaagtcac gcgtcaccat ctcaaaggac    660
aactctaaga tcaggtgtc actgaaactg tcatctgtga ccgcagccga caccgccgtg    720
tactattgcg ctaagcatta ctattatggc gggagctacg caatggatta ctggggacag    780
ggtactctgg tcaccgtgtc cagcaccact accccagcac cgaggccacc caccccggct    840
cctaccatcg cctcccagcc tctgtccctg cgtccggagg catgtagacc cgcagctggt    900
ggggccgtgc atacccgggg tcttgacttc gcctgcgata tctacatttg gcccctctg    960 gctggtactt gcggggtcct gctgctttca ctcgtgatca ctctttactg taagcgcggt   1020
cggaagaagc tgctgtacat ctttaagcaa cccttcatga ggcctgtgca gactactcaa   1080
gaggaggacg gctgttcatg ccggttccca gaggaggagg aaggcggctg cgaactgcgc   1140
gtgaaattca gccgcagcgc agatgctcca gcctacaagc aggggcagaa ccagctctac   1200
```

```
aacgaactca atcttggtcg agagaggag tacgacgtgc tggacaagcg agaggacgg     1260 gacccagaaa tgggcgggaa gccgcgcaga aagaatcccc aagagggcct gtacaacgag    1320
ctccaaaagg ataagatggc agaagcctat agcgagattg gtatgaaagg ggaacgcaga    1380
agaggcaaag gccacgacgg actgtaccag ggactcagca ccgccaccaa ggacacctat    1440
gacgctcttc acatgcaggc cctgccgcct cgg                                1473
```

<210> SEQ ID NO 94
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 94

```
atggccctcc ctgtcaccgc cctgctgctt ccgctggctc ttctgctcca cgccgctcgg     60
cccgaaattg tgatgaccca gtcacccgcc actcttagcc tttcacccgg tgagcgcgca    120
accctgtctt gcagagcctc ccaagacatc tcaaaatacc ttaattggta tcaacagaag    180
cccggacagg ctcctcgcct tctgatctac cacaccagcc ggctccattc tggaatccct    240
gccaggttca gcgtagcgg atctgggacc gactacaccc tcactatcag ctcactgcag    300
ccagaggact cgctgtcta tttctgtcag caagggaaca ccctgcccta cacctttgga    360
cagggcacca agctcgagat taaaggtgga ggtggcagcg aggaggtgg gtccggcggt    420 ggaggaagcg gaggcggtgg gagccaggtc caactccaag aaagcggacc gggtcttgtg    480
aagccatcag aaactctttc actgacttgt actgtgagcg gagtgtctct ccccgattac    540
ggggtgtctt ggatcagaca gccaccgggg aagggtctgg aatggattgg agtgatttgg    600
ggctctgaga ctacttacta caactcatcc ctcaagtcac gcgtcaccat ctcaaaggac    660
aactctaaga tcaggtgtc actgaaactg tcatctgtga ccgcagccga caccgccgtg    720
tactattgcg ctaagcatta ctattatggc gggagctacg caatggatta ctggggacag    780
ggtactctgg tcaccgtgtc cagcaccact accccagcac cgaggccacc cacccccggct    840 cctaccatcg cctcccagcc tctgtccctg cgtccggagg catgtagacc cgcagctggt    900
ggggccgtgc atacccgggg tcttgacttc gcctgcgata tctacatttg gcccctctg    960 gctggtactt gcggggtcct gctgctttca ctcgtgatca ctctttactg taagcgcggt   1020
cggaagaagc tgctgtacat ctttaagcaa cccttcatga ggcctgtgca gactactcaa   1080
gaggaggacg gctgttcatg ccggttccca gaggaggagg aaggcggctg cgaactgcgc   1140
gtgaaattca gccgcagcgc agatgctcca gcctacaagc aggggcagaa ccagctctac   1200
aacgaactca atcttggtcg agagaggag tacgacgtgc tggacaagcg agaggacgg    1260 gacccagaaa tgggcgggaa gccgcgcaga aagaatcccc aagagggcct gtacaacgag    1320
ctccaaaagg ataagatggc agaagcctat agcgagattg gtatgaaagg ggaacgcaga    1380
agaggcaaag gccacgacgg actgtaccag ggactcagca ccgccaccaa ggacacctat    1440
gacgctcttc acatgcaggc cctgccgcct cgg                                1473
```

<210> SEQ ID NO 95
<211> LENGTH: 1473
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95

| | |
|---|---|
| atggctctgc ccgtgaccgc actcctcctg ccactggctc tgctgcttca cgccgctcgc | 60 |
| ccacaagtcc agcttcaaga tcagggcct ggtctggtga agccatctga gactctgtcc | 120 |
| ctcacttgca ccgtgagcgg agtgtccctc ccagactacg gagtgagctg gattagacag | 180 |
| cctcccggaa agggactgga gtggatcgga gtgatttggg gtagcgaaac cacttactat | 240 |
| aactcttccc tgaagtcacg ggtcaccatt tcaaaggata actcaaagaa tcaagtgagc | 300 |
| ctcaagctct catcagtcac cgccgctgac accgccgtgt attactgtgc caagcattac | 360 |
| tactatggag ggtcctacgc catggactac tggggccagg gaactctggt cactgtgtca | 420 |
| tctggtggag gaggtagcgg aggaggcggg agcggtggag gtggctccgg aggtggcgga | 480 |
| agcgaaatcg tgatgaccca gagccctgca accctgtccc tttctcccgg ggaacgggct | 540 |
| acccttctt gtcgggcatc acaagatatc tcaaaatacc tcaattggta tcaacagaag | 600 |
| ccgggacagg cccctaggct tcttatctac cacacctctc gcctgcatag cgggattccc | 660 |
| gcacgcttta gcgggtctgg aagcgggacc gactacactc tgaccatctc atctctccag | 720 |
| cccgaggact cgccgtctca cttctgccag cagggtaaca ccctgccgta caccttcggc | 780 |
| cagggcacca gcttgagat caaaaccact actcccgctc caaggccacc cacccctgcc | 840 |
| ccgaccatcg cctctcagcc gctttccctg cgtccggagg catgtagacc cgcagctggt | 900 |
| ggggccgtgc atacccgggg tcttgacttc gcctgcgata tctacatttg gccccctctg | 960 |
| gctggtactt gcggggtcct gctgctttca ctcgtgatca ctctttactg taagcgcggt | 1020 |
| cggaagaagc tgctgtacat ctttaagcaa cccttcatga ggcctgtgca gactactcaa | 1080 |
| gaggaggacg gctgttcatg ccggttccca gaggaggagg aaggcggctg cgaactgcgc | 1140 |
| gtgaaattca gccgcagcgc agatgctcca gcctacaagc aggggcagaa ccagctctac | 1200 |
| aacgaactca atcttggtcg gagagaggag tacgacgtgc tggacaagcg gagaggacgg | 1260 |
| gacccagaaa tgggcgggaa gccgcgcaga aagaatcccc aagagggcct gtacaacgag | 1320 |
| ctccaaaagg ataagatggc agaagcctat agcgagattg tatgaaagg ggaacgcaga | 1380 |
| agaggcaaag gccacgacgg actgtaccag ggactcagca ccgccaccaa ggacacctat | 1440 |
| gacgctcttc acatgcaggc cctgccgcct cgg | 1473 |

<210> SEQ ID NO 96
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96

| | |
|---|---|
| atggccctcc ctgtcaccgc cctgctgctt ccgctggctc ttctgctcca cgccgctcgg | 60 |
| cccgaaattg tgatgaccca gtcacccgcc actcttagcc tttcaccgg tgagcgcgca | 120 |
| accctgtctt gcagagcctc ccaagacatc tcaaatacc ttaattggta tcaacagaag | 180 |
| cccggacagg ctcctcgcct tctgatctac cacaccagcc ggctccattc tggaatccct | 240 |
| gccaggttca gcgtagcgg atctgggacc gactacaccc tcactatcag ctcactgcag | 300 |
| ccagaggact cgctgtctca tttctgtcag caagggaaca ccctgcccta cacctttgga | 360 |

```
cagggcacca agctcgagat taaaggtgga ggtggcagcg gaggaggtgg gtccggcggt    420
ggaggaagcc aggtccaact ccaagaaagc ggaccgggtc ttgtgaagcc atcagaaact    480 cttcactga cttgtactgt gagcggagtg tctctccccg attacggggt gtcttggatc    540
agacagccac cggggaaggg tctgaatgg attggagtga tttggggctc tgagactact    600
tactacaact catccctcaa gtcacgcgtc accatctcaa aggacaactc taagaatcag    660
gtgtcactga aactgtcatc tgtgaccgca gccgacaccg ccgtgtacta ttgcgctaag    720
cattactatt atggcgggag ctacgcaatg gattactggg gacagggtac tctggtcacc    780
gtgtccagca ccactacccc agcaccgagg ccacccaccc cggctcctac catcgcctcc    840
cagcctctgt ccctgcgtcc ggaggcatgt agacccgcag ctggtggggc cgtgcatacc    900
cggggtcttg acttcgcctg cgatatctac atttgggccc ctctggctgg tacttgcggg    960
gtcctgctgc tttcactcgt gatcactctt tactgtaagc gcggtcggaa gaagctgctg   1020
tacatcttta gcaacccctt catgaggcct gtgcagacta ctcaagagga ggacggctgt   1080
tcatgccggt tcccagagga ggaggaaggc ggctgcgaac tgcgcgtgaa attcagccgc   1140
agcgcagatg ctccagccta caagcagggg cagaaccagc tctacaacga actcaatctt   1200
ggtcggagag aggagtacga cgtgctggac aagcggagag acgggacccc agaaatgggc   1260
gggaagccgc gcagaaagaa tccccaagag ggcctgtaca cgagctcca aaaggataag   1320 atggcagaag cctatagcga gattggtatg aaaggggaac gcagaagagg caaaggccac   1380
gacggactgt accagggact cagcaccgcc accaaggaca cctatgacgc tcttcacatg   1440
caggccctgc cgcctcgg                                                 1458

<210> SEQ ID NO 97
<211> LENGTH: 813
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
atggccctgc ccgtcaccgc tctgctgctg cccttgctc tgcttcttca tgcagcaagg     60
ccggacatcc agatgaccca aaccacctca tccctctctg cctctcttgg agacagggtg   120
accatttctt gtcgcgccag ccaggacatc agcaagtatc tgaactggta tcagcagaag   180
ccggacggaa ccgtgaagct cctgatctac catacctctc gcctgcatag cggcgtgccc   240
tcacgcttct ctggaagcgg atcaggaacc gattattctc tcactatttc aaatcttgag   300
caggaagata ttgccaccta tttctgccag caggtaata ccctgccta caccttcgga   360 ggagggacca agctcgaaat caccggtgga ggaggcagcg gcggtggagg gtctggtgga   420
ggtggttctg aggtgaagct gcaagaatca ggccctggac ttgtggcccc ttcacagtcc   480
ctgagcgtga cttgcaccgt gtccggagtc tccctgcccg actacggagt gcatggatc   540 agacaacctc cacggaaagg actggaatgg ctcggtgtca tctggggtag cgaaactact   600
tactacaatt cagccctcaa aagcaggctg actattatca aggacaacag caagtcccaa   660
gtctttctta agatgaactc actccagact gacgacaccg caatctacta ttgtgctaag   720
cactactact acggaggatc ctacgctatg gattactggg gacaaggtac ttccgtcact   780
gtctcttcac accatcatca ccatcaccat cac                                813
```

<210> SEQ ID NO 98
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 98

```
Met Ala Leu Pro Val Thr Ala Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
                100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Ser Gly Gly Gly Gly Ser Glu
        130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
                180                 185                 190

Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
        210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser His His His His His His
            260                 265                 270
```

<210> SEQ ID NO 99
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 99

```
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
```

```
ccagatggaa ctgttaaact cctgatctac catacatcaa gattacactc aggagtccca      240
tcaaggttca gtggcagtgg gtctggaaca gattattctc tcaccattag caacctggag      300
caagaagata ttgccactta cttttgccaa cagggtaata cgcttccgta cacgttcgga      360 gggggggacca agctggagat cacaggtggc ggtggctcgg gcggtggtgg gtcgggtggc      420
ggcggatctg aggtgaaact gcaggagtca ggacctggcc tggtggcgcc ctcacagagc      480
ctgtccgtca catgcactgt ctcaggggtc tcattacccg actatggtgt aagctggatt      540
cgccagcctc cacgaaaggg tctggagtgg ctgggagtaa tatgggggtag tgaaaccaca      600 tactataatt cagctctcaa atccagactg accatcatca aggacaactc caagagccaa      660
gttttcttaa aaatgaacag tctgcaaact gatgacacag ccatttacta ctgtgccaaa      720
cattattact acggtggtag ctatgctatg gactactggg gccaaggaac ctcagtcacc      780
gtctcctcaa ccacgacgcc agcgccgcga ccaccaacac cggcgcccac catcgcgtcg      840
cagcccctgt ccctgcgccc agaggcgtgc cggccagcgg cggggggcgc agtgcacacg      900
agggggctgg acttcgcctg tgatatctac atctgggcgc ccttggccgg acttgtgggg      960
gtccttctcc tgtcactggt tatcacccct tactgcaaac ggggcagaaa gaaactcctg     1020
tatatattca acaaccatt tatgagacca gtacaaacta ctcaagagga agatggctgt     1080
agctgccgat ttccagaaga agaagaagga ggatgtgaac tgagagtgaa gttcagcagg     1140
agcgcagacg ccccgcgta caagcagggc cagaaccagc tctataacga gctcaatcta     1200
ggacgaagag aggagtacga tgttttggac aagagacgtg gccgggaccc tgagatgggg     1260
ggaaagccga aaggaagaa ccctcaggaa ggcctgtaca atgaactgca gaaagataag     1320 atggcgagg cctacagtga gattgggatg aaaggcgagc gccggagggg caaggggcac     1380
gatggccttt accagggtct cagtacagcc accaaggaca cctacgacgc ccttcacatg     1440
caggccctgc cccctcgc                                                   1458
```

<210> SEQ ID NO 100
<211> LENGTH: 1184
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 100

```
cgtgaggctc cggtgcccgt cagtgggcag agcgcacatc gcccacagtc cccgagaagt       60 tgggggagg ggtcggcaat tgaaccggtg cctagagaag gtggcgcggg gtaaactggg      120
aaagtgatgt cgtgtactgg ctccgccttt ttcccgaggg tggggagaa ccgtatataa      180 gtgcagtagt cgccgtgaac gttctttttc gcaacgggtt tgccgccaga acacaggtaa      240
gtgccgtgtg tggttcccgc gggcctggcc tctttacggg ttatgcccct tgcgtgcctt      300
gaattacttc cacctggctg cagtacgtga ttcttgatcc cgagcttcgg gttggaagtg      360
ggtgggagag ttcgaggcct tgcgcttaag gagccccttc gcctcgtgct tgagttgagg      420
cctggcctgg gcgctgggc gccgcgtgc gaatctggtg gcaccttcgc gcctgtctcg      480
ctgctttcga taagtctcta gccatttaaa attttttgatg acctgctgcg acgcttttt      540 tctggcaaga tagtcttgta aatgcgggcc aagatctgca cactggtatt tcggtttttg      600
gggccgcggg cggcgacggg gcccgtgcgt cccagcgcac atgttcggcg aggcggggcc      660
```

```
tgcgagcgcg gccaccgaga atcggacggg ggtagtctca agctggccgg cctgctctgg      720
tgcctggcct cgcgccgccg tgtatcgccc cgccctgggc ggcaaggctg gcccggtcgg      780
caccagttgc gtgagcggaa agatggccgc ttcccggccc tgctgcaggg agctcaaaat      840
ggaggacgcg cgcgctcgga gagcgggcgg gtgagtcacc cacacaaagg aaaagggcct      900
ttccgtcctc agccgtcgct tcatgtgact ccacggagta ccgggcgccg tccaggcacc      960
tcgattagtt ctcgagcttt tggagtacgt cgtctttagg ttgggggggag gggtttttatg   1020 cgatggagtt tccccacact gagtgggtgg agactgaagt taggccagct tggcacttga     1080
tgtaattctc cttggaattt gcccttttg agtttggatc ttggttcatt ctcaagcctc      1140
agacagtggt tcaaagtttt tttcttccat ttcaggtgtc gtga                     1184
```

<210> SEQ ID NO 101
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 101

```
agagtgaagt tcagcaggag cgcagacgcc cccgcgtaca agcagggcca gaaccagctc       60
tataacgagc tcaatctagg acgaagagag gagtacgatg ttttggacaa gagacgtggc      120
cgggaccctg agatgggggg aaagccgaga aggaagaacc ctcaggaagg cctgtacaat      180
gaactgcaga aagataagat ggcggaggcc tacagtgaga ttgggatgaa aggcgagcgc      240
cggaggggca aggggcacga tggcctttac cagggtctca gtacagccac caaggacacc      300
tacgacgccc ttcacatgca ggccctgccc cctcgc                               336
```

<210> SEQ ID NO 102
<211> LENGTH: 230
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 102

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
```

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys Met
225                 230

<210> SEQ ID NO 103
<211> LENGTH: 690
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 103
gagagcaagt acggccctcc ctgccccct tgccctgccc ccgagttcct gggcggaccc      60
agcgtgttcc tgttcccccc caagcccaag acaccctga tgatcagccg gaccccgag     120 gtgacctgtg tggtggtgga cgtgtcccag gaggaccccg aggtccagtt caactggtac    180
gtggacggcg tggaggtgca caacgccaag accaagcccc gggaggagca gttcaatagc    240
acctaccggg tggtgtccgt gctgaccgtg ctgcaccagg actggctgaa cggcaaggaa    300
tacaagtgta aggtgtccaa caagggcctg cccagcagca tcgagaaaac catcagcaag    360
gccaagggcc agcctcggga gccccaggtg tacaccctgc cccctagcca agaggagatg    420
accaagaacc aggtgtccct gacctgcctg gtgaagggct tctacccag cgacatcgcc    480 gtggagtggg agagcaacgg ccagcccgag aacaactaca agaccacccc ccctgtgctg    540
gacagcgacg gcagcttctt cctgtacagc cggctgaccg tggacaagag ccggtggcag    600
gagggcaacg tctttagctg ctccgtgatg cacgaggccc tgcacaacca ctacacccag    660
aagagcctga gcctgtccct gggcaagatg                                     690

<210> SEQ ID NO 104
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 104
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa                                     150

<210> SEQ ID NO 105
<211> LENGTH: 40
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (5)..(40)
<223> OTHER INFORMATION: /replace=" "
<220> FEATURE:
<221> NAME/KEY: MISC_FEATURE
<222> LOCATION: (5)..(40)
<223> OTHER INFORMATION: /note="Variant residues given in the sequence
      have no preference with respect to those in the annotations for
      variant positions"
<220> FEATURE:
<221> NAME/KEY: MISC_FEATURE
<222> LOCATION: (1)..(40)
<223> OTHER INFORMATION: /note="This sequence may encompass 1-10
      "Gly Gly Gly Ser" repeating units"

<400> SEQUENCE: 105

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 106
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Gly Gly Gly Gly Ser Gly Gly Gly Ser Gly Gly Gly Gly Ser Gly
1               5                   10                  15

Gly Gly Gly Ser
            20

<210> SEQ ID NO 107
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Gly Gly Gly Gly Ser Gly Gly Gly Gly Ser Gly Gly Gly Gly Ser
1               5                   10                  15

<210> SEQ ID NO 108
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Gly Gly Gly Ser
1
```

<210> SEQ ID NO 109
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: Variation
<222> LOCATION: (51)..(5000)
<223> OTHER INFORMATION: /replace=" "
<220> FEATURE:
<221> NAME/KEY: MISC_FEATURE
<222> LOCATION: (51)..(5000)
<223> OTHER INFORMATION: /note="Variant bases given in the sequence have no preference with respect to those in the annotations for variant positions"

<400> SEQUENCE: 109

```
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaaaa aaaaaaaaaa aaaaaaaaaa     600
aaaaaaaaaa aaaaaaaaaa aaaaaaaaaa aaaaaaaaaa aaaaaaaaaa aaaaaaaaaa     660
aaaaaaaaaa aaaaaaaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaaaaaa    1020
aaaaaaaaaa aaaaaaaaaa aaaaaaaaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaaaaa aaaaaaaaaa aaaaaaaaaa aaaaaaaaaa    1200
aaaaaaaaaa aaaaaaaaaa aaaaaaaaaa aaaaaaaaaa aaaaaaaaaa aaaaaaaaaa    1260
aaaaaaaaaa aaaaaaaaaa aaaaaaaaaa aaaaaaaaaa aaaaaaaaaa aaaaaaaaaa    1320
aaaaaaaaaa aaaaaaaaaa aaaaaaaaaa aaaaaaaaaa aaaaaaaaaa aaaaaaaaaa    1380
aaaaaaaaaa aaaaaaaaaa aaaaaaaaaa aaaaaaaaaa aaaaaaaaaa aaaaaaaaaa    1440
aaaaaaaaaa aaaaaaaaaa aaaaaaaaaa aaaaaaaaaa aaaaaaaaaa aaaaaaaaaa    1500
aaaaaaaaaa aaaaaaaaaa aaaaaaaaaa aaaaaaaaaa aaaaaaaaaa aaaaaaaaaa    1560
aaaaaaaaaa aaaaaaaaaa aaaaaaaaaa aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaaa aaaaaaaaaa aaaaaaaaaa aaaaaaaaaa aaaaaaaaaa aaaaaaaaaa    1740
```

```
aaaaaaaaaa aaaaaaaaaa aaaaaaaaaa aaaaaaaaaa aaaaaaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaaaaaaa aaaaaaaaaa aaaaaaaaaa aaaaaaaaaa    1920
aaaaaaaaaa aaaaaaaaaa aaaaaaaaaa aaaaaaaaaa aaaaaaaaaa aaaaaaaaaa    1980
aaaaaaaaaa aaaaaaaaaa aaaaaaaaaa aaaaaaaaaa aaaaaaaaaa aaaaaaaaaa    2040
aaaaaaaaaa aaaaaaaaaa aaaaaaaaaa aaaaaaaaaa aaaaaaaaaa aaaaaaaaaa    2100
aaaaaaaaaa aaaaaaaaaa aaaaaaaaaa aaaaaaaaaa aaaaaaaaaa aaaaaaaaaa    2160
aaaaaaaaaa aaaaaaaaaa aaaaaaaaaa aaaaaaaaaa aaaaaaaaaa aaaaaaaaaa    2220
aaaaaaaaaa aaaaaaaaaa aaaaaaaaaa aaaaaaaaaa aaaaaaaaaa aaaaaaaaaa    2280
aaaaaaaaaa aaaaaaaaaa aaaaaaaaaa aaaaaaaaaa aaaaaaaaaa aaaaaaaaaa    2340
aaaaaaaaaa aaaaaaaaaa aaaaaaaaaa aaaaaaaaaa aaaaaaaaaa aaaaaaaaaa    2400
aaaaaaaaaa aaaaaaaaaa aaaaaaaaaa aaaaaaaaaa aaaaaaaaaa aaaaaaaaaa    2460
aaaaaaaaaa aaaaaaaaaa aaaaaaaaaa aaaaaaaaaa aaaaaaaaaa aaaaaaaaaa    2520
aaaaaaaaaa aaaaaaaaaa aaaaaaaaaa aaaaaaaaaa aaaaaaaaaa aaaaaaaaaa    2580
aaaaaaaaaa aaaaaaaaaa aaaaaaaaaa aaaaaaaaaa aaaaaaaaaa aaaaaaaaaa    2640
aaaaaaaaaa aaaaaaaaaa aaaaaaaaaa aaaaaaaaaa aaaaaaaaaa aaaaaaaaaa    2700
aaaaaaaaaa aaaaaaaaaa aaaaaaaaaa aaaaaaaaaa aaaaaaaaaa aaaaaaaaaa    2760
aaaaaaaaaa aaaaaaaaaa aaaaaaaaaa aaaaaaaaaa aaaaaaaaaa aaaaaaaaaa    2820
aaaaaaaaaa aaaaaaaaaa aaaaaaaaaa aaaaaaaaaa aaaaaaaaaa aaaaaaaaaa    2880
aaaaaaaaaa aaaaaaaaaa aaaaaaaaaa aaaaaaaaaa aaaaaaaaaa aaaaaaaaaa    2940
aaaaaaaaaa aaaaaaaaaa aaaaaaaaaa aaaaaaaaaa aaaaaaaaaa aaaaaaaaaa    3000
aaaaaaaaaa aaaaaaaaaa aaaaaaaaaa aaaaaaaaaa aaaaaaaaaa aaaaaaaaaa    3060
aaaaaaaaaa aaaaaaaaaa aaaaaaaaaa aaaaaaaaaa aaaaaaaaaa aaaaaaaaaa    3120
aaaaaaaaaa aaaaaaaaaa aaaaaaaaaa aaaaaaaaaa aaaaaaaaaa aaaaaaaaaa    3180
aaaaaaaaaa aaaaaaaaaa aaaaaaaaaa aaaaaaaaaa aaaaaaaaaa aaaaaaaaaa    3240
aaaaaaaaaa aaaaaaaaaa aaaaaaaaaa aaaaaaaaaa aaaaaaaaaa aaaaaaaaaa    3300
aaaaaaaaaa aaaaaaaaaa aaaaaaaaaa aaaaaaaaaa aaaaaaaaaa aaaaaaaaaa    3360
aaaaaaaaaa aaaaaaaaaa aaaaaaaaaa aaaaaaaaaa aaaaaaaaaa aaaaaaaaaa    3420
aaaaaaaaaa aaaaaaaaaa aaaaaaaaaa aaaaaaaaaa aaaaaaaaaa aaaaaaaaaa    3480
aaaaaaaaaa aaaaaaaaaa aaaaaaaaaa aaaaaaaaaa aaaaaaaaaa aaaaaaaaaa    3540
aaaaaaaaaa aaaaaaaaaa aaaaaaaaaa aaaaaaaaaa aaaaaaaaaa aaaaaaaaaa    3600
aaaaaaaaaa aaaaaaaaaa aaaaaaaaaa aaaaaaaaaa aaaaaaaaaa aaaaaaaaaa    3660
aaaaaaaaaa aaaaaaaaaa aaaaaaaaaa aaaaaaaaaa aaaaaaaaaa aaaaaaaaaa    3720
aaaaaaaaaa aaaaaaaaaa aaaaaaaaaa aaaaaaaaaa aaaaaaaaaa aaaaaaaaaa    3780
aaaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa aaaaaaaaaa aaaaaaaaaa aaaaaaaaaa    3900
aaaaaaaaaa aaaaaaaaaa aaaaaaaaaa aaaaaaaaaa aaaaaaaaaa aaaaaaaaaa    3960
aaaaaaaaaa aaaaaaaaaa aaaaaaaaaa aaaaaaaaaa aaaaaaaaaa aaaaaaaaaa    4020
aaaaaaaaaa aaaaaaaaaa aaaaaaaaaa aaaaaaaaaa aaaaaaaaaa aaaaaaaaaa    4080
```

| aaaaaaaaaa aaaaaaaaaa aaaaaaaaaa aaaaaaaaaa aaaaaaaaaa aaaaaaaaaa | 4140 |
| aaaaaaaaaa aaaaaaaaaa aaaaaaaaaa aaaaaaaaaa aaaaaaaaaa aaaaaaaaaa | 4200 |
| aaaaaaaaaa aaaaaaaaaa aaaaaaaaaa aaaaaaaaaa aaaaaaaaaa aaaaaaaaaa | 4260 |
| aaaaaaaaaa aaaaaaaaaa aaaaaaaaaa aaaaaaaaaa aaaaaaaaaa aaaaaaaaaa | 4320 |
| aaaaaaaaaa aaaaaaaaaa aaaaaaaaaa aaaaaaaaaa aaaaaaaaaa aaaaaaaaaa | 4380 |
| aaaaaaaaaa aaaaaaaaaa aaaaaaaaaa aaaaaaaaaa aaaaaaaaaa aaaaaaaaaa | 4440 |
| aaaaaaaaaa aaaaaaaaaa aaaaaaaaaa aaaaaaaaaa aaaaaaaaaa aaaaaaaaaa | 4500 |
| aaaaaaaaaa aaaaaaaaaa aaaaaaaaaa aaaaaaaaaa aaaaaaaaaa aaaaaaaaaa | 4560 |
| aaaaaaaaaa aaaaaaaaaa aaaaaaaaaa aaaaaaaaaa aaaaaaaaaa aaaaaaaaaa | 4620 |
| aaaaaaaaaa aaaaaaaaaa aaaaaaaaaa aaaaaaaaaa aaaaaaaaaa aaaaaaaaaa | 4680 |
| aaaaaaaaaa aaaaaaaaaa aaaaaaaaaa aaaaaaaaaa aaaaaaaaaa aaaaaaaaaa | 4740 |
| aaaaaaaaaa aaaaaaaaaa aaaaaaaaaa aaaaaaaaaa aaaaaaaaaa aaaaaaaaaa | 4800 |
| aaaaaaaaaa aaaaaaaaaa aaaaaaaaaa aaaaaaaaaa aaaaaaaaaa aaaaaaaaaa | 4860 |
| aaaaaaaaaa aaaaaaaaaa aaaaaaaaaa aaaaaaaaaa aaaaaaaaaa aaaaaaaaaa | 4920 |
| aaaaaaaaaa aaaaaaaaaa aaaaaaaaaa aaaaaaaaaa aaaaaaaaaa aaaaaaaaaa | 4980 |
| aaaaaaaaaa aaaaaaaaaa | 5000 |

<210> SEQ ID NO 110
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 110

| tttttttttt tttttttttt tttttttttt tttttttttt tttttttttt tttttttttt | 60 |
| tttttttttt tttttttttt tttttttttt tttttttttt | 100 |

<210> SEQ ID NO 111
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: Variation
<222> LOCATION: (51)..(5000)
<223> OTHER INFORMATION: /replace=" "
<220> FEATURE:
<221> NAME/KEY: MISC_FEATURE
<222> LOCATION: (51)..(5000)
<223> OTHER INFORMATION: /note="Variant bases given in the sequence have no preference with respect to those in the annotations for variant positions"

<400> SEQUENCE: 111

| tttttttttt tttttttttt tttttttttt tttttttttt tttttttttt tttttttttt | 60 |
| tttttttttt tttttttttt tttttttttt tttttttttt tttttttttt tttttttttt | 120 |
| tttttttttt tttttttttt tttttttttt tttttttttt tttttttttt tttttttttt | 180 |
| tttttttttt tttttttttt tttttttttt tttttttttt tttttttttt tttttttttt | 240 |
| tttttttttt tttttttttt tttttttttt tttttttttt tttttttttt tttttttttt | 300 |

-continued

| | | | | | | |
|---|---|---|---|---|---|---|
| tttttttttt | tttttttttt | tttttttttt | tttttttttt | tttttttttt | tttttttttt | 360 |
| tttttttttt | tttttttttt | tttttttttt | tttttttttt | tttttttttt | tttttttttt | 420 |
| tttttttttt | tttttttttt | tttttttttt | tttttttttt | tttttttttt | tttttttttt | 480 |
| tttttttttt | tttttttttt | tttttttttt | tttttttttt | tttttttttt | tttttttttt | 540 |
| tttttttttt | tttttttttt | tttttttttt | tttttttttt | tttttttttt | tttttttttt | 600 |
| tttttttttt | tttttttttt | tttttttttt | tttttttttt | tttttttttt | tttttttttt | 660 |
| tttttttttt | tttttttttt | tttttttttt | tttttttttt | tttttttttt | tttttttttt | 720 |
| tttttttttt | tttttttttt | tttttttttt | tttttttttt | tttttttttt | tttttttttt | 780 |
| tttttttttt | tttttttttt | tttttttttt | tttttttttt | tttttttttt | tttttttttt | 840 |
| tttttttttt | tttttttttt | tttttttttt | tttttttttt | tttttttttt | tttttttttt | 900 |
| tttttttttt | tttttttttt | tttttttttt | tttttttttt | tttttttttt | tttttttttt | 960 |
| tttttttttt | tttttttttt | tttttttttt | tttttttttt | tttttttttt | tttttttttt | 1020 |
| tttttttttt | tttttttttt | tttttttttt | tttttttttt | tttttttttt | tttttttttt | 1080 |
| tttttttttt | tttttttttt | tttttttttt | tttttttttt | tttttttttt | tttttttttt | 1140 |
| tttttttttt | tttttttttt | tttttttttt | tttttttttt | tttttttttt | tttttttttt | 1200 |
| tttttttttt | tttttttttt | tttttttttt | tttttttttt | tttttttttt | tttttttttt | 1260 |
| tttttttttt | tttttttttt | tttttttttt | tttttttttt | tttttttttt | tttttttttt | 1320 |
| tttttttttt | tttttttttt | tttttttttt | tttttttttt | tttttttttt | tttttttttt | 1380 |
| tttttttttt | tttttttttt | tttttttttt | tttttttttt | tttttttttt | tttttttttt | 1440 |
| tttttttttt | tttttttttt | tttttttttt | tttttttttt | tttttttttt | tttttttttt | 1500 |
| tttttttttt | tttttttttt | tttttttttt | tttttttttt | tttttttttt | tttttttttt | 1560 |
| tttttttttt | tttttttttt | tttttttttt | tttttttttt | tttttttttt | tttttttttt | 1620 |
| tttttttttt | tttttttttt | tttttttttt | tttttttttt | tttttttttt | tttttttttt | 1680 |
| tttttttttt | tttttttttt | tttttttttt | tttttttttt | tttttttttt | tttttttttt | 1740 |
| tttttttttt | tttttttttt | tttttttttt | tttttttttt | tttttttttt | tttttttttt | 1800 |
| tttttttttt | tttttttttt | tttttttttt | tttttttttt | tttttttttt | tttttttttt | 1860 |
| tttttttttt | tttttttttt | tttttttttt | tttttttttt | tttttttttt | tttttttttt | 1920 |
| tttttttttt | tttttttttt | tttttttttt | tttttttttt | tttttttttt | tttttttttt | 1980 |
| tttttttttt | tttttttttt | tttttttttt | tttttttttt | tttttttttt | tttttttttt | 2040 |
| tttttttttt | tttttttttt | tttttttttt | tttttttttt | tttttttttt | tttttttttt | 2100 |
| tttttttttt | tttttttttt | tttttttttt | tttttttttt | tttttttttt | tttttttttt | 2160 |
| tttttttttt | tttttttttt | tttttttttt | tttttttttt | tttttttttt | tttttttttt | 2220 |
| tttttttttt | tttttttttt | tttttttttt | tttttttttt | tttttttttt | tttttttttt | 2280 |
| tttttttttt | tttttttttt | tttttttttt | tttttttttt | tttttttttt | tttttttttt | 2340 |
| tttttttttt | tttttttttt | tttttttttt | tttttttttt | tttttttttt | tttttttttt | 2400 |
| tttttttttt | tttttttttt | tttttttttt | tttttttttt | tttttttttt | tttttttttt | 2460 |
| tttttttttt | tttttttttt | tttttttttt | tttttttttt | tttttttttt | tttttttttt | 2520 |
| tttttttttt | tttttttttt | tttttttttt | tttttttttt | tttttttttt | tttttttttt | 2580 |
| tttttttttt | tttttttttt | tttttttttt | tttttttttt | tttttttttt | tttttttttt | 2640 |

-continued

| | |
|---|---|
| tttttttttt tttttttttt tttttttttt tttttttttt tttttttttt tttttttttt | 2700 |
| tttttttttt tttttttttt tttttttttt tttttttttt tttttttttt tttttttttt | 2760 |
| tttttttttt tttttttttt tttttttttt tttttttttt tttttttttt tttttttttt | 2820 |
| tttttttttt tttttttttt tttttttttt tttttttttt tttttttttt tttttttttt | 2880 |
| tttttttttt tttttttttt tttttttttt tttttttttt tttttttttt tttttttttt | 2940 |
| tttttttttt tttttttttt tttttttttt tttttttttt tttttttttt tttttttttt | 3000 |
| tttttttttt tttttttttt tttttttttt tttttttttt tttttttttt tttttttttt | 3060 |
| tttttttttt tttttttttt tttttttttt tttttttttt tttttttttt tttttttttt | 3120 |
| tttttttttt tttttttttt tttttttttt tttttttttt tttttttttt tttttttttt | 3180 |
| tttttttttt tttttttttt tttttttttt tttttttttt tttttttttt tttttttttt | 3240 |
| tttttttttt tttttttttt tttttttttt tttttttttt tttttttttt tttttttttt | 3300 |
| tttttttttt tttttttttt tttttttttt tttttttttt tttttttttt tttttttttt | 3360 |
| tttttttttt tttttttttt tttttttttt tttttttttt tttttttttt tttttttttt | 3420 |
| tttttttttt tttttttttt tttttttttt tttttttttt tttttttttt tttttttttt | 3480 |
| tttttttttt tttttttttt tttttttttt tttttttttt tttttttttt tttttttttt | 3540 |
| tttttttttt tttttttttt tttttttttt tttttttttt tttttttttt tttttttttt | 3600 |
| tttttttttt tttttttttt tttttttttt tttttttttt tttttttttt tttttttttt | 3660 |
| tttttttttt tttttttttt tttttttttt tttttttttt tttttttttt tttttttttt | 3720 |
| tttttttttt tttttttttt tttttttttt tttttttttt tttttttttt tttttttttt | 3780 |
| tttttttttt tttttttttt tttttttttt tttttttttt tttttttttt tttttttttt | 3840 |
| tttttttttt tttttttttt tttttttttt tttttttttt tttttttttt tttttttttt | 3900 |
| tttttttttt tttttttttt tttttttttt tttttttttt tttttttttt tttttttttt | 3960 |
| tttttttttt tttttttttt tttttttttt tttttttttt tttttttttt tttttttttt | 4020 |
| tttttttttt tttttttttt tttttttttt tttttttttt tttttttttt tttttttttt | 4080 |
| tttttttttt tttttttttt tttttttttt tttttttttt tttttttttt tttttttttt | 4140 |
| tttttttttt tttttttttt tttttttttt tttttttttt tttttttttt tttttttttt | 4200 |
| tttttttttt tttttttttt tttttttttt tttttttttt tttttttttt tttttttttt | 4260 |
| tttttttttt tttttttttt tttttttttt tttttttttt tttttttttt tttttttttt | 4320 |
| tttttttttt tttttttttt tttttttttt tttttttttt tttttttttt tttttttttt | 4380 |
| tttttttttt tttttttttt tttttttttt tttttttttt tttttttttt tttttttttt | 4440 |
| tttttttttt tttttttttt tttttttttt tttttttttt tttttttttt tttttttttt | 4500 |
| tttttttttt tttttttttt tttttttttt tttttttttt tttttttttt tttttttttt | 4560 |
| tttttttttt tttttttttt tttttttttt tttttttttt tttttttttt tttttttttt | 4620 |
| tttttttttt tttttttttt tttttttttt tttttttttt tttttttttt tttttttttt | 4680 |
| tttttttttt tttttttttt tttttttttt tttttttttt tttttttttt tttttttttt | 4740 |
| tttttttttt tttttttttt tttttttttt tttttttttt tttttttttt tttttttttt | 4800 |
| tttttttttt tttttttttt tttttttttt tttttttttt tttttttttt tttttttttt | 4860 |
| tttttttttt tttttttttt tttttttttt tttttttttt tttttttttt tttttttttt | 4920 |
| tttttttttt tttttttttt tttttttttt tttttttttt tttttttttt tttttttttt | 4980 |
| tttttttttt tttttttttt | 5000 |

```
<210> SEQ ID NO 112
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: Variation
<222> LOCATION: (101)..(5000)
<223> OTHER INFORMATION: /replace=" "
<220> FEATURE:
<221> NAME/KEY: MISC_FEATURE
<222> LOCATION: (101)..(5000)
<223> OTHER INFORMATION: /note="Variant bases given in the sequence have
      no preference with respect to those in the annotations for variant
      positions"

<400> SEQUENCE: 112
```

| | | | | | | |
|---|---|---|---|---|---|---|
| aaaaaaaaaa | aaaaaaaaaa | aaaaaaaaaa | aaaaaaaaaa | aaaaaaaaaa | aaaaaaaaaa | 60 |
| aaaaaaaaaa | aaaaaaaaaa | aaaaaaaaaa | aaaaaaaaaa | aaaaaaaaaa | aaaaaaaaaa | 120 |
| aaaaaaaaaa | aaaaaaaaaa | aaaaaaaaaa | aaaaaaaaaa | aaaaaaaaaa | aaaaaaaaaa | 180 |
| aaaaaaaaaa | aaaaaaaaaa | aaaaaaaaaa | aaaaaaaaaa | aaaaaaaaaa | aaaaaaaaaa | 240 |
| aaaaaaaaaa | aaaaaaaaaa | aaaaaaaaaa | aaaaaaaaaa | aaaaaaaaaa | aaaaaaaaaa | 300 |
| aaaaaaaaaa | aaaaaaaaaa | aaaaaaaaaa | aaaaaaaaaa | aaaaaaaaaa | aaaaaaaaaa | 360 |
| aaaaaaaaaa | aaaaaaaaaa | aaaaaaaaaa | aaaaaaaaaa | aaaaaaaaaa | aaaaaaaaaa | 420 |
| aaaaaaaaaa | aaaaaaaaaa | aaaaaaaaaa | aaaaaaaaaa | aaaaaaaaaa | aaaaaaaaaa | 480 |
| aaaaaaaaaa | aaaaaaaaaa | aaaaaaaaaa | aaaaaaaaaa | aaaaaaaaaa | aaaaaaaaaa | 540 |
| aaaaaaaaaa | aaaaaaaaaa | aaaaaaaaaa | aaaaaaaaaa | aaaaaaaaaa | aaaaaaaaaa | 600 |
| aaaaaaaaaa | aaaaaaaaaa | aaaaaaaaaa | aaaaaaaaaa | aaaaaaaaaa | aaaaaaaaaa | 660 |
| aaaaaaaaaa | aaaaaaaaaa | aaaaaaaaaa | aaaaaaaaaa | aaaaaaaaaa | aaaaaaaaaa | 720 |
| aaaaaaaaaa | aaaaaaaaaa | aaaaaaaaaa | aaaaaaaaaa | aaaaaaaaaa | aaaaaaaaaa | 780 |
| aaaaaaaaaa | aaaaaaaaaa | aaaaaaaaaa | aaaaaaaaaa | aaaaaaaaaa | aaaaaaaaaa | 840 |
| aaaaaaaaaa | aaaaaaaaaa | aaaaaaaaaa | aaaaaaaaaa | aaaaaaaaaa | aaaaaaaaaa | 900 |
| aaaaaaaaaa | aaaaaaaaaa | aaaaaaaaaa | aaaaaaaaaa | aaaaaaaaaa | aaaaaaaaaa | 960 |
| aaaaaaaaaa | aaaaaaaaaa | aaaaaaaaaa | aaaaaaaaaa | aaaaaaaaaa | aaaaaaaaaa | 1020 |
| aaaaaaaaaa | aaaaaaaaaa | aaaaaaaaaa | aaaaaaaaaa | aaaaaaaaaa | aaaaaaaaaa | 1080 |
| aaaaaaaaaa | aaaaaaaaaa | aaaaaaaaaa | aaaaaaaaaa | aaaaaaaaaa | aaaaaaaaaa | 1140 |
| aaaaaaaaaa | aaaaaaaaaa | aaaaaaaaaa | aaaaaaaaaa | aaaaaaaaaa | aaaaaaaaaa | 1200 |
| aaaaaaaaaa | aaaaaaaaaa | aaaaaaaaaa | aaaaaaaaaa | aaaaaaaaaa | aaaaaaaaaa | 1260 |
| aaaaaaaaaa | aaaaaaaaaa | aaaaaaaaaa | aaaaaaaaaa | aaaaaaaaaa | aaaaaaaaaa | 1320 |
| aaaaaaaaaa | aaaaaaaaaa | aaaaaaaaaa | aaaaaaaaaa | aaaaaaaaaa | aaaaaaaaaa | 1380 |
| aaaaaaaaaa | aaaaaaaaaa | aaaaaaaaaa | aaaaaaaaaa | aaaaaaaaaa | aaaaaaaaaa | 1440 |
| aaaaaaaaaa | aaaaaaaaaa | aaaaaaaaaa | aaaaaaaaaa | aaaaaaaaaa | aaaaaaaaaa | 1500 |
| aaaaaaaaaa | aaaaaaaaaa | aaaaaaaaaa | aaaaaaaaaa | aaaaaaaaaa | aaaaaaaaaa | 1560 |
| aaaaaaaaaa | aaaaaaaaaa | aaaaaaaaaa | aaaaaaaaaa | aaaaaaaaaa | aaaaaaaaaa | 1620 |
| aaaaaaaaaa | aaaaaaaaaa | aaaaaaaaaa | aaaaaaaaaa | aaaaaaaaaa | aaaaaaaaaa | 1680 |

```
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
aaaaaaaaaa aaaaaaaaaa aaaaaaaaaa aaaaaaaaaa aaaaaaaaaa aaaaaaaaaa   3840
aaaaaaaaaa aaaaaaaaaa aaaaaaaaaa aaaaaaaaaa aaaaaaaaaa aaaaaaaaaa   3900
aaaaaaaaaa aaaaaaaaaa aaaaaaaaaa aaaaaaaaaa aaaaaaaaaa aaaaaaaaaa   3960
aaaaaaaaaa aaaaaaaaaa aaaaaaaaaa aaaaaaaaaa aaaaaaaaaa aaaaaaaaaa   4020
aaaaaaaaaa aaaaaaaaaa aaaaaaaaaa aaaaaaaaaa aaaaaaaaaa aaaaaaaaaa   4080
```

```
aaaaaaaaaa aaaaaaaaaa aaaaaaaaaa aaaaaaaaaa aaaaaaaaaa aaaaaaaaaa    4140
aaaaaaaaaa aaaaaaaaaa aaaaaaaaaa aaaaaaaaaa aaaaaaaaaa aaaaaaaaaa    4200
aaaaaaaaaa aaaaaaaaaa aaaaaaaaaa aaaaaaaaaa aaaaaaaaaa aaaaaaaaaa    4260
aaaaaaaaaa aaaaaaaaaa aaaaaaaaaa aaaaaaaaaa aaaaaaaaaa aaaaaaaaaa    4320
aaaaaaaaaa aaaaaaaaaa aaaaaaaaaa aaaaaaaaaa aaaaaaaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaaaaaa aaaaaaaaaa aaaaaaaaaa aaaaaaaaaa aaaaaaaaaa aaaaaaaaaa    4560
aaaaaaaaaa aaaaaaaaaa aaaaaaaaaa aaaaaaaaaa aaaaaaaaaa aaaaaaaaaa    4620
aaaaaaaaaa aaaaaaaaaa aaaaaaaaaa aaaaaaaaaa aaaaaaaaaa aaaaaaaaaa    4680
aaaaaaaaaa aaaaaaaaaa aaaaaaaaaa aaaaaaaaaa aaaaaaaaaa aaaaaaaaaa    4740
aaaaaaaaaa aaaaaaaaaa aaaaaaaaaa aaaaaaaaaa aaaaaaaaaa aaaaaaaaaa    4800
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
aaaaaaaaaa aaaaaaaaaa                                                5000

<210> SEQ ID NO 113
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: Variation
<222> LOCATION: (101)..(400)
<223> OTHER INFORMATION: /replace=" "
<220> FEATURE:
<221> NAME/KEY: MISC_FEATURE
<222> LOCATION: (101)..(400)
<223> OTHER INFORMATION: /note="Variant bases given in the sequence have
      no preference with respect to those in the annotations for variant
      positions"
<220> FEATURE:
<221> NAME/KEY: MISC_FEATURE
<222> LOCATION: (1)..(400)
<223> OTHER INFORMATION: /note="See specification as filed for detailed
      description of substitutions and preferred embodiments"

<400> SEQUENCE: 113
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa                           400

<210> SEQ ID NO 114
<211> LENGTH: 120
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic polypeptide"

<400> SEQUENCE: 114

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 115
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 116
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 117
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys
            100                 105

<210> SEQ ID NO 118
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: Variation
<222> LOCATION: (51)..(2000)
<223> OTHER INFORMATION: /replace=" "
<220> FEATURE:
<221> NAME/KEY: MISC_FEATURE
<222> LOCATION: (51)..(2000)
<223> OTHER INFORMATION: /note="Variant bases given in the sequence have
      no preference with respect to those in the annotations for variant
      positions"

<400> SEQUENCE: 118

| | | |
|---|---|---|
| aaaaaaaaaa aaaaaaaaaa aaaaaaaaaa aaaaaaaaaa aaaaaaaaaa aaaaaaaaaa | 60 |
| aaaaaaaaaa aaaaaaaaaa aaaaaaaaaa aaaaaaaaaa aaaaaaaaaa aaaaaaaaaa | 120 |
| aaaaaaaaaa aaaaaaaaaa aaaaaaaaaa aaaaaaaaaa aaaaaaaaaa aaaaaaaaaa | 180 |
| aaaaaaaaaa aaaaaaaaaa aaaaaaaaaa aaaaaaaaaa aaaaaaaaaa aaaaaaaaaa | 240 |
| aaaaaaaaaa aaaaaaaaaa aaaaaaaaaa aaaaaaaaaa aaaaaaaaaa aaaaaaaaaa | 300 |
| aaaaaaaaaa aaaaaaaaaa aaaaaaaaaa aaaaaaaaaa aaaaaaaaaa aaaaaaaaaa | 360 |
| aaaaaaaaaa aaaaaaaaaa aaaaaaaaaa aaaaaaaaaa aaaaaaaaaa aaaaaaaaaa | 420 |
| aaaaaaaaaa aaaaaaaaaa aaaaaaaaaa aaaaaaaaaa aaaaaaaaaa aaaaaaaaaa | 480 |
| aaaaaaaaaa aaaaaaaaaa aaaaaaaaaa aaaaaaaaaa aaaaaaaaaa aaaaaaaaaa | 540 |
| aaaaaaaaaa aaaaaaaaaa aaaaaaaaaa aaaaaaaaaa aaaaaaaaaa aaaaaaaaaa | 600 |
| aaaaaaaaaa aaaaaaaaaa aaaaaaaaaa aaaaaaaaaa aaaaaaaaaa aaaaaaaaaa | 660 |
| aaaaaaaaaa aaaaaaaaaa aaaaaaaaaa aaaaaaaaaa aaaaaaaaaa aaaaaaaaaa | 720 |
| aaaaaaaaaa aaaaaaaaaa aaaaaaaaaa aaaaaaaaaa aaaaaaaaaa aaaaaaaaaa | 780 |
| aaaaaaaaaa aaaaaaaaaa aaaaaaaaaa aaaaaaaaaa aaaaaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaaaaaaaa | 1020 |
| aaaaaaaaaa aaaaaaaaaa aaaaaaaaaa aaaaaaaaaa aaaaaaaaaa aaaaaaaaaa | 1080 |
| aaaaaaaaaa aaaaaaaaaa aaaaaaaaaa aaaaaaaaaa aaaaaaaaaa aaaaaaaaaa | 1140 |
| aaaaaaaaaa aaaaaaaaaa aaaaaaaaaa aaaaaaaaaa aaaaaaaaaa aaaaaaaaaa | 1200 |
| aaaaaaaaaa aaaaaaaaaa aaaaaaaaaa aaaaaaaaaa aaaaaaaaaa aaaaaaaaaa | 1260 |
| aaaaaaaaaa aaaaaaaaaa aaaaaaaaaa aaaaaaaaaa aaaaaaaaaa aaaaaaaaaa | 1320 |
| aaaaaaaaaa aaaaaaaaaa aaaaaaaaaa aaaaaaaaaa aaaaaaaaaa aaaaaaaaaa | 1380 |
| aaaaaaaaaa aaaaaaaaaa aaaaaaaaaa aaaaaaaaaa aaaaaaaaaa aaaaaaaaaa | 1440 |
| aaaaaaaaaa aaaaaaaaaa aaaaaaaaaa aaaaaaaaaa aaaaaaaaaa aaaaaaaaaa | 1500 |
| aaaaaaaaaa aaaaaaaaaa aaaaaaaaaa aaaaaaaaaa aaaaaaaaaa aaaaaaaaaa | 1560 |
| aaaaaaaaaa aaaaaaaaaa aaaaaaaaaa aaaaaaaaaa aaaaaaaaaa aaaaaaaaaa | 1620 |
| aaaaaaaaaa aaaaaaaaaa aaaaaaaaaa aaaaaaaaaa aaaaaaaaaa aaaaaaaaaa | 1680 |
| aaaaaaaaaa aaaaaaaaaa aaaaaaaaaa aaaaaaaaaa aaaaaaaaaa aaaaaaaaaa | 1740 |
| aaaaaaaaaa aaaaaaaaaa aaaaaaaaaa aaaaaaaaaa aaaaaaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaaaaaaa aaaaaaaaaa aaaaaaaaaa aaaaaaaaaa | 1920 |
| aaaaaaaaaa aaaaaaaaaa aaaaaaaaaa aaaaaaaaaa aaaaaaaaaa aaaaaaaaaa | 1980 |
| aaaaaaaaaa aaaaaaaaaa | 2000 |

```
<210> SEQ ID NO 119
<211> LENGTH: 373
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119
```

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
            245                 250                 255

Gly Gly Cys Glu Leu Arg Val Lys Phe Ser Arg Ser Ala Asp Ala Pro
        260                 265                 270

Ala Tyr Lys Gln Gly Gln Asn Gln Leu Tyr Asn Glu Leu Asn Leu Gly
    275                 280                 285

Arg Arg Glu Glu Tyr Asp Val Leu Asp Lys Arg Arg Gly Arg Asp Pro
290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
            325                 330                 335

Met Lys Gly Glu Arg Arg Arg Gly Lys Gly His Asp Gly Leu Tyr Gln
        340                 345                 350

Gly Leu Ser Thr Ala Thr Lys Asp Thr Tyr Asp Ala Leu His Met Gln
    355                 360                 365

Ala Leu Pro Pro Arg
    370

<210> SEQ ID NO 120
<211> LENGTH: 1182
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 120

```
atggccctcc ctgtcactgc cctgcttctc ccctcgcac tcctgctcca cgccgctaga      60
ccacccggat ggtttctgga ctctccggat cgcccgtgga atccccaac cttctcaccg     120
gcactcttgg ttgtgactga gggcgataat gcgaccttca cgtgctcgtt ctccaacacc    180
tccgaatcat tcgtgctgaa ctggtaccgc atgagcccgt caaaccagac cgacaagctc    240
gccgcgtttc cggaagatcg gtcgcaaccg ggacaggatt gtcggttccg cgtgactcaa    300
ctgccgaatg gcagagactt ccacatgagc gtggtccgcg ctaggcgaaa cgactccggg    360
acctacctgt gcgagccat ctcgctggcg cctaaggccc aaatcaaaga gagcttgagg     420
gccgaactga gagtgaccga gcgcagagct gaggtgccaa ctgcacatcc atccccatcg    480
cctcggcctg cggggcagtt tcagaccctg tcacgacca ctccggcgcc cgcccaccg     540
actccggccc caactatcgc gagccagccc tgtcgctga ggccggaagc atgccgccct     600
gccgccggag gtgctgtgca tacccgggga ttggacttcg catgcgacat ctacatttgg    660
gctcctctcg ccggaacttg tggcgtgctc cttctgtccc tggtcatcac cctgtactgc    720
aagcggggtc ggaaaaagct tctgtacatt ttcaagcagc ccttcatgag gcccgtgcaa    780
accacccagg aggaggacgg ttgctcctgc cggttccccg aagaggaaga aggaggttgc    840
gagctgcgcg tgaagttctc ccggagcgcc gacgcccccg cctataagca gggccagaac    900
cagctgtaca cgaactgaa cctgggacgg cgggaagagt acgatgtgct ggacaagcgg    960
cgcggccggg accccgaaat gggcgggaag cctagaagaa gaacccctca ggaaggcctg   1020
tataacgagc tgcagaagga caagatggcc gaggcctact ccgaaattgg gatgaaggga   1080
gagcggcgga ggggaaaggg gcacgacggc ctgtaccaag gactgtccac cgccaccaag   1140
gacacatacg atgccctgca catgcaggcc cttccccctc gc                      1182
```

<210> SEQ ID NO 121
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 121

```
Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
            100                 105                 110
```

-continued

```
Arg Ala Arg Arg Asn Asp Ser Gly Thr Tyr Leu Cys Gly Ala Ile Ser
            115                 120                 125

Leu Ala Pro Lys Ala Gln Ile Lys Glu Ser Leu Arg Ala Glu Leu Arg
        130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Pro Ala
                165                 170                 175

Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
        195                 200                 205

Arg Gly Leu Asp Phe Ala Cys Asp Ile Tyr Ile Trp Ala Pro Leu Ala
    210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Tyr Ile Phe Lys Gln Pro Phe Met
                245                 250                 255

Arg Pro Val Gln Thr Thr Gln Glu Glu Asp Gly Cys Ser Cys Arg Phe
            260                 265                 270

Pro Glu Glu Glu Glu Gly Gly Cys Glu Leu Arg Val Lys Phe Ser Arg
        275                 280                 285

Ser Ala Asp Ala Pro Ala Tyr Lys Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
    370                 375                 380

Ala Leu His Met Gln Ala Leu Pro Pro Arg
385                 390
```